United States Patent
Snir-Alkalay et al.

(10) Patent No.: US 12,138,265 B2
(45) Date of Patent: Nov. 12, 2024

(54) HETEROARYL COMPOUNDS, PHARMACEUTICAL COMPOSITIONS THEREOF, AND THEIR THERAPEUTIC USE

(71) Applicant: Yissum Research Development Company of the Hebrew University of Jerusalem Ltd., Jerusalem (IL)

(72) Inventors: Irit Snir-Alkalay, Mevasseret Zion (IL); Joseph P. Vacca, Telford, PA (US); Yinon Ben-Neriah, Mevasseret Zion (IL)

(73) Assignee: Yissum Research Development Company of the Hebrew University of Jerusalem Ltd, Jerusalem (IL)

( * ) Notice: Subject to any disclaimer, the term of this patent is extended or adjusted under 35 U.S.C. 154(b) by 0 days.

(21) Appl. No.: 18/159,176

(22) Filed: Jan. 25, 2023

(65) Prior Publication Data

US 2023/0233562 A1    Jul. 27, 2023

Related U.S. Application Data

(63) Continuation of application No. 16/968,273, filed as application No. PCT/IL2019/050151 on Feb. 7, 2019, now abandoned.

(60) Provisional application No. 62/627,921, filed on Feb. 8, 2018, provisional application No. 62/627,908, filed on Feb. 8, 2018.

(51) Int. Cl.
| | |
|---|---|
| *C07D 403/04* | (2006.01) |
| *A61K 31/506* | (2006.01) |
| *A61P 35/00* | (2006.01) |
| *C07D 405/14* | (2006.01) |
| *C07D 413/04* | (2006.01) |
| *C07D 495/04* | (2006.01) |

(52) U.S. Cl.
CPC ............ *A61K 31/506* (2013.01); *A61P 35/00* (2018.01); *C07D 403/04* (2013.01); *C07D 405/14* (2013.01); *C07D 413/04* (2013.01); *C07D 495/04* (2013.01)

(58) Field of Classification Search
CPC ... C07D 403/04; C07D 413/04; A61K 31/506
See application file for complete search history.

(56) References Cited

U.S. PATENT DOCUMENTS

| | | | |
|---|---|---|---|
| 10,376,511 B2 * | 8/2019 | Ben Neriah | .......... C07D 413/14 |
| 10,960,003 B2 * | 3/2021 | Ben Neriah | ............ A61P 35/02 |
| 11,072,599 B2 * | 7/2021 | Li | ........................ C07D 417/04 |

FOREIGN PATENT DOCUMENTS

WO    WO 2017/021969 A1 *    2/2017

OTHER PUBLICATIONS

Billin et al., Discovery of Novel Small Molecules that Activate Satellite Cell Proliferation and Enhance Repair of Damaged Muscle, ACS Chemical Biology, vol. 11, No. 2, pp. 518-529 (2015) [including Supporting Information pp. 1-75].*
Hulikal, Deuterium Labeled Compounds in Drug Discovery Process, Abstract, 2010.*
Pimlott, PubMed Abstract (Nucl Med Commun., 26(3):183-8), 2005.*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. 1: Principles and Practice, pp. 975-977, 1995.*

* cited by examiner

*Primary Examiner* — Deepak R Rao
(74) *Attorney, Agent, or Firm* — Giordano Law LLC; David A. Giordano

(57) ABSTRACT

Provided herein are heteroaryl compounds, for example, a compound of Formula I or IA, and pharmaceutical compositions thereof. Also provided herein are methods of their use for treating, ameliorating, or preventing one or more symptoms of a disorder, disease, or condition mediated by a casein kinase 1 (CK1), an interleukin-1 receptor associated kinase (IRAK1), or a cyclin-dependent kinase 9 (CDK9).

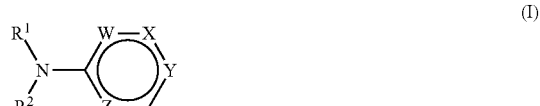

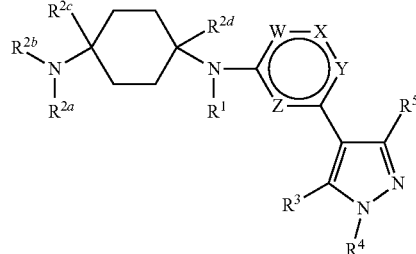

3 Claims, 1 Drawing Sheet

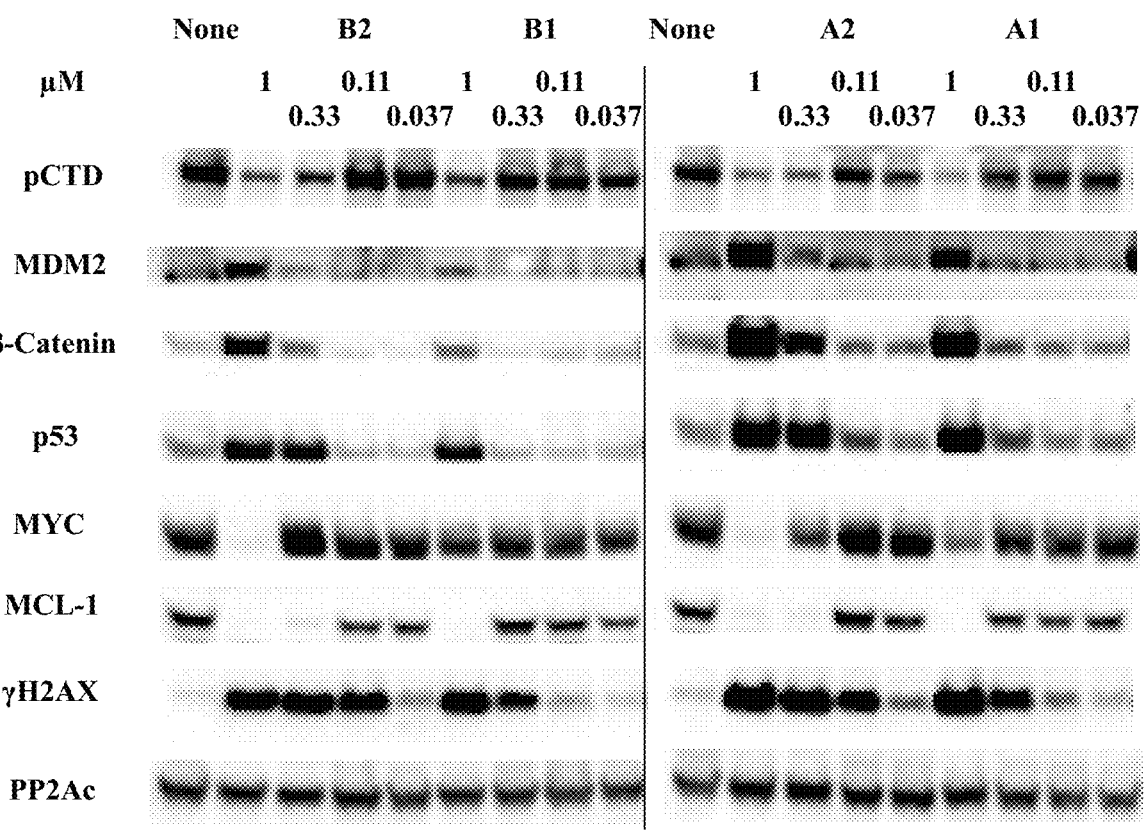

HETEROARYL COMPOUNDS, PHARMACEUTICAL COMPOSITIONS THEREOF, AND THEIR THERAPEUTIC USE

CROSS REFERENCE TO RELATED APPLICATIONS

This application is a continuation of U.S. application Ser. No. 16/968,273, filed Aug. 7, 2020; which is a National Stage of International Application No. PCT/IL2019/050151, filed Feb. 7, 2019; which claims the benefit of U.S. Provisional Application Nos. 62/627,908 and 62/627,921, filed Feb. 8, 2018; the disclosure of each of which is incorporated herein by reference in its entirety.

FIELD

Provided herein are heteroaryl compounds, and pharmaceutical compositions thereof. Also provided herein are methods of their use for treating, ameliorating, or preventing a disorder, disease, or condition mediated by a casein kinase 1 (CK1), an interleukin-1 receptor associated kinase (IRAK1), or a cyclin-dependent kinase 9 (CDK9).

BACKGROUND

Casein kinase 1α (CK1α), encoded by the Csnk1a1 gene, is a component of the β-catenin-degradation complex and a critical regulator of the Wnt signaling pathway. Schittek and Sinnberg, *Mol. Cancer* 2014, 13, 231; Cheong and Virshup, *J. Biochem. Cell Biol.* 2011, 43, 465-469; Elyada et al., *Nature* 2011, 470, 409-413. CK1α phosphorylates β-catenin at Ser45, which primes it for subsequent phosphorylation by GSK-3β. GSK-3β phosphorylates β-catenin at Ser33, Ser37, and Thr41, marking it for ubiquitination and proteasomal degradation. This CK1α-dependent phosphorylation functions as a molecular switch for the Wnt pathway. Amit et al., *Genes Dev.* 2002, 16, 1066-1076. A homozygous deficiency of CK1α results in embryonic lethality, suggesting a fundamental role for CK1α in embryogenesis. In a study of murine intestine epithelium, a CK1α deficiency was found to induce Wnt activation, and DNA damage response, with robust p53 activation and cellular senescence; this was also seen in other types of tissues such as in skin keratinocytes including tissue stem cells. Elyada et al., *Nature* 2011, 470, 409-413; Schneider et al., *Cancer Cell* 2014, 26, 509-520; Chang et al., *Proc. Natl. Acad. Sci. U.S.A.* 2017, 114, E8035-E8044. These facts suggest that CK1α plays an important role in cellular processes in various tissues, which is, at least, partly coordinated with p53. The well-known tumor suppressor protein, p53, is a transcription factor that plays a pivotal role in cellular responses to genotoxic stress and DNA damage. Levine and Oren, *Nat. Rev. Cancer* 2009, 9, 749-758. In the skin, p53 also acts as a central player against UV damage via the p53/POMC/α-MSH/MC1R/MITF skin tanning pathway and through the DNA repair/cell cycle arrest/apoptotic pathway. Cui et al., *Cell* 2007, 128, 853-864; Ogmundsdottir and Steingrimsson, *Pigment. Cell Melanoma Res.* 2014, 27, 154-155.

An interleukin-1 receptor associated kinase (IRAK1) is a serine/threonine kinase that mediates signals elicited from Toll-like receptor (TLR) and interleukin-1 receptor (IL1R). Janssens and Beyaert, *Mol. Cell.* 2003, 11, 293-302. Upon receptor activation, IRAK1 becomes phosphorylated, leading to recruitment of TRAF6 and activation of NF-κB and JNK pathways. IRAK1 has been identified as a therapeutic target for many proliferative diseases, including myelodysplastic syndrome (MDS), certain subsets of acute myeloid leukemia (AML), triple negative breast cancer, and head and neck cancer. Rhyasen et al., *Cancer Cell.* 2013, 24, 90-104; Rhyasen et al., *Exp. Hematol.* 2013, 41, 1005-1007; Wee et al., *Nat. Commun.* 2015, 6, 8746; Adams et al., *Oncotarget* 2015, 6, 43395-43407. For example, it has been demonstrated that IRAK-inhibition by a small molecule or the knockdown of IRAK1 impairs MDS cell proliferation, progenitor function, and viability in vitro and in vivo. Rhyasen et al., *Cancer Cell.* 2013, 24, 90-104; Rhyasen et al., *Exp. Hematol.* 2013, 41, 1005-1007. It has also been demonstrated that IRAK1 overexpression confers triple negative breast cancer cells (TNBC) a growth advantage through NF-κB-related cytokine secretion and metastatic TNBC cells exhibit gain of IRAK1 dependency, resulting in high susceptibility to genetic and pharmacologic inhibition of IRAK1. Wee et al., *Nat. Commun.* 2015, 6, 8746. It has been demonstrated that IRAK1 is essential for the cell survival of head and neck squamous cell carcinomas. Adams et al., *Oncotarget* 2015, 6, 43395-43407.

Cyclin-dependent kinase 9 (CDK9) is a prominent member of the transcriptional CDKs subfamily, a group of kinases whose function is to control the primary steps of mRNA synthesis and processing by eukaryotic RNA polymerase II. As a cyclin dependent kinase, CDK9 activation in vivo depends upon its association with T-type cyclins to assemble the positive transcription elongation factor (P-TEFb). Several cases of CDK9 deregulation have been linked to important human diseases, including various types of cancer and AIDS due to its essential role in HIV replication. Many human viruses including HIV have been shown to depend strongly on CDK9 activity to be transcribed within host cells. Paparidis et al., *Mol. Biosyst.* 2017, 13, 246-276.

Therefore, there is a need for a compound as an effective therapy for treating a disorder, disease, or condition mediated by a casein kinase 1, an interleukin-1 receptor associated kinase, or a cyclin-dependent kinase 9.

SUMMARY OF THE DISCLOSURE

Provided herein is a compound of Formula I:

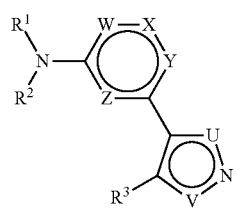

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

U and V are each independently —O— and =C($R^4$)—; or U and V are each independently =N— and —N($R^5$)—;

W, X, Y, and Z are each independently =C($R^6$)— or =N—, with the proviso that at least one of W, X, Y, and Z is =N—; or W, X, and Z are each independently =C($R^6$)—, —N($R^7$)—, =N—, —O—, or —S—; and Y is a bond;

R[1] and R[2] are each independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)R[1a], —C(O)OR[1a], —C(O)NR[1b]R[1c], —C(O)SR[1a], —C(NR[1a])NR[1b]R[1c], —C(S)R[1a], —C(S)OR[1a], —C(S)NR[1b]R[1c], —OR[1a], —OC(O)R[1a], —OC(O)OR[1a], —OC(O)NR[1b]R[1c], —OC(O)SR[1a], —OC(=NR[1a])NR[1b]R[1c], —OC(S)R[1a], —OC(S)OR[1a], —OC(S)NR[1b]R[1c], —OS(O)R[1a], —OS(O)$_2$R[1a], —OS(O)NR[1b]R[1c], —OS(O)$_2$NR[1b]R[1c], —NR[1b]R[1c], —NR[1a]C(O)R[1d], —NR[1a]C(O)OR[1d], —NR[1a]C(O)NR[1b]R[1c], —NR[1a]C(O)SR[1d], —NR[1a]C(=NR[1d])NR[1b]R[1c], —NR[1a]C(S)R[1d], —NR[1a]C(S)OR[1d], —NR[1a]C(S)NR[1b]R[1c], —NR[1a]S(O)R[1d], —NR[1a]S(O)$_2$R[1d], —NR[1a]S(O)NR[1b]R[1c], —NR[1a]S(O)$_2$NR[1b]R[1c], —S(O)R[1a], —S(O)$_2$R[1a], —S(O)NR[1b]R[1c], or —S(O)$_2$NR[1b]R[1c]; or R[1] and R[2] together with the N atom to which they are attached form heteroaryl or heterocyclyl;

each R[3], R[4], and R[6] is independently (a) hydrogen, deuterium, cyano, halo, or nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)R[1a], —C(O)OR[1a], —C(O)NR[1b]R[1c], —C(O)SR[1a], —C(NR[1a])NR[1b]R[1c], —C(S)R[1a], —C(S)OR[1a], —C(S)NR[1b]R[1c], —OR[1a], —OC(O)R[1a], —OC(O)OR[1a], —OC(O)NR[1b]R[1c], —OC(O)SR[1a], —OC(=NR[1a])NR[1b]R[1c], —OC(S)R[1a], —OC(S)OR[1a], —OC(S)NR[1b]R[1c], —OS(O)R[1a], —OS(O)$_2$R[1a], —OS(O)NR[1b]R[1c], —OS(O)$_2$NR[1b]R[1c], —NR[1b]R[1c], —NR[1a]C(O)R[1d], —NR[1a]C(O)OR[1d], —NR[1a]C(O)NR[1b]R[1c], —NR[1a]C(O)SR[1d], —NR[1a]C(=NR[1d])NR[1b]R[1c], —NR[1a]C(S)R[1d], —NR[1a]C(S)OR[1d], —NR[1a]C(S)NR[1b]R[1c], —NR[1a]S(O)R[1d], —NR[1a]S(O)$_2$R[1d], —NR[1a]S(O)NR[1b]R[1c], —NR[1a]S(O)$_2$NR[1b]R[1c], —SR[1a], —S(O)R[1a], —S(O)$_2$R[1a], —S(O)NR[1b]R[1c], or —S(O)$_2$NR[1b]R[1c];

R[5] and R[7] are each independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)R[1a], —C(O)OR[1a], —C(O)NR[1b]R[1c], —C(O)SR[1a], —C(NR[1a])NR[1b]R[1c], —C(S)R[1a], —C(S)OR[1a], —C(S)NR[1b]R[1c], —OR[1a], —OC(O)R[1a], —OC(O)OR[1a], —OC(O)NR[1b]R[1c], —OC(O)SR[1a], —OC(=NR[1a])NR[1b]R[1c], —OC(S)R[1a], —OC(S)OR[1a], —OC(S)NR[1b]R[1c], —OS(O)R[1a], —OS(O)$_2$R[1a], —OS(O)NR[1b]R[1c], —OS(O)$_2$NR[1b]R[1c], —NR[1b]R[1c], —NR[1a]C(O)R[1d], —NR[1a]C(O)OR[1d], —NR[1a]C(O)NR[1b]R[1c], —NR[1a]C(O)SR[1d], —NR[1a]C(=NR[1d])NR[1b]R[1c], —NR[1a]C(S)R[1d], —NR[1a]C(S)OR[1d], —NR[1a]C(S)NR[1b]R[1c], —NR[1a]S(O)R[1d], —NR[1a]S(O)$_2$R[1d], —NR[1a]S(O)NR[1b]R[1c], —NR[1a]S(O)$_2$NR[1b]R[1c], —S(O)R[1a], —S(O)$_2$R[1a], —S(O)NR[1b]R[1c], or —S(O)$_2$NR[1b]R[1c]; and each R[1a], R[1b], R[1c], and R[1d] is independently hydrogen, deuterium, $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or R[1a] and R[1c] together with the C and N atoms to which they are attached form heterocyclyl; or R[1b] and R[1c] together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents Q[a]; and (c) —C(O)R[a], —C(O)OR[a], —C(O)NR[b]R[c], —C(O)SR[a], —C(NR[a])NR[b]R[c], —C(S)R[a], —C(S)OR[a], —C(S)NR[b]R[c], —OR[a], —OC(O)R[a], —OC(O)OR[a], —OC(O)NR[b]R[c], —OC(O)SR[a], —OC(=NR[a])NR[b]R[c], —OC(S)R[a], —OC(S)OR[a], —OC(S)NR[b]R[c], —OS(O)R[a], —OS(O)$_2$R[a], —OS(O)NR[b]R[c], —OS(O)$_2$NR[b]R[c], —NR[b]R[c], —NR[a]C(O)R[d], —NR[a]C(O)OR[d], —NR[a]C(O)NR[b]R[c], —NR[a]C(O)SR[d], —NR[a]C(=NR[d])NR[b]R[c], —NR[a]C(S)R[d], —NR[a]C(S)OR[d], —NR[a]C(S)NR[b]R[c], —NR[a]S(O)R[d], —NR[a]S(O)$_2$R[d], —NR[a]S(O)NR[b]R[c], —NR[a]S(O)$_2$NR[b]R[c], —SR[a], —S(O)R[a], —S(O)$_2$R[a], —S(O)NR[b]R[c], and —S(O)$_2$NR[b]R[c], wherein each R[a], R[b], R[c], and R[d] is independently (i) hydrogen or deuterium; (ii) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents Q[a]; or (iii) R[b] and R[c] together with the N atom to which they are attached form heterocyclyl, optionally substituted with one or more, in one embodiment, one, two, three, or four, substituents Q[a];

wherein each Q[a] is independently selected from the group consisting of (a) deuterium, cyano, halo, and nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, and heterocyclyl; and (c) —C(O)R[e], —C(O)OR[e], —C(O)NR[f]R[g], —C(O)SR[e], —C(NR[e])NR[f]R[g], —C(S)R[e], —C(S)OR[e], —C(S)NR[f]R[g], —OR[e], —OC(O)R[e], —OC(O)OR[e], —OC(O)NR[f]R[g], —OC(O)SR[e], —OC(=NR[e])NR[f]R[g], —OC(S)R[e], —OC(S)OR[e], —OC(S)NR[f]R[g], —OS(O)R[e], —OS(O)$_2$R[e], —OS(O)NR[f]R[g], —OS(O)$_2$NR[f]R[g], —NR[f]R[g], —NR[e]C(O)R[h], —NR[e]C(O)OR[f], —NR[e]C(O)NR[f]R[g], —NR[e]C(O)SR[f], —NR[e]C(=NR[h])NR[f]R[g], —NR[e]C(S)R[h], —NR[e]C(S)OR[f], —NR[e]C(S)NR[f]R[g], —NR[e]S(O)R[h], —NR[e]S(O)$_2$R[h], —NR[e]S(O)NR[f]R[g], —NR[e]S(O)$_2$NR[f]R[g], —SR[e], —S(O)R[e], —S(O)$_2$R[e], —S(O)NR[f]R[g], and —S(O)$_2$NR[f]R[g]; wherein each R[e], R[f], R[g], and R[h] is independently (i) hydrogen or deuterium; (ii) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (iii) R[f] and R[g] together with the N atom to which they are attached form heterocyclyl.

Also provided herein is a compound of Formula I:

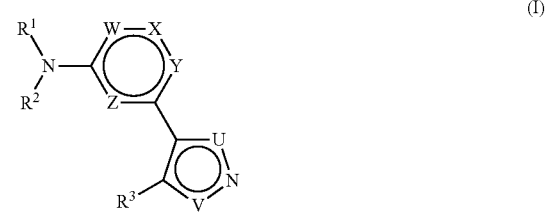

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

U and V are each independently —O— and =C(R[4])—; or U and V are each independently =N— and —N(R[5])—; or U is =N— and —N(R[5])—; and V is =C(R[4])—;

W, X, Y, and Z are each independently =C($R^6$)— or =N—, with the proviso that at least one of W, X, Y, and Z is =N—; or W, X, and Z are each independently =C($R^6$)—, —N($R^7$)—, =N—, —O—, or —S—; and Y is a bond;

$R^1$ and $R^2$ are each independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; or $R^1$ and $R^2$ together with the N atom to which they are attached form heteroaryl or heterocyclyl;

each $R^3$, $R^4$, and $R^6$ is independently (a) hydrogen, deuterium, cyano, halo, or nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^5$ and $R^7$ are each independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(=N$R^a$)N$R^bR^c$, —OC(S)$R^a$, —OC(S)O$R^a$, —OC(S)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(=N$R^d$)N$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(O)S$R^e$, —C(N$R^e$)N$R^fR^g$, —C(S)$R^e$, —C(S)O$R^e$, —C(S)N$R^fR^g$, —O$R^e$, —OC(O)$R^e$, —OC(O)O$R^e$, —OC(O)N$R^fR^g$, —OC(O)S$R^e$, —OC(=N$R^e$)N$R^fR^g$, —OC(S)$R^e$, —OC(S)O$R^e$, —OC(S)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(O)S$R^f$, —N$R^e$C(=N$R^h$)N$R^fR^g$, —N$R^e$C(S)$R^h$, —N$R^e$C(S)O$R^f$, —N$R^e$C(S)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Additionally provided herein is a compound of Formula IA:

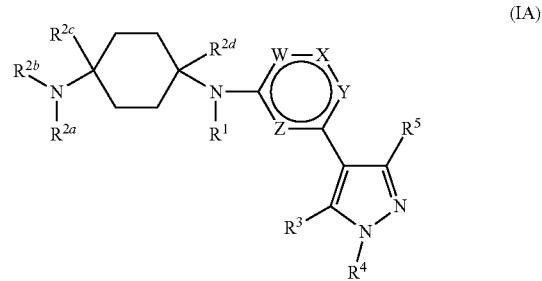

(IA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

W, X, Y, and Z are each independently $=C(R^6)$— or $=N$—, with the proviso that at least one of W, X, Y, and Z is $=N$—; or W, X, and Z are each independently $=C(R^6)$—, $-N(R^7)$—, $=N$—, $-O$—, or $-S$—; and Y is a bond;

each $R^1$, $R^4$, and $R^7$ is independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(O)SR^{1a}$, $-C(NR^{1a})NR^{1b}R^{1c}$, $-C(S)R^{1a}$, $-C(S)OR^{1a}$, $-C(S)NR^{1b}R^{1c}$, $-OR^{1a}$, $-OC(O)R^{1a}$, $-OC(O)OR^{1a}$, $-OC(O)NR^{1b}R^{1c}$, $-OC(O)SR^{1a}$, $-OC(=NR^{1a})NR^{1b}R^{1c}$, $-OC(S)R^{1a}$, $-OC(S)OR^{1a}$, $-OC(S)NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(O)SR^{1d}$, $-NR^{1a}C(=NR^{1d})NR^{1b}R^{1c}$, $-NR^{1a}C(S)R^{1d}$, $-NR^{1a}C(S)OR^{1d}$, $-NR^{1a}C(S)NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-S(O)R^{1a}$, $-S(O)_2R^{1a}$, $-S(O)NR^{1b}R^{1c}$, or $-S(O)_2NR^{1b}R^{1c}$;

$R^{2a}$, $R^{2b}$, $R^{2c}$, and $R^{2d}$ are (i) or (ii):

(i) $R^{2a}$ and $R^{2b}$ are each independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(O)SR^{1a}$, $-C(NR^{1a})NR^{1b}R^{1c}$, $-C(S)R^{1a}$, $-C(S)OR^{1a}$, $-C(S)NR^{1b}R^{1c}$, $-OR_{1a}$, $-OC(O)R^{1a}$, $-OC(O)OR^{1a}$, $-OC(O)NR^{1b}R^{1c}$, $-OC(O)SR^{1a}$, $-OC(=NR^{1a})NR^{1b}R^{1c}$, $-OC(S)R^{1a}$, $-OC(S)OR^{1a}$, $-OC(S)NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR_{1b}R_{1c}$, $-NR^{1a}C(O)R^{1d}$, $-NR^{1a}C(O)OR^{1d}$, $-NR^{1a}C(O)NR^{1b}R^{1c}$, $-NR^{1a}C(O)SR^{1d}$, $-NR^{1a}C(=NR^{1d})NR^{1b}R^{1c}$, $-NR^{1a}C(S)R^{1d}$, $-NR^{1a}C(S)OR^{1d}$, $-NR^{1a}C(S)NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-S(O)R^{1a}$, $-S(O)_2R^{1a}$, $-S(O)NR^{1b}R^{1c}$, or $-S(O)_2NR^{1b}R^{1c}$; or $R^{2a}$ and $R^{2b}$ together with the N atom to which they are attached form heteroaryl or heterocyclyl; and $R^{2c}$ and $R^{2d}$ are each independently (a) hydrogen, deuterium, or cyano; or (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or $R^{2c}$ and $R^{2d}$ are linked together to form $-O$—, $C_{1-6}$ alkylene, $C_{1-6}$ heteroalkylene, $C_{2-6}$ alkenylene, or $C_{2-6}$ alkynylene; or (ii) $R^{2a}$ and $R^{2c}$ together with the C and N atoms to which they are attached form heterocyclyl;

$R^{2b}$ is (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(O)SR^{1a}$, $-C(NR^{1a})NR^{1b}R^{1c}$, $-C(S)R^{1a}$, $-C(S)OR^{1a}$, $-C(S)NR^{1b}R^{1c}$, $-OR^{1a}$, $-OC(O)R^{1a}$, $-OC(O)OR^{1a}$, $-OC(O)NR^{1b}R^{1c}$, $-OC(O)SR^{1a}$, $-OC(=NR^{1a})NR^{1b}R^{1c}$, $-OC(S)R^{1a}$, $-OC(S)OR^{1a}$, $-OC(S)NR^{1b}R^{1c}$, $-OS(O)R^{1a}$, $-OS(O)_2R^{1a}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(O)SR^{1d}$, $-NR^{1a}C(=NR^{1d})NR^{1b}R^{1c}$, $-NR^{1a}C(S)R^{1d}$, $-NR^{1a}C(S)OR^{1d}$, $-NR^{1a}C(S)NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-S(O)R^{1a}$, $-S(O)_2R^{1a}$, $-S(O)NR^{1b}R^{1c}$, or $-S(O)_2NR^{1b}R^{1c}$; and $R^{2d}$ is (a) hydrogen, deuterium, or cyano; or (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl;

each $R^3$, $R^5$, and $R^6$ is independently (a) hydrogen, deuterium, cyano, halo, or nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(O)SR^{1a}$, $-C(NR^{1a})NR^{1b}R^{1c}$, $-C(S)R^{1a}$, $-C(S)OR^{1a}$, $-C(S)NR^{1b}R^{1c}$, $-OR^{1a}$, $-OC(O)R^{1a}$, $-OC(O)OR^{1a}$, $-OC(O)NR^{1b}R^{1c}$, $-OC(O)SR^{1a}$, $-OC(=NR^{1a})NR^{1b}R^{1c}$, $-OC(S)R^{1a}$, $-OC(S)OR^{1a}$, $-OC(S)NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(O)SR^{1d}$, $-NR^{1a}C(=NR^{1d})NR^{1b}R^{1c}$, $-NR^{1a}C(S)R^{1d}$, $-NR^{1a}C(S)OR^{1d}$, $-NR^{1a}C(S)NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-SR^{1a}$, $-S(O)R^1$, $-S(O)_2R^{1a}$, $-S(O)NR^{1b}R^{1c}$, or $-S(O)_2NR^{1b}R^{1c}$; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkylene, heteroalkylene, alkenyl, alkenylene, alkynyl, alkynylene, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) $-C(O)R^a$, $-C(O)OR^a$, $-C(O)NR^bR^c$, $-C(O)SR^a$, $-C(NR^a)NR^bR^c$, $-C(S)R^a$, $-C(S)OR^a$, $-C(S)NR^bR^c$, $-OR^a$, $-OC(O)R^a$, $-OC(O)OR^a$, $-OC(O)NR^bR^c$, $-OC(O)SR^a$, $-OC(=NR^a)NR^bR^c$, $-OC(S)R^a$, $-OC(S)OR^a$, $-OC(S)NR^bR^c$, $-OS(O)R^a$, $-OS(O)_2R^a$, $-OS(O)NR^bR^c$, $-OS(O)_2NR^bR^c$, $-NR^bR^c$, $-NR^aC(O)R^d$, $-NR^aC(O)OR^d$, $-NR^aC(O)NR^bR^c$, $-NR^aC(O)SR^d$, $-NR^aC(=NR^d)NR^bR^c$, $-NR^aC(S)R^d$, $-NR^aC(S)OR^d$, $-NR^aC(S)NR^bR^c$, $-NR^aS(O)R^d$, $-NR^aS(O)_2R^d$, $-NR^aS(O)NR^bR^c$, $-NR^aS(O)_2NR^bR^c$, $-SR^a$, $-S(O)R^a$, $-S(O)_2R^a$, $-S(O)NR^bR^c$, and $-S(O)_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b)

$C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(=NR$^h$)NR$^b$R$^c$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

Furthermore provided herein is a pharmaceutical composition, comprising a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, and a pharmaceutically acceptable excipient.

Provided herein is a method of treating, preventing, or ameliorating one or more symptoms of a proliferative disease in a subject, comprising administering to the subject a therapeutically effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of treating, preventing, or ameliorating one or more symptoms of acquired immune deficiency syndrome (AIDS) in a subject, comprising administering to the subject a therapeutically effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of treating or preventing a viral infection in a subject, comprising administering to the subject a therapeutically effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of treating, ameliorating, or preventing a skin disorder, disease, or condition in a subject, comprising administering to the subject a therapeutically effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of protecting a subject from ultraviolet radiation, comprising administering to the subject a therapeutically effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of increasing skin pigmentation in a subject, comprising administering to the subject a therapeutically effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of increasing eumelanin level in a subject, comprising administering to the subject a therapeutically effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of treating one or more symptoms of a disorder, disease, or condition mediated by a casein kinase 1 (CK1) in a subject, comprising administering to the subject a therapeutically effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of treating one or more symptoms of a disorder, disease, or condition mediated by an interleukin-1 receptor associated kinase (IRAK1) in a subject, comprising administering to the subject a therapeutically effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of treating one or more symptoms of a disorder, disease, or condition mediated by a cyclin-dependent kinase 9 (CDK9) in a subject, comprising administering to the subject a therapeutically effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of inhibiting the activity of a CK1 in a cell, comprising contacting the cell with an effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of inhibiting the activity of an IRAK1 in a cell, comprising contacting the cell with an effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of inhibiting the activity of a CDK9 in a cell, comprising contacting the cell with an effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of inhibiting the growth of a cell, comprising contacting the cell with an effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method for inhibiting replication of a virus in a host, comprising administering to the host a therapeutically effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of increasing eumelanin level in a skin cell, comprising contacting the cell with an effective amount of a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

BRIEF DESCRIPTION OF THE DRAWINGS

FIG. 1 shows the effects of compounds A1, A2, B1, and B2 on the protein expression levels of β-catenin, MDM2, MCL-1, MYC, and p53; and on the phosphorylation of RNA POL2-CTD (pCTD) and H2AX (γH2AX), following 16 h-treatment of RKO cells, where PP2Ac was used as a loading control.

DETAILED DESCRIPTION

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The term "host" refers to a unicellular or multicellular organism in which a virus can replicate, including, but not limited to, a cell, cell line, and animal, such as a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, *Remington: The Science and Practice of Pharmacy,* 22nd ed.; Allen Ed.: Philadelphia, PA, 2012; *Handbook of Pharmaceutical Excipients,* 8th ed.; Sheskey et al., Eds.; The Pharmaceutical Press and the American Pharmacists Association: 2017; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, FL, 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer of a compound described herein.

The terms "drug," "therapeutic agent," and "chemotherapeutic agent" refer to a compound or a pharmaceutical composition thereof, which is administered to a subject for treating, preventing, or ameliorating one or more symptoms of a disorder, disease, or condition.

The term "alkyl" refers to a linear or branched saturated monovalent hydrocarbon radical, wherein the alkyl is optionally substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkylene" refers to a linear or branched saturated divalent hydrocarbon radical, wherein the alkylene may optionally be substituted with one or more substituents Q as described herein. For example, $C_{1-6}$ alkylene refers to a linear saturated divalent hydrocarbon radical of 1 to 6 carbon atoms or a branched saturated divalent hydrocarbon radical of 3 to 6 carbon atoms. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms).

The term "heteroalkylene" refers to a linear or branched saturated divalent hydrocarbon radical that contains one or more heteroatoms each independently selected from O, S, and N in the hydrocarbon chain. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkylene groups are also referred as "lower heteroalkylene." Examples of heteroalkylene groups include, but are not limited to, —$CH_2O$—, —$CH_2OCH_2$—, —$CH_2CH_2O$—, —$CH_2NH$—, —$CH_2NHCH_2$—, —$CH_2CH_2NH$—, —$C(O)NH$—, —$C(O)NHCH_2$—, —$CH_2C(O)NH$—, —$CH_2S$—, —$CH_2SCH_2$—, —$CH_2CH_2S$—, —$CH_2S(O)_2NH$—, —$CH_2S(O)_2NHCH_2$—, and —$CH_2CH_2S(O)_2NH$—. In certain embodiments, heteroalkylene may also be optionally substituted with one or more substituents Q as described herein.

The term "alkenyl" refers to a linear or branched monovalent hydrocarbon radical, which contains one or more, in one embodiment, one, two, three, four, or five, in another embodiment, one, carbon-carbon double bond(s). The alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more carbon-carbon double bond(s), in one embodiment, one to five carbon-carbon double bond(s), in another embodiment, one carbon-carbon double bond. The alkenylene may be optionally substituted with one or more substituents Q as described herein. The term "alkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene.

The term "alkynyl" refers to a linear or branched monovalent hydrocarbon radical, which contains one or more, in one embodiment, one, two, three, four, or five, in another embodiment, one, carbon-carbon triple bond(s). The alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "alkynylene" refers to a linear or branched divalent hydrocarbon radical, which contains one or more, in one embodiment, one, two, three, four, or five, in another embodiment, one or two, carbon-carbon triple bond(s). The alkynylene may be optionally substituted with one or more substituents Q as described herein. For example, $C_{2-6}$ alkynylene refers to a linear unsaturated divalent hydrocarbon radical of 2 to 6 carbon atoms or a branched unsaturated divalent hydrocarbon radical of 4 to 6 carbon atoms. In certain embodiments, the alkynylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynylene groups include, but are not limited to, ethynylene, propynylene (including all isomeric forms, e.g., 1-propynylene and propargylene), butynylene (including all isomeric forms, e.g., 1-butyn-1-ylene and 2-butyn-1-ylene), pentynylene (including all isomeric forms, e.g., 1-pentyn-1-ylene and 1-methyl-2-butyn-1-ylene), and hexynylene (including all isomeric forms, e.g., 1-hexyn-1-ylene).

The term "cycloalkyl" refers to a cyclic monovalent hydrocarbon radical, which is optionally substituted with one or more substituents Q as described herein. In one embodiment, the cycloalkyl is a saturated or unsaturated but non-aromatic, and/or bridged or non-bridged, and/or fused bicyclic group. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. In one embodiment, the cycloalkyl is monocyclic. In another embodiment, the cycloalkyl is bicyclic. In yet another embodiment, the cycloalkyl is polycyclic. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "aryl" refers to a monovalent monocyclic aromatic hydrocarbon radical and/or monovalent polycyclic aromatic hydrocarbon radical that contain at least one aromatic carbon ring. In certain embodiments, the aryl has from 6 to 20 ($C_{6-20}$), from 6 to 15 ($C_{6-15}$), or from 6 to 10 ($C_{6-10}$) ring carbon atoms. Examples of aryl groups include, but are not limited to, phenyl, naphthyl, fluorenyl, azulenyl, anthryl, phenanthryl, pyrenyl, biphenyl, and terphenyl. The aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In one embodiment, the aryl is monocyclic. In another embodiment, the aryl is polycyclic. In yet another embodiment, the aryl is bicyclic. In still another embodiment, the aryl is tricyclic. In certain embodiments, the aryl is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, the aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each independently selected from O, S, and N, in the ring. The heteroaryl is bonded to the rest of a molecule through the aromatic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. In one embodiment, the heteroaryl is monocyclic. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In another embodiment, the heteroaryl is bicyclic. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. In yet another embodiment, the heteroaryl is tricyclic. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. The heterocyclyl is bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclyls and heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "halogen", "halide," or "halo" refers to fluorine, chlorine, bromine, and/or iodine.

The term "optionally substituted" is intended to mean that a group or substituent, such as an alkyl, alkylene, heteroalkylene, alkenyl, alkenylene, alkynyl, alkynylene, cycloalkyl, aryl, aralkyl, heteroaryl, or heterocyclyl group, may be substituted with one or more, one, two, three, or four, substituents Q, each of which is independently selected from, e.g., (a) deuterium (-D), cyano (—CN), halo, and nitro (—NO$_2$); (b) C$_{1-6}$ alkyl, C$_{2-6}$ alkenyl, C$_{2-6}$ alkynyl, C$_{3-12}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(O)SR$^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(=NR$^a$)NR$^b$R$^c$, —OC(S)R$^a$, —OC(S)OR$^a$, —OC(S)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(=NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) C$_{1-6}$ alkyl, C$_{2-6}$ alkenyl, C$_{2-6}$ alkynyl, C$_{3-12}$ cycloalkyl, C$_{6-14}$ aryl, C$_{7-15}$ aralkyl, heteroaryl, or heterocyclyl, each of which is optionally substituted with one or more, in one embodiment, one, two, three, or four, substituents Q$^a$; or (iii) R$^b$ and R$^c$ together with the N atom to which they are attached form heterocyclyl, optionally substituted with one or more, in one embodiment, one, two, three, or four, substituents Q$^a$. As used herein, all groups that can be substituted are "optionally substituted," unless otherwise specified.

In one embodiment, each Q$^a$ is independently selected from the group consisting of (a) deuterium, cyano, halo, and nitro; (b) C$_{1-6}$ alkyl, C$_{2-6}$ alkenyl, C$_{2-6}$ alkynyl, C$_{3-12}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(=NR$^h$)NR$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^b$R$^c$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-12}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an isotopically enriched compound is in an unstable form, that is, radioactive. In certain embodiments, an isotopically enriched compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, as example, or any carbon can be $^{13}$C, as example, or any nitrogen can be $^{15}$N, as example, or any oxygen can be $^{18}$O, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^1$H for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium ($^1$H), deuterium ($^2$H or D), and tritium ($^3$H), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}C$) and carbon-13 ($^{13}C$) in their natural abundances. Carbon-12 is the most common carbon isotope having a natural abundance of more than 98.89%. Carbon-13 is a less prevalent carbon isotope having a natural abundance of about 1.110%.

The term "carbon-13 enrichment" or "$^{13}C$ enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.110% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof" has the same meaning as the phrase "(i) an enantiomer, a mixture of enantiomers, a mixture of two or more diastereomers, a tautomer, a mixture of two or more tautomers, or an isotopic variant of the compound referenced therein; or (ii) a pharmaceutically acceptable salt, solvate, hydrate, or prodrug of the compound referenced therein; or (iii) a pharmaceutically acceptable salt, solvate, hydrate, or prodrug of an enantiomer, a mixture of enantiomers, a mixture of two or more diastereomers, a tautomer, a mixture of two or more tautomers, or an isotopic variant of the compound referenced therein."

Compounds

In one embodiment, provided herein is a compound of Formula I:

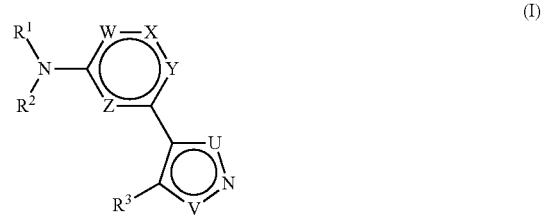

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

U and V are each independently —O— and =C($R^4$)—; or U and V are each independently =N— and —N($R^5$)—;

W, X, Y, and Z are each independently =C($R^6$)— or =N—, with the proviso that at least one of W, X, Y, and Z is =N—; or W, X, and Z are each independently =C($R^6$)—, —N($R^7$)—, =N—, —O—, or —S—; and Y is a bond;

$R^1$ and $R^2$ are each independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)NR$^{1b}$R$^{1c}$, —C(O)S$R^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)

$NR^{1b}R^{1c}$, —$NR^{1a}C(S)R^{1d}$, —$NR^{1a}C(S)OR^{1d}$, —$NR^{1a}C(S)NR^{1b}R^{1c}$, —$NR^{1a}S(O)R^{1d}$, —$NR^{1a}S(O)_2 R^{1d}$, —$NR^{1a}S(O)NR^{1b}R^{1c}$, —$NR^{1a}S(O)_2NR^{1b}R^{1c}$, —$S(O)R^{1a}$, —$S(O)_2R^{1a}$, —$S(O)NR^{1b}R^{1c}$, or —$S(O)_2NR^{1b}R^{1c}$; or $R^1$ and $R^2$ together with the N atom to which they are attached form heteroaryl or heterocyclyl;

each $R^3$, $R^4$, and $R^6$ is independently (a) hydrogen, deuterium, cyano, halo, or nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(O)SR^{1a}$, —$C(NR^{1a})NR^{1b}R^{1c}$, —$C(S)R^{1a}$, —$C(S)OR^{1a}$, —$C(S)NR^{1b}R^{1c}$, —$OR^{1a}$, —$OC(O)R^{1a}$, —$OC(O)OR^{1a}$, —$OC(O)NR^{1b}R^{1c}$, —$OC(O)SR^{1a}$, —$OC(=NR^{1a})NR^{1b}R^{1c}$, —$OC(S)R^{1a}$, —$OC(S)OR^{1a}$, —$OC(S)NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(O)SR^{1d}$, —$NR^{1a}C(=NR^{1d})NR^{1b}R^{1c}$, —$NR^{1a}C(S)R^{1d}$, —$NR^{1a}C(S)OR^{1d}$, —$NR^{1a}C(S)NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$;

$R^5$ and $R^7$ are each independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(O)SR^{1a}$, —$C(NR^{1a})NR^{1b}R^{1c}$, —$C(S)R^{1a}$, —$C(S)OR^{1a}$, —$C(S)NR^{1b}R^{1c}$, —$OR^{1a}$, —$OC(O)R^{1a}$, —$OC(O)OR^{1a}$, —$OC(O)NR^{1b}R^{1c}$, —$OC(O)SR^{1a}$, —$OC(=NR^{1a})NR^{1b}R^{1c}$, —$OC(S)R^{1a}$, —$OC(S)OR^{1a}$, —$OC(S)NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(O)SR^{1d}$, —$NR^{1a}C(=NR^{1d})NR^{1b}R^{1c}$, —$NR^{1a}C(S)R^{1d}$, —$NR^{1a}C(S)OR^{1d}$, —$NR^{1a}C(S)NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$S(O)R^{1a}$, —$S(O)_2R^{1a}$, —$S(O)NR^{1b}R^{1c}$, or —$S(O)_2NR^{1b}R^{1c}$; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —$C(O)R^a$, —$C(O)OR^a$, —$C(O)NR^bR^c$, —$C(O)SR^a$, —$C(NR^a)NR^bR^c$, —$C(S)R^a$, —$C(S)OR^a$, —$C(S)NR^bR^c$, —$OR^a$, —$OC(O)R^a$, —$OC(O)OR^a$, —$OC(O)NR^bR^c$, —$OC(O)SR^a$, —$OC(=NR^a)NR^bR^c$, —$OC(S)R^a$, —$OC(S)OR^a$, —$OC(S)NR^bR^c$, —$OS(O)R^a$, —$OS(O)_2R^a$, —$OS(O)NR^bR^c$, —$OS(O)_2NR^bR^c$, —$NR^bR^c$, —$NR^aC(O)R^d$, —$NR^aC(O)OR^d$, —$NR^aC(O)NR^bR^c$, —$NR^aC(O)SR^d$, —$NR^aC(=NR^d)NR^bR^c$, —$NR^aC(S)R^d$, —$NR^aC(S)OR^d$, —$NR^aC(S)NR^bR^c$, —$NR^aS(O)R^d$, —$NR^aS(O)_2R^d$, —$NR^aS(O)NR^bR^c$, —$NR^aS(O)_2NR^bR^c$, —$SR^a$, —$S(O)R^a$, —$S(O)_2R^a$, —$S(O)NR^bR^c$, and —$S(O)_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, and heterocyclyl; and (c) —$C(O)R^e$, —$C(O)OR^e$, —$C(O)NR^fR^g$, —$C(O)SR^e$, —$C(NR^e)NR^fR^g$, —$C(S)R^e$, —$C(S)OR^e$, —$C(S)NR^fR^g$, —$OR^e$, —$OC(O)R^e$, —$OC(O)OR^e$, —$OC(O)NR^fR^g$, —$OC(O)SR^e$, —$OC(=NR^e)NR^fR^g$, —$OC(S)R^e$, —$OC(S)OR^e$, —$OC(S)NR^fR^g$, —$OS(O)R^e$, —$OS(O)_2R^e$, —$OS(O)NR^fR^g$, —$OS(O)_2NR^fR^g$, —$NR^fR^g$, —$NR^eC(O)R^h$, —$NR^eC(O)OR^f$, —$NR^eC(O)NR^fR^g$, —$NR^eC(O)SR^f$, —$NR^eC(=NR^h)NR^fR^g$, —$NR^eC(S)R^h$, —$NR^eC(S)OR^f$, —$NR^eC(S)NR^fR^g$, —$NR^eS(O)R^h$, —$NR^eS(O)_2R^h$, —$NR^eS(O)NR^fR^g$, —$NR^eS(O)_2NR^fR^g$, —$SR^e$, —$S(O)R^e$, —$S(O)_2R^e$, —$S(O)NR^fR^g$, and —$S(O)_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In another embodiment, provided herein is a compound of Formula I:

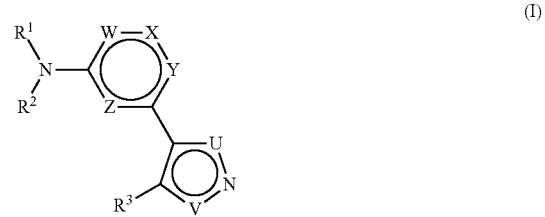

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

U and V are each independently —O— and =C($R^4$)—; or U and V are each independently =N— and —N($R^5$)—; or U is =N— and —N($R^5$)—; and V is =C($R^4$)—;

W, X, Y, and Z are each independently =C($R^6$)— or =N—, with the proviso that at least one of W, X, Y, and Z is =N—; or W, X, and Z are each independently =C($R^6$)—, —N($R^7$)—, =N—, —O—, or —S—; and Y is a bond;

$R^1$ and $R^2$ are each independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(O)SR^{1a}$, —$C(NR^{1a})NR^{1b}R^{1c}$, —$C(S)$ $R^{1a}$, —C(S)$OR^{1a}$, —C(S)$NR^{1b}R^{1c}$, —$OR^{1a}$, —OC(O)$R^{1a}$, —OC(O)$OR^{1a}$, —OC(O)$NR^{1b}R^{1c}$, —OC(O)$SR^{1a}$, —OC(=$NR^{1a}$)$NR^{1b}R^{1c}$, —OC(S)$R^{1a}$, —OC(S)$OR^{1a}$, —OC(S)$NR^{1b}R^{1c}$, —OS(O)$R^{1a}$, —OS(O)$_2R^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)$OR^{1d}$, —$NR^{1a}$C(O)$NR^{1b}R^{1c}$, —$NR^{1a}$C(O)$SR^{1d}$, —$NR^{1a}$C(=$NR^{1d}$)$NR^{1b}R^{1c}$, —$NR^{1a}$C(S)$R^{1d}$, —$NR^{1a}$C(S)$OR^{1d}$, —$NR^{1a}$C(S)$NR^{1b}R^{1c}$, —$NR^{1a}$S(O)$R^{1d}$, —$NR^{1a}$S(O)$_2R^{1d}$, —$NR^{1a}$S(O)$NR^{1b}R^{1c}$, —$NR^{1a}$S(O)$_2NR^{1b}R^{1c}$, —S(O)$R^{1a}$, —S(O)$_2R^{1a}$, —S(O)$NR^{1b}R^{1c}$, or —S(O)$_2NR^{1b}R^{1c}$; or $R^1$ and $R^2$ together with the N atom to which they are attached form heteroaryl or heterocyclyl;

each $R^3$, $R^4$, and $R^6$ is independently (a) hydrogen, deuterium, cyano, halo, or nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)$R^{1a}$, —C(O)$OR^{1a}$, —C(O)$NR^{1b}R^{1c}$, —C(O)$SR^{1a}$, —C($NR^{1a}$)$NR^{1b}R^{1c}$, —C(S)$R^{1a}$, —C(S)$OR^{1a}$, —C(S)$NR^{1b}R^{1c}$, —$OR^{1a}$, —OC(O)$R^{1a}$, —OC(O)$OR^{1a}$, —OC(O)$NR_{1b}R^{1c}$, —OC(O)$SR^{1a}$, —OC(=$NR^{1a}$)$NR^{1b}R^{1c}$, —OC(S)$R^{1a}$, —OC(S)$OR^{1a}$, —OC(S)$NR^{1b}R^{1c}$, —OS(O)$R^{1a}$, —OS(O)$_2R^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)$OR^{1d}$, —$NR^{1a}$C(O)$NR^{1b}R^{1c}$, —$NR^{1a}$C(O)$SR^{1d}$, —$NR^{1a}$C(=$NR^{1d}$)$NR^{1b}R^{1c}$, —$NR^{1a}$C(S)$R^{1d}$, —$NR^{1a}$C(S)$OR^{1d}$, —$NR^{1a}$C(S)$NR^{1b}R^{1c}$, —$NR^{1a}$S(O)$R^{1d}$, —$NR^{1a}$S(O)$_2R^{1d}$, —$NR^{1a}$S(O)$NR^{1b}R^{1c}$, —$NR^{1a}$S(O)$_2NR^{1b}R^{1c}$, —$SR^{1a}$, —S(O)$R^{1a}$, —S(O)$_2R^{1a}$, —S(O)$NR^{1b}R^{1c}$, or —S(O)$_2NR^{1b}R^{1c}$;

$R^5$ and $R^7$ are each independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)$R^{1a}$, —C(O)$OR^{1a}$, —C(O)$NR^{1b}R^{1c}$, —C(O)$SR^{1a}$, —C($NR^{1a}$)$NR^{1b}R^{1c}$, —C(S)$R^{1a}$, —C(S)$OR^{1a}$, —C(S)$NR^{1b}R^{1c}$, —$OR^{1a}$, —OC(O)$R^{1a}$, —OC(O)$OR^{1a}$, —OC(O)$NR^{1b}R^{1c}$, —OC(O)$SR^{1a}$, —OC(=$NR^{1a}$)$NR^{1b}R^{1c}$, —OC(S)$R^{1a}$, —OC(S)$OR^{1a}$, —OC(S)$NR^{1b}R^{1c}$, —OS(O)$R^{1a}$, —OS(O)$_2R^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)$OR^{1d}$, —$NR^{1a}$C(O)$NR^{1b}R^{1c}$, —$NR^{1a}$C(O)$SR^{1d}$, —$NR^{1a}$C(=$NR^{1d}$)$NR^{1b}R^{1c}$, —$NR^{1a}$C(S)$R^{1d}$, —$NR^{1a}$C(S)$OR^{1d}$, —$NR^{1a}$C(S)$NR^{1b}R^{1c}$, —$NR^{1a}$S(O)$R^{1d}$, —$NR^{1a}$S(O)$_2R^{1d}$, —$NR^{1a}$S(O)$NR^{1b}R^{1c}$, —$NR^{1a}$S(O)$_2NR^{1b}R^{1c}$, —S(O)$R^{1a}$, —S(O)$_2R^{1a}$, —S(O)$NR^{1b}R^{1c}$, or —S(O)$_2NR^{1b}R^{1c}$; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)$OR^a$, —C(O)$NR^bR^c$, —C(O)$SR^a$, —C($NR^a$)$NR^bR^c$, —C(S)$R^a$, —C(S)$OR^a$, —C(S)$NR^bR^c$, —$OR^a$, —OC(O)$R^a$, —OC(O)$OR^a$, —OC(O)$NR^bR^c$, —OC(O)$SR^a$, —OC(=$NR^a$)$NR^bR^c$, —OC(S)$R^a$, —OC(S)$OR^a$, —OC(S)$NR^bR^c$, —OS(O)$R^a$, —OS(O)$_2R^a$, —OS(O)$NR^bR^c$, —OS(O)$_2NR^bR^c$, —$NR^bR^c$, —$NR^a$C(O)$R^d$, —$NR^a$C(O)$OR^d$, —$NR^a$C(O)$NR^bR^c$, —$NR^a$C(O)$SR^d$, —$NR^a$C(=$NR^d$)$NR^bR^c$, —$NR^a$C(S)$R^d$, —$NR^a$C(S)$OR^d$, —$NR^a$C(S)$NR^bR^c$, —$NR^a$S(O)$R^d$, —$NR^a$S(O)$_2R^d$, —$NR^a$S(O)$NR^bR^c$, —$NR^a$S(O)$_2NR^bR^c$, —$SR^a$, —S(O)$R^a$, —S(O)$_2R^a$, —S(O)$NR^bR^c$, and —S(O)$_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, and heterocyclyl; and (c) —C(O)$R^e$, —C(O)$OR^e$, —C(O)$NR^fR^g$, —C(O)$SR^e$, —C($NR^e$)$NR^fR^g$, —C(S)$R^e$, —C(S)$OR^e$, —C(S)$NR^fR^g$, —$OR^e$, —OC(O)$R^e$, —OC(O)$OR^e$, —OC(O)$NR^fR^g$, —OC(O)$SR^e$, —OC(=$NR^e$)$NR^fR^g$, —OC(S)$R^e$, —OC(S)$OR^e$, —OC(S)$NR^fR^g$, —OS(O)$R^e$, —OS(O)$_2R^e$, —OS(O)$NR^fR^g$, —OS(O)$_2NR^fR^g$, —$NR^fR^g$, —$NR^e$C(O)$R^h$, —$NR^e$C(O)$OR^f$, —$NR^e$C(O)$NR^fR^g$, —$NR^e$C(O)$SR^f$, —$NR^e$C(=$NR^h$)$NR^fR^g$, —$NR^e$C(S)$R^h$, —$NR^e$C(S)$OR^f$, —$NR^e$C(S)$NR^fR^g$, —$NR^e$S(O)$R^h$, —$NR^e$S(O)$_2R^h$, —$NR^e$S(O)$NR^fR^g$, —$NR^e$S(O)$_2NR^fR^g$, —$SR^e$, —S(O)$R^e$, —S(O)$_2R^e$, —S(O)$NR^fR^g$, and —S(O)$_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In one embodiment, in Formula I, $R^1$ is hydrogen or $C_{1-6}$ alkyl; and $R^2$ is $C_{3-12}$ cycloalkyl or heterocyclyl; wherein each alkyl, cycloalkyl, and heterocyclyl is optionally substituted with one or more substituents Q as defined herein.

In another embodiment, in Formula I, $R^1$ is hydrogen or $C_{1-6}$ alkyl; and $R^2$ is monocyclic $C_{3-12}$ cycloalkyl, bicyclic $C_{3-12}$ cycloalkyl, or bicyclic heterocyclyl; wherein each alkyl, cycloalkyl, and heterocyclyl is optionally substituted with one or more substituents Q as defined herein.

In yet another embodiment, in Formula I, $R^1$ is hydrogen or $C_{1-6}$ alkyl; and $R^2$ is monocyclic $C_{3-12}$ cycloalkyl, bridged $C_{3-12}$ cycloalkyl, or spiro heterocyclyl, wherein each alkyl, cycloalkyl, and heterocyclyl is optionally substituted with one or more substituents Q as defined herein.

In still another embodiment, in Formula I, $R^1$ is hydrogen or methyl; and $R^2$ is cyclohexyl, bicyclo[2.2.1]heptyl, or bicyclo[2.2.2]octyl, each of which is substituted with one or two substituents, wherein each substituent is independently $C_{1-6}$ alkyl or —$NR^{1b}R^{1c}$, where the alkyl is optionally substituted with one or more substituents Q as defined herein and $R^{1b}$ and $R^{1c}$ are each as defined herein.

In yet another embodiment, provided herein is a compound of Formula II:

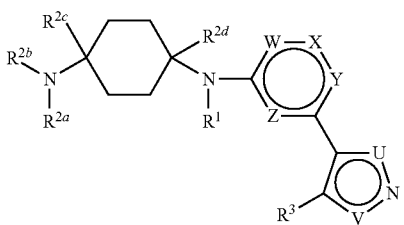

(II)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

$R^{2a}$, $R^{2b}$, $R^{2c}$, and $R^{2d}$ are (i) or (ii):

(i) $R^{2a}$ and $R^{2b}$ are each independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; or $R^{2a}$ and $R^{2b}$ together with the N atom to which they are attached form heteroaryl or heterocyclyl, each of which is optionally substituted with one or more substituents Q; and $R^{2c}$ and $R^{2d}$ are each independently (a) hydrogen, deuterium, or cyano; or (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl, each of which is optionally substituted with one or more substituents Q; or $R^{2c}$ and $R^{2d}$ are linked together to form —O—, $C_{1-6}$ alkylene, $C_{1-6}$ heteroalkylene, $C_{2-6}$ alkenylene, or $C_{2-6}$ alkynylene, wherein the alkylene, heteroalkylene, alkenylene, and alkynylene are each optionally substituted with one or more substituents Q; or (ii) $R^{2a}$ and $R^{2c}$ together with the C and N atoms to which they are attached form heterocyclyl, which is optionally substituted with one or more substituents Q;

$R^{2b}$ is (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; and $R^{2d}$ is (a) hydrogen, deuterium, or cyano; or (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl, each of which is optionally substituted with one or more substituents Q; and $R^1$, $R^3$, $R^{1a}$, $R^{1b}$, $R^{1c}$, $R^{1d}$, Q, U, V, W, X, Y, and Z are each as defined herein.

In one embodiment, in Formula II,

U is —O— and V is =C($R^4$)—; or U is =N— and V is —N($R^5$)—;

W, X, Y, and Z are each independently =C($R^6$)— or =N—;

$R^1$ is hydrogen or $C_{1-6}$ alkyl;

$R^{2a}$, $R^{2b}$, $R^{2c}$, and $R^{2d}$ are (i) or (ii):

(i) $R^{2a}$ and $R^{2b}$ are each independently hydrogen, $C_{1-6}$ alkyl, $C_{2-6}$ alkynyl, $C_{6-14}$ aryl, $C_{6-14}$ aralkyl, or —C(O)$R^{1a}$; or $R^{2a}$ and $R^{2b}$ together with the N atom to which they are attached form heteroaryl or heterocyclyl; and $R^{2c}$ and $R^{2d}$ are each independently hydrogen or $C_{1-6}$ alkyl; or $R^{2c}$ and $R^{2d}$ are linked together to form —O—, $C_{1-6}$ alkylene, or $C_{1-6}$ heteroalkylene; or (ii) $R^{2a}$ and $R^{2c}$ together with the C and N atoms to which they are attached form heteroaryl or heterocyclyl; and $R^{2b}$ and $R^{2d}$ are each hydrogen;

$R^3$ is $C_{1-6}$ alkyl;

$R^4$ and $R^5$ are each independently $C_{1-6}$ alkyl, $C_{3-12}$ cycloalkyl, or heterocyclyl;

each $R^6$ is independently hydrogen, halo, $C_{1-6}$ alkyl, —O$R^{1a}$, or —N$R^{1b}R^{1c}$; and each $R^{1a}$, $R^{1b}$, and $R^{1c}$ is as defined herein;

wherein each alkyl, alkylene, heteroalkylene, alkynyl, cycloalkyl, aryl, aralkyl, heteroaryl, and heterocyclyl is optionally substituted with one or more, in one embodiment, one, two, three, or four, substituents Q.

In another embodiment, in Formula II,

U is —O— and V is =C($R^4$)—; or U is =N— and V is —N($R^5$)—;

W, X, Y, and Z are each independently =C($R^6$)— or =N—;

$R^1$ is hydrogen or $C_{1-6}$ alkyl;

$R^{2a}$, $R^{2b}$, $R^{2c}$, and $R^{2d}$ are (i) or (ii):

(i) $R^{2a}$ and $R^{2b}$ are each independently hydrogen, $C_{1-6}$ alkyl, $C_{2-6}$ alkynyl, 5- or 6-membered heteroaryl-$C_{1-6}$ alkyl, $C_{6-14}$ aryl, $C_{6-14}$ aralkyl, —C(O)—$C_{1-6}$ alkyl, —C(O)—$C_{2-6}$ alkynyl, or —C(O)-5-membered heteroaryl; or $R^{2a}$ and $R^{2b}$ together with the N atom to which they are attached form 5-membered heteroaryl or 4- to 6-membered heterocyclyl; and $R^{2c}$ is hydrogen or $C_{1-6}$ alkyl; and $R^{2d}$ is hydrogen; or $R^{2c}$ and $R^{2d}$ are linked together to form $C_{2-6}$ alkylene; or (ii) $R^{2a}$ and $R^{2c}$ together with the C and N atoms to which they are attached form 5-membered heteroaryl or 5-membered heterocyclyl; and $R^{2b}$ and $R^{2d}$ are each hydrogen;

$R^3$ is $C_{1-6}$ alkyl or $C_{3-12}$ cycloalkyl-$C_{1-6}$ alkyl;

$R^4$ and $R^5$ are each independently $C_{1-6}$ alkyl, $C_{3-12}$ cycloalkyl, or 4- to 6-membered heterocyclyl; and each $R^6$ is independently hydrogen, fluoro, chloro, $C_{1-6}$ alkyl, hydroxyl, or amino;

wherein each alkyl, alkylene, alkynyl, cycloalkyl, aryl, aralkyl, heteroaryl, and heterocyclyl is optionally substituted with one or more, in one embodiment, one, two, three, or four, substituents Q.

In yet another embodiment, in Formula II,

U is —O— and V is =C($R^4$)—; or U is =N— and V is —N($R^5$)—;

W, X, Y, and Z are each independently =C($R^6$)— or =N—;

$R^1$ is hydrogen or methyl;

$R^{2a}$, $R^{2b}$, $R^{2c}$, and $R^{2d}$ are (i) or (ii):

(i) $R^{2a}$ is hydrogen, methyl, trifluoroethyl, methoxyethyl, pentynyl, phenyl, benzyl, (pyrazolyl)methyl, (methylpyrazolyl)methyl, (pyrazolyl)ethyl, (pyridinyl)methyl, pentanoyl, methoxyacetyl, butynylcarbonyl, or (pyrazolyl)carbonyl; and $R^{2b}$ is hydrogen, methyl, trifluoroethyl, or (pyrazolyl)methyl; or $R^{2a}$ and $R^{2b}$ together with the N atom to which they are attached form azetidinyl, pyrrolidinyl, piperidinyl, morpholinyl, pyrazolyl, methylpyrazolyl, or imidazolyl; and $R^{2c}$ is hydrogen, methyl, or hydroxymethyl; and $R^{2d}$ is hydrogen; or $R^{2c}$ and $R^{2d}$ are linked together to form methylene or ethylene; or (ii) $R^{2a}$ and $R^{2c}$ together with the C and N atoms to which they are attached form pyrrolidinylene-one, imidazolidinylene-dione, or oxazolidinylene-one; and $R^{2b}$ and $R^{2d}$ are each hydrogen;

$R^3$ is butylmethyl, cyclopropylmethyl, methylcyclopropylmethyl, hydroxy(cyclopropylmethyl), cyclobutylmethyl, or cyclopentylmethyl;

$R^4$ and $R^5$ are each independently methyl, isopropyl, cyclopentyl, oxetanyl, tetrahydrofuryl, or tetrahydropyranyl; and each $R^6$ is independently hydrogen, fluoro, chloro, methyl, trifluoromethyl, hydroxyl, or amino.

In yet another embodiment, in Formula II,

U is —O— and V is =C($R^4$)—; or U is =N— and V is —N($R^5$)—;

W, X, Y, and Z are each independently =C(H)—, =C(F)—, =C(Cl)—, =C(CH$_3$)—, =C(CF$_3$)—, =C(OH)—, =C(NH$_2$)—, or =N—;

$R^1$ is hydrogen;

$R^{2a}$, $R^{2b}$, $R^{2c}$, and $R^{2d}$ are (i) or (ii):

(i) $R^{2a}$ is hydrogen, methyl, 2,2,2-trifluoroethyl, 2-methoxyethyl, pent-4-ynyl, phenyl, benzyl, (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, (pyridin-3-yl)methyl, pentanoyl, 2-methoxyacetyl, but-3-ynylcarbonyl, or (pyrazol-4-yl)carbonyl; and $R^{2b}$ is hydrogen, methyl, 2,2,2-trifluoroethyl, or (pyrazol-4-yl)methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; and $R^{2c}$ is hydrogen, methyl, or hydroxymethyl; and $R^{2d}$ is hydrogen; or $R^{2c}$ and $R^{2d}$ are linked together to form methylene or eth-1,2-ylene; or (ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and $R^{2b}$ and $R^{2d}$ are each hydrogen;

$R^3$ is t-butylmethyl, cyclopropylmethyl, 1-methylcyclopropylmethyl, 1-hydroxy(cyclopropylmethyl), cyclobutylmethyl, or cyclopentylmethyl; and $R^4$ and $R^5$ are each independently methyl, isopropyl, cyclopentyl, oxetan-3-yl, tetrahydrofur-3-yl, tetrahydropyran-4-yl, or tetrahydropyran-3-yl.

In yet another embodiment, in Formula II,

U is —O— and V is =C($R^4$)—; or U is =N— and V is —N($R^5$)—;

W and Z are each independently =C(H)— or =N—;

X is =C(H)—, =C(OH)—, or =C(NH$_2$)—;

Y is =C(H)—, =C(F)—, =C(Cl)—, =C(CH$_3$)—, =C(CF$_3$)—, or =N—;

$R^1$ is hydrogen;

$R^{2a}$, $R^{2b}$, $R^{2c}$, and $R^{2d}$ are (i) or (ii):

(i) $R^{2a}$ is hydrogen, methyl, 2,2,2-trifluoroethyl, 2-methoxyethyl, pent-4-ynyl, phenyl, benzyl, (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, (pyridin-3-yl)methyl, pentanoyl, 2-methoxyacetyl, but-3-ynylcarbonyl, or (pyrazol-4-yl)carbonyl; and $R^{2b}$ is hydrogen, methyl, 2,2,2-trifluoroethyl, or (pyrazol-4-yl)methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; and $R^{2c}$ is hydrogen, methyl, or hydroxymethyl; and $R^{2d}$ is hydrogen; or $R^{2c}$ and $R^{2d}$ are linked together to form methylene or 1,2-ethylene; or (ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and $R^{2b}$ and $R^{2d}$ are each hydrogen;

$R^3$ is t-butylmethyl, cyclopropylmethyl, 1-methylcyclopropylmethyl, 1-hydroxy(cyclopropylmethyl), cyclobutylmethyl, or cyclopentylmethyl; and $R^4$ and $R^5$ are each independently methyl, isopropyl, cyclopentyl, oxetan-3-yl, tetrahydrofur-3-yl, tetrahydropyran-4-yl, or tetrahydropyran-3-yl.

In still another embodiment, in Formula II,

U is —O— and V is =C(CH$_3$)—; or U is =N— and V is —N(CH$_3$)—;

W and Z are each independently =C(H)— or =N—;

X is =C(H)—;

Y is =C(H)—, =C(F)—, or =C(Cl)—;

$R^1$ is hydrogen;

$R^{2a}$, $R^{2b}$, $R^{2c}$, and $R^{2d}$ are (i) or (ii):

(i) $R^{2a}$ is hydrogen, methyl, 2,2,2-trifluoroethyl, 2-methoxyethyl, pent-4-ynyl, pentanoyl, 2-methoxyacetyl, or but-3-ynylcarbonyl; and $R^{2b}$ is hydrogen or methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; and $R^{2c}$ and $R^{2d}$ are each hydrogen; or $R^{2c}$ and $R^{2d}$ are linked together to form methylene or eth-1,2-ylene; or (ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and $R^{2b}$ and $R^{2d}$ are each hydrogen; and $R^3$ is cyclopropylmethyl.

In yet another embodiment, provided herein is a compound of Formula IIa:

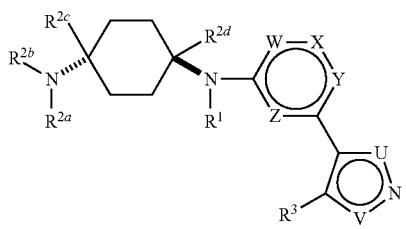

(IIa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, U, V, W, X, Y, and Z are each as defined herein.

In one embodiment, in Formula IIa,
U is —O— and V is $=C(R^4)$—; or U is $=N$— and V is —$N(R^5)$—;
W, X, Y, and Z are each independently $=C(R^6)$— or $=N$—;
$R^1$ is hydrogen or $C_{1-6}$ alkyl;
$R^{2a}$, $R^{2b}$, $R^{2c}$, and $R^{2d}$ are (i) or (ii):
(i) $R^{2a}$ and $R^{2b}$ are each independently hydrogen, $C_{1-6}$ alkyl, $C_{2-6}$ alkynyl, $C_{6-14}$ aryl, $C_{6-14}$ aralkyl, or —C(O)$R^{1a}$; or $R^{2a}$ and $R^{2b}$ together with the N atom to which they are attached form heteroaryl or heterocyclyl; and $R^{2c}$ and $R^{2d}$ are each independently hydrogen or $C_{1-6}$ alkyl; or
(ii) $R^{2a}$ and $R^{2c}$ together with the C and N atoms to which they are attached form heteroaryl or heterocyclyl; and $R^{2b}$ and $R^{2d}$ are each hydrogen;
$R^3$ is $C_{1-6}$ alkyl;
$R^4$ and $R^5$ are each independently $C_{1-6}$ alkyl, $C_{3-12}$ cycloalkyl, or heterocyclyl;
each $R^6$ is independently hydrogen, halo, $C_{1-6}$ alkyl, —$OR^{1a}$, or —$NR^{1b}R^{1c}$; and
each $R^{1a}$, $R^{1b}$, and $R^{1c}$ is as defined herein;
wherein each alkyl, alkynyl, cycloalkyl, aryl, aralkyl, heteroaryl, and heterocyclyl is optionally substituted with one or more, in one embodiment, one, two, three, or four, substituents Q.

In another embodiment, in Formula IIa,
U is —O— and V is $=C(R^4)$—; or U is $=N$— and V is —$N(R^5)$—;
W, X, Y, and Z are each independently $=C(R^6)$— or $=N$—;
$R^1$ is hydrogen or $C_{1-6}$ alkyl;
$R^{2a}$, $R^{2b}$, $R^{2c}$, and $R^{2d}$ are (i) or (ii):
(i) $R^{2a}$ and $R^{2b}$ are each independently hydrogen, $C_{1-6}$ alkyl, $C_{2-6}$ alkynyl, 5- or 6-membered heteroaryl-$C_{1-6}$ alkyl, $C_{6-14}$ aryl, $C_{6-14}$ aralkyl, —C(O)—$C_{1-6}$ alkyl, —C(O)—$C_{2-6}$ alkynyl, or —C(O)-5-membered heteroaryl; or $R^{2a}$ and $R^{2b}$ together with the N atom to which they are attached form 5-membered heteroaryl or 4- to 6-membered heterocyclyl;
$R^{2c}$ is hydrogen or $C_{1-6}$ alkyl; and
$R^{2d}$ is hydrogen; or
(ii) $R^{2a}$ and $R^{2c}$ together with the C and N atoms to which they are attached form 5-membered heteroaryl or 5-membered heterocyclyl; and
$R^{2b}$ and $R^{2d}$ are each hydrogen;
$R^3$ is $C_{1-6}$ alkyl or $C_{3-12}$ cycloalkyl-$C_{1-6}$ alkyl;
$R^4$ and $R^5$ are each independently $C_{1-6}$ alkyl, $C_{3-12}$ cycloalkyl, or 4- to 6-membered heterocyclyl; and each $R^6$ is independently hydrogen, fluoro, chloro, $C_{1-6}$ alkyl, hydroxyl, or amino;
wherein each alkyl, alkynyl, cycloalkyl, aryl, aralkyl, heteroaryl, and heterocyclyl is optionally substituted with one or more, in one embodiment, one, two, three, or four, substituents Q.

In yet another embodiment, in Formula IIa,
U is —O— and V is $=C(R^4)$—; or U is $=N$— and V is —$N(R^5)$—;
W, X, Y, and Z are each independently $=C(R^6)$— or $=N$—;
$R^1$ is hydrogen or methyl;
$R^{2a}$, $R^{2b}$, $R^{2c}$, and $R^{2d}$ are (i) or (ii):
(i) $R^{2a}$ is hydrogen, methyl, trifluoroethyl, methoxyethyl, pentynyl, phenyl, benzyl, (pyrazolyl)methyl, (methylpyrazolyl)methyl, (pyrazolyl)ethyl, (pyridinyl)methyl, pentanoyl, methoxyacetyl, butynylcarbonyl, or (pyrazolyl)carbonyl; and $R^{2b}$ is hydrogen, methyl, trifluoroethyl, or (pyrazolyl)methyl; or $R^{2a}$ and $R^{2b}$ together with the N atom to which they are attached form azetidinyl, pyrrolidinyl, piperidinyl, morpholinyl, pyrazolyl, methylpyrazolyl, or imidazolyl;
$R^{2c}$ is hydrogen, methyl, or hydroxymethyl; and
$R^{2d}$ is hydrogen; or
(ii) $R^{2a}$ and $R^{2c}$ together with the C and N atoms to which they are attached form pyrrolidinylene-one, imidazolidinylene-dione, or oxazolidinylene-one; and
$R^{2b}$ and $R^{2d}$ are each hydrogen;
$R^3$ is butylmethyl, cyclopropylmethyl, methylcyclopropylmethyl, hydroxy(cyclopropylmethyl), cyclobutylmethyl, or cyclopentylmethyl;
$R^4$ and $R^5$ are each independently methyl, isopropyl, cyclopentyl, oxetanyl, tetrahydrofuryl, or tetrahydropyranyl; and
each $R^6$ is independently hydrogen, fluoro, chloro, methyl, trifluoromethyl, hydroxyl, or amino.

In yet another embodiment, in Formula IIa,
U is —O— and V is $=C(R^4)$—; or U is $=N$— and V is —$N(R^5)$—; W, X, Y, and Z are each independently $=C(H)$—, $=C(F)$—, $=C(Cl)$—, $=C(CH_3)$—, $=C(CF_3)$—, $=C(OH)$—, $=C(NH_2)$—, or $=N$—;
$R^1$ is hydrogen;
$R^{2a}$, $R^{2b}$, $R^{2c}$, and $R^{2d}$ are (i) or (ii):
(i) $R^{2a}$ is hydrogen, methyl, 2,2,2-trifluoroethyl, 2-methoxyethyl, pent-4-ynyl, phenyl, benzyl, (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, (pyridin-3-yl)methyl, pentanoyl, 2-methoxyacetyl, but-3-ynylcarbonyl, or (pyrazol-4-yl)carbonyl; and $R^{2b}$ is hydrogen, methyl, 2,2,2-trifluoroethyl, or (pyrazol-4-yl)methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl;
$R^{2c}$ is hydrogen, methyl, or hydroxymethyl; and
$R^{2d}$ is hydrogen; or
(ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and
$R^{2b}$ and $R^{2d}$ are each hydrogen;
$R^3$ is t-butylmethyl, cyclopropylmethyl, 1-methylcyclopropylmethyl, 1-hydroxy(cyclopropylmethyl), cyclobutylmethyl, or cyclopentylmethyl; and R⁴ and R⁵ are each independently methyl, isopropyl, cyclopentyl, oxetan-3-yl, tetrahydrofur-3-yl, tetrahydropyran-4-yl, or tetrahydropyran-3-yl.

In yet another embodiment, in Formula IIa,
U is —O— and V is =C(R⁴)—; or U is =N— and V is —N(R⁵)—;
W and Z are each independently =C(H)— or =N—;
X is =C(H)—, =C(OH)—, or =C(NH₂)—;
Y is =C(H)—, =C(F)—, =C(Cl)—, =C(CH₃)—, =C(CF₃)—, or =N—;
R¹ is hydrogen;
R²ᵃ, R²ᵇ, R²ᶜ, and R²ᵈ are (i) or (ii):
(i) R²ᵃ is hydrogen, methyl, 2,2,2-trifluoroethyl, 2-methoxyethyl, pent-4-ynyl, phenyl, benzyl, (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, (pyridin-3-yl)methyl, pentanoyl, 2-methoxyacetyl, but-3-ynylcarbonyl, or (pyrazol-4-yl)carbonyl; and R²ᵇ is hydrogen, methyl, 2,2,2-trifluoroethyl, or (pyrazol-4-yl)methyl; or R²ᵃ and R²ᵇ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; R²ᶜ is hydrogen, methyl, or hydroxymethyl; and R²ᵈ is hydrogen; or
(ii) R²ᵃ and R²ᶜ together with the C and N atoms to which they are attached form pyrrolidin-5,5-ylene-2-one, imidazolidin-5,5-ylene-2,4-dione, or oxazolidin-4,4-ylene-2-one; and
R²ᵇ and R²ᵈ are each hydrogen;
R³ is t-butylmethyl, cyclopropylmethyl, 1-methylcyclopropylmethyl, 1-hydroxy(cyclopropylmethyl), cyclobutylmethyl, or cyclopentylmethyl; and
R⁴ and R⁵ are each independently methyl, isopropyl, cyclopentyl, oxetan-3-yl, tetrahydrofur-3-yl, tetrahydropyran-4-yl, or tetrahydropyran-3-yl.

In still another embodiment, in Formula IIa,
U is —O— and V is =C(CH₃)—; or U is =N— and V is —N(CH₃)—;
W and Z are each independently =C(H)— or =N—;
X is =C(H)—;
Y is =C(H)—, =C(F)—, or =C(Cl)—;
R¹ is hydrogen;
R²ᵃ, R²ᵇ, R²ᶜ, and R²ᵈ are (i) or (ii):
(i) R²ᵃ is hydrogen, methyl, 2,2,2-trifluoroethyl, 2-methoxyethyl, pent-4-ynyl, pentanoyl, 2-methoxyacetyl, or but-3-ynylcarbonyl; and R²ᵇ is hydrogen or methyl; or R²ᵃ and R²ᵇ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; and
R²ᶜ and R²ᵈ are each hydrogen; or
(ii) R²ᵃ and R²ᶜ together with the C and N atoms to which they are attached form pyrrolidin-5,5-ylene-2-one, imidazolidin-5,5-ylene-2,4-dione, or oxazolidin-4,4-ylene-2-one; and
R²ᵇ and R²ᵈ are each hydrogen; and
R³ is cyclopropylmethyl.

In Formula I, II, or IIa, in one embodiment, W and X are =N—; in another embodiment, W and Y are =N—; in yet another embodiment, W and Z are =N—; in yet another embodiment, X and Y are =N—; in yet another embodiment, X and Z are =N—; and in still another embodiment, Y and Z are =N—.

In yet another embodiment, provided herein is a compound of Formula III:

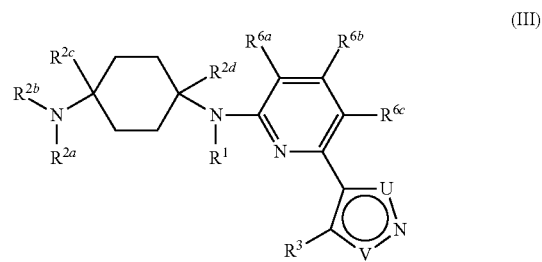

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein R⁶ᵃ, R⁶ᵇ, and R⁶ᶜ are each independently R⁶; and R¹, R³, R²ᵃ, R²ᵇ, R²ᶜ, R²ᵈ, R⁶, U, and V are each as defined herein. In Formula III, in one embodiment, U is —O— and V is =C(R⁴)—, in another embodiment, U is =N— and V is —N(R⁵)—, wherein R⁴ and R⁵ are each as defined herein.

In yet another embodiment, provided herein is a compound of Formula IIIa:

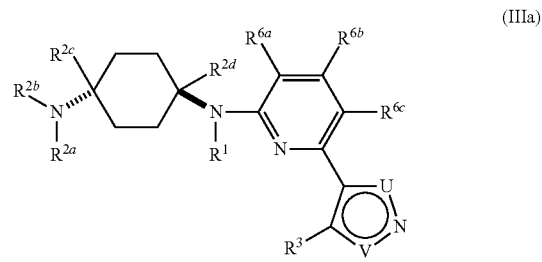

or a tautomer, a mixture of two or more tautomers, or an isotopic variant thereof; or a pharmaceutically acceptable salt, solvate, hydrate, or prodrug thereof; wherein R¹, R³, R²ᵃ, R²ᵇ, R²ᶜ, R²ᵈ, R⁶ᵃ, R⁶ᵇ, R⁶ᶜ, U, and V are each as defined herein. In Formula IIIa, in one embodiment, U is —O— and V is =C(R⁴)—, in another embodiment, U is =N— and V is —N(R⁵)—, wherein R⁴ and R⁵ are each as defined herein.

In yet another embodiment, provided herein is a compound of Formula IV:

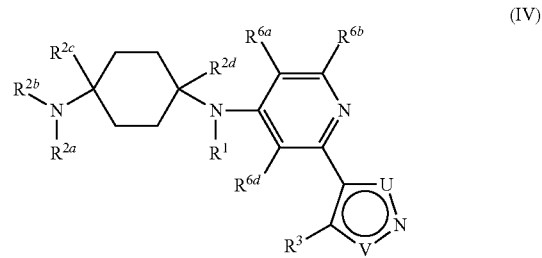

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof;

wherein $R^{6d}$ is $R^6$; and $R^1$, $R^3$, $R^6$, $R^{2a}$, $R^{2b}$, $R^{2c}$, $R^{2d}$, $R^{6a}$, $R^{6b}$, U, and V are each as defined herein. In Formula IV, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula IVa:

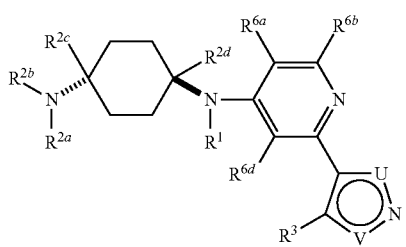

(IVa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6a}$, $R^{6b}$, $R^{6d}$, U, and V are each as defined herein. In Formula IVa, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula V:

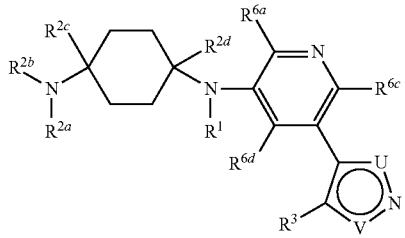

(V)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6a}$, $R^{6c}$, $R^{6d}$, U, and V are each as defined herein. In Formula V, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula Va:

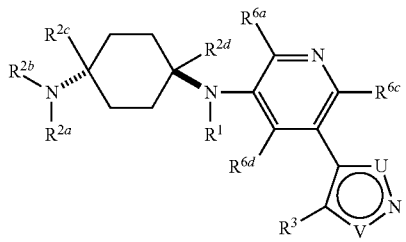

(Va)

or aa tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6a}$, $R^{6c}$, $R^{6d}$, U, and V are each as defined herein. In Formula Va, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula VI:

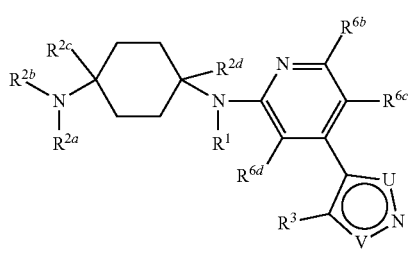

(VI)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6b}$, $R^{6c}$, $R^{6d}$, U, and V are each as defined herein. In Formula VI, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula VIa:

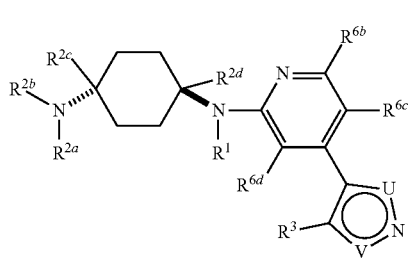

(VIa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6b}$, $R^{6c}$, $R^{6d}$, U, and V are each as defined herein. In Formula VIa, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula VII:

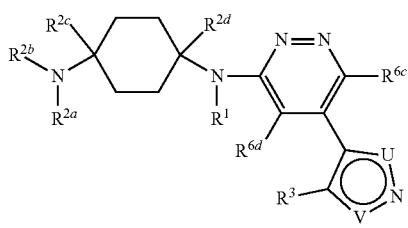

(VII)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6c}$, $R^{6d}$, U, and V are each as defined herein. In Formula VII, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula VIIa:

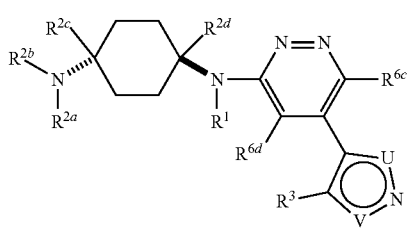

(VIIa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6c}$, $R^{6d}$, U, and V are each as defined herein. In Formula VIIa, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula VIII:

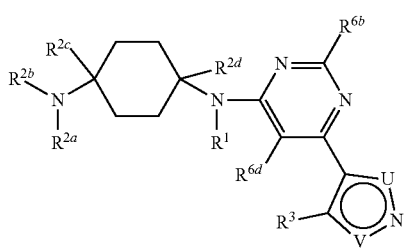

(VIII)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6b}$, $R^{6d}$, U, and V are each as defined herein. In Formula VIII, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula VIIIa:

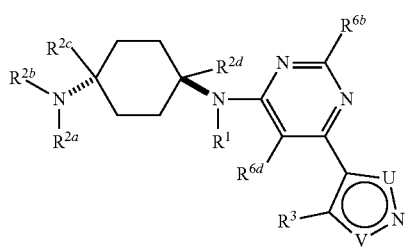

(VIIIa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6b}$, $R^{6d}$, U, and V are each as defined herein. In Formula VIIIa, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula IX:

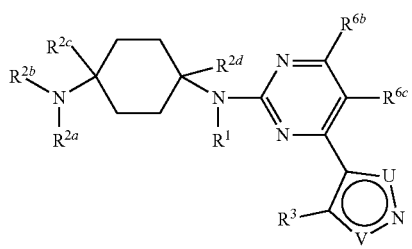

(IX)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6b}$, $R^{6c}$, U, and V are each as defined herein. In Formula IX, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula IXa:

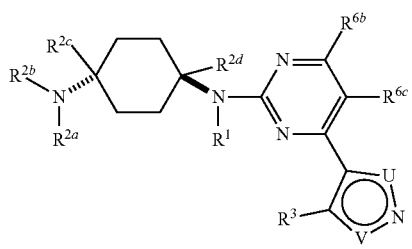

(IXa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6b}$, $R^{6c}$, U, and V are each as defined herein. In Formula IXa, in one embodiment, U is —O— and V is =C(R⁴)—, in another embodiment, U is =N— and V is —N(R⁵)—, wherein R⁴ and R⁵ are each as defined herein.

In yet another embodiment, provided herein is a compound of Formula X:

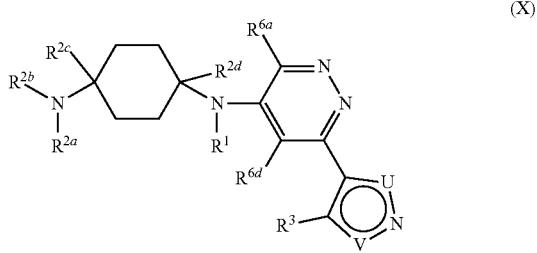

(X)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6a}$, $R^{6d}$, U, and V are each as defined herein. In Formula X, in one embodiment, U is —O— and V is =C(R⁴)—, in another embodiment, U is =N— and V is —N(R⁵)—, wherein R⁴ and R⁵ are each as defined herein.

In yet another embodiment, provided herein is a compound of Formula Xa:

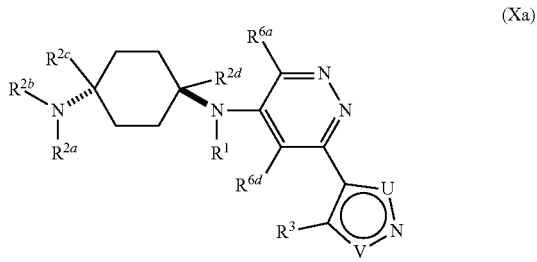

(Xa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6a}$, $R^{6d}$, U, and V are each as defined herein. In Formula Xa, in one embodiment, U is —O— and V is =C(R⁴)—, in another embodiment, U is =N— and V is —N(R⁵)—, wherein R⁴ and R⁵ are each as defined herein.

In yet another embodiment, provided herein is a compound of Formula XI:

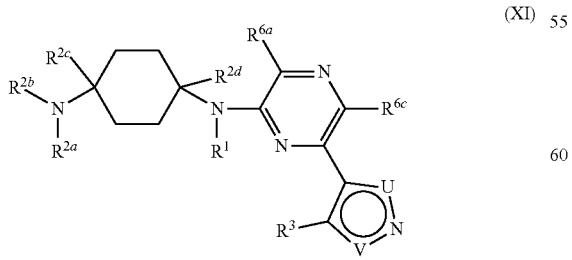

(XI)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6a}$, $R^{6c}$, U, and V are each as defined herein. In Formula XI, in one embodiment, U is —O— and V is =C(R⁴)—, in another embodiment, U is =N— and V is —N(R⁵)—, wherein R⁴ and R⁵ are each as defined herein.

In yet another embodiment, provided herein is a compound of Formula XIa:

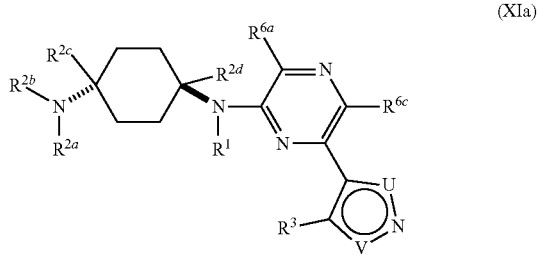

(XIa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6a}$, $R^{6c}$, U, and V are each as defined herein. In Formula XIa, in one embodiment, U is —O— and V is =C(R⁴)—, in another embodiment, U is =N— and V is —N(R⁵)—, wherein R⁴ and R⁵ are each as defined herein.

In yet another embodiment, provided herein is a compound of Formula XII:

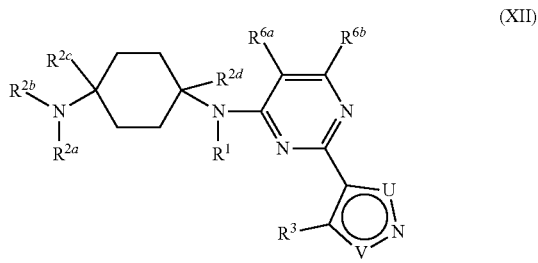

(XII)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6a}$, $R^{6b}$, U, and V are each as defined herein. In Formula XII, in one embodiment, U is —O— and V is =C(R⁴)—, in another embodiment, U is =N— and V is —N(R⁵)—, wherein R⁴ and R⁵ are each as defined herein.

In yet another embodiment, provided herein is a compound of Formula XIIa:

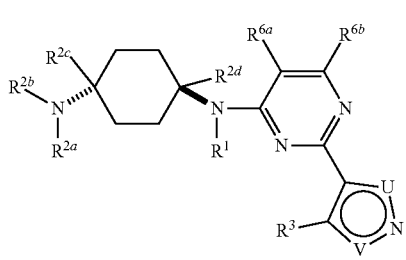

(XIIa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6a}$, $R^{6b}$, U, and V are each as defined herein. In Formula XIIa, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XIII:

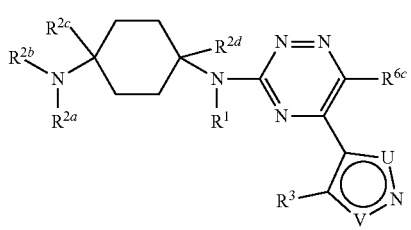

(XIII)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6c}$, U, and V are each as defined herein. In Formula XIII, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XIIIa:

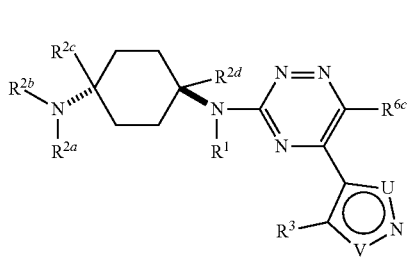

(XIIIa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6c}$, U, and V are each as defined herein. In Formula XIIIa, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XIV:

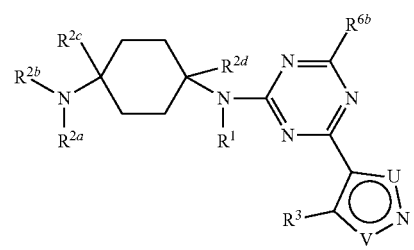

(XIV)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6b}$, U, and V are each as defined herein. In Formula XIV, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XIVa:

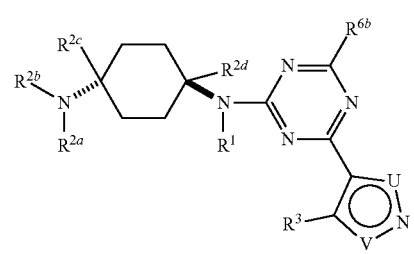

(XIVa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6b}$, U, and V are each as defined herein. In Formula XIVa, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XV:

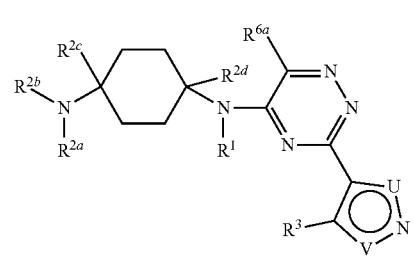

(XV)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6a}$, U, and V are each as defined herein. In Formula XV, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XVa:

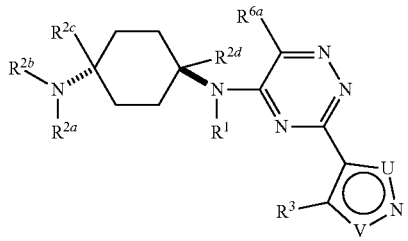

(XVa)

or tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6a}$, U, and V are each as defined herein. In Formula XVa, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XVI:

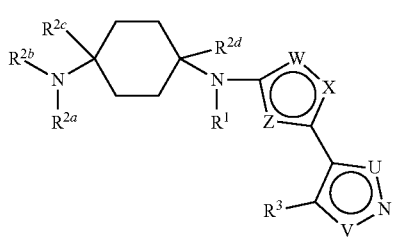

(XVI)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, U, V, W, X, and Z are each as defined herein. In Formula XVI, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XVIa:

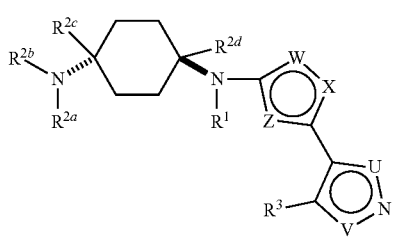

(XVIa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, U, V, W, X, and Z are each as defined herein. In Formula XVIa, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XVII:

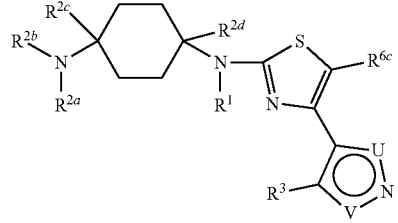

(XVII)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6c}$, U, and V are each as defined herein. In Formula XVII, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XVIIa:

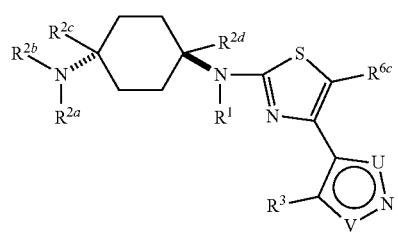

(XVIIa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6c}$, U, and V are each as defined herein. In Formula XVIIa, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XVIII:

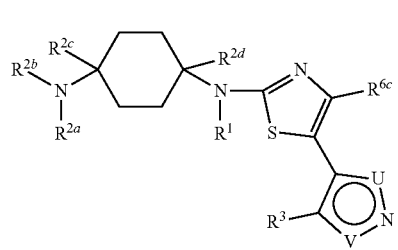

(XVIII)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof;

wherein $R^1$, $R^3$, $R^{2a}$, $R^{2b}$, $R^{2c}$, $R^{2d}$, $R^{6c}$, U, and V are each as defined herein. In Formula XVIII, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XVIIIa:

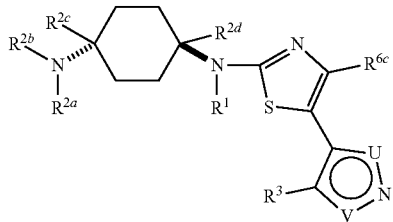

(XVIIIa)

or a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{2c}$, $R^{2d}$, $R^{6c}$, U, and V are each as defined herein. In Formula XVIIIa, in one embodiment, U is —O— and V is =C($R^4$)—, in another embodiment, U is =N— and V is —N($R^5$)—, wherein $R^4$ and $R^5$ are each as defined herein.

In yet another embodiment, provided herein is a compound of Formula XIX:

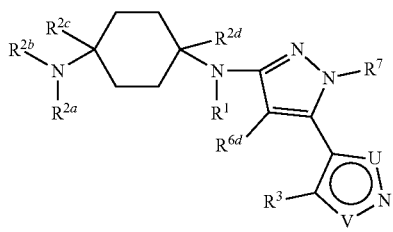

(XIX)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^7$, $R^{2a}$, $R^{2b}$, $R^{2c}$, $R^{2d}$, $R^{6c}$, U, and V are each as defined herein. In Formula XIX, in one embodiment, U is —O— and V is =C($R^4$)—, in another embodiment, U is =N— and V is —N($R^5$)—, wherein $R^4$ and $R^5$ are each as defined herein.

In still another embodiment, provided herein is a compound of Formula XIXa:

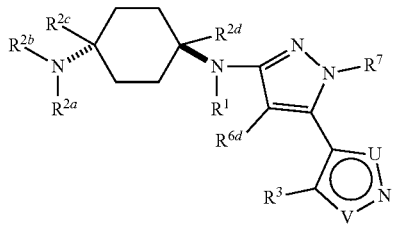

(XIXa)

or a tautomer, a mixture of two or more tautomers, or an isotopic variant thereof; or a pharmaceutically acceptable salt, solvate, hydrate, or prodrug thereof; wherein $R^1$, $R^3$, $R^7$, $R^{2a}$, $R^{2b}$, $R^{2c}$, $R^{2d}$, $R^{6c}$, U, and V are each as defined herein. In Formula XIXa, in one embodiment, U is —O— and V is =C($R^4$)—, in another embodiment, U is =N— and V is —N($R^5$)—, wherein $R^4$ and $R^5$ are each as defined herein.

In one embodiment, in any one of Formulae III to XIX,
U is —O— and V is =C($R^4$)—; or U is =N— and V is —N($R^5$)—;
$R^1$ is hydrogen or $C_{1-6}$ alkyl;
$R^{2a}$, $R^{2b}$, $R^{2c}$, and $R^{2d}$ are (i) or (ii):
(i) $R^{2a}$ and $R^{2b}$ are each independently hydrogen, $C_{1-6}$ alkyl, $C_{2-6}$ alkynyl, $C_{6-14}$ aryl, $C_{6-14}$ aralkyl, or —C(O)$R^{1a}$; or $R^{2a}$ and $R^{2b}$ together with the N atom to which they are attached form heteroaryl or heterocyclyl; and $R^{2c}$ and $R^{2d}$ are each independently hydrogen or $C_{1-6}$ alkyl; or $R^{2c}$ and $R^{2d}$ are linked together to form —O—, $C_{1-6}$ alkylene, or $C_{1-6}$ heteroalkylene; or
(ii) $R^{2a}$ and $R^{2c}$ together with the C and N atoms to which they are attached form heteroaryl or heterocyclyl; and $R^{2b}$ and $R^{2d}$ are each hydrogen;
$R^3$ is $C_{1-6}$ alkyl;
$R^4$ and $R^5$ are each independently $C_{1-6}$ alkyl, $C_{3-12}$ cycloalkyl, or heterocyclyl;
$R^{6a}$, $R^{6b}$, $R^{6c}$, and $R^{6d}$, if present, are each independently hydrogen, halo, $C_{1-6}$ alkyl, —$OR^{1a}$, or —$NR^{1b}R^{1c}$;
$R^7$, if present, is hydrogen or $C_{1-6}$ alkyl; and
each $R^{1a}$, $R^{1b}$, and $R^{1c}$ is as defined herein;
wherein each alkyl, alkylene, heteroalkylene, alkynyl, cycloalkyl, aryl, aralkyl, heteroaryl, and heterocyclyl is optionally substituted with one or more, in one embodiment, one, two, three, or four, substituents Q.

In another embodiment, in any one of Formulae III to XIX,
U is —O— and V is =C($R^4$)—; or U is =N— and V is —N($R^5$)—;
$R^1$ is hydrogen or $C_{1-6}$ alkyl;
$R^{2a}$, $R^{2b}$, $R^{2c}$, and $R^{2d}$ are (i) or (ii):
(i) $R^{2a}$ and $R^{2b}$ are each independently hydrogen, $C_{1-6}$ alkyl, $C_{2-6}$ alkynyl, 5- or 6-membered heteroaryl-$C_{1-6}$ alkyl, $C_{6-14}$ aryl, $C_{6-14}$ aralkyl, —C(O)—$C_{1-6}$ alkyl, —C(O)—$C_{2-6}$ alkynyl, or —C(O)-5-membered heteroaryl; or $R^{2a}$ and $R^{2b}$ together with the N atom to which they are attached form 5-membered heteroaryl or 4- to 6-membered heterocyclyl; and
$R^{2c}$ is hydrogen or $C_{1-6}$ alkyl; and $R^{2d}$ is hydrogen; or $R^{2c}$ and $R^{2d}$ are linked together to form $C_{2-6}$ alkylene; or
(ii) $R^{2a}$ and $R^{2c}$ together with the C and N atoms to which they are attached form 5-membered heteroaryl or 5-membered heterocyclyl; and $R^{2b}$ and $R^{2d}$ are each hydrogen;
$R^3$ is $C_{1-6}$ alkyl or $C_{3-12}$ cycloalkyl-$C_{1-6}$ alkyl;
$R^4$ and $R^5$ are each independently $C_{1-6}$ alkyl, $C_{3-12}$ cycloalkyl, or 4- to 6-membered heterocyclyl;
$R^{6a}$, $R^{6b}$, $R^{6c}$, and $R^{6d}$, if present, are each independently hydrogen, fluoro, chloro, $C_{1-6}$ alkyl, hydroxyl, or amino; and
$R^7$, if present, is hydrogen or methyl;
wherein each alkyl, alkylene, alkynyl, cycloalkyl, aryl, aralkyl, heteroaryl, and heterocyclyl is optionally substituted with one or more, in one embodiment, one, two, three, or four, substituents Q.

In yet another embodiment, in any one of Formulae III to XIX,
U is —O— and V is =C($R^4$)—; or U is =N— and V is —N($R^5$)—;

$R^1$ is hydrogen;
$R^{2a}$, $R^{2b}$, $R^{2c}$, and $R^{2d}$ are (i) or (ii):
(i) $R^{2a}$ is hydrogen, methyl, 2,2,2-trifluoroethyl, 2-methoxyethyl, pent-4-ynyl, phenyl, benzyl, (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, (pyridin-3-yl)methyl, pentanoyl, 2-methoxyacetyl, but-3-ynylcarbonyl, or (pyrazol-4-yl)carbonyl; and $R^{2b}$ is hydrogen, methyl, 2,2,2-trifluoroethyl, or (pyrazol-4-yl)methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; and
$R^{2c}$ is hydrogen, methyl, or hydroxymethyl; and $R^{2d}$ is hydrogen; or $R^{2c}$ and $R^{2d}$ are linked together to form methylene or 1,2-ethylene; or
(ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and
$R^{2b}$ and $R^{2d}$ are each hydrogen;
$R^3$ is t-butylmethyl, cyclopropylmethyl, 1-methylcyclopropylmethyl, 1-hydroxy(cyclopropylmethyl), cyclobutylmethyl, or cyclopentylmethyl;
$R^4$ and $R^5$ are each independently methyl, isopropyl, cyclopentyl, oxetan-3-yl, tetrahydrofur-3-yl, tetrahydropyran-4-yl, or tetrahydropyran-3-yl;
$R^{6a}$, $R^{6b}$, and $R^{6d}$, if present, are each independently hydrogen;
$R^{6c}$, if present, is hydrogen, fluoro, chloro, methyl, or trifluoromethyl; and
$R^7$, if present, is hydrogen or methyl.

In still another embodiment, in any one of Formulae III to XIX,
U is —O— and V is =C(CH$_3$)—; or U is =N— and V is —N(CH$_3$)—;
$R^1$ is hydrogen;
$R^{2a}$, $R^{2b}$, $R^{2c}$, and $R^{2d}$ are (i) or (ii):
(i) $R^{2a}$ is hydrogen, methyl, 2,2,2-trifluoroethyl, 2-methoxyethyl, pent-4-ynyl, pentanoyl, 2-methoxyacetyl, or but-3-ynylcarbonyl; and $R^{2b}$ is hydrogen or methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; and
$R^{2c}$ and $R^{2d}$ are each hydrogen; or $R^{2c}$ and $R^{2d}$ are linked together to form methylene or eth-1,2-ylene; or
(ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and
$R^{2b}$ and $R^{2d}$ are each hydrogen;
$R^3$ is cyclopropylmethyl;
$R^{6a}$, $R^{6b}$, and $R^{6d}$, if present, are each independently hydrogen;
$R^{6c}$, if present, is hydrogen, fluoro, or chloro; and
$R^7$, if present, is hydrogen or methyl.

In one embodiment, in any one of Formulae IIIa to XIXa,
U is —O— and V is =C(R$^4$)—; or U is =N— and V is —N(R$^5$)—;
$R^1$ is hydrogen or $C_{1-6}$ alkyl;
$R^{2a}$, $R^{2b}$, $R^{2c}$, and $R^{2d}$ are (i) or (ii):
(i) $R^{2a}$ and $R^{2b}$ are each independently hydrogen, $C_{1-6}$ alkyl, $C_{2-6}$ alkynyl, $C_{6-14}$ aryl, $C_{6-14}$ aralkyl, or —C(O)R$^{1a}$; or $R^{2a}$ and $R^{2b}$ together with the N atom to which they are attached form heteroaryl or heterocyclyl; and
$R^{2c}$ and $R^{2d}$ are each independently hydrogen or $C_{1-6}$ alkyl; or
(ii) $R^{2a}$ and $R^{2c}$ together with the C and N atoms to which they are attached form heteroaryl or heterocyclyl; and
$R^{2b}$ and $R^{2d}$ are each hydrogen;
$R^3$ is $C_{1-6}$ alkyl;
$R^4$ and $R^5$ are each independently $C_{1-6}$ alkyl, $C_{3-12}$ cycloalkyl, or heterocyclyl;
$R^{6a}$, $R^{6b}$, $R^{6c}$, and $R^{6d}$, if present, are each independently hydrogen, halo, $C_{1-6}$ alkyl, —OR$^{1a}$, or —NR$^{1b}$R$^{1c}$;
$R^7$, if present, is hydrogen or $C_{1-6}$ alkyl; and
each $R^{1a}$, $R^{1b}$, and $R^{1c}$ is as defined herein;
wherein each alkyl, alkynyl, cycloalkyl, aryl, aralkyl, heteroaryl, and heterocyclyl is optionally substituted with one or more, in one embodiment, one, two, three, or four, substituents Q.

In another embodiment, in any one of Formulae IIIa to XIXa,
U is —O— and V is =C(R$^4$)—; or U is =N— and V is —N(R$^5$)—;
$R^1$ is hydrogen or $C_{1-6}$ alkyl;
$R^{2a}$, $R^{2b}$, $R^{2c}$, and $R^{2d}$ are (i) or (ii):
(i) $R^{2a}$ and $R^{2b}$ are each independently hydrogen, $C_{1-6}$ alkyl, $C_{2-6}$ alkynyl, 5- or 6-membered heteroaryl-$C_{1-6}$ alkyl, $C_{6-14}$ aryl, $C_{6-14}$ aralkyl, —C(O)—$C_{1-6}$ alkyl, —C(O)—$C_{2-6}$ alkynyl, or —C(O)-5-membered heteroaryl; or $R^{2a}$ and $R^{2b}$ together with the N atom to which they are attached form 5-membered heteroaryl or 4- to 6-membered heterocyclyl;
$R^{2c}$ is hydrogen or $C_{1-6}$ alkyl; and
$R^{2d}$ is hydrogen; or
(ii) $R^{2a}$ and $R^{2c}$ together with the C and N atoms to which they are attached form 5-membered heteroaryl or 5-membered heterocyclyl; and
$R^{2b}$ and $R^{2d}$ are each hydrogen;
$R^3$ is $C_{1-6}$ alkyl or $C_{3-12}$ cycloalkyl-$C_{1-6}$ alkyl;
$R^4$ and $R^5$ are each independently $C_{1-6}$ alkyl, $C_{3-12}$ cycloalkyl, or 4- to 6-membered heterocyclyl;
$R^{6a}$, $R^{6b}$, $R^{6c}$, and $R^{6d}$, if present, are each independently hydrogen, fluoro, chloro, $C_{1-6}$ alkyl, hydroxyl, or amino; and
$R^7$, if present, is hydrogen or methyl;
wherein each alkyl, alkynyl, cycloalkyl, aryl, aralkyl, heteroaryl, and heterocyclyl is optionally substituted with one or more, in one embodiment, one, two, three, or four, substituents Q.

In yet another embodiment, in any one of Formulae IIIa to XIXa,
U is —O— and V is =C(R$^4$)—; or U is =N— and V is —N(R$^5$)—;
$R^1$ is hydrogen;
$R^{2a}$, $R^{2b}$, $R^{2c}$, and $R^{2d}$ are (i) or (ii):
(i) $R^{2a}$ is hydrogen, methyl, 2,2,2-trifluoroethyl, 2-methoxyethyl, pent-4-ynyl, phenyl, benzyl, (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, (pyridin-3-yl)methyl, pentanoyl, 2-methoxyacetyl, but-3-ynylcarbonyl, or (pyrazol-4-yl)carbonyl; and $R^{2b}$ is hydrogen, methyl, 2,2,2-trifluoroethyl, or (pyrazol-4-yl)methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; $R^{2c}$ is hydrogen, methyl, or hydroxymethyl; and $R^{2d}$ is hydrogen; or (ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and
$R^{2b}$ and $R^{2d}$ are each hydrogen;

$R^3$ is t-butylmethyl, cyclopropylmethyl, 1-methylcyclopropylmethyl, 1-hydroxy(cyclopropylmethyl), cyclobutylmethyl, or cyclopentylmethyl;

$R^4$ and $R^5$ are each independently methyl, isopropyl, cyclopentyl, oxetan-3-yl, tetrahydrofur-3-yl, tetrahydropyran-4-yl, or tetrahydropyran-3-yl;

$R^{6a}$, $R^{6b}$, and $R^{6d}$, if present, are each independently hydrogen;

$R^{6c}$, if present, is hydrogen, fluoro, chloro, methyl, or trifluoromethyl; and $R^7$, if present, is hydrogen or methyl.

In still another embodiment, in any one of Formulae IIIa to XIXa,

U is —O— and V is =C(CH$_3$)—; or U is =N— and V is —N(CH$_3$)—;
$R^1$ is hydrogen;
$R^{2a}$, $R^{2b}$, $R^{2c}$, and $R^{2d}$ are (i) or (ii):

(i) $R^{2a}$ is hydrogen, methyl, 2,2,2-trifluoroethyl, 2-methoxyethyl, pent-4-ynyl, pentanoyl, 2-methoxyacetyl, or but-3-ynylcarbonyl; and $R^{2b}$ is hydrogen or methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; and
$R^{2c}$ and $R^{2d}$ are each hydrogen; or (ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and
$R^{2b}$ and $R^{2d}$ are each hydrogen;

$R^3$ is cyclopropylmethyl;
$R^{6a}$, $R^{6b}$, and $R^{6d}$, if present, are each independently hydrogen;
$R^{6c}$, if present, is hydrogen, fluoro, or chloro; and
$R^7$, if present, is hydrogen or methyl.

In one embodiment, provided herein is a compound of:

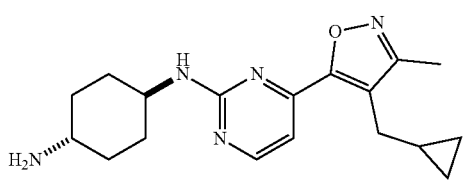

A1

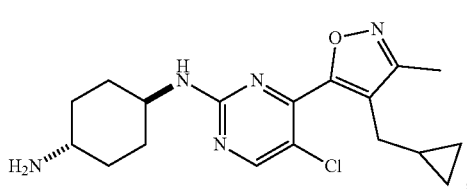

A2 or a tautomer, a mixture of two or more tautomers, or an isotopic variant thereof; or a pharmaceutically acceptable salt, solvate, hydrate, or a prodrug thereof.

In another embodiment, provided herein is a compound of:

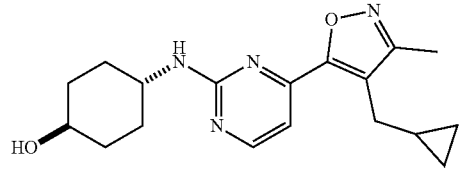

C3

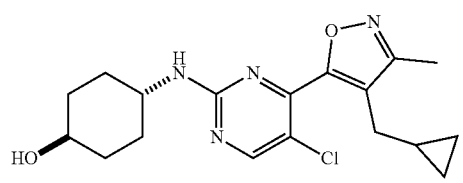

C4 or a tautomer, a mixture of two or more tautomers, or an isotopic variant thereof; or a pharmaceutically acceptable salt, solvate, hydrate, or a prodrug thereof.

In yet another embodiment, provided herein is a compound of:

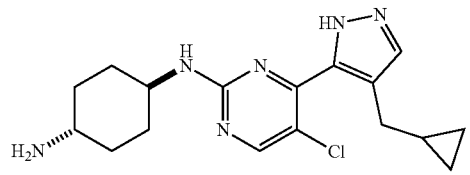

C14

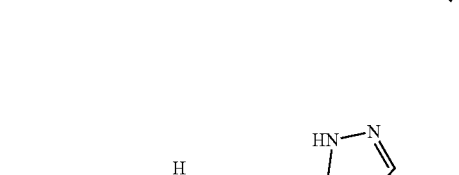

C15 or a tautomer, a mixture of two or more tautomers, or an isotopic variant thereof; or a pharmaceutically acceptable salt, solvate, hydrate, or a prodrug thereof.

In yet another embodiment, provided herein is a compound of:

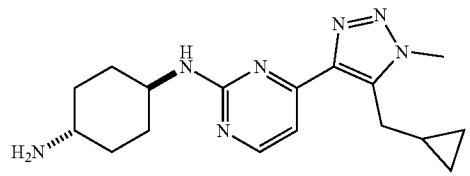

B1

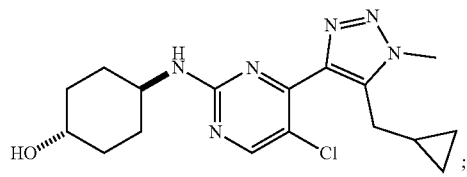
B2 or a tautomer, a mixture of two or more tautomers, or an isotopic variant thereof; or a pharmaceutically acceptable salt, solvate, hydrate, or a prodrug thereof.

In yet another embodiment, provided herein is a compound of:

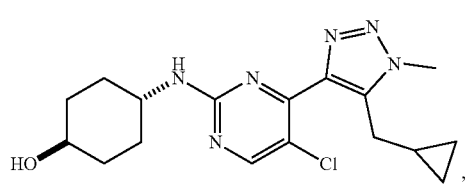
C5

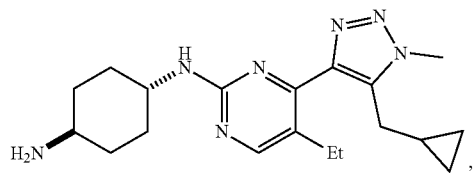
C6

C7
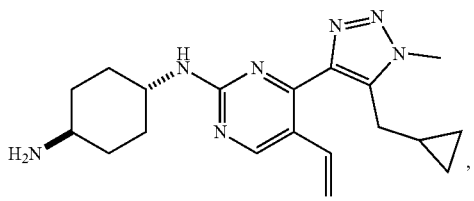

C8
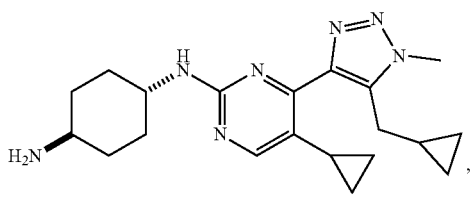

C9
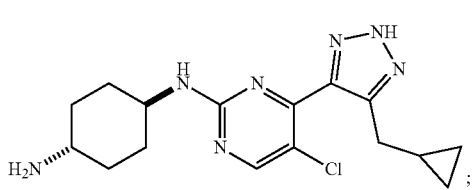

C10
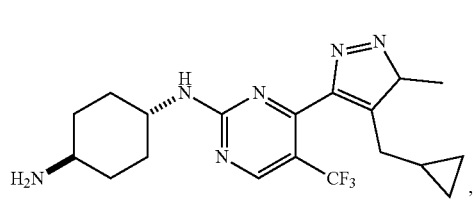

C11
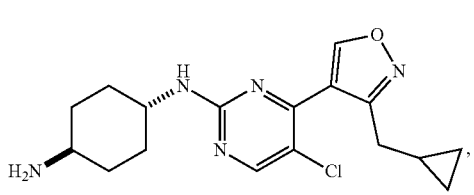

C12
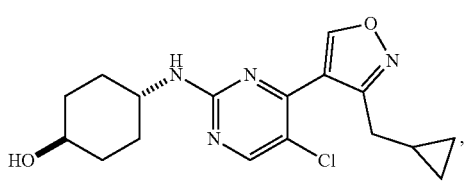
or

C13
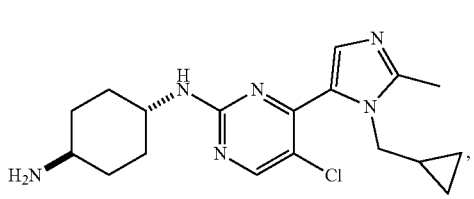
;

or a tautomer, a mixture of two or more tautomers, or an isotopic variant thereof; or a pharmaceutically acceptable salt, solvate, hydrate, or a prodrug thereof.

In still another embodiment, provided herein is a compound of:

C1

C2

C16
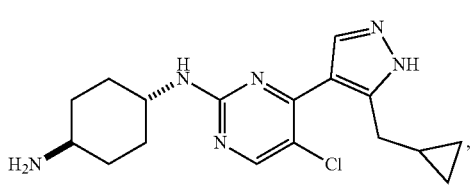

C17
or

-continued

C18

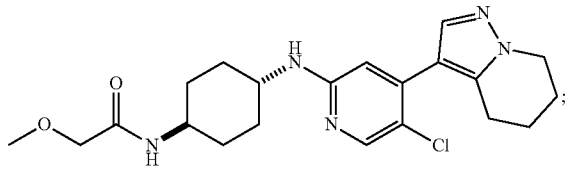

or a tautomer, a mixture of two or more tautomers, or an isotopic variant thereof; or a pharmaceutically acceptable salt, solvate, hydrate, or a prodrug thereof.

In one embodiment, provided herein is an isolated compound C17. In another embodiment, provided herein is a purified compound C17.

In one embodiment, provided herein is a compound of Formula IA:

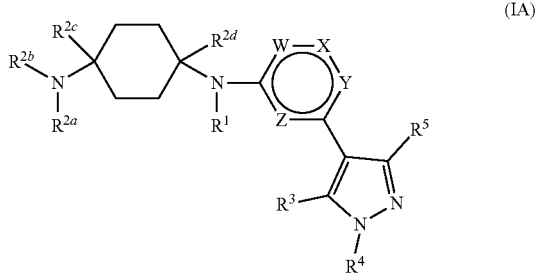

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

W, X, Y, and Z are each independently =C($R^6$)— or =N—, with the proviso that at least one of W, X, Y, and Z is =N—; or W, X, and Z are each independently =C($R^6$)—, —N($R^7$)—, =N—, —O—, or —S—; and Y is a bond;

each $R^1$, $R^4$, and $R^7$ is independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{2a}$, $R^{2b}$, $R^{2c}$, and $R^{2d}$ are (i) or (ii):
(i) $R^{2a}$ and $R^{2b}$ are each independently (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)$R^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$; or $R^{2a}$ and $R^{2b}$ together with the N atom to which they are attached form heteroaryl or heterocyclyl; and $R^{2c}$ and $R^{2d}$ are each independently (a) hydrogen, deuterium, or cyano; or (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or $R^{2c}$ and $R^{2d}$ are linked together to form —O—, $C_{1-6}$ alkylene, $C_{1-6}$ heteroalkylene, $C_{2-6}$ alkenylene, or $C_{2-6}$ alkynylene; or (ii) $R^{2a}$ and $R^{2c}$ together with the C and N atoms to which they are attached form heterocyclyl;

$R^{2b}$ is (a) hydrogen or deuterium; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)$R^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$; and $R^{2d}$ is (a) hydrogen, deuterium, or cyano; or (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl;

each $R^3$, $R^5$, and $R^6$ is independently (a) hydrogen, deuterium, cyano, halo, or nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (c) —C(O)$R^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkylene, heteroalkylene, alkenyl, alkenylene, alkynyl, alkynylene, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^b R^c$, —C(O)S$R^a$, —C(N$R^a$)N$R^b R^c$, —C(S)$R^a$, —C(S)O$R^a$, —C(S)N$R^b R^c$, —O$R^a$, —OC(O)$R^a$, —OC(O)O$R^a$, —OC(O)N$R^b R^c$, —OC(O)S$R^a$, —OC(=N$R^a$)N$R^b R^c$, —OC(S)$R^a$, —OC(S)O$R^a$, —OC(S)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(O)S$R^d$, —N$R^a$C(=N$R^d$)N$R^b R^c$, —N$R^a$C(S)$R^d$, —N$R^a$C(S)O$R^d$, —N$R^a$C(S)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —S$R^a$, —S(O)$R^a$, —S(O)$_2 R^a$, —S(O)N$R^b R^c$, and —S(O)$_2$N$R^b R^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f R^g$, —C(O)S$R^e$, —C(N$R^e$)N$R^f R^g$, —C(S)$R^e$, —C(S)O$R^e$, —C(S)N$R^f R^g$, —O$R^e$, —OC(O)$R^e$, —OC(O)O$R^e$, —OC(O)N$R^f R^g$, —OC(O)S$R^e$, —OC(=N$R^e$)N$R^f R^g$, —OC(S)$R^e$, —OC(S)O$R^e$, —OC(S)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^f$, —N$R^e$C(O)N$R^f R^g$, —N$R^e$C(O)S$R^f$, —N$R^e$C(=N$R^h$)N$R^f R^g$, —N$R^e$C(S)$R^h$, —N$R^e$C(S)O$R^f$, —N$R^e$C(S)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S$R^e$, —S(O)$R^e$, —S(O)$_2$R, —S(O)N$R^f R^g$, and —S(O)$_2$N$R^f R^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-12}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In another embodiment, provided herein is a compound of Formula IAa:

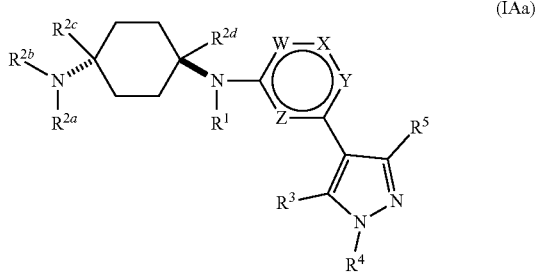

(IAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, W, X, Y, and Z are each as defined herein.

In yet another embodiment, provided herein is a compound of Formula IAb:

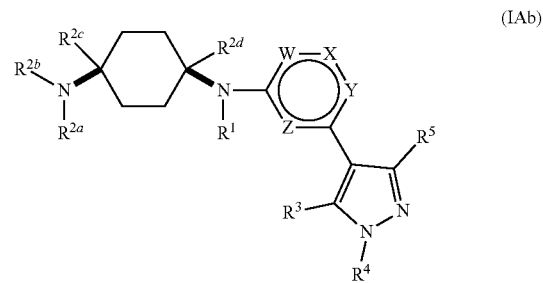

(IAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, W, X, Y, and Z are each as defined herein.

In one embodiment, in Formula IA, IAa, or IAb,

W, X, Y, and Z are each independently =C($R^6$)— or =N—;

$R^1$ and $R^5$ are each independently hydrogen or $C_{1-6}$ alkyl; $R^{2a}$, $R^{2b}$, $R^{2c}$, and $R^{2d}$ are (i) or (ii):

(i) $R^{2a}$ and $R^{2b}$ are each independently hydrogen, $C_{1-6}$ alkyl, $C_{2-6}$ alkynyl, $C_{6-14}$ aryl, $C_{6-14}$ aralkyl, or —C(O)$R^{1a}$; or $R^{2a}$ and $R^{2b}$ together with the N atom to which they are attached form heteroaryl or heterocyclyl; and $R^{2c}$ and $R^{2d}$ are each independently hydrogen or $C_{1-6}$ alkyl; or $R^{2c}$ and $R^{2d}$ in Formula I or Ib are linked together to form —O—, $C_{1-6}$ alkylene, or $C_{1-6}$ heteroalkylene; or (ii) $R^{2a}$ and $R^{2c}$ together with the C and N atoms to which they are attached form heteroaryl or heterocyclyl; and $R^{2b}$ and $R^{2d}$ are each hydrogen;

$R^3$ is $C_{1-6}$ alkyl;

$R^4$ is $C_{1-6}$ alkyl, $C_{3-12}$ cycloalkyl, or heterocyclyl;

each $R^6$ is independently hydrogen, halo, $C_{1-6}$ alkyl, —O$R^{1a}$, or —N$R^{1b}R^{1c}$; and each $R^{1a}$, $R^{1b}$, and $R^{1c}$ is as defined herein;

wherein each alkyl, alkylene, heteroalkylene, alkynyl, cycloalkyl, aryl, aralkyl, heteroaryl, and heterocyclyl is optionally substituted with one or more, in one embodiment, one, two, three, or four, substituents Q.

In another embodiment, in Formula IA, IAa, or IAb,

W, X, Y, and Z are each independently =C($R^6$)— or =N—;

$R^1$ and $R^5$ are each independently hydrogen or $C_{1-6}$ alkyl; $R^{2a}$, $R^{2b}$, $R^{2c}$, and $R^{2d}$ are (i) or (ii):

(i) $R^{2a}$ and $R^{2b}$ are each independently hydrogen, $C_{1-6}$ alkyl, $C_{2-6}$ alkynyl, 5- or 6-membered heteroaryl-$C_{1-6}$ alkyl, $C_{6-14}$ aryl, $C_{6-14}$ aralkyl, —C(O)—$C_{1-6}$ alkyl, —C(O)—$C_2$-6 alkyl, —C(O)—$C_{2-6}$ alkynyl, or —C(O)-5-membered heteroaryl; or $R^{2a}$ and $R^{2b}$ together with the N atom to which they are attached form 5-membered heteroaryl or 4- to 6-membered heterocyclyl; and $R^{2c}$ is hydrogen or $C_{1-6}$ alkyl; and $R^{2d}$ is hydrogen; or $R^{2c}$ and $R^{2d}$ in Formula I or Ib are linked together to form $C_{2-6}$ alkylene; or (ii) $R^{2a}$ and $R^{2c}$ together with the C and N atoms to which they are attached form 5-membered heteroaryl or 5-membered heterocyclyl; and
$R^{2b}$ and $R^{2d}$ are each hydrogen;
$R^3$ is $C_{1-6}$ alkyl or $C_{3-12}$ cycloalkyl-$C_{1-6}$ alkyl;
$R^4$ is $C_{1-6}$ alkyl, $C_{3-12}$ cycloalkyl, or 4- to 6-membered heterocyclyl; and
each $R^6$ is independently hydrogen, fluoro, chloro, $C_{1-6}$ alkyl, hydroxyl, or amino;
wherein each alkyl, alkylene, alkynyl, cycloalkyl, aryl, aralkyl, heteroaryl, and heterocyclyl is optionally substituted with one or more, in one embodiment, one, two, three, or four, substituents Q.

In yet another embodiment, in Formula IA, IAa, or IAb, W, X, Y, and Z are each independently =C($R^6$)— or =N—;
$R^1$ and $R^5$ are each independently hydrogen or methyl;
$R^{2a}$, $R^{2b}$, $R^{2c}$, and $R^{2d}$ are (i) or (ii):
(i) $R^{2a}$ is hydrogen, methyl, trifluoroethyl, methoxyethyl, pentynyl, phenyl, benzyl, (pyrazolyl)methyl, (methylpyrazolyl)methyl, (pyrazolyl)ethyl, (pyridinyl)methyl, pentanoyl, methoxyacetyl, butynylcarbonyl, or (pyrazolyl)carbonyl; and $R^{2b}$ is hydrogen, methyl, trifluoroethyl, or (pyrazolyl)methyl; or $R^{2a}$ and $R^{2b}$ together with the N atom to which they are attached form azetidinyl, pyrrolidinyl, piperidinyl, morpholinyl, pyrazolyl, methylpyrazolyl, or imidazolyl; and
$R^{2c}$ is hydrogen, methyl, or hydroxymethyl; and $R^{2d}$ is hydrogen; or $R^{2c}$ and $R^{2d}$ in Formula I or Ib are linked together to form methylene or ethylene; or
(ii) $R^{2a}$ and $R^{2c}$ together with the C and N atoms to which they are attached form pyrrolidinylene-one, imidazolidinylene-dione, or oxazolidinylene-one; and
$R^{2b}$ and $R^{2d}$ are each hydrogen;
$R^3$ is butylmethyl, cyclopropylmethyl, methylcyclopropylmethyl, hydroxy(cyclopropylmethyl), cyclobutylmethyl, or cyclopentylmethyl;
$R^4$ is methyl, isopropyl, cyclopentyl, oxetanyl, tetrahydrofuryl, or tetrahydropyranyl; and
each $R^6$ is independently hydrogen, fluoro, chloro, methyl, trifluoromethyl, hydroxyl, or amino.

In yet another embodiment, in Formula IA, IAa, or IAb, W, X, Y, and Z are each independently =C(H)—, =C(F)—, =C(Cl)—, =C($CH_3$)—, =C($CF_3$)—, =C(OH)—, =C($NH_2$)—, or =N—;
$R^1$ and $R^5$ are each hydrogen;
$R^{2a}$, $R^{2b}$, $R^{2c}$, and $R^{2d}$ are (i) or (ii):
(i) $R^{2a}$ is hydrogen, methyl, 2,2,2-trifluoroethyl, 2-methoxyethyl, pent-4-ynyl, phenyl, benzyl, (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, (pyridin-3-yl)methyl, pentanoyl, 2-methoxyacetyl, but-3-ynylcarbonyl, or (pyrazol-4-yl)carbonyl; and $R^{2b}$ is hydrogen, methyl, 2,2,2-trifluoroethyl, or (pyrazol-4-yl)methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; and
$R^{2c}$ is hydrogen, methyl, or hydroxymethyl; and $R^{2d}$ is hydrogen; or $R^{2c}$ and $R^{2d}$ in Formula I or Ib are linked together to form methylene or eth-1,2-ylene; or
(ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and
$R^{2b}$ and $R^{2d}$ are each hydrogen;
$R^3$ is t-butylmethyl, cyclopropylmethyl, 1-methylcyclopropylmethyl, 1-hydroxy(cyclopropylmethyl), cyclobutylmethyl, or cyclopentylmethyl; and
$R^4$ is methyl, isopropyl, cyclopentyl, oxetan-3-yl, tetrahydrofur-3-yl, tetrahydropyran-4-yl, or tetrahydropyran-3-yl.

In yet another embodiment, in Formula IA,
W and Z are each independently =C(H)— or =N—;
X is =C(H)—, =C(OH)—, or =C($NH_2$)—;
Y is =C(H)—, =C(F)—, =C(Cl)—, =C($CH_3$)—, =C($CF_3$)—, or =N—;
$R^1$ and $R^5$ are each hydrogen;
$R^{2a}$, $R^{2b}$, $R^{2c}$, and $R^{2d}$ are (i) or (ii):
(i) $R^{2a}$ is hydrogen, methyl, 2,2,2-trifluoroethyl, 2-methoxyethyl, pent-4-ynyl, phenyl, benzyl, (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, (pyridin-3-yl)methyl, pentanoyl, 2-methoxyacetyl, but-3-ynylcarbonyl, or (pyrazol-4-yl)carbonyl; and $R^{2b}$ is hydrogen, methyl, 2,2,2-trifluoroethyl, or (pyrazol-4-yl)methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; and
$R^{2c}$ is hydrogen, methyl, or hydroxymethyl; and $R^{2d}$ is hydrogen; or $R^{2c}$ and $R^{2d}$ in Formula I or Ib are linked together to form methylene or 1,2-ethylene; or
(ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and
$R^{2b}$ and $R^{2d}$ are each hydrogen;
$R^3$ is t-butylmethyl, cyclopropylmethyl, 1-methylcyclopropylmethyl, 1-hydroxy(cyclopropylmethyl), cyclobutylmethyl, or cyclopentylmethyl; and
$R^4$ is methyl, isopropyl, cyclopentyl, oxetan-3-yl, tetrahydrofur-3-yl, tetrahydropyran-4-yl, or tetrahydropyran-3-yl.

In still another embodiment, in Formula IA,
W and Z are each independently =C(H)— or =N—;
X is =C(H)—;
Y is =C(H)—, =C(F)—, or =C(Cl)—;
$R^1$ and $R^5$ are each hydrogen;
$R^{2a}$, $R^{2b}$, $R^{2c}$, and $R^{2d}$ are (i) or (ii):
(i) $R^{2a}$ is hydrogen, methyl, 2,2,2-trifluoroethyl, 2-methoxyethyl, pent-4-ynyl, pentanoyl, 2-methoxyacetyl, or but-3-ynylcarbonyl; and $R^{2b}$ is hydrogen or methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; and
$R^{2c}$ and $R^{2d}$ are each hydrogen; or $R^{2c}$ and $R^{2d}$ in Formula I or Ib are linked together to form methylene or eth-1,2-ylene; or
(ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and
$R^{2b}$ and $R^{2d}$ are each hydrogen;

$R^3$ is cyclopropylmethyl; and
$R^4$ is methyl.

In one embodiment, in Formula IA, IAa, or IAb,
W, X, Y, and Z are each independently $=C(R^6)$— or $=N$—;
$R^1$ and $R^5$ are each independently hydrogen or $C_{1-6}$ alkyl;
$R^{2a}$ and $R^{2b}$ are each independently hydrogen, $C_{2-6}$ alkynyl, or —C(O)$R^{1a}$;
$R^{2c}$ and $R^{2d}$ are each independently hydrogen or $C_{1-6}$ alkyl;
$R^3$ is $C_{1-6}$ alkyl;
$R^4$ is $C_{1-6}$ alkyl, $C_{3-12}$ cycloalkyl, or heterocyclyl;
each $R^6$ is independently hydrogen, halo, $C_{1-6}$ alkyl, —OR$^{1a}$, or —NR$^{1b}$R$^{1c}$; and
each $R^{1a}$, $R^{1b}$, and $R^{1c}$ is as defined herein;
wherein each alkyl, alkynyl, cycloalkyl, and heterocyclyl is optionally substituted with one or more, in one embodiment, one, two, three, or four, substituents Q.

In another embodiment, in Formula IA, IAa, or IAb,
W, X, Y, and Z are each independently $=C(R^6)$— or $=N$—;
$R^1$ and $R^5$ are each independently hydrogen or $C_{1-6}$ alkyl;
$R^{2a}$ and $R^{2b}$ are each independently hydrogen, $C_{2-6}$ alkynyl, —C(O)—$C_{2-6}$ alkyl, or —C(O)—$C_{2-6}$ alkynyl;
$R^{2c}$ is hydrogen or $C_{1-6}$ alkyl;
$R^{2d}$ is hydrogen;
$R^3$ is $C_{1-6}$ alkyl or $C_{3-12}$ cycloalkyl-$C_{1-6}$ alkyl;
$R^4$ is $C_{1-6}$ alkyl, $C_{3-12}$ cycloalkyl, or 4- to 6-membered heterocyclyl; and
each $R^6$ is independently hydrogen, fluoro, chloro, $C_{1-6}$ alkyl, hydroxyl, or amino;
wherein each alkyl, alkynyl, cycloalkyl, and heterocyclyl is optionally substituted with one or more, in one embodiment, one, two, three, or four, substituents Q.

In yet another embodiment, in Formula IA, IAa, or IAb,
W, X, Y, and Z are each independently $=C(R^6)$— or $=N$—;
$R^1$ and $R^5$ are each independently hydrogen or methyl;
$R^{2a}$ is pentynyl, pentanoyl, or butynylcarbonyl;
$R^{2b}$ is hydrogen, methyl, trifluoroethyl, or (pyrazolyl)methyl;
$R^{2c}$ is hydrogen, methyl, or hydroxymethyl;
$R^{2d}$ is hydrogen;
$R^3$ is butylmethyl, cyclopropylmethyl, methylcyclopropylmethyl, hydroxy(cyclopropylmethyl), cyclobutylmethyl, or cyclopentylmethyl;
$R^4$ is methyl, isopropyl, cyclopentyl, oxetanyl, tetrahydrofuryl, or tetrahydropyranyl; and
each $R^6$ is independently hydrogen, fluoro, chloro, methyl, trifluoromethyl, hydroxyl, or amino.

In still another embodiment, in Formula IA, IAa, or IAb,
W and Z are each independently $=C(H)$— or $=N$—;
X is $=C(H)$—;
Y is $=C(H)$—, $=C(F)$—, or $=C(Cl)$—;
$R^1$ and $R^5$ are each hydrogen;
$R^{2a}$ is pent-4-ynyl, pentanoyl, or but-3-ynylcarbonyl;
$R^{2b}$ is hydrogen or methyl;
$R^{2c}$ and $R^{2d}$ are each hydrogen;
$R^3$ is cyclopropylmethyl; and
$R^4$ is methyl.

In one embodiment, in Formula IA or IAb,
W, X, Y, and Z are each independently $=C(R^6)$— or $=N$—;
$R^1$ and $R^5$ are each independently hydrogen or $C_{1-6}$ alkyl;
$R^{2a}$ and $R^{2b}$ are each independently hydrogen, $C_{1-6}$ alkyl, $C_{3-6}$ alkynyl, $C_{6-14}$ aryl, $C_{6-14}$ aralkyl, or —C(O)$R^{1a}$; or $R^{2a}$ and $R^{2b}$ together with the N atom to which they are attached form heteroaryl or heterocyclyl;
$R^{2c}$ and $R^{2d}$ are linked together to form —O—, $C_{1-6}$ alkylene, or $C_{1-6}$ heteroalkylene;
$R^3$ is $C_{1-6}$ alkyl;
$R^4$ is $C_{1-6}$ alkyl, $C_{3-12}$ cycloalkyl, or heterocyclyl;
each $R^6$ is independently hydrogen, halo, $C_{1-6}$ alkyl, —OR$^{1a}$, or —NR$^{1b}$R$^{1c}$; and
each $R^{1a}$, $R^{1b}$, and $R^{1c}$ is as defined herein;
wherein each alkyl, alkylene, heteroalkylene, alkynyl, cycloalkyl, aryl, aralkyl, heteroaryl, and heterocyclyl is optionally substituted with one or more, in one embodiment, one, two, three, or four, substituents Q.

In another embodiment, in Formula IA or IAb,
W, X, Y, and Z are each independently $=C(R^6)$— or $=N$—;
$R^1$ and $R^5$ are each independently hydrogen or $C_{1-6}$ alkyl;
$R^{2a}$ and $R^{2b}$ are each independently hydrogen, $C_{1-6}$ alkyl, $C_{2-6}$ alkynyl, 5- or 6-membered heteroaryl-$C_{1-6}$ alkyl, $C_{6-14}$ aryl, $C_{6-14}$ aralkyl, —C(O)—$C_{1-6}$ alkyl, —C(O)—$C_{2-6}$ alkynyl, or —C(O)-5-membered heteroaryl; or $R^{2a}$ and $R^{2b}$ together with the N atom to which they are attached form 5-membered heteroaryl or 4- to 6-membered heterocyclyl;
$R^{2c}$ and $R^{2d}$ are linked together to form $C_{2-6}$ alkylene;
$R^3$ is $C_{1-6}$ alkyl or $C_{3-12}$ cycloalkyl-$C_{1-6}$ alkyl;
$R^4$ is $C_{1-6}$ alkyl, $C_{3-12}$ cycloalkyl, or 4- to 6-membered heterocyclyl; and
each $R^6$ is independently hydrogen, fluoro, chloro, $C_{1-6}$ alkyl, hydroxyl, or amino;
wherein each alkyl, alkylene, alkynyl, cycloalkyl, aryl, aralkyl, heteroaryl, and heterocyclyl is optionally substituted with one or more, in one embodiment, one, two, three, or four, substituents Q.

In yet another embodiment, in Formula IA or IAb,
W, X, Y, and Z are each independently $=C(R^6)$— or $=N$—;
$R^1$ and $R^5$ are each independently hydrogen or methyl;
$R^{2a}$ is hydrogen, methyl, trifluoroethyl, methoxyethyl, pentynyl, phenyl, benzyl, (pyrazolyl)methyl, (methylpyrazolyl)methyl, (pyrazolyl)ethyl, (pyridinyl)methyl, pentanoyl, methoxyacetyl, butynylcarbonyl, or (pyrazolyl)carbonyl; and $R^{2b}$ is hydrogen, methyl, trifluoroethyl, or (pyrazolyl)methyl; or $R^{2a}$ and $R^{2b}$ together with the N atom to which they are attached form azetidinyl, pyrrolidinyl, piperidinyl, morpholinyl, pyrazolyl, methylpyrazolyl, or imidazolyl;
$R^{2c}$ and $R^{2d}$ are linked together to form methylene or ethylene;
$R^3$ is butylmethyl, cyclopropylmethyl, methylcyclopropylmethyl, hydroxy(cyclopropylmethyl), cyclobutylmethyl, or cyclopentylmethyl;
$R^4$ is methyl, isopropyl, cyclopentyl, oxetanyl, tetrahydrofuryl, or tetrahydropyranyl; and
each $R^6$ is independently hydrogen, fluoro, chloro, methyl, trifluoromethyl, hydroxyl, or amino.

In yet another embodiment, in Formula IA or IAb,
W, X, Y, and Z are each independently $=C(H)$—, $=C(F)$—, $=C(Cl)$—, $=C(CH_3)$—, $=C(CF_3)$—, $=C(OH)$—, $=C(NH_2)$—, or $=N$—;
$R^1$ and $R^5$ are each hydrogen;
$R^{2a}$ is hydrogen, methyl, trifluoroethyl, methoxyethyl, pentynyl, phenyl, benzyl, (pyrazolyl)methyl, (1-methylpyrazolyl)methyl, (3-methylpyrazolyl)methyl, (pyrazol-yl)ethyl, (pyridinyl)methyl, pentanoyl, methoxyacetyl, butynylcarbonyl, or (pyrazolyl)carbonyl; and $R^{2b}$ is hydrogen, methyl, trifluoroethyl, or (pyrazolyl)

methyl; or $R^{2a}$ and $R^{2b}$ together with the N atom to which they are attached form azetidinyl, pyrrolidinyl, piperidineyl, morpholinyl, pyrazolyl, methylpyrazolyl, or imidazolyl;

$R^{2c}$ and $R^{2d}$ are linked together to form methylene or ethylene;

$R^3$ is t-butylmethyl, cyclopropylmethyl, methylcyclopropylmethyl, hydroxy(cyclopropylmethyl), cyclobutylmethyl, or cyclopentylmethyl; and $R^4$ is methyl, isopropyl, cyclopentyl, oxetanyl, tetrahydrofuryl, tetrahydropyranyl, or tetrahydropyranyl.

In yet another embodiment, in Formula IA or IAb,

W and Z are each independently =C(H)— or =N—;

X is =C(H)—, =C(OH)—, or =C(NH$_2$)—;

Y is =C(H)—, =C(F)—, =C(Cl)—, =C(CH$_3$)—, =C(CF$_3$)—, or =N—;

$R^1$ and $R^5$ are each hydrogen;

$R^{2a}$ is hydrogen, methyl, 2,2,2-trifluoroethyl, 2-methoxyethyl, pent-4-ynyl, phenyl, benzyl, (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, (pyridin-3-yl)methyl, pentanoyl, 2-methoxyacetyl, but-3-ynylcarbonyl, or (pyrazol-4-yl)carbonyl; and $R^{2b}$ is hydrogen, methyl, 2,2,2-trifluoroethyl, or (pyrazol-4-yl)methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl;

$R^{2c}$ and $R^{2d}$ are linked together to form methylene or 1,2-ethylene;

$R^3$ is t-butylmethyl, cyclopropylmethyl, 1-methylcyclopropylmethyl, 1-hydroxy(cyclopropylmethyl), cyclobutylmethyl, or cyclopentylmethyl; and $R^4$ is methyl, isopropyl, cyclopentyl, oxetan-3-yl, tetrahydrofur-3-yl, tetrahydropyran-4-yl, or tetrahydropyran-3-yl.

In still another embodiment, in Formula IA or IAb,

W and Z are each independently =C(H)— or =N—;

X is =C(H)—;

Y is =C(H)—, =C(F)—, or =C(Cl)—;

$R^1$ and $R^5$ are each hydrogen;

$R^{2a}$ is hydrogen, methyl, 2,2,2-trifluoroethyl, 2-methoxyethyl, pent-4-ynyl, pentanoyl, 2-methoxyacetyl, or but-3-ynylcarbonyl; and $R^{2b}$ is hydrogen or methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl;

$R^{2c}$ and $R^{2d}$ are linked together to form methylene or eth-1,2-ylene;

$R^3$ is cyclopropylmethyl; and $R^4$ is methyl.

In Formula IA, IAa, or IAb, in one embodiment, W and X are =N—; in another embodiment, W and Y are =N—; in yet another embodiment, W and Z are =N—; in yet another embodiment, X and Y are =N—; in yet another embodiment, X and Z are =N—; and in still another embodiment, Y and Z are =N—.

In yet another embodiment, provided herein is a compound of Formula IIA:

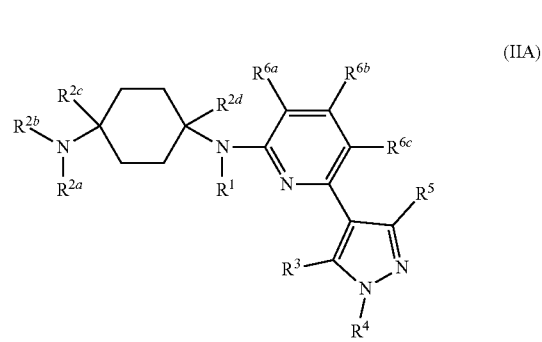

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^{6a}$, $R^{6b}$, and $R^{6c}$ are each independently $R^6$; and $R^1$, $R^3$, $R^4$, $R^5$, $R^6$, $R^{2a}$, $R^{2b}$, $R^{2c}$, and $R^{2d}$ are each as defined herein.

In yet another embodiment, provided herein is a compound of Formula IIAa:

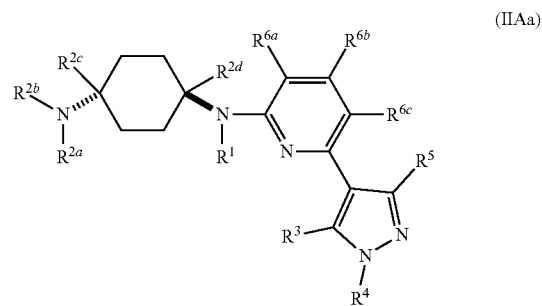

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, $R^{6b}$ and $R^{6c}$ are each as defined herein.

In yet another embodiment, provided herein is a compound of Formula IIAb:

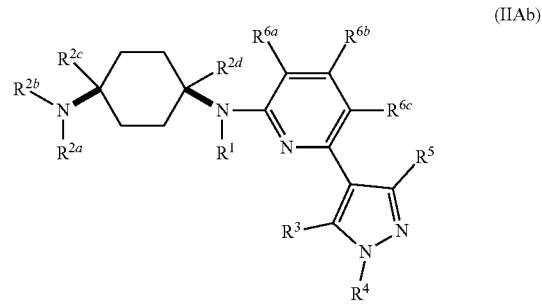

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, $R^{6b}$, and $R^{6c}$ are each as defined herein.

In yet another embodiment, provided herein is a compound of Formula IIIA:

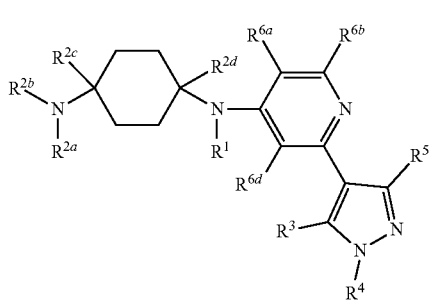

(IIIA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^{6d}$ is $R^6$; and $R^1$, $R^3$, $R^4$, $R^5$, $R^6$, $R^{2a}$, $R^{2b}$, $R^{2c}$, $R^{2d}$, $R^{6a}$, and $R^{6b}$ are each as defined herein.

In yet another embodiment, provided herein is a compound of Formula IIIAa:

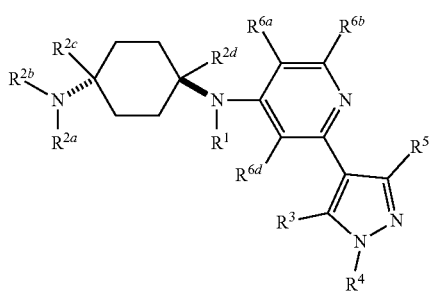

(IIIAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, $R^{6b}$, and $R^{6d}$ are each as defined herein.

In yet another embodiment, provided herein is a compound of Formula IIIAb:

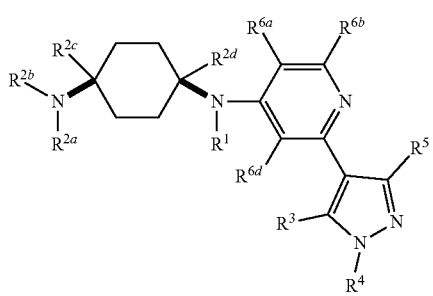

(IIIAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, $R^{6b}$, and $R^{6d}$ are each as defined herein.

In yet another embodiment, provided herein is a compound of Formula IVA:

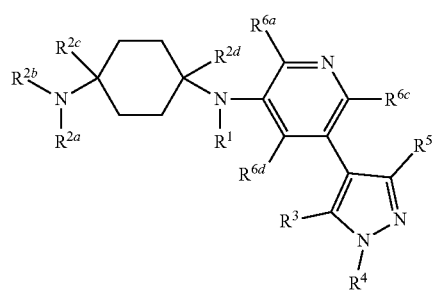

(IVA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, $R^{6c}$, and $R^{6d}$ are each as defined herein.

In yet another embodiment, provided herein is a compound of Formula IVAa:

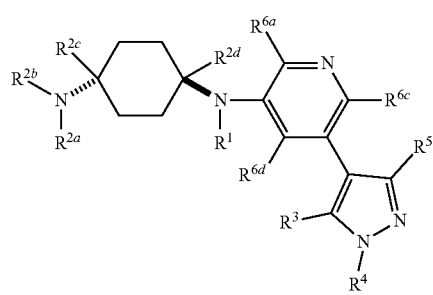

(IVAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, $R^{6c}$, and $R^{6d}$ are each as defined herein.

In yet another embodiment, provided herein is a compound of Formula IVAb:

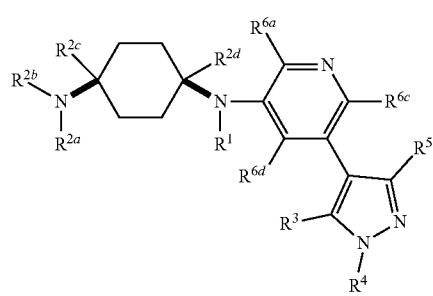

(IVAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, $R^{6c}$, and $R^{6d}$ are each as defined herein.

In yet another embodiment, provided herein is a compound of Formula VA:

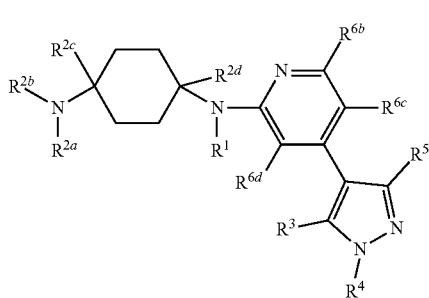

(VA)

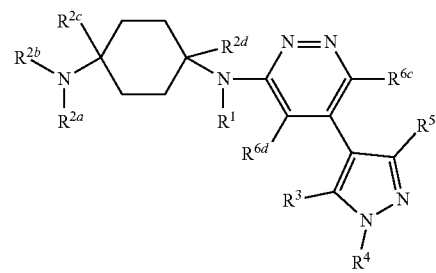

(VIA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6b}$, $R^{6c}$, and $R^{6d}$ are each as defined herein.

In yet another embodiment, provided herein is a compound of Formula VAa:

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6c}$, and $R^{6d}$ are each as defined herein.

In yet another embodiment, provided herein is a compound of Formula VIAa:

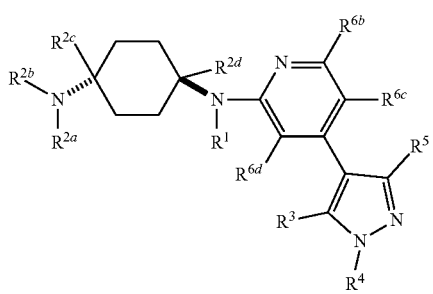

(VAa)

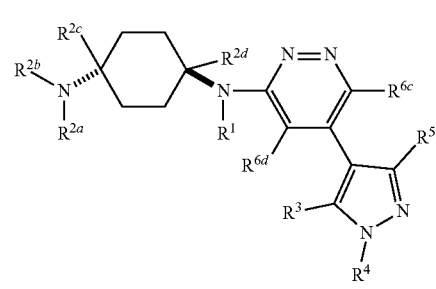

(VIAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6b}$, $R^{6c}$, and $R^{6d}$ are each as defined herein.

In yet another embodiment, provided herein is a compound of Formula VAb:

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6c}$, and $R^{6d}$ are each as defined herein.

In yet another embodiment, provided herein is a compound of Formula VIAb:

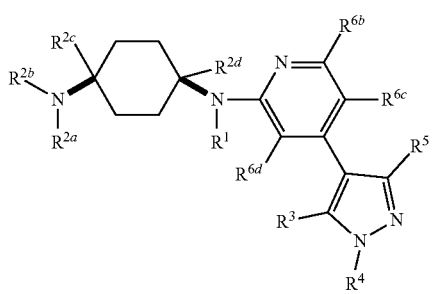

(VAb)

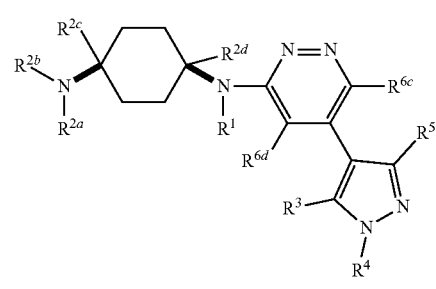

(VIAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6b}$, $R^{6c}$, and $R^{6d}$ are each as defined herein.

In yet another embodiment, provided herein is a compound of Formula VIA:

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6c}$, and $R^{6d}$ are each as defined herein.

In yet another embodiment, provided herein is a compound of Formula VIIA:

(VIIA)

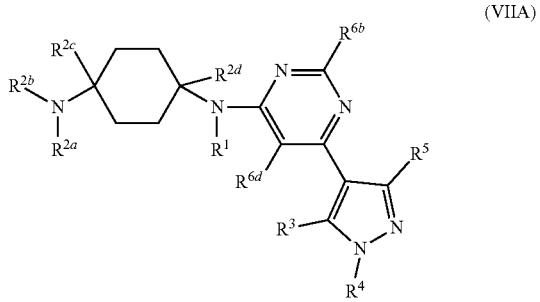

(VIIIA)

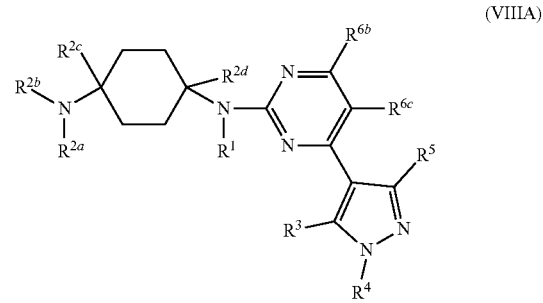

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6b}$, and $R^{6d}$ are each as defined herein.

In yet another embodiment, provided herein is a compound of Formula VIIAa:

(VIIAa)

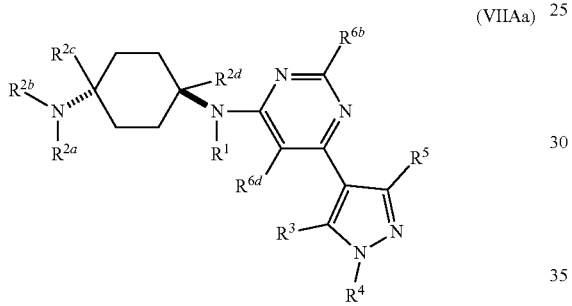

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6b}$, and $R^{6d}$ are each as defined herein.

In yet another embodiment, provided herein is a compound of Formula VIIAb:

(VIIAb)

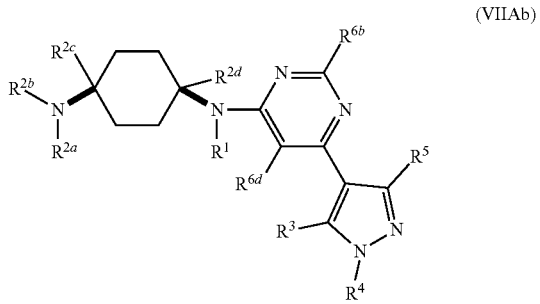

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6b}$, and $R^{6d}$ are each as defined herein.

In yet another embodiment, provided herein is a compound of Formula VIIIA:

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6b}$, and $R^{6c}$ are each as defined herein.

In yet another embodiment, provided herein is a compound of Formula VIIIAa:

(VIIIAa)

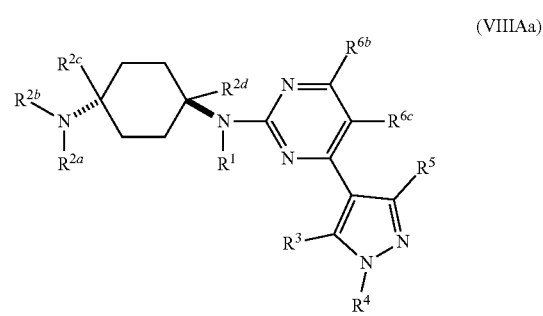

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6b}$, and $R^{6c}$ are each as defined herein.

In yet another embodiment, provided herein is a compound of Formula VIIIAb:

(VIIIAb)

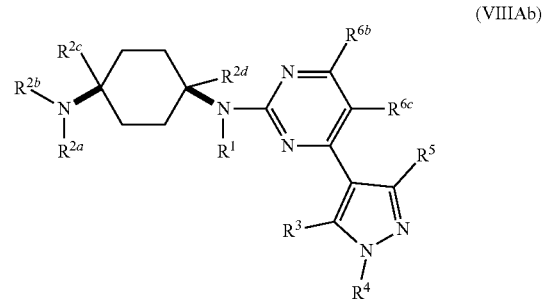

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6b}$, and $R^{6c}$ are each as defined herein.

In yet another embodiment, provided herein is a compound of Formula IXA:

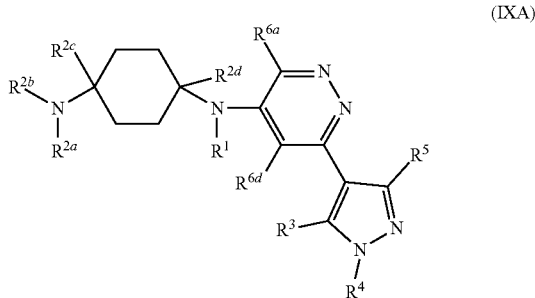

(IXA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, and $R^{6d}$ are each as defined herein.

In yet another embodiment, provided herein is a compound of Formula IXAa:

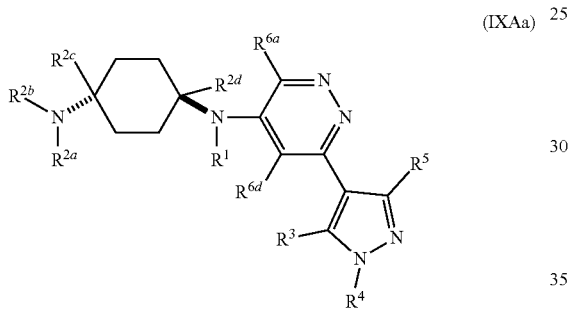

(IXAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, and $R^{6d}$ are each as defined herein.

In yet another embodiment, provided herein is a compound of Formula IXAb:

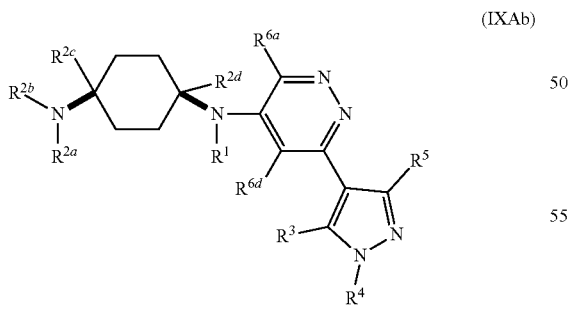

(IXAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, and $R^{6d}$ are each as defined herein.

In yet another embodiment, provided herein is a compound of Formula XA:

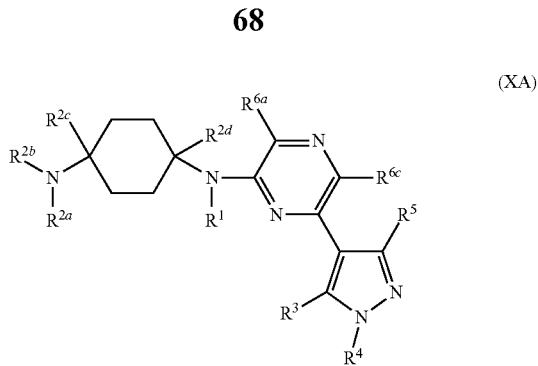

(XA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, and $R^{6c}$ are each as defined herein.

In yet another embodiment, provided herein is a compound of Formula XAa:

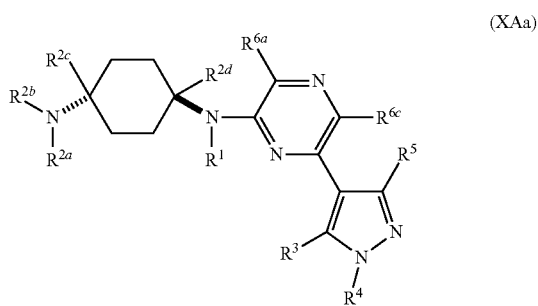

(XAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, and $R^{6c}$ are each as defined herein.

In yet another embodiment, provided herein is a compound of Formula XAb:

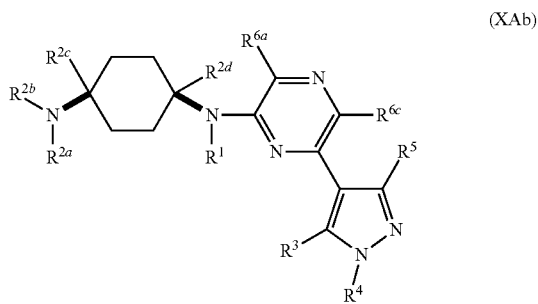

(XAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, and $R^{6c}$ are each as defined herein.

In yet another embodiment, provided herein is a compound of Formula XIA:

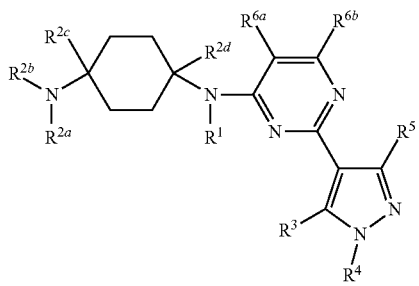

(XIA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, and $R^{6b}$ are each as defined herein.

In yet another embodiment, provided herein is a compound of Formula XIAa:

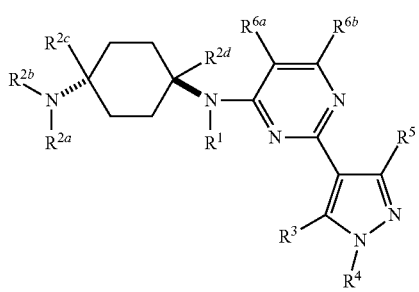

(XIAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, and $R^{6b}$ are each as defined herein.

In yet another embodiment, provided herein is a compound of Formula XIAb:

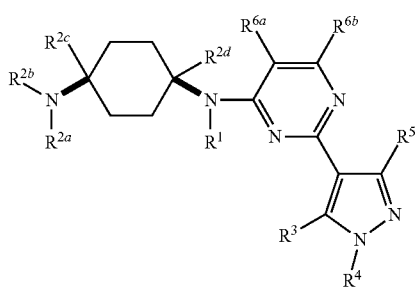

(XIAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, $R^{6a}$, and $R^{6b}$ are each as defined herein.

In yet another embodiment, provided herein is a compound of Formula XIIA:

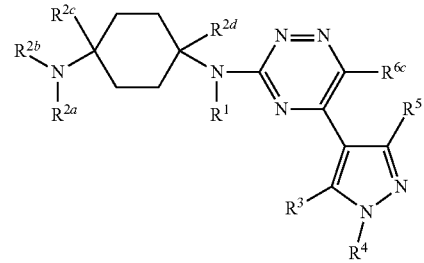

(XIIA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6c}$ are each as defined herein.

In yet another embodiment, provided herein is a compound of Formula XIIAa:

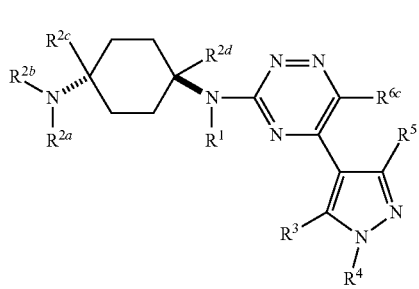

(XIIAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6c}$ are each as defined herein.

In yet another embodiment, provided herein is a compound of Formula XIIAb:

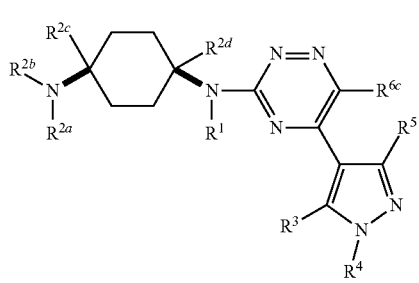

(XIIAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6c}$ are each as defined herein.

In yet another embodiment, provided herein is a compound of Formula XIIIA:

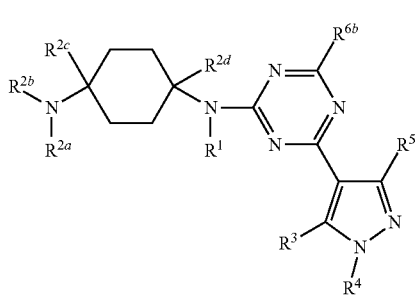
(XIIIA)

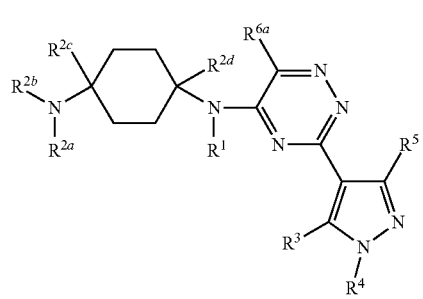
(XIVA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6b}$ are each as defined herein.

In yet another embodiment, provided herein is a compound of Formula XIIIAa:

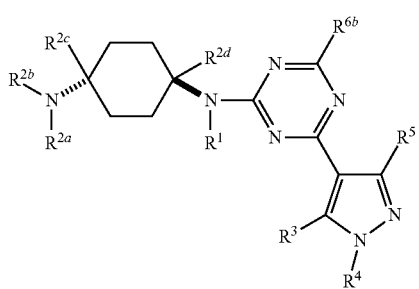
(XIIIAa)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6a}$ are each as defined herein.

In yet another embodiment, provided herein is a compound of Formula XIVAa:

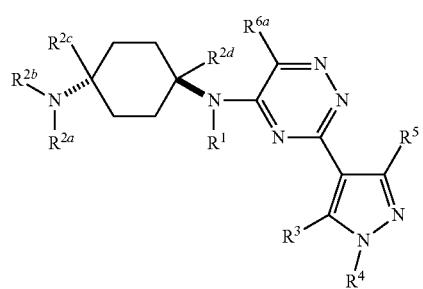
(XIVAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6b}$ are each as defined herein.

In yet another embodiment, provided herein is a compound of Formula XIIIAb:

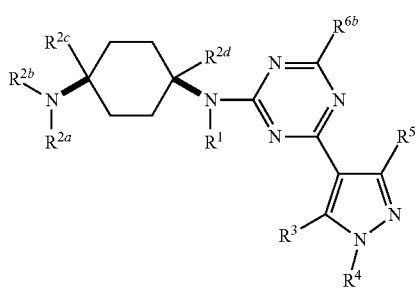
(XIIIAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6a}$ are each as defined herein.

In yet another embodiment, provided herein is a compound of Formula XIVAb:

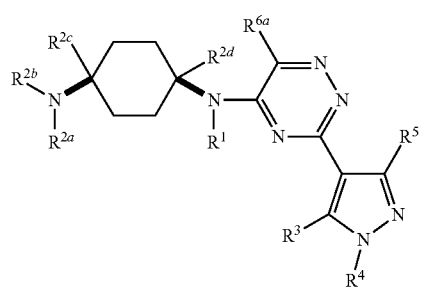
(XIVAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6b}$ are each as defined herein.

In yet another embodiment, provided herein is a compound of Formula XIVA:

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6a}$ are each as defined herein.

In yet another embodiment, provided herein is a compound of Formula XVA:

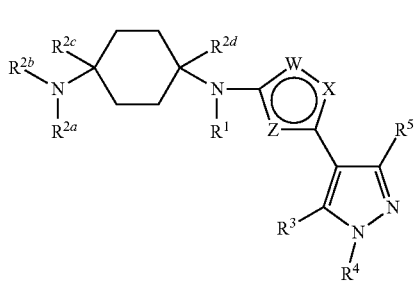 (XVA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, W, X, and Z are each as defined herein.

In yet another embodiment, provided herein is a compound of Formula XVAa:

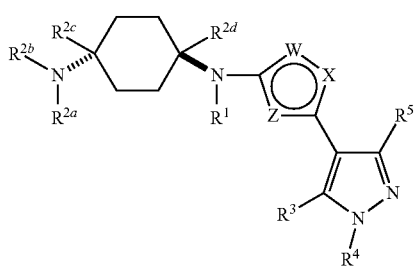 (XVAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, W, X, and Z are each as defined herein.

In yet another embodiment, provided herein is a compound of Formula XVAb:

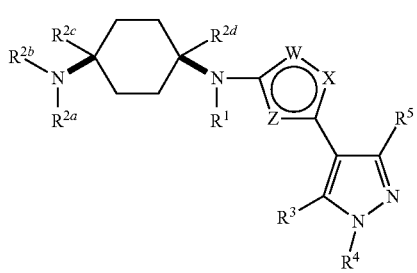 (XVAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, W, X, and Z are each as defined herein.

In yet another embodiment, provided herein is a compound of Formula XVIA:

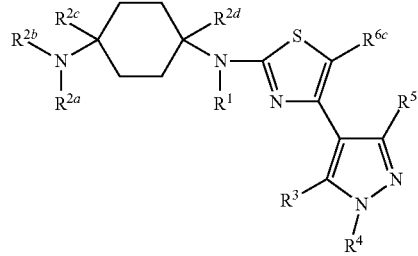 (XVIA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6c}$ are each as defined herein.

In yet another embodiment, provided herein is a compound of Formula XVIAa:

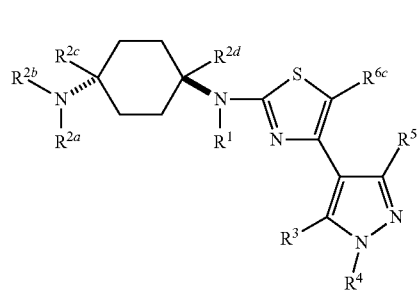 (XVIAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6c}$ are each as defined herein.

In yet another embodiment, provided herein is a compound of Formula XVIAb:

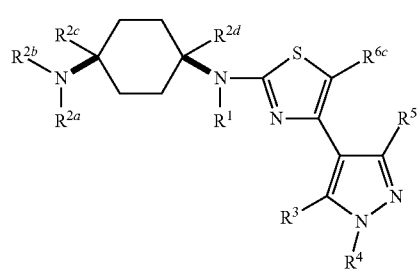 (XVIAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6c}$ are each as defined herein.

In yet another embodiment, provided herein is a compound of Formula XVIIA:

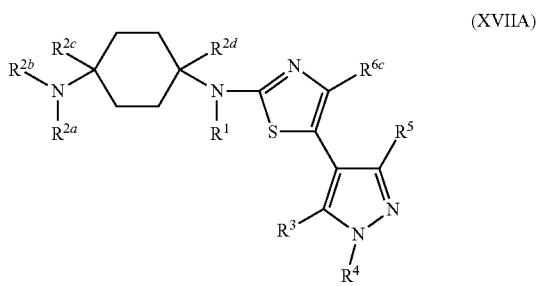

(XVIIA)

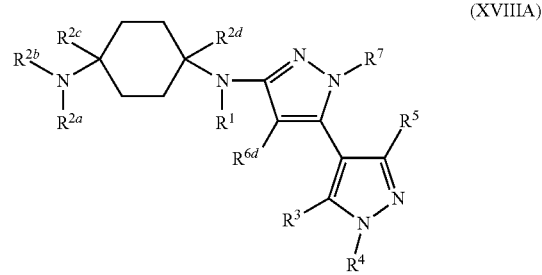

(XVIIIA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6c}$ are each as defined herein.

In yet another embodiment, provided herein is a compound of Formula XVIIAa:

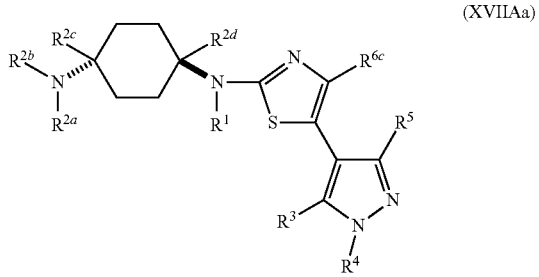

(XVIIAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6c}$ are each as defined herein.

In yet another embodiment, provided herein is a compound of Formula XVIIAb:

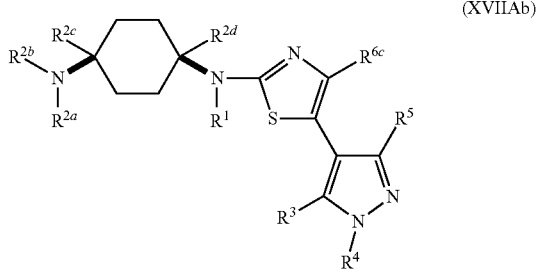

(XVIIAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^{2a}$, $R^{2b}$, $R^{2c}$, $R^{2d}$, and $R^{6c}$ are each as defined herein.

In yet another embodiment, provided herein is a compound of Formula XVIIIA:

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^7$, $R^{2a}$, $R^{2b}$, $R^{2c}$, $R^{2d}$, and $R^{6d}$ are each as defined herein.

In yet another embodiment, provided herein is a compound of Formula XVIIIAa:

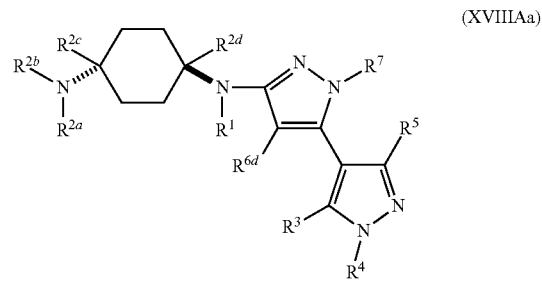

(XVIIIAa)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^7$, $R^{2a}$, $R^{2b}$, $R^{2c}$, $R^{2d}$, and $R^{6d}$ are each as defined herein.

In yet another embodiment, provided herein is a compound of Formula XVIIIAb:

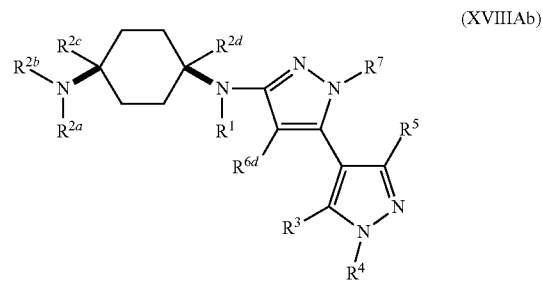

(XVIIIAb)

or a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^7$, $R^{2a}$, $R^{2b}$, $R^{2c}$, $R^{2d}$, and $R^{6d}$ are each as defined herein.

In one embodiment, in any one of Formulae IIA to XVIIIA, IIAa to XVIIIAa, and IIAb to XVIIIAb, $R^1$ and $R^5$ are each independently hydrogen or $C_{1-6}$ alkyl; $R^{2a}$, $R^{2b}$, $R^{2c}$, and $R^{2d}$ are (i) or (ii):

(i) $R^{2a}$ and $R^{2b}$ are each independently hydrogen, $C_{1-6}$ alkyl, $C_{2-6}$ alkynyl, $C_{6-14}$ aryl, $C_{6-14}$ aralkyl, or —C(O)

$R^{1a}$; or $R^{2a}$ and $R^{2b}$ together with the N atom to which they are attached form heteroaryl or heterocyclyl; and $R^{2c}$ and $R^{2d}$ are each independently hydrogen or $C_{1-6}$ alkyl; or $R^{2c}$ and $R^{2d}$ in any one of Formulae IIA to XVIIIA and IIAb to XVIIIAb are linked together to form —O—, $C_{1-6}$ alkylene, or $C_{1-6}$ heteroalkylene; or (ii) $R^{2a}$ and $R^{2c}$ together with the C and N atoms to which they are attached form heteroaryl or heterocyclyl; and $R^{2b}$ and $R^{2d}$ are each hydrogen;

$R^3$ is $C_{1-6}$ alkyl;

$R^4$ is $C_{1-6}$ alkyl, $C_{3-12}$ cycloalkyl, or heterocyclyl;

$R^{6a}$, $R^{6b}$, $R^{6c}$, and $R^{6d}$, if present, are each independently hydrogen, halo, $C_{1-6}$ alkyl, —$OR^{1a}$, or —$NR^{1b}R^{1c}$;

$R^7$, if present, is hydrogen or $C_{1-6}$ alkyl; and each $R^{1a}$, $R^{1b}$, and $R^{1c}$ is as defined herein;

wherein each alkyl, alkylene, heteroalkylene, alkynyl, cycloalkyl, aryl, aralkyl, heteroaryl, and heterocyclyl is optionally substituted with one or more, in one embodiment, one, two, three, or four, substituents Q.

In another embodiment, in any one of Formulae IIA to XVIIIA, IIAa to XVIIIAa, and IIAb to XVIIIAb, $R^1$ and $R^5$ are each independently hydrogen or $C_{1-6}$ alkyl;

$R^{2a}$, $R^{2b}$, $R^{2c}$, and $R^{2d}$ are (i) or (ii):

(i) $R^{2a}$ and $R^{2b}$ are each independently hydrogen, $C_{1-6}$ alkyl, $C_{2-6}$ alkynyl, 5- or 6-membered heteroaryl-$C_{1-6}$ alkyl, $C_{6-14}$ aryl, $C_{6-14}$ aralkyl, —C(O)—$C_{1-6}$ alkyl, —C(O)—$C_{2-6}$ alkyl, —C(O)—$C_{2-6}$ alkynyl, or —C(O)-5-membered heteroaryl; or $R^{2a}$ and $R^{2b}$ together with the N atom to which they are attached form 5-membered heteroaryl or 4- to 6-membered heterocyclyl; and $R^{2c}$ is hydrogen or $C_{1-6}$ alkyl; and $R^{2d}$ is hydrogen; or $R^{2c}$ and $R^{2d}$ in any one of Formulae IIA to XVIIIA and IIAb to XVIIIAb are linked together to form $C_{2-6}$ alkylene; or (ii) $R^{2a}$ and $R^{2c}$ together with the C and N atoms to which they are attached form 5-membered heteroaryl or 5-membered heterocyclyl; and $R^{2b}$ and $R^{2d}$ are each hydrogen;

$R^3$ is $C_{1-6}$ alkyl or $C_{3-12}$ cycloalkyl-$C_{1-6}$ alkyl;

$R^4$ is $C_{1-6}$ alkyl, $C_{3-12}$ cycloalkyl, or 4- to 6-membered heterocyclyl;

$R^{6a}$, $R^{6b}$, $R^{6c}$, and $R^{6d}$, if present, are each independently hydrogen, fluoro, chloro, $C_{1-6}$ alkyl, hydroxyl, or amino; and $R^7$, if present, is hydrogen or methyl;

wherein each alkyl, alkylene, alkynyl, cycloalkyl, aryl, aralkyl, heteroaryl, and heterocyclyl is optionally substituted with one or more, in one embodiment, one, two, three, or four, substituents Q.

In yet another embodiment, in any one of Formulae IIA to XVIIIA, IIAa to XVIIIAa, and IIAb to XVIIIAb, $R^1$ and $R^5$ are each hydrogen;

$R^{2a}$, $R^{2b}$, $R^{2c}$, and $R^{2d}$ are (i) or (ii):

(i) $R^{2a}$ is hydrogen, methyl, 2,2,2-trifluoroethyl, 2-methoxyethyl, pent-4-ynyl, phenyl, benzyl, (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, (pyridin-3-yl)methyl, pentanoyl, 2-methoxyacetyl, but-3-ynylcarbonyl, or (pyrazol-4-yl)carbonyl; and $R^{2b}$ is hydrogen, methyl, 2,2,2-trifluoroethyl, or (pyrazol-4-yl)methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; and $R^{2c}$ is hydrogen, methyl, or hydroxymethyl; and $R^{2d}$ is hydrogen; or $R^{2c}$ and $R^{2d}$ in any one of Formulae IIA to XVIIIA and IIAb to XVIIIAb are linked together to form methylene or 1,2-ethylene; or (ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and $R^{2b}$ and $R^{2d}$ are each hydrogen;

$R^3$ is t-butylmethyl, cyclopropylmethyl, 1-methylcyclopropylmethyl, 1-hydroxy(cyclopropylmethyl), cyclobutylmethyl, or cyclopentylmethyl;

$R^4$ is methyl, isopropyl, cyclopentyl, oxetan-3-yl, tetrahydrofur-3-yl, tetrahydropyran-4-yl, or tetrahydropyran-3-yl;

$R^{6a}$, $R^{6b}$, and $R^{6d}$, if present, are each independently hydrogen;

$R^{6c}$, if present, is hydrogen, fluoro, chloro, methyl, or trifluoromethyl; and $R^7$, if present, is hydrogen or methyl.

In still another embodiment, in any one of Formulae IIA to XVIIIA, IIAa to XVIIIAa, and IIAb to XVIIIAb, $R^1$ and $R^5$ are each hydrogen;

$R^{2a}$, $R^{2b}$, $R^{2c}$, and $R^{2d}$ are (i) or (ii):

(i) $R^{2a}$ is hydrogen, methyl, 2,2,2-trifluoroethyl, 2-methoxyethyl, pent-4-ynyl, pentanoyl, 2-methoxyacetyl, or but-3-ynylcarbonyl; and $R^{2b}$ is hydrogen or methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl; and $R^{2c}$ and $R^{2d}$ are each hydrogen; or $R^{2c}$ and $R^{2d}$ in any one of Formulae IIA to XVIIIA and IIAb to XVIIIAb are linked together to form methylene or eth-1,2-ylene; or (ii) $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one; and $R^{2b}$ and $R^{2d}$ are each hydrogen;

$R^3$ is cyclopropylmethyl;

$R^4$ is methyl;

$R^{6a}$, $R^{6b}$, and $R^{6d}$, if present, are each independently hydrogen;

$R^{6c}$, if present, is hydrogen, fluoro, or chloro; and $R^7$, if present, is hydrogen or methyl.

In one embodiment, in any one of Formulae IIA to XVIIIA and IIAb to XVIIIAb, $R^1$ and $R^5$ are each independently hydrogen or $C_{1-6}$ alkyl;

$R^{2a}$ and $R^{2b}$ are each independently hydrogen, $C_{1-6}$ alkyl, $C_{3-6}$ alkynyl, $C_{6-14}$ aryl, $C_{6-14}$ aralkyl, or —C(O)$R^{1a}$; or $R^{2a}$ and $R^{2b}$ together with the N atom to which they are attached form heteroaryl or heterocyclyl;

$R^{2c}$ and $R^{2d}$ are linked together to form —O—, $C_{1-6}$ alkylene, or $C_{1-6}$ heteroalkylene;

$R^3$ is $C_{1-6}$ alkyl;

$R^4$ is $C_{1-6}$ alkyl, $C_{3-12}$ cycloalkyl, or heterocyclyl;

$R^{6a}$, $R^{6b}$, $R^{6c}$, and $R^{6d}$, if present, are each independently hydrogen, halo, $C_{1-6}$ alkyl, —$OR^{1a}$, or —$NR^{1b}R^{1c}$;

$R^7$, if present, is hydrogen or $C_{1-6}$ alkyl; and each $R^{1a}$, $R^{1b}$, and $R^{1c}$ is as defined herein;

wherein each alkyl, alkylene, heteroalkylene, alkynyl, cycloalkyl, aryl, aralkyl, heteroaryl, and heterocyclyl is optionally substituted with one or more, in one embodiment, one, two, three, or four, substituents Q.

In another embodiment, in any one of Formulae IIA to XVIIIA and IIAb to XVIIIAb, $R^1$ and $R^5$ are each independently hydrogen or $C_{1-6}$ alkyl;
$R^{2a}$ and $R^{2b}$ are each independently hydrogen, $C_{1-6}$ alkyl, $C_{2-6}$ alkynyl, 5- or 6-membered heteroaryl-$C_{1-6}$ alkyl, $C_{6-14}$ aryl, $C_{6-14}$ aralkyl, —C(O)—$C_{1-6}$ alkyl, —C(O)—$C_{2-6}$ alkynyl, or —C(O)-5-membered heteroaryl; or $R^{2a}$ and $R^{2b}$ together with the N atom to which they are attached form 5-membered heteroaryl or 4- to 6-membered heterocyclyl;
$R^{2c}$ and $R^{2d}$ are linked together to form $C_{2-6}$ alkylene;
$R^3$ is $C_{1-6}$ alkyl or $C_{3-12}$ cycloalkyl-$C_{1-6}$ alkyl;
$R^4$ is $C_{1-6}$ alkyl, $C_{3-12}$ cycloalkyl, or 4- to 6-membered heterocyclyl;
$R^{6a}$, $R^{6b}$, $R^{6c}$, and $R^{6d}$, if present, are each independently hydrogen, fluoro, chloro, $C_{1-6}$ alkyl, hydroxyl, or amino; and
$R^7$, if present, is hydrogen or methyl;
wherein each alkyl, alkylene, alkynyl, cycloalkyl, aryl, aralkyl, heteroaryl, and heterocyclyl is optionally substituted with one or more, in one embodiment, one, two, three, or four, substituents Q.

In yet another embodiment, in any one of Formulae IIA to XVIIIA and IIAb to XVIIIAb, $R^1$ and $R^5$ are each independently hydrogen or methyl;
$R^{2a}$ is hydrogen, methyl, trifluoroethyl, methoxyethyl, pentynyl, phenyl, benzyl, (pyrazolyl)methyl, (methylpyrazolyl)methyl, (pyrazolyl)ethyl, (pyridinyl)methyl, pentanoyl, methoxyacetyl, butynylcarbonyl, or (pyrazolyl)carbonyl; and $R^{2b}$ is hydrogen, methyl, trifluoroethyl, or (pyrazolyl)methyl; or $R^{2a}$ and $R^{2b}$ together with the N atom to which they are attached form azetidinyl, pyrrolidinyl, piperidinyl, morpholinyl, pyrazolyl, methylpyrazolyl, or imidazolyl;
$R^{2c}$ and $R^{2d}$ are linked together to form methylene or ethylene;
$R^3$ is butylmethyl, cyclopropylmethyl, methylcyclopropylmethyl, hydroxy(cyclopropylmethyl), cyclobutylmethyl, or cyclopentylmethyl;
$R^4$ is methyl, isopropyl, cyclopentyl, oxetanyl, tetrahydrofuryl, or tetrahydropyranyl;
$R^{6a}$, $R^{6b}$, and $R^{6d}$, if present, are each independently hydrogen;
$R^{6c}$, if present, is hydrogen, fluoro, chloro, methyl, or trifluoromethyl; and
$R^7$, if present, is hydrogen or methyl.

In yet another embodiment, in any one of Formulae IIA to XVIIIA and IIAb to XVIIIAb, $R^1$ and $R^5$ are each hydrogen;
$R^{2a}$ is hydrogen, methyl, trifluoroethyl, methoxyethyl, pentynyl, phenyl, benzyl, (pyrazolyl)methyl, (1-methylpyrazolyl)methyl, (3-methylpyrazolyl)methyl, (pyrazol-yl)ethyl, (pyridinyl)methyl, pentanoyl, methoxyacetyl, butynylcarbonyl, or (pyrazolyl)carbonyl; and $R^{2b}$ is hydrogen, methyl, trifluoroethyl, or (pyrazolyl)methyl; or $R^{2a}$ and $R^{2b}$ together with the N atom to which they are attached form azetidinyl, pyrrolidinyl, piperidineyl, morpholinyl, pyrazolyl, methylpyrazolyl, or imidazolyl;
$R^{2c}$ and $R^{2d}$ are linked together to form methylene or ethylene;
$R^3$ is t-butylmethyl, cyclopropylmethyl, methylcyclopropylmethyl, hydroxy(cyclopropylmethyl), cyclobutylmethyl, or cyclopentylmethyl; and $R^4$ is methyl, isopropyl, cyclopentyl, oxetanyl, tetrahydrofuryl, tetrahydropyranyl, or tetrahydropyranyl.

In yet another embodiment, in any one of Formulae IIA to XVIIIA and IIAb to XVIIIAb, W and Z are each independently =C(H)— or =N—;
X is =C(H)—, =C(OH)—, or =C(NH$_2$)—;
Y is =C(H)—, =C(F)—, =C(Cl)—, =C(CH$_3$)—, =C(CF$_3$)—, or =N—;
$R^1$ and $R^5$ are each hydrogen;
$R^{2a}$ is hydrogen, methyl, 2,2,2-trifluoroethyl, 2-methoxyethyl, pent-4-ynyl, phenyl, benzyl, (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, (pyridin-3-yl)methyl, pentanoyl, 2-methoxyacetyl, but-3-ynylcarbonyl, or (pyrazol-4-yl)carbonyl; and $R^{2b}$ is hydrogen, methyl, 2,2,2-trifluoroethyl, or (pyrazol-4-yl)methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl;
$R^{2c}$ and $R^{2d}$ are linked together to form methylene or 1,2-ethylene;
$R^3$ is t-butylmethyl, cyclopropylmethyl, 1-methylcyclopropylmethyl, 1-hydroxy(cyclopropylmethyl), cyclobutylmethyl, or cyclopentylmethyl;
$R^4$ is methyl, isopropyl, cyclopentyl, oxetan-3-yl, tetrahydrofur-3-yl, tetrahydropyran-4-yl, or tetrahydropyran-3-yl;
$R^{6a}$, $R^{6b}$, and $R^{6d}$, if present, are each independently hydrogen;
$R^{6c}$, if present, is hydrogen, fluoro, chloro, methyl, or trifluoromethyl; and
$R^7$, if present, is hydrogen or methyl.

In still another embodiment, in any one of Formulae IIA to XVIIIA and IIAb to XVIIIAb, $R^1$ and $R^5$ are each hydrogen;
$R^{2a}$ is hydrogen, methyl, 2,2,2-trifluoroethyl, 2-methoxyethyl, pent-4-ynyl, pentanoyl, 2-methoxyacetyl, or but-3-ynylcarbonyl; and $R^{2b}$ is hydrogen or methyl; or $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl;
$R^{2c}$ and $R^{2d}$ are linked together to form methylene or eth-1,2-ylene;
$R^3$ is cyclopropylmethyl;
$R^4$ is methyl;
$R^{6a}$, $R^{6b}$, and $R^{6d}$, if present, are each independently hydrogen;
$R^{6c}$, if present, is hydrogen, fluoro, or chloro; and
$R^7$, if present, is hydrogen or methyl.

In one embodiment, provided herein is a compound of:

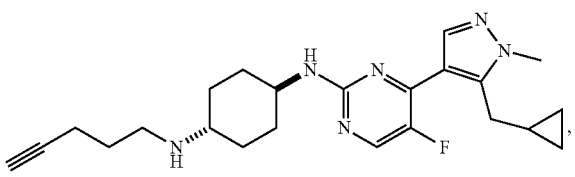

AA1

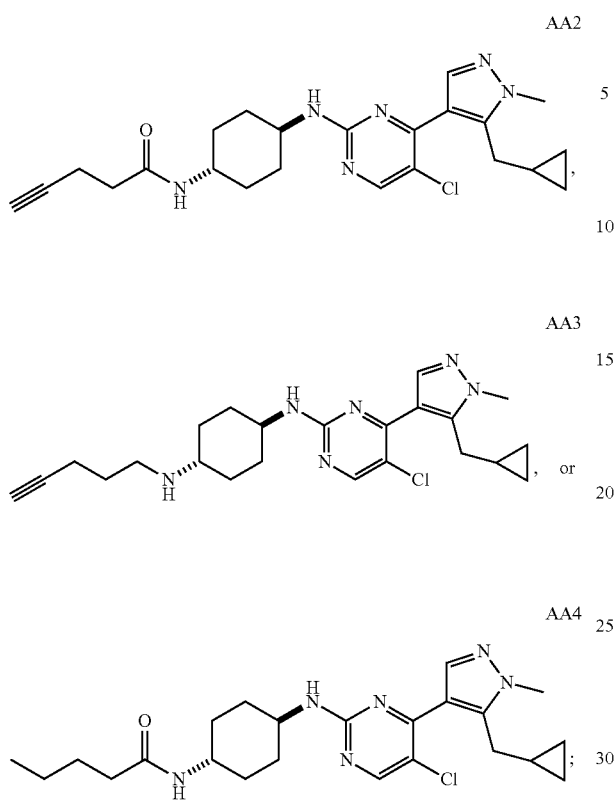

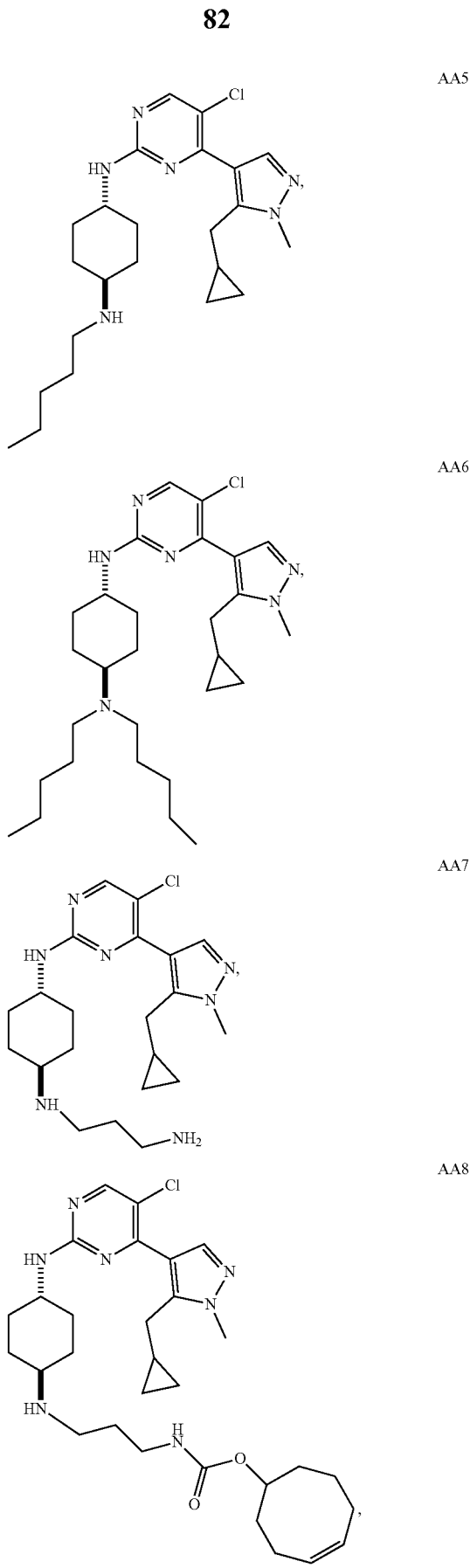

or a tautomer, a mixture of two or more tautomers, or an isotopic variant thereof; or a pharmaceutically acceptable salt, solvate, hydrate, or a prodrug thereof.

In another embodiment, provided herein is a compound of:

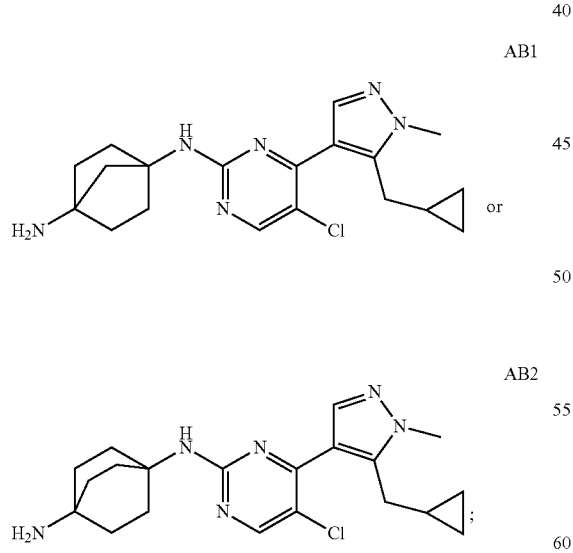

or a tautomer, a mixture of two or more tautomers, or an isotopic variant thereof; or a pharmaceutically acceptable salt, solvate, hydrate, or a prodrug thereof.

In yet another embodiment, provided herein is a compound of:

AA9

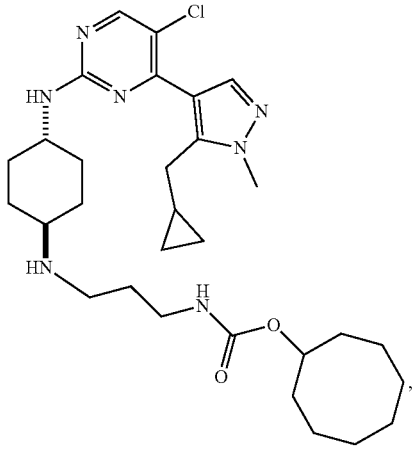

AA10

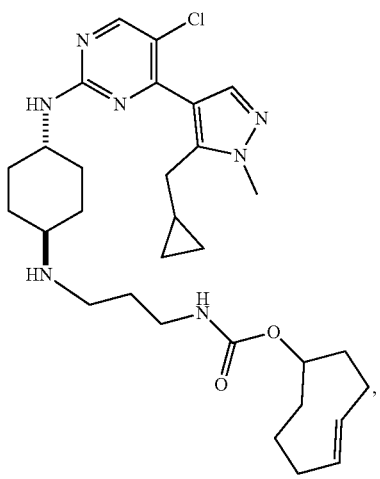

AA11

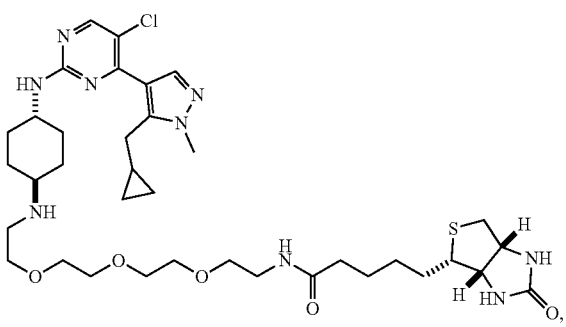

AA12

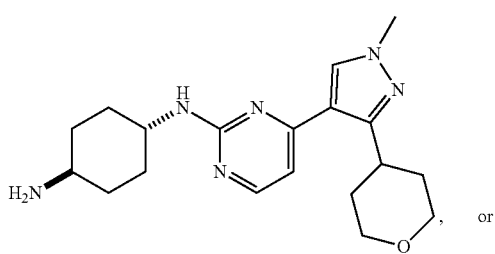 or

AA13

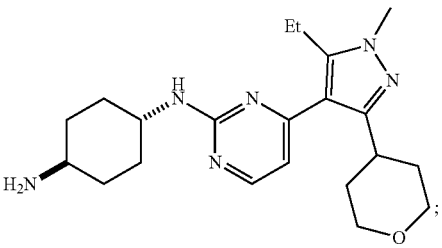

or a tautomer, a mixture of two or more tautomers, or an isotopic variant thereof; or a pharmaceutically acceptable salt, solvate, hydrate, or a prodrug thereof.

The groups, $R^1$, $R^2$, $R^3$, $R^4$, $R^5$, $R^6$, $R^7$, $R^{2a}$, $R^{2b}$, $R^{2c}$, $R^{2d}$, $R^{6a}$, $R^{6b}$, $R^{6a}$, $R^{6d}$, U, V, W, X, Y, and Z, in formulae described herein, including Formulae I to XIX, Formulae IIa to XIXa, Formulae IA to XVIIIA, Formulae IAa to XVII-IAa, and Formulae IAb to XVIIIAb, are further defined in the embodiments described herein. All combinations of the embodiments provided herein for such groups are within the scope of this disclosure.

In certain embodiments, $R^1$ is hydrogen. In certain embodiments, $R^1$ is deuterium. In certain embodiments, $R^1$ is $C_{1-6}$ alkyl, optionally substituted with one or more substituents Q. In certain embodiments, $R^1$ is methyl, optionally substituted with one or more substituents Q. In certain embodiments, $R^1$ is $C_{2-6}$ alkenyl, optionally substituted with one or more substituents Q. In certain embodiments, $R^1$ is $C_{2-6}$ alkynyl, optionally substituted with one or more substituents Q. In certain embodiments, $R^1$ is $C_{3-12}$ cycloalkyl, optionally substituted with one or more substituents Q. In certain embodiments, $R^1$ is $C_{6-14}$ aryl, optionally substituted with one or more substituents Q. In certain embodiments, $R^1$ is $C_{7-15}$ aralkyl, optionally substituted with one or more substituents Q. In certain embodiments, $R^1$ is heteroaryl, optionally substituted with one or more substituents Q. In certain embodiments, $R^1$ is heterocyclyl, optionally substituted with one or more substituents Q.

In certain embodiments, $R^1$ is —C(O)$R^{1a}$, wherein $R^{1a}$ is as defined herein. In certain embodiments, $R^1$ is —C(O)O$R^{1a}$, wherein $R^{1a}$ is as defined herein. In certain embodiments, $R^1$ is —C(O)NR$^{1b}$R$^{1c}$, wherein $R^{1b}$ and $R^{1c}$ are each as defined herein. In certain embodiments, $R^1$ is —C(O)SR$^{1a}$, wherein $R^{1a}$ is as defined herein. In certain embodiments, $R^1$ is —C(NR$^{1a}$)NR$^{1b}$R$^{1c}$, wherein $R^{1a}$, $R^{1b}$, and $R^{1c}$ are each as defined herein. In certain embodiments, $R^1$ is —C(S)$R^{1a}$, wherein $R^{1a}$ is as defined herein. In certain embodiments, $R^1$ is —C(S)OR$^{1a}$, wherein $R^{1a}$ is as defined herein. In certain embodiments, $R^1$ is —C(S)NR$^{1b}$R$^{1c}$, wherein $R^{1b}$ and $R^{1c}$ are each as defined herein. In certain embodiments, $R^1$ is —OR$^{1a}$, wherein $R^{1a}$ is as defined herein. In certain embodiments, $R^1$ is —OC(O)R$^{1a}$, wherein $R^{1a}$ is as defined herein. In certain embodiments, $R^1$ is —OC(O)OR$^{1a}$, wherein $R^{1a}$ is as defined herein. In certain embodiments, $R^1$ is —OC(O)NR$^{1b}$R$^{1c}$, wherein $R^{1b}$ and $R^{1c}$ are each as defined herein. In certain embodiments, $R^1$ is —OC(O)SR$^{1a}$, wherein $R^{1a}$ is as defined herein. In certain embodiments, $R^1$ is —OC(=NR$^{1a}$)NR$^{1b}$R$^{1c}$, wherein $R^{1a}$, $R^{1b}$, and $R^{1c}$ are each as defined herein. In certain embodiments, $R^1$ is —OC(S)R$^{1a}$, wherein $R^{1a}$ is as defined herein. In certain embodiments, $R^1$ is —OC(S)OR$^{1a}$, wherein $R^{1a}$ is as defined herein. In certain embodiments, $R^1$ is —OC(S)NR$^{1b}$R$^{1c}$, wherein $R^{1b}$ and $R^{1c}$ are each as defined herein. In certain embodiments, $R^1$ is —OS(O)R$^{1a}$, wherein $R^{1a}$ is as defined herein. In certain embodiments, $R^1$ is $-OS(O)_2R^{1a}$, wherein $R^{1a}$ is as defined herein. In certain embodiments, $R^1$ is $-OS(O)NR^{1b}R^{1c}$, wherein $R^{1b}$ and $R^{1c}$ are each as defined herein. In certain embodiments, $R^1$ is $-OS(O)_2NR^{1b}R^{1c}$, wherein $R^{1b}$ and $R^{1c}$ are each as defined herein. In certain embodiments, $R^1$ is $-NR^{1b}R^{1c}$, wherein $R^{1b}$ and $R^{1c}$ are each as defined herein. In certain embodiments, $R^1$ is $-NR^{1a}C(O)R^{1d}$, wherein $R^{1a}$ and $R^{1d}$ are each as defined herein. In certain embodiments, $R^1$ is $-NR^{1a}C(O)OR^{1d}$, wherein $R^{1a}$ and $R^{1d}$ are each as defined herein. In certain embodiments, $R^1$ is $-NR^{1a}C(O)NR^{1b}R^{1c}$, wherein $R^{1a}$, $R^{1b}$, and $R^{1c}$ are each as defined herein. In certain embodiments, $R^1$ is $-NR^{1a}C(O)SR^{1d}$, wherein $R^{1a}$ and $R^{1d}$ are each as defined herein. In certain embodiments, $R^1$ is $-NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^1$ is $-NR^{1a}C(S)R^{1d}$, wherein $R^{1a}$ and $R^{1d}$ are each as defined herein. In certain embodiments, $R^1$ is $-NR^{1a}C(S)OR^{1d}$, wherein $R^{1a}$ and $R^{1d}$ are each as defined herein. In certain embodiments, $R^1$ is $-NR^{1a}C(S)NR^{1b}R^{1c}$, wherein $R^{1a}$, $R^{1b}$, and $R^{1c}$ are each as defined herein. In certain embodiments, $R^1$ is $-NR^{1a}S(O)R^{1d}$, wherein $R^{1a}$ and $R^{1d}$ are each as defined herein. In certain embodiments, $R^1$ is $-NR^{1a}S(O)_2R^{1d}$, wherein $R^{1a}$ and $R^{1d}$ are each as defined herein. In certain embodiments, $R^1$ is $-NR^{1a}S(O)NR^{1b}R^{1c}$, wherein $R^{1a}$, $R^{1b}$, and $R^{1c}$ are each as defined herein. In certain embodiments, $R^1$ is $-NR^{1a}S(O)_2NR^{1b}R^{1c}$, wherein $R^{1a}$, $R^{1b}$, and $R^{1c}$ are each as defined herein. In certain embodiments, $R^1$ is $-S(O)R^{1a}$, wherein $R^{1a}$ is as defined herein. In certain embodiments, $R^1$ is $-S(O)_2R^{1a}$, wherein $R^{1a}$ is as defined herein. In certain embodiments, $R^1$ is $-S(O)NR^{1b}R^{1c}$, wherein $R^{1b}$ and $R^{1c}$ are each as defined herein. In certain embodiments, $R^1$ is $-S(O)_2NR^{1b}R^{1c}$, wherein $R^{1b}$ and $R^{1c}$ are each as defined herein.

In certain embodiments, $R^2$ is hydrogen. In certain embodiments, $R^2$ is deuterium. In certain embodiments, $R^2$ is $C_{1-6}$ alkyl, optionally substituted with one or more substituents Q. In certain embodiments, $R^2$ is methyl, optionally substituted with one or more substituents Q. In certain embodiments, $R^2$ is $C_{2-6}$ alkenyl, optionally substituted with one or more substituents Q. In certain embodiments, $R^2$ is $C_{2-6}$ alkynyl, optionally substituted with one or more substituents Q. In certain embodiments, $R^2$ is $C_{3-12}$ cycloalkyl, optionally substituted with one or more substituents Q. In certain embodiments, $R^2$ is $C_{3-12}$ cycloalkyl, optionally substituted with one or more substituents Q. In certain embodiments, $R^2$ is monocyclic $C_{3-12}$ cycloalkyl, optionally substituted with one or more substituents Q. In certain embodiments, $R^2$ is cyclobutyl, cyclopentyl, cyclohexyl, or cycloheptyl, each optionally substituted with one or more substituents Q. In certain embodiments, $R^2$ is cyclopentyl or cyclohexyl, each optionally substituted with one or more substituents Q. In certain embodiments, $R^2$ is cyclohexyl, optionally substituted with one or more substituents Q. In certain embodiments, $R^2$ is bicyclic $C_{3-12}$ cycloalkyl, optionally substituted with one or more substituents Q. In certain embodiments, $R^2$ is bicyclic $C_{3-12}$ cycloalkyl, optionally substituted with one or more substituents Q. In certain embodiments, $R^2$ is bridged $C_{3-12}$ cycloalkyl, optionally substituted with one or more substituents Q. In certain embodiments, $R^2$ is bicyclo[2.2.1]heptyl or bicyclo[2.2.2]octyl, each optionally substituted with one or more substituents Q. In certain embodiments, $R^2$ is cyclohexyl, bicyclo[2.2.1]heptyl, or bicyclo[2.2.2]octyl, each of which is substituted with one or two substituents, wherein each substituent is independently $C_{1-6}$ alkyl or $-NR^{1b}R^{1c}$, where the alkyl is optionally substituted with one or more substituents Q as defined herein and $R^{1b}$ and $R^{1c}$ are each as defined herein. In certain embodiments, $R^2$ is $C_{6-14}$ aryl, optionally substituted with one or more substituents Q. In certain embodiments, $R^2$ is $C_{7-15}$ aralkyl, optionally substituted with one or more substituents Q. In certain embodiments, $R^2$ is heteroaryl, optionally substituted with one or more substituents Q. In certain embodiments, $R^2$ is heterocyclyl, optionally substituted with one or more substituents Q. In certain embodiments, $R^2$ is bicyclic heterocyclyl, optionally substituted with one or more substituents Q. In certain embodiments, $R^2$ is spiro heterocyclyl, optionally substituted with one or more substituents Q. In certain embodiments, $R^2$ is 4- to 6-membered heterocyclyl, optionally substituted with one or more substituents Q.

In certain embodiments, $R^2$ is $-C(O)R^{1a}$, wherein $R^{1a}$ is as defined herein. In certain embodiments, $R^2$ is $-C(O)OR^{1a}$, wherein $R^{1a}$ is as defined herein. In certain embodiments, $R^2$ is $-C(O)NR^{1b}R^{1c}$, wherein $R^{1b}$ and $R^{1c}$ are each as defined herein. In certain embodiments, $R^2$ is $-C(O)SR^{1a}$, wherein $R^{1a}$ is as defined herein. In certain embodiments, $R^2$ is $-C(NR^{1a})NR^{1b}R^{1c}$, wherein $R^{1a}$, $R^{1b}$, and $R^{1c}$ are each as defined herein. In certain embodiments, $R^2$ is $-C(S)R^{1a}$, wherein $R^{1a}$ is as defined herein. In certain embodiments, $R^2$ is $-C(S)OR^{1a}$, wherein $R^{1a}$ is as defined herein. In certain embodiments, $R^2$ is $-C(S)NR^{1b}R^{1c}$, wherein $R^{1b}$ and $R^{1c}$ are each as defined herein. In certain embodiments, $R^2$ is $-OR^{1a}$, wherein $R^{1a}$ is as defined herein. In certain embodiments, $R^2$ is $-OC(O)R^{1a}$, wherein $R^{1a}$ is as defined herein. In certain embodiments, $R^2$ is $-OC(O)OR^{1a}$, wherein $R^{1a}$ is as defined herein. In certain embodiments, $R^2$ is $-OC(O)NR^{1b}R^{1c}$, wherein $R^{1b}$ and $R^{1c}$ are each as defined herein. In certain embodiments, $R^2$ is $-OC(O)SR^{1a}$, wherein $R^{1a}$ is as defined herein. In certain embodiments, $R^2$ is $-OC(=NR^{1a})NR^{1b}R^{1c}$, wherein $R^{1a}$, $R^{1b}$, and $R^{1c}$ are each as defined herein. In certain embodiments, $R^2$ is $-OC(S)R^{1a}$, wherein $R^{1a}$ is as defined herein. In certain embodiments, $R^2$ is $-OC(S)OR^{1a}$, wherein $R^{1a}$ is as defined herein. In certain embodiments, $R^2$ is $-OC(S)NR^{1b}R^{1c}$, wherein $R^{1b}$ and $R^{1c}$ are each as defined herein. In certain embodiments, $R^2$ is $-OS(O)R^{1a}$, wherein $R^{1a}$ is as defined herein. In certain embodiments, $R^2$ is $-OS(O)_2R^{1a}$, wherein $R^{1a}$ is as defined herein. In certain embodiments, $R^2$ is $-OS(O)NR^{1b}R^{1c}$, wherein $R^{1b}$ and $R^{1c}$ are each as defined herein. In certain embodiments, $R^2$ is $-OS(O)_2NR^{1b}R^{1c}$, wherein $R^{1b}$ and $R^{1c}$ are each as defined herein. In certain embodiments, $R^2$ is $-NR^{1b}R^{1c}$, wherein $R^{1b}$ and $R^{1c}$ are each as defined herein. In certain embodiments, $R^2$ is $-NR^{1a}C(O)R^{1d}$, wherein $R^{1a}$ and $R^{1d}$ are each as defined herein. In certain embodiments, $R^2$ is $-NR^{1a}C(O)OR^{1d}$, wherein $R^{1a}$ and $R^{1d}$ are each as defined herein. In certain embodiments, $R^2$ is $-NR^{1a}C(O)NR^{1b}R^{1c}$, wherein $R^{1a}$, $R^{1b}$, and $R^{1c}$ are each as defined herein. In certain embodiments, $R^2$ is $-NR^{1a}C(O)SR^{1d}$, wherein $R^{1a}$ and $R^{1d}$ are each as defined herein. In certain embodiments, $R^2$ is $-NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^2$ is $-NR^{1a}C(S)R^{1d}$, wherein $R^{1a}$ and $R^{1d}$ are each as defined herein. In certain embodiments, $R^2$ is $-NR^{1a}C(S)OR^{1d}$, wherein $R^{1a}$ and $R^{1d}$ are each as defined herein. In certain embodiments, $R^2$ is $-NR^{1a}C(S)NR^{1b}R^{1c}$, wherein $R^{1a}$, $R^{1b}$, and $R^{1c}$ are each as defined herein. In certain embodiments, $R^2$ is $-NR^{1a}S(O)R^{1d}$, wherein $R^{1a}$ and $R^{1d}$ are each as defined herein. In certain embodiments, $R^2$ is $-NR^{1a}S(O)_2R^{1d}$, wherein $R^{1a}$ and $R^{1d}$ are each as defined herein. In certain embodiments, $R^2$ is $-NR^{1a}S(O)NR^{1b}R^{1c}$, wherein $R^{1a}$, $R^{1b}$, and $R^{1c}$ are each as defined herein. In certain embodiments, $R^2$ is $-NR^{1a}S(O)_2NR^{1b}R^{1c}$, wherein $R^{1a}$, $R^{1b}$, and $R^{1c}$ are each as defined herein. In certain embodiments, $R^2$ is —S(O)$R^{1a}$, wherein $R^{1a}$ is as defined herein. In certain embodiments, $R^2$ is —S(O)$_2R^{1a}$, wherein $R^{1a}$ is as defined herein. In certain embodiments, $R^2$ is —S(O)NR$^{1b}R^{1c}$, wherein $R^{1b}$ and $R^{1c}$ are each as defined herein. In certain embodiments, $R^2$ is —S(O)$_2$NR$^{1b}R^{1c}$, wherein $R^{1b}$ and $R^{1c}$ are each as defined herein.

In certain embodiments, $R^3$ is hydrogen. In certain embodiments, $R^3$ is deuterium. In certain embodiments, $R^3$ is cyano. In certain embodiments, $R^3$ is halo. In certain embodiments, $R^3$ is fluoro. In certain embodiments, $R^3$ is chloro. In certain embodiments, $R^3$ is nitro. In certain embodiments, $R^3$ is $C_{1-6}$ alkyl, optionally substituted with one or more substituents Q. In certain embodiments, $R^3$ is $C_{3-12}$ cycloalkyl-$C_{1-6}$ alkyl, where the alkyl and cycloalkyl are each independently and optionally substituted with one or more substituents Q. In certain embodiments, $R^3$ is t-butylmethyl, cyclopropylmethyl, 1-methylcyclopropylmethyl, 1-hydroxy(cyclopropylmethyl), cyclobutylmethyl, or cyclopentylmethyl. In certain embodiments, $R^3$ is cyclopropylmethyl. In certain embodiments, $R^3$ is $C_{2-6}$ alkenyl, optionally substituted with one or more substituents Q. In certain embodiments, $R^3$ is $C_{2-6}$ alkynyl, optionally substituted with one or more substituents Q. In certain embodiments, $R^3$ is $C_{3-12}$ cycloalkyl, optionally substituted with one or more substituents Q. In certain embodiments, $R^3$ is cyclopentyl, optionally substituted with one or more substituents Q. In certain embodiments, $R^3$ is $C_{6-14}$ aryl, optionally substituted with one or more substituents Q. In certain embodiments, $R^3$ is $C_{7-15}$ aralkyl, optionally substituted with one or more substituents Q. In certain embodiments, $R^3$ is heteroaryl, optionally substituted with one or more substituents Q. In certain embodiments, $R^3$ is heterocyclyl, optionally substituted with one or more substituents Q.

In certain embodiments, $R^3$ is —C(O)$R^{1a}$, wherein $R^{1a}$ is as defined herein. In certain embodiments, $R^3$ is —C(O)O$R^{1a}$, wherein $R^{1a}$ is as defined herein. In certain embodiments, $R^3$ is —C(O)NR$^{1b}R^{1c}$, wherein $R^{1b}$ and $R^{1c}$ are each as defined herein. In certain embodiments, $R^3$ is —C(O)S$R^{1a}$, wherein $R^{1a}$ is as defined herein. In certain embodiments, $R^3$ is —C(NR$^{1a}$)NR$^{1b}R^{1c}$, wherein $R^{1a}$, $R^{1b}$, and $R^{1c}$ are each as defined herein. In certain embodiments, $R^3$ is —C(S)$R^{1a}$, wherein $R^{1a}$ is as defined herein. In certain embodiments, $R^3$ is —C(S)O$R^{1a}$, wherein $R^{1a}$ is as defined herein. In certain embodiments, $R^3$ is —C(S)NR$^{1b}R^{1c}$, wherein $R^{1b}$ and $R^{1c}$ are each as defined herein. In certain embodiments, $R^3$ is —O$R^{1a}$, wherein $R^{1a}$ is as defined herein. In certain embodiments, $R^3$ is —OC(O)$R^{1a}$, wherein $R^{1a}$ is as defined herein. In certain embodiments, $R^3$ is —OC(O)O$R^{1a}$, wherein $R^{1a}$ is as defined herein. In certain embodiments, $R^3$ is —OC(O)NR$^{1b}R^{1c}$, wherein $R^{1b}$ and $R^{1c}$ are each as defined herein. In certain embodiments, $R^3$ is —OC(O)S$R^{1a}$, wherein $R^{1a}$ is as defined herein. In certain embodiments, $R^3$ is —OC(=NR$^{1a}$)NR$^{1b}R^{1c}$, wherein $R^{1a}$, $R^{1b}$, and $R^{1c}$ are each as defined herein. In certain embodiments, $R^3$ is —OC(S)$R^{1a}$, wherein $R^{1a}$ is as defined herein. In certain embodiments, $R^3$ is —OC(S)O$R^{1a}$, wherein $R^{1a}$ is as defined herein. In certain embodiments, $R^3$ is —OC(S)NR$^{1b}R^{1c}$, wherein $R^{1b}$ and $R^{1c}$ are each as defined herein. In certain embodiments, $R^3$ is —OS(O)$R^{1a}$, wherein $R^{1a}$ is as defined herein. In certain embodiments, $R^3$ is —OS(O)$_2R^{1a}$, wherein $R^{1a}$ is as defined herein. In certain embodiments, $R^3$ is —OS(O)NR$^{1b}R^{1c}$, wherein $R^{1b}$ and $R^{1c}$ are each as defined herein. In certain embodiments, $R^3$ is —OS(O)$_2$NR$^{1b}R^{1c}$, wherein $R^{1b}$ and $R^{1c}$ are each as defined herein. In certain embodiments, $R^3$ is —NR$^{1b}R^{1c}$, wherein $R^{1b}$ and $R^{1c}$ are each as defined herein. In certain embodiments, $R^3$ is —NR$^{1a}$C(O)$R^{1d}$, wherein $R^{1a}$ and $R^{1d}$ are each as defined herein. In certain embodiments, $R^3$ is —NR$^{1a}$C(O)O$R^{1d}$, wherein $R^{1a}$ and $R^{1d}$ are each as defined herein. In certain embodiments, $R^3$ is —NR$^{1a}$C(O)NR$^{1b}R^{1c}$, wherein $R^{1a}$, $R^{1b}$, and $R^{1c}$ are each as defined herein. In certain embodiments, $R^3$ is —NR$^{1a}$C(O)S$R^{1d}$, wherein $R^{1a}$ and $R^{1d}$ are each as defined herein. In certain embodiments, $R^3$ is —NR$^{1a}$C(=NR$^{1d}$)NR$^{1b}R^{1c}$, wherein $R^{1a}$, $R^{1b}$, $R^{1c}$, and $R^{1d}$ are each as defined herein. In certain embodiments, $R^3$ is —NR$^{1a}$C(S)$R^{1d}$, wherein $R^{1a}$ and $R^{1d}$ are each as defined herein. In certain embodiments, $R^3$ is —NR$^{1a}$C(S)O$R^{1d}$, wherein $R^{1a}$ and $R^{1d}$ are each as defined herein. In certain embodiments, $R^3$ is —NR$^{1a}$C(S)NR$^{1b}R^{1c}$, wherein $R^{1a}$, $R^{1b}$, and $R^{1c}$ are each as defined herein. In certain embodiments, $R^3$ is —NR$^{1a}$S(O)$R^{1d}$, wherein $R^{1a}$ and $R^{1d}$ are each as defined herein. In certain embodiments, $R^3$ is —NR$^{1a}$S(O)$_2R^{1d}$, wherein $R^{1a}$ and $R^{1d}$ are each as defined herein. In certain embodiments, $R^3$ is —NR$^{1a}$S(O)NR$^{1b}R^{1c}$, wherein $R^{1a}$, $R^{1b}$, and $R^{1c}$ are each as defined herein. In certain embodiments, $R^3$ is —NR$^{1a}$S(O)$_2$NR$^{1b}R^{1c}$, wherein $R^{1a}$, $R^{1b}$, and $R^{1c}$ are each as defined herein. In certain embodiments, $R^3$ is —S$R^{1a}$, wherein $R^{1a}$ is as defined herein. In certain embodiments, $R^3$ is —S(O)$R^{1a}$, wherein $R^{1a}$ is as defined herein. In certain embodiments, $R^3$ is —S(O)$_2R^{1a}$, wherein $R^{1a}$ is as defined herein. In certain embodiments, $R^3$ is —S(O)NR$^{1b}R^{1c}$, wherein $R^{1b}$ and $R^{1c}$ are each as defined herein. In certain embodiments, $R^3$ is —S(O)$_2$NR$^{1b}R^{1c}$, wherein $R^{1b}$ and $R^{1c}$ are each as defined herein.

In certain embodiments, $R^4$ is hydrogen. In certain embodiments, $R^4$ is deuterium. In certain embodiments, $R^4$ is cyano. In certain embodiments, $R^4$ is halo. In certain embodiments, $R^4$ is fluoro. In certain embodiments, $R^4$ is chloro. In certain embodiments, $R^4$ is nitro. In certain embodiments, $R^4$ is $C_{1-6}$ alkyl, optionally substituted with one or more substituents Q. In certain embodiments, $R^4$ is methyl, ethyl, or propyl, each optionally substituted with one or more substituents Q. In certain embodiments, $R^4$ is methyl or isopropyl, each optionally substituted with one or more substituents Q. In certain embodiments, $R^4$ is $C_{2-6}$ alkenyl, optionally substituted with one or more substituents Q. In certain embodiments, $R^4$ is $C_{2-6}$ alkynyl, optionally substituted with one or more substituents Q. In certain embodiments, $R^4$ is $C_{3-12}$ cycloalkyl, optionally substituted with one or more substituents Q. In certain embodiments, $R^4$ is $C_{6-14}$ aryl, optionally substituted with one or more substituents Q. In certain embodiments, $R^4$ is $C_{7-15}$ aralkyl, optionally substituted with one or more substituents Q. In certain embodiments, $R^4$ is heteroaryl, optionally substituted with one or more substituents Q. In certain embodiments, $R^4$ is heterocyclyl, optionally substituted with one or more substituents Q. In certain embodiments, $R^4$ is 4- to 6-membered heterocyclyl, optionally substituted with one or more substituents Q. In certain embodiments, $R^4$ is oxetanyl, tetrahydrofuryl, or tetrahydropyranyl, each optionally substituted with one or more substituents Q.

In certain embodiments, $R^4$ is —C(O)$R^{1a}$, wherein $R^{1a}$ is as defined herein. In certain embodiments, $R^4$ is —C(O)O$R^{1a}$, wherein $R^{1a}$ is as defined herein. In certain embodiments, $R^4$ is —C(O)NR$^{1b}R^{1c}$, wherein $R^{1b}$ and $R^{1c}$ are each as defined herein. In certain embodiments, $R^4$ is —C(O)S$R^{1a}$, wherein $R^{1a}$ is as defined herein. In certain embodiments, $R^4$ is —C(NR$^{1a}$)NR$^{1b}R^{1c}$, wherein $R^{1a}$, $R^{1b}$, and $R^{1c}$ are each as defined herein. In certain embodiments, $R^4$ is —C(S)$R^{1a}$, wherein $R^{1a}$ is as defined herein. In certain embodiments, $R^4$ is —C(S)O$R^{1a}$, wherein $R^{1a}$ is as defined herein. In certain embodiments, $R^4$ is —C(S)NR$^{1b}R^{1c}$, wherein $R^{1b}$ and $R^{1c}$ are each as defined herein. In certain embodiments, $R^4$ is —$OR^{1a}$, wherein $R^{1a}$ is as defined herein. In certain embodiments, $R^4$ is —OH. In certain embodiments, $R^4$ is —$OC(O)R^{1a}$, wherein $R^{1a}$ is as defined herein. In certain embodiments, $R^4$ is —$OC(O)OR^{1a}$, wherein $R^{1a}$ is as defined herein. In certain embodiments, $R^4$ is —$OC(O)NR^{1b}R^{1c}$, wherein $R^{1b}$ and $R^{1c}$ are each as defined herein. In certain embodiments, $R^4$ is —$OC(O)SR^{1a}$, wherein $R^{1a}$ is as defined herein. In certain embodiments, $R^4$ is —$OC(=NR^{1a})NR^{1b}R^{1c}$, wherein $R^{1a}$, $R^{1b}$, and $R^{1c}$ are each as defined herein. In certain embodiments, $R^4$ is —$OC(S)R^{1a}$, wherein $R^{1a}$ is as defined herein. In certain embodiments, $R^4$ is —$OC(S)OR^{1a}$, wherein $R^{1a}$ is as defined herein. In certain embodiments, $R^4$ is —$OC(S)NR^{1b}R^{1c}$, wherein $R^{1b}$ and $R^{1c}$ are each as defined herein. In certain embodiments, $R^4$ is —$OS(O)R^{1a}$, wherein $R^{1a}$ is as defined herein. In certain embodiments, $R^4$ is —$OS(O)_2R^{1a}$, wherein $R^{1a}$ is as defined herein. In certain embodiments, $R^4$ is —$OS(O)NR^{1b}R^{1c}$, wherein $R^{1b}$ and $R^{1c}$ are each as defined herein. In certain embodiments, $R^4$ is —$OS(O)_2NR^{1b}R^{1c}$, wherein $R^{1b}$ and $R^{1c}$ are each as defined herein. In certain embodiments, $R^4$ is —$NR^{1b}R^{1c}$, wherein $R^{1b}$ and $R^{1c}$ are each as defined herein. In certain embodiments, $R^4$ is —$NH_2$. In certain embodiments, $R^4$ is —$NR^{1a}C(O)R^{1d}$, wherein $R^{1a}$ and $R^{1d}$ are each as defined herein. In certain embodiments, $R^4$ is —$NR^{1a}C(O)OR^{1d}$, wherein $R^{1a}$ and $R^{1d}$ are each as defined herein. In certain embodiments, $R^4$ is —$NR^{1a}C(O)NR^{1b}R^{1c}$, wherein $R^{1a}$, $R^{1b}$, and $R^{1c}$ are each as defined herein. In certain embodiments, $R^4$ is —$NR^{1a}C(O)SR^{1d}$, wherein $R^{1a}$ and $R^{1d}$ are each as defined herein. In certain embodiments, $R^4$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^4$ is —$NR^{1a}C(S)R^{1d}$, wherein $R^{1a}$ and $R^{1d}$ are each as defined herein. In certain embodiments, $R^4$ is —$NR^{1a}C(S)OR^{1d}$, wherein $R^{1a}$ and $R^{1d}$ are each as defined herein. In certain embodiments, $R^4$ is —$NR^{1a}C(S)NR^{1b}R^{1c}$, wherein $R^{1a}$, $R^{1b}$, and $R^{1c}$ are each as defined herein. In certain embodiments, $R^4$ is —$NR^{1a}S(O)R^{1d}$, wherein $R^{1a}$ and $R^{1d}$ are each as defined herein. In certain embodiments, $R^4$ is —$NR^{1a}S(O)_2R^{1d}$, wherein $R^{1a}$ and $R^{1d}$ are each as defined herein. In certain embodiments, $R^4$ is —$NR^{1a}S(O)NR^{1b}R^{1c}$, wherein $R^{1a}$, $R^{1b}$, and $R^{1c}$ are each as defined herein. In certain embodiments, $R^4$ is —$NR^{1a}S(O)_2NR^{1b}R^{1c}$, wherein $R^{1a}$, $R^{1b}$, and $R^{1c}$ are each as defined herein. In certain embodiments, $R^4$ is —$SR^{1a}$, wherein $R^{1a}$ is as defined herein. In certain embodiments, $R^4$ is —$S(O)R^{1a}$, wherein $R^{1a}$ is as defined herein. In certain embodiments, $R^4$ is —$S(O)_2R^{1a}$, wherein $R^{1a}$ is as defined herein. In certain embodiments, $R^4$ is —$S(O)NR^{1b}R^{1c}$, wherein $R^{1b}$ and $R^{1c}$ are each as defined herein. In certain embodiments, $R^4$ is —$S(O)_2NR^{1b}R^{1c}$, wherein $R^{1b}$ and $R^{1c}$ are each as defined herein.

In certain embodiments, $R^5$ is hydrogen. In certain embodiments, $R^5$ is deuterium. In certain embodiments, $R^5$ is $C_{1-6}$ alkyl, optionally substituted with one or more substituents Q. In certain embodiments, $R^5$ is methyl, ethyl, or propyl, each optionally substituted with one or more substituents Q. In certain embodiments, $R^5$ is methyl or isopropyl, each optionally substituted with one or more substituents Q. In certain embodiments, $R^5$ is $C_{2-6}$ alkenyl, optionally substituted with one or more substituents Q. In certain embodiments, $R^5$ is $C_{2-6}$ alkynyl, optionally substituted with one or more substituents Q. In certain embodiments, $R^5$ is $C_{3-12}$ cycloalkyl, optionally substituted with one or more substituents Q. In certain embodiments, $R^5$ is cyclopentyl, optionally substituted with one or more substituents Q. In certain embodiments, $R^5$ is $C_{6-14}$ aryl, optionally substituted with one or more substituents Q. In certain embodiments, $R^5$ is $C_{7-15}$ aralkyl, optionally substituted with one or more substituents Q. In certain embodiments, $R^5$ is heteroaryl, optionally substituted with one or more substituents Q. In certain embodiments, $R^5$ is heterocyclyl, optionally substituted with one or more substituents Q. In certain embodiments, $R^5$ is 4- to 6-membered heterocyclyl, optionally substituted with one or more substituents Q. In certain embodiments, $R^5$ is oxetanyl, tetrahydrofuryl, or tetrahydropyranyl, each optionally substituted with one or more substituents Q.

In certain embodiments, $R^5$ is —$C(O)R^{1a}$, wherein $R^{1a}$ is as defined herein. In certain embodiments, $R^5$ is —$C(O)OR^{1a}$, wherein $R^{1a}$ is as defined herein. In certain embodiments, $R^5$ is —$C(O)NR^{1b}R^{1c}$, wherein $R^{1b}$ and $R^{1c}$ are each as defined herein. In certain embodiments, $R^5$ is —$C(O)SR^{1a}$, wherein $R^{1a}$ is as defined herein. In certain embodiments, $R^5$ is —$C(NR^{1a})NR^{1b}R^{1c}$, wherein $R^{1a}$, $R^{1b}$, and $R^{1c}$ are each as defined herein. In certain embodiments, $R^5$ is —$C(S)R^{1a}$, wherein $R^{1a}$ is as defined herein. In certain embodiments, $R^5$ is —$C(S)OR^{1a}$, wherein $R^{1a}$ is as defined herein. In certain embodiments, $R^5$ is —$C(S)NR^{1b}R^{1c}$, wherein $R^{1b}$ and $R^{1c}$ are each as defined herein. In certain embodiments, $R^5$ is —$OR^{1a}$, wherein $R^{1a}$ is as defined herein. In certain embodiments, $R^5$ is —$OC(O)R^{1a}$, wherein $R^{1a}$ is as defined herein. In certain embodiments, $R^5$ is —$OC(O)OR^{1a}$, wherein $R^{1a}$ is as defined herein. In certain embodiments, $R^5$ is —$OC(O)NR^{1b}R^{1c}$, wherein $R^{1b}$ and $R^{1c}$ are each as defined herein. In certain embodiments, $R^5$ is —$OC(O)SR^{1a}$, wherein $R^{1a}$ is as defined herein. In certain embodiments, $R^5$ is —$OC(=NR^{1a})NR^{1b}R^{1c}$, wherein $R^{1a}$, $R^{1b}$, and $R^{1c}$ are each as defined herein. In certain embodiments, $R^5$ is —$OC(S)R^{1a}$, wherein $R^{1a}$ is as defined herein. In certain embodiments, $R^5$ is —$OC(S)OR^{1a}$, wherein $R^{1a}$ is as defined herein. In certain embodiments, $R^5$ is —$OC(S)NR^{1b}R^{1c}$, wherein $R^{1b}$ and $R^{1c}$ are each as defined herein. In certain embodiments, $R^5$ is —$OS(O)R^{1a}$, wherein $R^{1a}$ is as defined herein. In certain embodiments, $R^5$ is —$OS(O)_2R^{1a}$, wherein $R^{1a}$ is as defined herein. In certain embodiments, $R^5$ is —$OS(O)NR^{1b}R^{1c}$, wherein $R^{1b}$ and $R^{1c}$ are each as defined herein. In certain embodiments, $R^5$ is —$OS(O)_2NR^{1b}R^{1c}$, wherein $R^{1b}$ and $R^{1c}$ are each as defined herein. In certain embodiments, $R^5$ is —$NR^{1b}R^{1c}$, wherein $R^{1b}$ and $R^{1c}$ are each as defined herein. In certain embodiments, $R^5$ is —$NR^{1a}C(O)R^{1d}$, wherein $R^{1a}$ and $R^{1d}$ are each as defined herein. In certain embodiments, $R^5$ is —$NR^{1a}C(O)OR^{1d}$, wherein $R^{1a}$ and $R^{1d}$ are each as defined herein. In certain embodiments, $R^5$ is —$NR^{1a}C(O)NR^{1b}R^{1c}$, wherein $R^{1a}$, $R^{1b}$, and $R^{1c}$ are each as defined herein. In certain embodiments, $R^5$ is —$NR^{1a}C(O)SR^{1d}$, wherein $R^{1a}$ and $R^{1d}$ are each as defined herein. In certain embodiments, $R^5$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^5$ is —$NR^{1a}C(S)R^{1d}$, wherein $R^{1a}$ and $R^{1d}$ are each as defined herein. In certain embodiments, $R^5$ is —$NR^{1a}C(S)OR^{1d}$, wherein $R^{1a}$ and $R^{1d}$ are each as defined herein. In certain embodiments, $R^5$ is —$NR^{1a}C(S)NR^{1b}R^{1c}$, wherein $R^{1a}$, $R^{1b}$, and $R^{1c}$ are each as defined herein. In certain embodiments, $R^5$ is —$NR^{1a}S(O)R^{1d}$, wherein $R^{1a}$ and $R^{1d}$ are each as defined herein. In certain embodiments, $R^5$ is —$NR^{1a}S(O)_2R^{1d}$, wherein $R^{1a}$ and $R^{1d}$ are each as defined herein. In certain embodiments, $R^5$ is —$NR^{1a}S(O)NR^{1b}R^{1c}$, wherein $R^{1a}$, $R^{1b}$, and $R^{1c}$ are each as defined herein. In certain embodiments, $R^5$ is —$NR^{1a}S(O)_2NR^{1b}R^{1c}$, wherein $R^{1a}$, $R^{1b}$, and $R^{1c}$ are each as defined herein. In certain embodiments, $R^5$ is —$S(O)R^{1a}$, wherein $R^{1a}$ is as defined herein. In certain embodiments, $R^5$ is —$S(O)_2R^{1a}$, wherein $R^{1a}$ is as defined herein. In certain embodiments, $R^5$ is —$S(O)$ $NR^{1b}R^{1c}$, wherein $R^{1b}$ and $R^{1c}$ are each as defined herein. In certain embodiments, $R^5$ is —$S(O)_2NR^{1b}R^{1c}$, wherein $R^{1b}$ and $R^{1c}$ are each as defined herein.

In certain embodiments, $R^6$ is hydrogen. In certain embodiments, $R^6$ is deuterium. In certain embodiments, $R^6$ is cyano. In certain embodiments, $R^6$ is halo. In certain embodiments, $R^6$ is fluoro. In certain embodiments, $R^6$ is chloro. In certain embodiments, $R^6$ is nitro. In certain embodiments, $R^6$ is $C_{1-6}$ alkyl, optionally substituted with one or more substituents Q. In certain embodiments, $R^6$ is methyl, optionally substituted with one or more substituents Q. In certain embodiments, $R^6$ is methyl or trifluoromethyl. In certain embodiments, $R^6$ is $C_{2-6}$ alkenyl, optionally substituted with one or more substituents Q. In certain embodiments, $R^6$ is $C_{2-6}$ alkynyl, optionally substituted with one or more substituents Q. In certain embodiments, $R^6$ is $C_{3-12}$ cycloalkyl, optionally substituted with one or more substituents Q. In certain embodiments, $R^6$ is $C_{6-14}$ aryl, optionally substituted with one or more substituents Q. In certain embodiments, $R^6$ is $C_{7-15}$ aralkyl, optionally substituted with one or more substituents Q. In certain embodiments, $R^6$ is heteroaryl, optionally substituted with one or more substituents Q. In certain embodiments, $R^6$ is heterocyclyl, optionally substituted with one or more substituents Q. In certain embodiments, $R^6$ is 4- to 6-membered heterocyclyl, optionally substituted with one or more substituents Q. In certain embodiments, $R^6$ is oxetanyl, tetrahydrofuryl, or tetrahydropyranyl, each optionally substituted with one or more substituents Q.

In certain embodiments, $R^6$ is —$C(O)R^{1a}$, wherein $R^{1a}$ is as defined herein. In certain embodiments, $R^6$ is —$C(O)OR^{1a}$, wherein $R^{1a}$ is as defined herein. In certain embodiments, $R^6$ is —$C(O)NR^{1b}R^{1c}$, wherein $R^{1b}$ and $R^{1c}$ are each as defined herein. In certain embodiments, $R^6$ is —$C(O)SR^{1a}$, wherein $R^{1a}$ is as defined herein. In certain embodiments, $R^6$ is —$C(NR^{1a})NR^{1b}R^{1c}$, wherein $R^{1a}$, $R^{1b}$, and $R^{1c}$ are each as defined herein. In certain embodiments, $R^6$ is —$C(S)R^{1a}$, wherein $R^{1a}$ is as defined herein. In certain embodiments, $R^6$ is —$C(S)OR^{1a}$, wherein $R^{1a}$ is as defined herein. In certain embodiments, $R^6$ is —$C(S)NR^{1b}R^{1c}$, wherein $R^{1b}$ and $R^{1c}$ are each as defined herein. In certain embodiments, $R^6$ is —$OR^{1a}$, wherein $R^{1a}$ is as defined herein. In certain embodiments, $R^6$ is —OH. In certain embodiments, $R^6$ is —$OC(O)R^{1a}$, wherein $R^{1a}$ is as defined herein. In certain embodiments, $R^6$ is —$OC(O)OR^{1a}$, wherein $R^{1a}$ is as defined herein. In certain embodiments, $R^6$ is —$OC(O)NR^{1b}R^{1c}$, wherein $R^{1b}$ and $R^{1c}$ are each as defined herein. In certain embodiments, $R^6$ is —$OC(O)SR^{1a}$, wherein $R^{1a}$ is as defined herein. In certain embodiments, $R^6$ is —$OC(=NR^{1a})NR^{1b}R^{1c}$, wherein $R^{1a}$, $R^{1b}$, and $R^{1c}$ are each as defined herein. In certain embodiments, $R^6$ is —$OC(S)R^{1a}$, wherein $R^{1a}$ is as defined herein. In certain embodiments, $R^6$ is —$OC(S)OR^{1a}$, wherein $R^{1a}$ is as defined herein. In certain embodiments, $R^6$ is —$OC(S)NR^{1b}R^{1c}$, wherein $R^{1b}$ and $R^{1c}$ are each as defined herein. In certain embodiments, $R^6$ is —$OS(O)R^{1a}$, wherein $R^{1a}$ is as defined herein. In certain embodiments, $R^6$ is —$OS(O)_2R^{1a}$, wherein $R^{1a}$ is as defined herein. In certain embodiments, $R^6$ is —$OS(O)NR^{1b}R^{1c}$, wherein $R^{1b}$ and $R^{1c}$ are each as defined herein. In certain embodiments, $R^6$ is —$OS(O)_2NR^{1b}R^{1c}$, wherein $R^{1b}$ and $R^{1c}$ are each as defined herein. In certain embodiments, $R^6$ is —$NR^{1b}R^{1c}$, wherein $R^{1b}$ and $R^{1c}$ are each as defined herein. In certain embodiments, $R^6$ is —$NH_2$. In certain embodiments, $R^6$ is —$NR^{1a}C(O)R^{1d}$, wherein $R^{1a}$ and $R^{1d}$ are each as defined herein. In certain embodiments, $R^6$ is —$NR^{1a}C(O)OR^{1d}$, wherein $R^{1a}$ and $R^{1d}$ are each as defined herein. In certain embodiments, $R^6$ is —$NR^{1a}C(O)NR^{1b}R^{1c}$, wherein $R^{1a}$, $R^{1b}$, and $R^{1c}$ are each as defined herein. In certain embodiments, $R^6$ is —$NR^{1a}C(O)SR^{1d}$, wherein $R^{1a}$ and $R^{1d}$ are each as defined herein. In certain embodiments, $R^6$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^6$ is —$NR^{1a}C(S)R^{1d}$, wherein $R^{1a}$ and $R^{1d}$ are each as defined herein. In certain embodiments, $R^6$ is —$NR^{1a}C(S)OR^{1d}$, wherein $R^{1a}$ and $R^{1d}$ are each as defined herein. In certain embodiments, $R^6$ is —$NR^{1a}C(S)NR^{1b}R^{1c}$, wherein $R^{1a}$, $R^{1b}$, and $R^{1c}$ are each as defined herein. In certain embodiments, $R^6$ is —$NR^{1a}S(O)R^{1d}$, wherein $R^{1a}$ and $R^{1d}$ are each as defined herein. In certain embodiments, $R^6$ is —$NR^{1a}S(O)_2R^{1d}$, wherein $R^{1a}$ and $R^{1d}$ are each as defined herein. In certain embodiments, $R^6$ is —$NR^{1a}S(O)NR^{1b}R^{1c}$, wherein $R^{1a}$, $R^{1b}$, and $R^{1c}$ are each as defined herein. In certain embodiments, $R^6$ is —$NR^{1a}S(O)_2NR^{1b}R^{1c}$, wherein $R^{1a}$, $R^{1b}$, and $R^{1c}$ are each as defined herein. In certain embodiments, $R^6$ is —$SR^{1a}$, wherein $R^{1a}$ is as defined herein. In certain embodiments, $R^6$ is —$S(O)R^{1a}$, wherein $R^{1a}$ is as defined herein. In certain embodiments, $R^6$ is —$S(O)_2R^{1a}$, wherein $R^{1a}$ is as defined herein. In certain embodiments, $R^6$ is —$S(O)NR^{1b}R^{1c}$, wherein $R^{1b}$ and $R^{1c}$ are each as defined herein. In certain embodiments, $R^6$ is —$S(O)_2NR^{1b}R^{1c}$, wherein $R^{1b}$ and $R^{1c}$ are each as defined herein.

In certain embodiments, $R^7$ is hydrogen. In certain embodiments, $R^7$ is deuterium. In certain embodiments, $R^7$ is $C_{1-6}$ alkyl, optionally substituted with one or more substituents Q. In certain embodiments, $R^7$ is methyl, optionally substituted with one or more substituents Q. In certain embodiments, $R^7$ is $C_{2-6}$ alkenyl, optionally substituted with one or more substituents Q. In certain embodiments, $R^7$ is $C_{2-6}$ alkynyl, optionally substituted with one or more substituents Q. In certain embodiments, $R^7$ is $C_{3-12}$ cycloalkyl, optionally substituted with one or more substituents Q. In certain embodiments, $R^7$ is cyclopentyl, optionally substituted with one or more substituents Q. In certain embodiments, $R^7$ is $C_{6-14}$ aryl, optionally substituted with one or more substituents Q. In certain embodiments, $R^7$ is $C_{7-15}$ aralkyl, optionally substituted with one or more substituents Q. In certain embodiments, $R^7$ is heteroaryl, optionally substituted with one or more substituents Q. In certain embodiments, $R^7$ is heterocyclyl, optionally substituted with one or more substituents Q. In certain embodiments, $R^7$ is 4- to 6-membered heterocyclyl, optionally substituted with one or more substituents Q.

In certain embodiments, $R^7$ is —$C(O)R^{1a}$, wherein $R^{1a}$ is as defined herein. In certain embodiments, $R^7$ is —$C(O)OR^{1a}$, wherein $R^{1a}$ is as defined herein. In certain embodiments, $R^7$ is —$C(O)NR^{1b}R^{1c}$, wherein $R^{1b}$ and $R^{1c}$ are each as defined herein. In certain embodiments, $R^7$ is —$C(O)SR^{1a}$, wherein $R^{1a}$ is as defined herein. In certain embodiments, $R^7$ is —$C(NR^{1a})NR^{1b}R^{1c}$, wherein $R^{1a}$, $R^{1b}$, and $R^{1c}$ are each as defined herein. In certain embodiments, $R^7$ is —$C(S)R^{1a}$, wherein $R^{1a}$ is as defined herein. In certain embodiments, $R^7$ is —$C(S)OR^{1a}$, wherein $R^{1a}$ is as defined herein. In certain embodiments, $R^7$ is —$C(S)NR^{1b}R^{1c}$, wherein $R^{1b}$ and $R^{1c}$ are each as defined herein. In certain embodiments, $R^7$ is —$OR^{1a}$, wherein $R^{1a}$ is as defined herein. In certain embodiments, $R^7$ is —$OC(O)R^{1a}$, wherein $R^{1a}$ is as defined herein. In certain embodiments, $R^7$ is —$OC(O)OR^{1a}$, wherein $R^{1a}$ is as defined herein. In certain embodiments, $R^7$ is —$OC(O)NR^{1b}R^{1c}$, wherein $R^{1b}$ and $R^{1c}$ are each as defined herein. In certain embodiments, $R^7$ is —$OC(O)SR^{1a}$, wherein $R^{1a}$ is as defined herein. In certain embodiments, $R^7$ is —$OC(=NR^{1a})NR^{1b}R^{1c}$, wherein $R^{1a}$, $R^{1b}$, and $R^{1c}$ are each as defined herein. In certain embodiments, $R^7$ is —OC(S)$R^{1a}$, wherein $R^{1a}$ is as defined herein. In certain embodiments, $R^7$ is —OC(S)O$R^{1a}$, wherein $R^{1a}$ is as defined herein. In certain embodiments, $R^7$ is —OC(S)N$R^{1b}R^{1c}$, wherein $R^{1b}$ and $R^{1c}$ are each as defined herein. In certain embodiments, $R^7$ is —OS(O)$R^{1a}$, wherein $R^{1a}$ is as defined herein. In certain embodiments, $R^7$ is —OS(O)$_2R^{1a}$, wherein $R^{1a}$ is as defined herein. In certain embodiments, $R^7$ is —OS(O)N$R^{1b}R^{1c}$, wherein $R^{1b}$ and $R^{1c}$ are each as defined herein. In certain embodiments, $R^7$ is —OS(O)$_2$N$R^{1b}R^{1c}$, wherein $R^{1b}$ and $R^{1c}$ are each as defined herein. In certain embodiments, $R^7$ is —N$R^{1b}R^{1c}$, wherein $R^{1b}$ and $R^{1c}$ are each as defined herein. In certain embodiments, $R^7$ is —N$R^{1a}$C(O)$R^{1d}$, wherein $R^{1a}$ and $R^{1d}$ are each as defined herein. In certain embodiments, $R^7$ is —N$R^{1a}$C(O)O$R^{1d}$, wherein $R^{1a}$ and $R^{1d}$ are each as defined herein. In certain embodiments, $R^7$ is —N$R^{1a}$C(O)N$R^{1b}R^{1c}$, wherein $R^{1a}$, $R^{1b}$, and $R^{1c}$ are each as defined herein. In certain embodiments, $R^7$ is —N$R^{1a}$C(O)S$R^{1d}$, wherein $R^{1a}$ and $R^{1d}$ are each as defined herein. In certain embodiments, $R^7$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^7$ is —N$R^{1a}$C(S)$R^{1d}$, wherein $R^{1a}$ and $R^{1d}$ are each as defined herein. In certain embodiments, $R^7$ is —N$R^{1a}$C(S)O$R^{1d}$, wherein $R^{1a}$ and $R^{1d}$ are each as defined herein. In certain embodiments, $R^7$ is —N$R^{1a}$C(S)N$R^{1b}R^{1c}$, wherein $R^{1a}$, $R^{1b}$, and $R^{1c}$ are each as defined herein. In certain embodiments, $R^7$ is —N$R^{1a}$S(O)$R^{1d}$, wherein $R^{1a}$ and $R^{1d}$ are each as defined herein. In certain embodiments, $R^7$ is —N$R^{1a}$S(O)$_2R^{1d}$, wherein $R^{1a}$ and $R^{1d}$ are each as defined herein. In certain embodiments, $R^7$ is —N$R^{1a}$S(O)N$R^{1b}R^{1c}$, wherein $R^{1a}$, $R^{1b}$, and $R^{1c}$ are each as defined herein. In certain embodiments, $R^7$ is —N$R^{1a}$S(O)$_2$N$R^{1b}R^{1c}$, wherein $R^{1a}$, $R^{1b}$, and $R^{1c}$ are each as defined herein. In certain embodiments, $R^7$ is —S(O)$R^{1a}$, wherein $R^{1a}$ is as defined herein. In certain embodiments, $R^7$ is —S(O)$_2R^{1a}$, wherein $R^{1a}$ is as defined herein. In certain embodiments, $R^7$ is —S(O)N$R^{1b}R^{1c}$, wherein $R^{1b}$ and $R^{1c}$ are each as defined herein. In certain embodiments, $R^7$ is —S(O)$_2$N$R^{1b}R^{1c}$, wherein $R^{1b}$ and $R^{1c}$ are each as defined herein.

In certain embodiments, $R^{2a}$ is hydrogen. In certain embodiments, $R^{2a}$ is deuterium. In certain embodiments, $R^{2a}$ is $C_{1-6}$ alkyl, optionally substituted with one or more substituents Q. In certain embodiments, $R^{2a}$ is methyl or ethyl, each optionally substituted with one or more substituents Q. In certain embodiments, $R^{2a}$ is methyl, 2,2,2-trifluoroethyl, or 2-methoxyethyl. In certain embodiments, $R^{2a}$ is heteroaryl-$C_{1-6}$ alkyl, where the alkyl and heteroaryl are each optionally substituted with one or more substituents Q. In certain embodiments, $R^{2a}$ is 5-membered heteroaryl-$C_{1-6}$ alkyl, where the alkyl and heteroaryl are each optionally substituted with one or more substituents Q. In certain embodiments, $R^{2a}$ is 6-membered heteroaryl-$C_{1-6}$ alkyl, where the alkyl and heteroaryl are each optionally substituted with one or more substituents Q. In certain embodiments, $R^{2a}$ is (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, or (pyridin-3-yl)methyl. In certain embodiments, $R^{2a}$ is $C_{2-6}$ alkenyl, optionally substituted with one or more substituents Q. In certain embodiments, $R^{2a}$ is $C_{2-6}$ alkynyl, optionally substituted with one or more substituents Q. In certain embodiments, $R^{2a}$ is pent-4-ynyl. In certain embodiments, $R^{2a}$ is $C_{3-12}$ cycloalkyl, optionally substituted with one or more substituents Q. In certain embodiments, $R^{2a}$ is $C_{6-14}$ aryl, optionally substituted with one or more substituents Q. In certain embodiments, $R^{2a}$ is phenyl, optionally substituted with one or more substituents Q. In certain embodiments, $R^{2a}$ is $C_{7-15}$ aralkyl, optionally substituted with one or more substituents Q. In certain embodiments, $R^{2a}$ is benzyl, optionally substituted with one or more substituents Q. In certain embodiments, $R^{2a}$ is heteroaryl, optionally substituted with one or more substituents Q. In certain embodiments, $R^{2a}$ is heterocyclyl, optionally substituted with one or more substituents Q.

In certain embodiments, $R^{2a}$ is —C(O)$R^{1a}$, wherein $R^{1a}$ is as defined herein. In certain embodiments, $R^{2a}$ is —C(O)$R^{1a}$, wherein $R^{1a}$ is $C_{1-6}$ alkyl, $C_{2-6}$ alkyl, $C_{2-6}$ alkynyl, or heteroaryl, each of which is optionally substituted with one or more substituents Q. In certain embodiments, $R^{2a}$ is 2-methoxyacetyl, pentanoyl, but-3-ynylcarbonyl, or (pyrazol-4-yl)carbonyl. In certain embodiments, $R^{2a}$ is —C(O)O$R^{1a}$, wherein $R^{1a}$ is as defined herein. In certain embodiments, $R^{2a}$ is —C(O)N$R^{1b}R^{1c}$, wherein $R^{1b}$ and $R^{1c}$ are each as defined herein. In certain embodiments, $R^{2a}$ is —C(O)S$R^{1a}$, wherein $R^{1a}$ is as defined herein. In certain embodiments, $R^{2a}$ is —C(N$R^{1a}$)N$R^{1b}R^{1c}$, wherein $R^{1a}$, $R^{1b}$, and $R^{1c}$ are each as defined herein. In certain embodiments, $R^{2a}$ is —C(S)$R^{1a}$, wherein $R^{1a}$ is as defined herein. In certain embodiments, $R^{2a}$ is —C(S)O$R^{1a}$, wherein $R^{1a}$ is as defined herein. In certain embodiments, $R^{2a}$ is —C(S)N$R^{1b}R^{1c}$, wherein $R^{1b}$ and $R^{1c}$ are each as defined herein. In certain embodiments, $R^{2a}$ is —O$R^{1a}$, wherein $R^{1a}$ is as defined herein. In certain embodiments, $R^{2a}$ is —OC(O)$R^{1a}$, wherein $R^{1a}$ is as defined herein. In certain embodiments, $R^{2a}$ is —OC(O)O$R^{1a}$, wherein $R^{1a}$ is as defined herein. In certain embodiments, $R^{2a}$ is —OC(O)N$R^{1b}R^{1c}$, wherein $R^{1b}$ and $R^{1c}$ are each as defined herein. In certain embodiments, $R^{2a}$ is —OC(O)S$R^{1a}$, wherein $R^{1a}$ is as defined herein. In certain embodiments, $R^{2a}$ is —OC(=N$R^{1a}$)N$R^{1b}R^{1c}$, wherein $R^{1a}$, $R^{1b}$, and $R^{1c}$ are each as defined herein. In certain embodiments, $R^{2a}$ is —OC(S)$R^{1a}$, wherein $R^{1a}$ is as defined herein. In certain embodiments, $R^{2a}$ is —OC(S)O$R^{1a}$, wherein $R^{1a}$ is as defined herein. In certain embodiments, $R^{2a}$ is —OC(S)N$R^{1b}R^{1c}$, wherein $R^{1b}$ and $R^{1c}$ are each as defined herein. In certain embodiments, $R^{2a}$ is —OS(O)$R^{1a}$, wherein $R^{1a}$ is as defined herein. In certain embodiments, $R^{2a}$ is —OS(O)$_2R^{1a}$, wherein $R^{1a}$ is as defined herein. In certain embodiments, $R^{2a}$ is —OS(O)N$R^{1b}R^{1c}$, wherein $R^{1b}$ and $R^{1c}$ are each as defined herein. In certain embodiments, $R^{2a}$ is —OS(O)$_2$N$R^{1b}R^{1c}$, wherein $R^{1b}$ and $R^{1c}$ are each as defined herein. In certain embodiments, $R^{2a}$ is —N$R^{1b}R^{1c}$, wherein $R^{1b}$ and $R^{1c}$ are each as defined herein. In certain embodiments, $R^{2a}$ is —N$R^{1a}$C(O)$R^{1d}$, wherein $R^{1a}$ and $R^{1d}$ are each as defined herein. In certain embodiments, $R^{2a}$ is —N$R^{1a}$C(O)O$R^{1d}$, wherein $R^{1a}$ and $R^{1d}$ are each as defined herein. In certain embodiments, $R^{2a}$ is —N$R^{1a}$C(O)N$R^{1b}R^{1c}$, wherein $R^{1a}$, $R^{1b}$, and $R^{1c}$ are each as defined herein. In certain embodiments, $R^{2a}$ is —N$R^{1a}$C(O)S$R^{1d}$, wherein $R^{1a}$ and $R^{1d}$ are each as defined herein. In certain embodiments, $R^{2a}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{2a}$ is —N$R^{1a}$C(S)$R^{1d}$, wherein $R^{1a}$ and $R^{1d}$ are each as defined herein. In certain embodiments, $R^{2a}$ is —N$R^{1a}$C(S)O$R^{1d}$, wherein $R^{1a}$ and $R^{1d}$ are each as defined herein. In certain embodiments, $R^{2a}$ is —N$R^{1a}$C(S)N$R^{1b}R^{1c}$, wherein $R^{1a}$, $R^{1b}$, and $R^{1c}$ are each as defined herein. In certain embodiments, $R^{2a}$ is —N$R^{1a}$S(O)$R^{1d}$, wherein $R^{1a}$ and $R^{1d}$ are each as defined herein. In certain embodiments, $R^{2a}$ is —N$R^{1a}$S(O)$_2R^{1d}$, wherein $R^{1a}$ and $R^{1d}$ are each as defined herein. In certain embodiments, $R^{2a}$ is —N$R^{1a}$S(O)N$R^{1b}R^{1c}$, wherein $R^{1a}$, $R^{1b}$, and $R^{1c}$ are each as defined herein. In certain embodiments, $R^{2a}$ is —N$R^{1a}$S(O)$_2$N$R^{1b}R^{1c}$, wherein $R^{1a}$, $R^{1b}$, and $R^{1c}$ are each as defined herein. In certain embodiments, $R^{2a}$ is —S(O)$R^{1a}$, wherein $R^{1a}$ is as defined herein.

In certain embodiments, $R^{2a}$ is —S(O)$_2$R$^{1a}$, wherein $R^{1a}$ is as defined herein. In certain embodiments, $R^{2a}$ is —S(O)NR$^{1b}$R$^{1c}$, wherein $R^{1b}$ and $R^{1c}$ are each as defined herein. In certain embodiments, $R^{2a}$ is —S(O)$_2$NR$^{1b}$R$^{1c}$, wherein $R^{1b}$ and $R^{1c}$ are each as defined herein.

In certain embodiments, $R^{2b}$ is hydrogen. In certain embodiments, $R^{2b}$ is deuterium. In certain embodiments, $R^{2b}$ is C$_{1-6}$ alkyl, optionally substituted with one or more substituents Q. In certain embodiments, $R^{2b}$ is methyl or ethyl, each optionally substituted with one or more substituents Q. In certain embodiments, $R^{2b}$ is methyl, 2,2,2-trifluoroethyl, or 2-methoxyethyl. In certain embodiments, $R^{2b}$ is heteroaryl-C$_{1-6}$ alkyl, where the alkyl and heteroaryl are each optionally substituted with one or more substituents Q. In certain embodiments, $R^{2b}$ is 5-membered heteroaryl-C$_{1-6}$ alkyl, where the alkyl and heteroaryl are each optionally substituted with one or more substituents Q. In certain embodiments, $R^{2b}$ is 6-membered heteroaryl-C$_{1-6}$ alkyl, where the alkyl and heteroaryl are each optionally substituted with one or more substituents Q. In certain embodiments, $R^{2b}$ is (pyrazol-3-yl)methyl, (pyrazol-4-yl)methyl, (1-methylpyrazol-4-yl)methyl, (3-methylpyrazol-4-yl)methyl, 1-(pyrazol-4-yl)ethyl, or (pyridin-3-yl)methyl. In certain embodiments, $R^{2b}$ is C$_{2-6}$ alkenyl, optionally substituted with one or more substituents Q. In certain embodiments, $R^{2b}$ is C$_{2-6}$ alkynyl, optionally substituted with one or more substituents Q. In certain embodiments, $R^{2b}$ is pent-4-ynyl. In certain embodiments, $R^{2b}$ is C$_{3-12}$ cycloalkyl, optionally substituted with one or more substituents Q. In certain embodiments, $R^{2b}$ is C$_{6-14}$ aryl, optionally substituted with one or more substituents Q. In certain embodiments, $R^{2b}$ is phenyl, optionally substituted with one or more substituents Q. In certain embodiments, $R^{2b}$ is C$_{7-15}$ aralkyl, optionally substituted with one or more substituents Q. In certain embodiments, $R^{2b}$ is benzyl, optionally substituted with one or more substituents Q. In certain embodiments, $R^{2b}$ is heteroaryl, optionally substituted with one or more substituents Q. In certain embodiments, $R^{2b}$ is heterocyclyl, optionally substituted with one or more substituents Q.

In certain embodiments, $R^{2b}$ is —C(O)R$^{1a}$, wherein $R^{1a}$ is as defined herein. In certain embodiments, $R^{2b}$ is —C(O)R$^{1a}$, wherein $R^{1a}$ is C$_{1-6}$ alkyl, C$_{2-6}$ alkyl, C$_{2-6}$ alkynyl, or heteroaryl, each of which is optionally substituted with one or more substituents Q. In certain embodiments, $R^{2b}$ is 2-methoxyacetyl, pentanoyl, but-3-ynylcarbonyl, or (pyrazol-4-yl)carbonyl. In certain embodiments, $R^{2b}$ is —C(O)OR$^{1a}$, wherein $R^{1a}$ is as defined herein. In certain embodiments, $R^{2b}$ is —C(O)NR$^{1b}$R$^{1c}$, wherein $R^{1b}$ and $R^{1c}$ are each as defined herein. In certain embodiments, $R^{2b}$ is —C(O)SR$^{1a}$, wherein $R^{1a}$ is as defined herein. In certain embodiments, $R^{2b}$ is —C(NR$^{1a}$)NR$^{1b}$R$^{1c}$, wherein $R^{1a}$, $R^{1b}$, and $R^{1c}$ are each as defined herein. In certain embodiments, $R^{2b}$ is —C(S)R$^{1a}$, wherein $R^{1a}$ is as defined herein. In certain embodiments, $R^{2b}$ is —C(S)OR$^{1a}$, wherein $R^{1a}$ is as defined herein. In certain embodiments, $R^{2b}$ is —C(S)NR$^{1b}$R$^{1c}$, wherein $R^{1b}$ and $R^{1c}$ are each as defined herein. In certain embodiments, $R^{2b}$ is —OR$^{1a}$, wherein $R^{1a}$ is as defined herein. In certain embodiments, $R^{2b}$ is —OC(O)R$^{1a}$, wherein $R^{1a}$ is as defined herein. In certain embodiments, $R^{2b}$ is —OC(O)OR$^{1a}$, wherein $R^{1a}$ is as defined herein. In certain embodiments, $R^{2b}$ is —OC(O)NR$^{1b}$R$^{1c}$, wherein $R^{1b}$ and $R^{1c}$ are each as defined herein. In certain embodiments, $R^{2b}$ is —OC(O)SR$^{1a}$, wherein $R^{1a}$ is as defined herein. In certain embodiments, $R^{2b}$ is —OC(=NR$^{1a}$)NR$^{1b}$R$^{1c}$, wherein $R^{1a}$, $R^{1b}$, and $R^{1c}$ are each as defined herein. In certain embodiments, $R^{2b}$ is —OC(S)R$^{1a}$, wherein $R^{1a}$ is as defined herein. In certain embodiments, $R^{2b}$ is —OC(S)OR$^{1a}$, wherein $R^{1a}$ is as defined herein. In certain embodiments, $R^{2b}$ is —OC(S)NR$^{1b}$R$^{1c}$, wherein $R^{1b}$ and $R^{1c}$ are each as defined herein. In certain embodiments, $R^{2b}$ is —OS(O)R$^{1a}$, wherein $R^{1a}$ is as defined herein. In certain embodiments, $R^{2b}$ is —OS(O)$_2$R$^{1a}$, wherein $R^{1a}$ is as defined herein. In certain embodiments, $R^{2b}$ is —OS(O)NR$^{1b}$R$^{1c}$, wherein $R^{1b}$ and $R^{1c}$ are each as defined herein. In certain embodiments, $R^{2b}$ is —OS(O)$_2$NR$^{1b}$R$^{1c}$, wherein $R^{1b}$ and $R^{1c}$ are each as defined herein. In certain embodiments, $R^{2b}$ is —NR$^{1b}$R$^{1c}$, wherein $R^{1b}$ and $R^{1c}$ are each as defined herein. In certain embodiments, $R^{2b}$ is —NR$^{1a}$C(O)R$^{1d}$, wherein $R^{1a}$ and $R^{1d}$ are each as defined herein. In certain embodiments, $R^{2b}$ is —NR$^{1a}$C(O)OR$^{1d}$, wherein $R^{1a}$ and $R^{1d}$ are each as defined herein. In certain embodiments, $R^{2b}$ is —NR$^{1a}$C(O)NR$^{1b}$R$^{1c}$, wherein $R^{1a}$, $R^{1b}$, and $R^{1c}$ are each as defined herein. In certain embodiments, $R^{2b}$ is —NR$^{1a}$C(O)SR$^{1d}$, wherein $R^{1a}$ and $R^{1d}$ are each as defined herein. In certain embodiments, $R^{2b}$ is —NR$^{1a}$C(=NR$^{1d}$)NR$^{1b}$R$^{1c}$, wherein $R^{1a}$, $R^{1b}$, $R^{1c}$, and $R^{1d}$ are each as defined herein. In certain embodiments, $R^{2b}$ is —NR$^{1a}$C(S)R$^{1d}$, wherein $R^{1a}$ and $R^{1d}$ are each as defined herein. In certain embodiments, $R^{2b}$ is —NR$^{1a}$C(S)OR$^{1d}$, wherein $R^{1a}$ and $R^{1d}$ are each as defined herein. In certain embodiments, $R^{2b}$ is —NR$^{1a}$C(S)NR$^{1b}$R$^{1c}$, wherein $R^{1a}$, $R^{1b}$, and $R^{1c}$ are each as defined herein. In certain embodiments, $R^{2b}$ is —NR$^{1a}$S(O)R$^{1d}$, wherein $R^{1a}$ and $R^{1d}$ are each as defined herein. In certain embodiments, $R^{2b}$ is —NR$^{1a}$S(O)$_2$R$^{1d}$, wherein $R^{1a}$ and $R^{1d}$ are each as defined herein. In certain embodiments, $R^{2b}$ is —NR$^{1a}$S(O)NR$^{1b}$R$^{1c}$, wherein $R^{1a}$, $R^{1b}$, and $R^{1c}$ are each as defined herein. In certain embodiments, $R^{2b}$ is —NR$^{1a}$S(O)$_2$NR$^{1b}$R$^{1c}$, wherein $R^{1a}$, $R^{1b}$, and $R^{1c}$ are each as defined herein. In certain embodiments, $R^{2b}$ is —S(O)R$^{1a}$, wherein $R^{1a}$ is as defined herein. In certain embodiments, $R^{2b}$ is —S(O)$_2$R$^{1a}$, wherein $R^{1a}$ is as defined herein. In certain embodiments, $R^{2b}$ is —S(O)NR$^{1b}$R$^{1c}$, wherein $R^{1b}$ and $R^{1c}$ are each as defined herein. In certain embodiments, $R^{2b}$ is —S(O)$_2$NR$^{1b}$R$^{1c}$, wherein $R^{1b}$ and $R^{1c}$ are each as defined herein.

In certain embodiments, $R^{2a}$ and $R^{2b}$ together with the N atom to which they are attached form heteroaryl, optionally substituted with one or more substituents Q. In certain embodiments, $R^{2a}$ and $R^{2b}$ together with the N atom to which they are attached form 5-membered heteroaryl, optionally substituted with one or more substituents Q. In certain embodiments, $R^{2a}$ and $R^{2b}$ together with the N atom to which they are attached form heterocyclyl, optionally substituted with one or more substituents Q. In certain embodiments, $R^{2a}$ and $R^{2b}$ together with the N atom to which they are attached form 5-membered heterocyclyl, optionally substituted with one or more substituents Q. In certain embodiments, $R^{2a}$ and $R^{2b}$ together with the N atom to which they are attached form azetidinyl, pyrrolidinyl, piperidinyl, morpholinyl, pyrazolyl, or imidazolyl, each of which is independently and optionally substituted with one or more substituents Q. In certain embodiments, $R^{2a}$ and $R^{2b}$ together with the N atom to which they are attached form azetidin-1-yl, pyrrolidin-1-yl, piperidine-1-yl, morpholin-4-yl, pyrazol-1-yl, 3-methylpyrazol-1-yl, 4-methylpyrazol-1-yl, 5-methylpyrazol-1-yl, or imidazol-1-yl.

In certain embodiments, $R^{2c}$ is hydrogen. In certain embodiments, $R^{2c}$ is deuterium. In certain embodiments, $R^{2c}$ is cyano. In certain embodiments, $R^{2c}$ is C$_{1-6}$ alkyl, optionally substituted with one or more substituents Q. In certain embodiments, $R^{2c}$ is methyl, optionally substituted with one or more substituents Q. In certain embodiments, $R^{2c}$ is methyl or hydroxymethyl. In certain embodiments, $R^{2c}$ is C$_{2-6}$ alkenyl, optionally substituted with one or more substituents Q. In certain embodiments, $R^{2c}$ is $C_{2-6}$ alkynyl, optionally substituted with one or more substituents Q. In certain embodiments, $R^{2c}$ is $C_{3-12}$ cycloalkyl, optionally substituted with one or more substituents Q. In certain embodiments, $R^{2c}$ is $C_{6-14}$ aryl, optionally substituted with one or more substituents Q. In certain embodiments, $R^{2c}$ is $C_{7-15}$ aralkyl, optionally substituted with one or more substituents Q. In certain embodiments, $R^{2c}$ is heteroaryl, optionally substituted with one or more substituents Q. In certain embodiments, $R^{2c}$ is heterocyclyl, optionally substituted with one or more substituents Q.

In certain embodiments, $R^{2a}$ and $R^{2c}$ together with the C and N atoms to which they are attached form heterocyclyl, optionally substituted with one or more substituents Q. In certain embodiments, $R^{2a}$ and $R^{2c}$ together with the C and N atoms to which they are attached form 5-membered heterocyclyl, optionally substituted with one or more substituents Q. In certain embodiments, $R^{2a}$ and $R^{2c}$ together with the C and N atoms to which they are attached form pyrrolidin-5,5-ylene-2-one, imidazolidin-5,5-ylene-2,4-dione, or oxazolidin-4,4-ylene-2-one.

In certain embodiments, $R^{2d}$ is hydrogen. In certain embodiments, $R^{2d}$ is deuterium. In certain embodiments, $R^{2d}$ is cyano. In certain embodiments, $R^{2d}$ is $C_{1-6}$ alkyl, optionally substituted with one or more substituents Q. In certain embodiments, $R^{2d}$ is $C_{2-6}$ alkenyl, optionally substituted with one or more substituents Q. In certain embodiments, $R^{2d}$ is $C_{2-6}$ alkynyl, optionally substituted with one or more substituents Q. In certain embodiments, $R^{2d}$ is $C_{3-12}$ cycloalkyl, optionally substituted with one or more substituents Q. In certain embodiments, $R^{2d}$ is $C_{6-14}$ aryl, optionally substituted with one or more substituents Q. In certain embodiments, $R^{2d}$ is $C_{7-15}$ aralkyl, optionally substituted with one or more substituents Q. In certain embodiments, $R^{2d}$ is heteroaryl, optionally substituted with one or more substituents Q. In certain embodiments, $R^{2d}$ is heterocyclyl, optionally substituted with one or more substituents Q.

In certain embodiments, $R^{2c}$ and $R^{2d}$ are linked together to form —O—. In certain embodiments, $R^{2c}$ and $R^{2d}$ are linked together to form $C_{1-6}$ alkylene, optionally substituted with one or more substituents Q. In certain embodiments, $R^{2c}$ and $R^{2d}$ are linked together to form methylene or ethylene, each optionally substituted with one or more substituents Q. In certain embodiments, $R^{2c}$ and $R^{2d}$ are linked together to form methylene or eth-1,2-ylene, each optionally substituted with one or more substituents Q. In certain embodiments, $R^{2c}$ and $R^{2d}$ are linked together to form $C_{1-6}$ heteroalkylene, optionally substituted with one or more substituents Q. In certain embodiments, $R^{2c}$ and $R^{2d}$ are linked together to form $C_{2-6}$ alkenylene, optionally substituted with one or more substituents Q. In certain embodiments, $R^{2c}$ and $R^{2d}$ are linked together to form $C_{2-6}$ alkynylene, optionally substituted with one or more substituents Q.

In certain embodiments, $R^{6a}$ is hydrogen. In certain embodiments, $R^{6a}$ is deuterium. In certain embodiments, $R^{6a}$ is cyano. In certain embodiments, $R^{6a}$ is halo. In certain embodiments, $R^{6a}$ is fluoro. In certain embodiments, $R^{6a}$ is chloro. In certain embodiments, $R^{6a}$ is nitro. In certain embodiments, $R^{6a}$ is $C_{1-6}$ alkyl, optionally substituted with one or more substituents Q. In certain embodiments, $R^{6a}$ is methyl, optionally substituted with one or more substituents Q. In certain embodiments, $R^{6a}$ is $C_{2-6}$ alkenyl, optionally substituted with one or more substituents Q. In certain embodiments, $R^{6a}$ is $C_{2-6}$ alkynyl, optionally substituted with one or more substituents Q. In certain embodiments, $R^{6a}$ is $C_{3-12}$ cycloalkyl, optionally substituted with one or more substituents Q. In certain embodiments, $R^{6a}$ is $C_{6-14}$ aryl, optionally substituted with one or more substituents Q. In certain embodiments, $R^{6a}$ is $C_{7-15}$ aralkyl, optionally substituted with one or more substituents Q. In certain embodiments, $R^{6a}$ is heteroaryl, optionally substituted with one or more substituents Q. In certain embodiments, $R^{6a}$ is heterocyclyl, optionally substituted with one or more substituents Q. In certain embodiments, $R^{6a}$ is 4- to 6-membered heterocyclyl, optionally substituted with one or more substituents Q. In certain embodiments, $R^{6a}$ is oxetanyl, tetrahydrofuryl, or tetrahydropyranyl, each optionally substituted with one or more substituents Q.

In certain embodiments, $R^{6a}$ is —C(O)$R^{1a}$, wherein $R^{1a}$ is as defined herein. In certain embodiments, $R^{6a}$ is —C(O)O$R^{1a}$, wherein $R^{1a}$ is as defined herein. In certain embodiments, $R^{6a}$ is —C(O)N$R^{1b}R^{1c}$, wherein $R^{1b}$ and $R^{1c}$ are each as defined herein. In certain embodiments, $R^{6a}$ is —C(O)S$R^{1a}$, wherein $R^{1a}$ is as defined herein. In certain embodiments, $R^{6a}$ is —C(N$R^{1a}$)N$R^{1b}R^{1c}$, wherein $R^{1a}$, $R^{1b}$, and $R^{1c}$ are each as defined herein. In certain embodiments, $R^{6a}$ is —C(S)$R^{1a}$, wherein $R^{1a}$ is as defined herein. In certain embodiments, $R^{6a}$ is —C(S)O$R^{1a}$, wherein $R^{1a}$ is as defined herein. In certain embodiments, $R^{6a}$ is —C(S)N$R^{1b}R^{1c}$, wherein $R^{1b}$ and $R^{1c}$ are each as defined herein. In certain embodiments, $R^{6a}$ is —O$R^{1a}$, wherein $R^{1a}$ is as defined herein. In certain embodiments, $R^{6a}$ is —OH. In certain embodiments, $R^{6a}$ is —OC(O)$R^{1a}$, wherein $R^{1a}$ is as defined herein. In certain embodiments, $R^{6a}$ is —OC(O)O$R^{1a}$, wherein $R^{1a}$ is as defined herein. In certain embodiments, $R^{6a}$ is —OC(O)N$R^{1b}R^{1c}$, wherein $R^{1b}$ and $R^{1c}$ are each as defined herein. In certain embodiments, $R^{6a}$ is —OC(O)S$R^{1a}$, wherein $R^{1a}$ is as defined herein. In certain embodiments, $R^{6a}$ is —OC(=N$R^{1a}$)N$R^{1b}R^{1c}$, wherein $R^{1a}$, $R^{1b}$, and $R^{1c}$ are each as defined herein. In certain embodiments, $R^{6a}$ is —OC(S)$R^{1a}$, wherein $R^{1a}$ is as defined herein. In certain embodiments, $R^{6a}$ is —OC(S)O$R^{1a}$, wherein $R^{1a}$ is as defined herein. In certain embodiments, $R^{6a}$ is —OC(S)N$R^{1b}R^{1c}$, wherein $R^{1b}$ and $R^{1c}$ are each as defined herein. In certain embodiments, $R^{6a}$ is —OS(O)$R^{1a}$, wherein $R^{1a}$ is as defined herein. In certain embodiments, $R^{6a}$ is —OS(O)$_2R^{1a}$, wherein $R^{1a}$ is as defined herein. In certain embodiments, $R^{6a}$ is —OS(O)N$R^{1b}R^{1c}$, wherein $R^{1b}$ and $R^{1c}$ are each as defined herein. In certain embodiments, $R^{6a}$ is —OS(O)$_2$N$R^{1b}R^{1c}$, wherein $R^{1b}$ and $R^{1c}$ are each as defined herein. In certain embodiments, $R^{6a}$ is —N$R^{1b}R^{1c}$, wherein $R^{1b}$ and $R^{1c}$ are each as defined herein. In certain embodiments, $R^{6a}$ is —NH$_2$. In certain embodiments, $R^{6a}$ is —N$R^{1a}$C(O)$R^{1d}$, wherein $R^{1a}$ and $R^{1d}$ are each as defined herein. In certain embodiments, $R^{6a}$ is —N$R^{1a}$C(O)O$R^{1d}$, wherein $R^{1a}$ and $R^{1d}$ are each as defined herein. In certain embodiments, $R^{6a}$ is —N$R^{1a}$C(O)N$R^{1b}R^{1c}$, wherein $R^{1a}$, $R^{1b}$, and $R^{1c}$ are each as defined herein. In certain embodiments, $R^{6a}$ is —N$R^{1a}$C(O)S$R^{1d}$, wherein $R^{1a}$ and $R^{1d}$ are each as defined herein. In certain embodiments, $R^{6a}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{6a}$ is —N$R^{1a}$C(S)$R^{1d}$, wherein $R^{1a}$ and $R^{1d}$ are each as defined herein. In certain embodiments, $R^{6a}$ is —N$R^{1a}$C(S)O$R^{1d}$, wherein $R^{1a}$ and $R^{1d}$ are each as defined herein. In certain embodiments, $R^{6a}$ is —N$R^{1a}$C(S)N$R^{1b}R^{1c}$, wherein $R^{1a}$, $R^{1b}$, and $R^{1c}$ are each as defined herein. In certain embodiments, $R^{6a}$ is —N$R^{1a}$S(O)$R^{1d}$, wherein $R^{1a}$ and $R^{1d}$ are each as defined herein. In certain embodiments, $R^{6a}$ is —N$R^{1a}$S(O)$_2R^{1d}$, wherein $R^{1a}$ and $R^{1d}$ are each as defined herein. In certain embodiments, $R^{6a}$ is —N$R^{1a}$S(O)N$R^{1b}R^{1c}$, wherein $R^{1a}$, $R^{1b}$, and $R^{1c}$ are each as defined herein. In certain embodiments, $R^{6a}$ is —N$R^{1a}$S(O)$_2$N$R^{1b}R^{1c}$, wherein $R^{1a}$, $R^{1b}$, and $R^{1c}$ are each as defined herein. In certain embodiments, $R^{6a}$ is —$SR^{1a}$, wherein $R^{1a}$ is as defined herein. In certain embodiments, $R^{6a}$ is —$S(O)R^{1a}$, wherein $R^{1a}$ is as defined herein. In certain embodiments, $R^{6a}$ is —$S(O)_2R^{1a}$, wherein $R^{1a}$ is as defined herein. In certain embodiments, $R^{6a}$ is —$S(O)NR^{1b}R^{1c}$, wherein $R^{1b}$ and $R^{1c}$ are each as defined herein. In certain embodiments, $R^{6a}$ is —$S(O)_2NR^{1b}R^{1c}$, wherein $R^{1b}$ and $R^{1c}$ are each as defined herein.

In certain embodiments, $R^{6b}$ is hydrogen. In certain embodiments, $R^{6b}$ is deuterium. In certain embodiments, $R^{6b}$ is cyano. In certain embodiments, $R^{6b}$ is halo. In certain embodiments, $R^{6b}$ is fluoro. In certain embodiments, $R^{6b}$ is chloro. In certain embodiments, $R^{6b}$ is nitro. In certain embodiments, $R^{6b}$ is $C_{1-6}$ alkyl, optionally substituted with one or more substituents Q. In certain embodiments, $R^{6b}$ is methyl, optionally substituted with one or more substituents Q. In certain embodiments, $R^{6b}$ is $C_{2-6}$ alkenyl, optionally substituted with one or more substituents Q. In certain embodiments, $R^{6b}$ is $C_{2-6}$ alkynyl, optionally substituted with one or more substituents Q. In certain embodiments, $R^{6b}$ is $C_{3-12}$ cycloalkyl, optionally substituted with one or more substituents Q. In certain embodiments, $R^{6b}$ is $C_{6-14}$ aryl, optionally substituted with one or more substituents Q. In certain embodiments, $R^{6b}$ is $C_{7-15}$ aralkyl, optionally substituted with one or more substituents Q. In certain embodiments, $R^{6b}$ is heteroaryl, optionally substituted with one or more substituents Q. In certain embodiments, $R^{6b}$ is heterocyclyl, optionally substituted with one or more substituents Q. In certain embodiments, $R^{6b}$ is 4- to 6-membered heterocyclyl, optionally substituted with one or more substituents Q. In certain embodiments, $R^{6b}$ is oxetanyl, tetrahydrofuryl, or tetrahydropyranyl, each optionally substituted with one or more substituents Q.

In certain embodiments, $R^{6b}$ is —$C(O)R^{1a}$, wherein $R^{1a}$ is as defined herein. In certain embodiments, $R^{6b}$ is —$C(O)OR^{1a}$, wherein $R^{1a}$ is as defined herein. In certain embodiments, $R^{6b}$ is —$C(O)NR^{1b}R^{1c}$, wherein $R^{1b}$ and $R^{1c}$ are each as defined herein. In certain embodiments, $R^{6b}$ is —$C(O)SR^{1a}$, wherein $R^{1a}$ is as defined herein. In certain embodiments, $R^{6b}$ is —$C(NR^{1a})NR^{1b}R^{1c}$, wherein $R^{1a}$, $R^{1b}$, and $R^{1c}$ are each as defined herein. In certain embodiments, $R^{6b}$ is —$C(S)R^{1a}$, wherein $R^{1a}$ is as defined herein. In certain embodiments, $R^{6b}$ is —$C(S)OR^{1a}$, wherein $R^{1a}$ is as defined herein. In certain embodiments, $R^{6b}$ is —$C(S)NR^{1b}R^{1c}$, wherein $R^{1b}$ and $R^{1c}$ are each as defined herein. In certain embodiments, $R^{6b}$ is —$OR^{1a}$, wherein $R^{1a}$ is as defined herein. In certain embodiments, $R^{6b}$ is —OH. In certain embodiments, $R^{6b}$ is —$OC(O)R^{1a}$, wherein $R^{1a}$ is as defined herein. In certain embodiments, $R^{6b}$ is —$OC(O)OR^{1a}$, wherein $R^{1a}$ is as defined herein. In certain embodiments, $R^{6b}$ is —$OC(O)NR^{1b}R^{1c}$, wherein $R^{1b}$ and $R^{1c}$ are each as defined herein. In certain embodiments, $R^{6b}$ is —$OC(O)SR^{1a}$, wherein $R^{1a}$ is as defined herein. In certain embodiments, $R^{6b}$ is —$OC(=NR^{1a})NR^{1b}R^{1c}$, wherein $R^{1a}$, $R^{1b}$, and $R^{1c}$ are each as defined herein. In certain embodiments, $R^{6b}$ is —$OC(S)R^{1a}$, wherein $R^{1a}$ is as defined herein. In certain embodiments, $R^{6b}$ is —$OC(S)OR^{1a}$, wherein $R^{1a}$ is as defined herein. In certain embodiments, $R^{6b}$ is —$OC(S)NR^{1b}R^{1c}$, wherein $R^{1b}$ and $R^{1c}$ are each as defined herein. In certain embodiments, $R^{6b}$ is —$OS(O)R^{1a}$, wherein $R^{1a}$ is as defined herein. In certain embodiments, $R^{6b}$ is —$OS(O)_2R^{1a}$, wherein $R^{1a}$ is as defined herein. In certain embodiments, $R^{6b}$ is —$OS(O)NR^{1b}R^{1c}$, wherein $R^{1b}$ and $R^{1c}$ are each as defined herein. In certain embodiments, $R^{6b}$ is —$OS(O)_2NR^{1b}R^{1c}$, wherein $R^{1b}$ and $R^{1c}$ are each as defined herein. In certain embodiments, $R^{6b}$ is —$NR^{1b}R^{1c}$, wherein $R^{1b}$ and $R^{1c}$ are each as defined herein. In certain embodiments, $R^{6b}$ is —$NH_2$. In certain embodiments, $R^{6b}$ is —$NR^{1a}C(O)R^{1d}$, wherein $R^{1a}$ and $R^{1d}$ are each as defined herein. In certain embodiments, $R^{6b}$ is —$NR^{1a}C(O)OR^{1d}$, wherein $R^{1a}$ and $R^{1d}$ are each as defined herein. In certain embodiments, $R^{6b}$ is —$NR^{1a}C(O)NR^{1b}R^{1c}$, wherein $R^{1a}$, $R^{1b}$, and $R^{1c}$ are each as defined herein. In certain embodiments, $R^{6b}$ is —$NR^{1a}C(O)SR^{1d}$, wherein $R^{1a}$ and $R^{1d}$ are each as defined herein. In certain embodiments, $R^{6b}$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^{6b}$ is —$NR^{1a}C(S)R^{1d}$, wherein $R^{1a}$ and $R^{1d}$ are each as defined herein. In certain embodiments, $R^{6b}$ is —$NR^{1a}C(S)OR^{1d}$, wherein $R^{1a}$ and $R^{1d}$ are each as defined herein. In certain embodiments, $R^{6b}$ is —$NR^{1a}C(S)NR^{1b}R^{1c}$, wherein $R^{1a}$, $R^{1b}$, and $R^{1c}$ are each as defined herein. In certain embodiments, $R^{6b}$ is —$NR^{1a}S(O)R^{1d}$, wherein $R^{1a}$ and $R^{1d}$ are each as defined herein. In certain embodiments, $R^{6b}$ is —$NR^{1a}S(O)_2R^{1d}$, wherein $R^{1a}$ and $R^{1d}$ are each as defined herein. In certain embodiments, $R^{6b}$ is —$NR^{1a}S(O)NR^{1b}R^{1c}$, wherein $R^{1a}$, $R^{1b}$, and $R^{1c}$ are each as defined herein. In certain embodiments, $R^{6b}$ is —$NR^{1a}S(O)_2NR^{1b}R^{1c}$, wherein $R^{1a}$, $R^{1b}$, and $R^{1c}$ are each as defined herein. In certain embodiments, $R^{6b}$ is —$SR^{1a}$, wherein $R^{1a}$ is as defined herein. In certain embodiments, $R^{6b}$ is —$S(O)R^{1a}$, wherein $R^{1a}$ is as defined herein. In certain embodiments, $R^{6b}$ is —$S(O)_2R^{1a}$, wherein $R^{1a}$ is as defined herein. In certain embodiments, $R^{6b}$ is —$S(O)NR^{1b}R^{1c}$, wherein $R^{1b}$ and $R^{1c}$ are each as defined herein. In certain embodiments, $R^{6b}$ is —$S(O)_2NR^{1b}R^{1c}$, wherein $R^{1b}$ and $R^{1c}$ are each as defined herein.

In certain embodiments, $R^{6c}$ is hydrogen. In certain embodiments, $R^{6c}$ is deuterium. In certain embodiments, $R^{6c}$ is cyano. In certain embodiments, $R^{6c}$ is halo. In certain embodiments, $R^{6c}$ is fluoro. In certain embodiments, $R^{6c}$ is chloro. In certain embodiments, $R^{6c}$ is nitro. In certain embodiments, $R^{6c}$ is $C_{1-6}$ alkyl, optionally substituted with one or more substituents Q. In certain embodiments, $R^{6c}$ is methyl, optionally substituted with one or more substituents Q. In certain embodiments, $R^{6c}$ is methyl or trifluoromethyl. In certain embodiments, $R^{6c}$ is $C_{2-6}$ alkenyl, optionally substituted with one or more substituents Q. In certain embodiments, $R^{6c}$ is $C_{2-6}$ alkynyl, optionally substituted with one or more substituents Q. In certain embodiments, $R^{6c}$ is $C_{3-12}$ cycloalkyl, optionally substituted with one or more substituents Q. In certain embodiments, $R^{6c}$ is $C_{6-14}$ aryl, optionally substituted with one or more substituents Q. In certain embodiments, $R^{6c}$ is $C_{7-15}$ aralkyl, optionally substituted with one or more substituents Q. In certain embodiments, $R^{6c}$ is heteroaryl, optionally substituted with one or more substituents Q. In certain embodiments, $R^{6c}$ is heterocyclyl, optionally substituted with one or more substituents Q. In certain embodiments, $R^{6c}$ is 4- to 6-membered heterocyclyl, optionally substituted with one or more substituents Q. In certain embodiments, $R^{6c}$ is oxetanyl, tetrahydrofuryl, or tetrahydropyranyl, each optionally substituted with one or more substituents Q.

In certain embodiments, $R^{6c}$ is —$C(O)R^{1a}$, wherein $R^{1a}$ is as defined herein. In certain embodiments, $R^{6c}$ is —$C(O)OR^{1a}$, wherein $R^{1a}$ is as defined herein. In certain embodiments, $R^{6c}$ is —$C(O)NR^{1b}R^{1c}$, wherein $R^{1b}$ and $R^{1c}$ are each as defined herein. In certain embodiments, $R^{6c}$ is —$C(O)SR^{1a}$, wherein $R^{1a}$ is as defined herein. In certain embodiments, $R^{6c}$ is —$C(NR^{1a})NR^{1b}R^{1c}$, wherein $R^{1a}$, $R^{1b}$, and $R^{1c}$ are each as defined herein. In certain embodiments, $R^{6c}$ is —$C(S)R^{1a}$, wherein $R^{1a}$ is as defined herein. In certain embodiments, $R^{6c}$ is —$C(S)OR^{1a}$, wherein $R^{1a}$ is as defined herein. In certain embodiments, $R^{6c}$ is —$C(S)NR^{1b}R^{1c}$, wherein $R^{1b}$ and $R^{1c}$ are each as defined herein. In certain embodiments, $R^{6c}$ is —$OR^{1a}$, wherein $R^{1a}$ is as defined herein. In certain embodiments, $R^{6c}$ is —OH. In certain embodiments, $R^{6c}$ is —OC(O)$R^{1a}$, wherein $R^{1a}$ is as defined herein. In certain embodiments, $R^{6c}$ is —OC(O)O$R^{1a}$, wherein $R^{1a}$ is as defined herein. In certain embodiments, $R^{6c}$ is —OC(O)N$R^{1b}R^{1c}$, wherein $R^{1b}$ and $R^{1c}$ are each as defined herein. In certain embodiments, $R^{6c}$ is —OC(O)S$R^{1a}$, wherein $R^{1a}$ is as defined herein. In certain embodiments, $R^{6c}$ is —OC(=N$R^{1a}$)N$R^{1b}R^{1c}$, wherein $R^{1a}$, $R^{1b}$, and $R^{1c}$ are each as defined herein. In certain embodiments, $R^{6c}$ is —OC(S)$R^{1a}$, wherein $R^{1a}$ is as defined herein. In certain embodiments, $R^{6c}$ is —OC(S)O$R^{1a}$, wherein $R^{1a}$ is as defined herein. In certain embodiments, $R^{6c}$ is —OC(S)N$R^{1b}R^{1c}$, wherein $R^{1b}$ and $R^{1c}$ are each as defined herein. In certain embodiments, $R^{6c}$ is —OS(O)$R^{1a}$, wherein $R^{1a}$ is as defined herein. In certain embodiments, $R^{6c}$ is —OS(O)$_2$$R^{1a}$, wherein $R^{1a}$ is as defined herein. In certain embodiments, $R^{6c}$ is —OS(O)N$R^{1b}R^{1c}$, wherein $R^{1b}$ and $R^{1c}$ are each as defined herein. In certain embodiments, $R^{6c}$ is —OS(O)$_2$N$R^{1b}R^{1c}$, wherein $R^{1b}$ and $R^{1c}$ are each as defined herein. In certain embodiments, $R^{6c}$ is —N$R^{1b}R^{1c}$, wherein $R^{1b}$ and $R^{1c}$ are each as defined herein. In certain embodiments, $R^{6c}$ is —NH$_2$. In certain embodiments, $R^{6c}$ is —N$R^{1a}$C(O)$R^{1d}$, wherein $R^{1a}$ and $R^{1d}$ are each as defined herein. In certain embodiments, $R^{6c}$ is —N$R^{1a}$C(O)O$R^{1d}$, wherein $R^{1a}$ and $R^{1d}$ are each as defined herein. In certain embodiments, $R^{6c}$ is —N$R^{1a}$C(O)N$R^{1b}R^{1c}$, wherein $R^{1a}$, $R^{1b}$, and $R^{1c}$ are each as defined herein. In certain embodiments, $R^{6c}$ is —N$R^{1a}$C(O)S$R^{1d}$, wherein $R^{1a}$ and $R^{1d}$ are each as defined herein. In certain embodiments, $R^{6c}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{6c}$ is —N$R^{1a}$C(S)$R^{1d}$, wherein $R^{1a}$ and $R^{1d}$ are each as defined herein. In certain embodiments, $R^{6c}$ is —N$R^{1a}$C(S)O$R^{1d}$, wherein $R^{1a}$ and $R^{1d}$ are each as defined herein. In certain embodiments, $R^{6c}$ is —N$R^{1a}$C(S)N$R^{1b}R^{1c}$, wherein $R^{1a}$, $R^{1b}$, and $R^{1c}$ are each as defined herein. In certain embodiments, $R^{6c}$ is —N$R^{1a}$S(O)$R^{1d}$, wherein $R^{1a}$ and $R^{1d}$ are each as defined herein. In certain embodiments, $R^{6c}$ is —N$R^{1a}$S(O)$_2$$R^{1d}$, wherein $R^{1a}$ and $R^{1d}$ are each as defined herein. In certain embodiments, $R^{6c}$ is —N$R^{1a}$S(O)N$R^{1b}R^{1c}$, wherein $R^{1a}$, $R^{1b}$, and $R^{1c}$ are each as defined herein. In certain embodiments, $R^{6c}$ is —N$R^{1a}$S(O)$_2$N$R^{1b}R^{1c}$, wherein $R^{1a}$, $R^{1b}$, and $R^{1c}$ are each as defined herein. In certain embodiments, $R^{6c}$ is —S$R^{1a}$, wherein $R^{1a}$ is as defined herein. In certain embodiments, $R^{6c}$ is —S(O)$R^{1a}$, wherein $R^{1a}$ is as defined herein. In certain embodiments, $R^{6c}$ is —S(O)$_2$$R^{1a}$, wherein $R^{1a}$ is as defined herein. In certain embodiments, $R^{6c}$ is —S(O)N$R^{1b}R^{1c}$, wherein $R^{1b}$ and $R^{1c}$ are each as defined herein. In certain embodiments, $R^{6c}$ is —S(O)$_2$N$R^{1b}R^{1c}$, wherein $R^{1b}$ and $R^{1c}$ are each as defined herein.

In certain embodiments, $R^{6d}$ is hydrogen. In certain embodiments, $R^{6d}$ is deuterium. In certain embodiments, $R^{6d}$ is cyano. In certain embodiments, $R^{6d}$ is halo. In certain embodiments, $R^{6d}$ is fluoro. In certain embodiments, $R^{6d}$ is chloro. In certain embodiments, $R^{6d}$ is nitro. In certain embodiments, $R^{6d}$ is $C_{1-6}$ alkyl, optionally substituted with one or more substituents Q. In certain embodiments, $R^{6d}$ is methyl, optionally substituted with one or more substituents Q. In certain embodiments, $R^{6d}$ is $C_{2-6}$ alkenyl, optionally substituted with one or more substituents Q. In certain embodiments, $R^{6d}$ is $C_{2-6}$ alkynyl, optionally substituted with one or more substituents Q. In certain embodiments, $R^{6d}$ is $C_{3-12}$ cycloalkyl, optionally substituted with one or more substituents Q. In certain embodiments, $R^{6d}$ is $C_{6-14}$ aryl, optionally substituted with one or more substituents Q. In certain embodiments, $R^{6d}$ is $C_{7-15}$ aralkyl, optionally substituted with one or more substituents Q. In certain embodiments, $R^{6d}$ is heteroaryl, optionally substituted with one or more substituents Q. In certain embodiments, $R^{6d}$ is heterocyclyl, optionally substituted with one or more substituents Q. In certain embodiments, $R^{6d}$ is 4- to 6-membered heterocyclyl, optionally substituted with one or more substituents Q. In certain embodiments, $R^{6d}$ is oxetanyl, tetrahydrofuryl, or tetrahydropyranyl, each optionally substituted with one or more substituents Q.

In certain embodiments, $R^{6d}$ is —C(O)$R^{1a}$, wherein $R^{1a}$ is as defined herein. In certain embodiments, $R^{6d}$ is —C(O)O$R^{1a}$, wherein $R^{1a}$ is as defined herein. In certain embodiments, $R^{6d}$ is —C(O)N$R^{1b}R^{1c}$, wherein $R^{1b}$ and $R^{1c}$ are each as defined herein. In certain embodiments, $R^{6d}$ is —C(O)S$R^{1a}$, wherein $R^{1a}$ is as defined herein. In certain embodiments, $R^{6d}$ is —C(N$R^{1a}$)N$R^{1b}R^{1c}$, wherein $R^{1a}$, $R^{1b}$, and $R^{1c}$ are each as defined herein. In certain embodiments, $R^{6d}$ is —C(S)$R^{1a}$, wherein $R^{1a}$ is as defined herein. In certain embodiments, $R^{6d}$ is —C(S)O$R^{1a}$, wherein $R^{1a}$ is as defined herein. In certain embodiments, $R^{6d}$ is —C(S)N$R^{1b}R^{1c}$, wherein $R^{1b}$ and $R^{1c}$ are each as defined herein. In certain embodiments, $R^{6d}$ is —O$R^{1a}$, wherein $R^{1a}$ is as defined herein. In certain embodiments, $R^{6d}$ is —OH. In certain embodiments, $R^{6d}$ is —OC(O)$R^{1a}$, wherein $R^{1a}$ is as defined herein. In certain embodiments, $R^{6d}$ is —OC(O)O$R^{1a}$, wherein $R^{1a}$ is as defined herein. In certain embodiments, $R^{6d}$ is —OC(O)N$R^{1b}R^{1c}$, wherein $R^{1b}$ and $R^{1c}$ are each as defined herein. In certain embodiments, $R^{6d}$ is —OC(O)S$R^{1a}$, wherein $R^{1a}$ is as defined herein. In certain embodiments, $R^{6d}$ is —OC(=N$R^{1a}$)N$R^{1b}R^{1c}$, wherein $R^{1a}$, $R^{1b}$, and $R^{1c}$ are each as defined herein. In certain embodiments, $R^{6d}$ is —OC(S)$R^{1a}$, wherein $R^{1a}$ is as defined herein. In certain embodiments, $R^{6d}$ is —OC(S)O$R^{1a}$, wherein $R^{1a}$ is as defined herein. In certain embodiments, $R^{6d}$ is —OC(S)N$R^{1b}R^{1c}$, wherein $R^{1b}$ and $R^{1c}$ are each as defined herein. In certain embodiments, $R^{6d}$ is —OS(O)$R^{1a}$, wherein $R^{1a}$ is as defined herein. In certain embodiments, $R^{6d}$ is —OS(O)$_2$$R^{1a}$, wherein $R^{1a}$ is as defined herein. In certain embodiments, $R^{6d}$ is —OS(O)N$R^{1b}R^{1c}$, wherein $R^{1b}$ and $R^{1c}$ are each as defined herein. In certain embodiments, $R^{6d}$ is —OS(O)$_2$N$R^{1b}R^{1c}$, wherein $R^{1b}$ and $R^{1c}$ are each as defined herein. In certain embodiments, $R^{6d}$ is —N$R^{1b}R^{1c}$, wherein $R^{1b}$ and $R^{1c}$ are each as defined herein. In certain embodiments, $R^{6d}$ is —NH$_2$. In certain embodiments, $R^{6d}$ is —N$R^{1a}$C(O)$R^{1d}$, wherein $R^{1a}$ and $R^{1d}$ are each as defined herein. In certain embodiments, $R^{6d}$ is —N$R^{1a}$C(O)O$R^{1d}$, wherein $R^{1a}$ and $R^{1d}$ are each as defined herein. In certain embodiments, $R^{6d}$ is —N$R^{1a}$C(O)N$R^{1b}R^{1c}$, wherein $R^{1a}$, $R^{1b}$, and $R^{1c}$ are each as defined herein. In certain embodiments, $R^{6d}$ is —N$R^{1a}$C(O)S$R^{1d}$, wherein $R^{1a}$ and $R^{1d}$ are each as defined herein. In certain embodiments, $R^{6d}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{6d}$ is —N$R^{1a}$C(S)$R^{1d}$, wherein $R^{1a}$ and $R^{1d}$ are each as defined herein. In certain embodiments, $R^{6d}$ is —N$R^{1a}$C(S)O$R^{1d}$, wherein $R^{1a}$ and $R^{1d}$ are each as defined herein. In certain embodiments, $R^{6d}$ is —N$R^{1a}$C(S)N$R^{1b}R^{1c}$, wherein $R^{1a}$, $R^{1b}$, and $R^{1c}$ are each as defined herein. In certain embodiments, $R^{6d}$ is —N$R^{1a}$S(O)$R^{1d}$, wherein $R^{1a}$ and $R^{1d}$ are each as defined herein. In certain embodiments, $R^{6d}$ is —N$R^{1a}$S(O)$_2$$R^{1d}$, wherein $R^{1a}$ and $R^{1d}$ are each as defined herein. In certain embodiments, $R^{6d}$ is —N$R^{1a}$S(O)N$R^{1b}R^{1c}$, wherein $R^{1a}$, $R^{1b}$, and $R^{1c}$ are each as defined herein. In certain embodiments, $R^{6d}$ is —N$R^{1a}$S(O)$_2$N$R^{1b}R^{1c}$, wherein $R^{1a}$, $R^{1b}$, and $R^{1c}$ are each as defined herein. In certain embodiments, $R^{6d}$ is —S$R^{1a}$, wherein $R^{1a}$ is as defined herein. In certain embodiments, $R^{6d}$ is —S(O)$R^{1a}$, wherein $R^{1a}$ is as defined herein. In certain embodiments, $R^{6d}$ is —S(O)$_2$$R^{1a}$, wherein $R^{1a}$ is as defined herein. In certain embodiments, $R^{6d}$ is —S(O)NR$^{1b}$R$^{1c}$, wherein $R^{1b}$ and $R^{1c}$ are each as defined herein. In certain embodiments, $R^{6d}$ is —S(O)$_2$NR$^{1b}$R$^{1c}$, wherein $R^{1b}$ and $R^{1c}$ are each as defined herein.

In certain embodiments, U is —O—. In certain embodiments, U is =C(R$^4$)—, wherein R$^4$ is as defined herein. In certain embodiments, U is =C(H)—. In certain embodiments, U is =C(CH$_3$)—. In certain embodiments, U is =N—. In certain embodiments, U is —N(R$^5$)—, wherein R$^5$ is as defined herein. In certain embodiments, U is —N(H)—. In certain embodiments, U is —N(CH$_3$)—.

In certain embodiments, V is —O—. In certain embodiments, V is =C(R$^4$)—, wherein R$^4$ is as defined herein. In certain embodiments, V is =C(H)—. In certain embodiments, V is =C(CH$_3$)—. In certain embodiments, V is =N—. In certain embodiments, V is —N(R$^5$)—, wherein R$^5$ is as defined herein. In certain embodiments, V is —N(H)—. In certain embodiments, V is —N(CH$_3$)—.

In certain embodiments, W is =C(R$^6$)—, wherein R$^6$ is as defined herein. In certain embodiments, W is =C(H)—, =C(F)—, =C(Cl)—, =C(CH$_3$)—, =C(CF$_3$)—, =C(OH)—, or =C(NH$_2$)—. In certain embodiments, W is =N—. In certain embodiments, W is —NR$^7$—, wherein R$^7$ is as defined herein. In certain embodiments, W is —NH—. In certain embodiments, W is —O—. In certain embodiments, W is —S—.

In certain embodiments, X is =C(R$^6$)—, wherein R$^6$ is as defined herein. In certain embodiments, X is =C(H)—, =C(F)—, =C(Cl)—, =C(CH$_3$)—, =C(CF$_3$)—, =C(OH)—, or =C(NH$_2$)—. In certain embodiments, X is =N—. In certain embodiments, X is —NR$^7$—, wherein R$^7$ is as defined herein. In certain embodiments, X is —NH—. In certain embodiments, X is —O—. In certain embodiments, X is —S—.

In certain embodiments, Y is =C(R$^6$)—, wherein R$^6$ is as defined herein. In certain embodiments, Y is =C(H)—, =C(F)—, =C(Cl)—, =C(CH$_3$)—, =C(CF$_3$)—, =C(OH)—, or =C(NH$_2$)—. In certain embodiments, Y is =N—. In certain embodiments, Y is a bond.

In certain embodiments, Z is =C(R$^6$)—, wherein R$^6$ is as defined herein. In certain embodiments, Z is =C(H)—, =C(F)—, =C(Cl)—, =C(CH$_3$)—, =C(CF$_3$)—, =C(OH)—, or =C(NH$_2$)—. In certain embodiments, Z is =N—. In certain embodiments, Z is —NR$^7$—, wherein R$^7$ is as defined herein. In certain embodiments, Z is —NH—. In certain embodiments, Z is —O—. In certain embodiments, Z is —S—.

In certain embodiments, a compound provided herein is deuterium-enriched. In certain embodiments, a compound provided herein is carbon-13 enriched. In certain embodiments, a compound provided herein is carbon-14 enriched. In certain embodiments, a compound provided herein contains one or more less prevalent isotopes for other elements, including, but not limited to, $^{16}$N for nitrogen; $^{17}$O or $^{18}$O for oxygen, and $^{33}$S, $^{34}$S, or $^{37}$S for sulfur.

In certain embodiments, a compound provided herein has an isotopic enrichment factor of no less than about 6, no less than about 10, no less than about 20, no less than about 30, no less than about 40, no less than about 60, no less than about 70, no less than about 70, no less than about 80, no less than about 90, no less than about 100, no less than about 200, no less than about 600, no less than about 1,000, no less than about 2,000, no less than about 6,000, or no less than about 10,000. In any events, however, an isotopic enrichment factor for a specified isotope is no greater than the maximum isotopic enrichment factor for the specified isotope, which is the isotopic enrichment factor when a compound at a given position is 100% enriched with the specified isotope. Thus, the maximum isotopic enrichment factor is different for different isotopes. The maximum isotopic enrichment factor is 7410 for deuterium and 90 for carbon-13.

In certain embodiments, a compound provided herein has a deuterium enrichment factor of no less than about 74 (about 1% deuterium enrichment), no less than about 130 (about 2% deuterium enrichment), no less than about 320 (about 6% deuterium enrichment), no less than about 740 (about 10% deuterium enrichment), no less than about 1,300 (about 20% deuterium enrichment), no less than about 3,200 (about 60% deuterium enrichment), no less than about 4,800 (about 76% deuterium enrichment), no less than about 6,130 (about 80% deuterium enrichment), no less than about 6,460 (about 86% deuterium enrichment), no less than about 6,770 (about 90% deuterium enrichment), no less than about 7,090 (about 96% deuterium enrichment), no less than about 7,220 (about 97% deuterium enrichment), no less than about 7,280 (about 98% deuterium enrichment), no less than about 7,360 (about 99% deuterium enrichment), or no less than about 7,380 (about 99.6% deuterium enrichment). The deuterium enrichment can be determined using conventional analytical methods known to one of ordinary skill in the art, including mass spectrometry and nuclear magnetic resonance spectroscopy.

In certain embodiments, a compound provided herein has a carbon-13 enrichment factor of no less than about 1.8 (about 2% carbon-13 enrichment), no less than about 4.6 (about 6% carbon-13 enrichment), no less than about 9 (about 10% carbon-13 enrichment), no less than about 18 (about 20% carbon-13 enrichment), no less than about 46 (about 60% carbon-13 enrichment), no less than about 78 (about 76% carbon-13 enrichment), no less than about 72 (about 80% carbon-13 enrichment), no less than about 77 (about 86% carbon-13 enrichment), no less than about 81 (about 90% carbon-13 enrichment), no less than about 87 (about 96% carbon-13 enrichment), no less than about 87 (about 97% carbon-13 enrichment), no less than about 88 (about 98% carbon-13 enrichment), no less than about 89 (about 99% carbon-13 enrichment), or no less than about 90 (about 99.6% carbon-13 enrichment). The carbon-13 enrichment can be determined using conventional analytical methods known to one of ordinary skill in the art, including mass spectrometry and nuclear magnetic resonance spectroscopy.

In certain embodiments, at least one of the atoms of a compound provided herein, as specified as isotopically enriched, has isotopic enrichment of no less than about 1%, no less than about 2%, no less than about 6%, no less than about 10%, no less than about 20%, no less than about 60%, no less than about 70%, no less than about 80%, no less than about 90%, or no less than about 98%. In certain embodiments, the atoms of a compound provided herein, as specified as isotopically enriched, have isotopic enrichment of no less than about 10%, no less than about 2%, no less than about 6%, no less than about 10%, no less than about 20%, no less than about 60%, no less than about 70%, no less than about 80%, no less than about 90%, or no less than about 98%. In any events, the isotopic enrichment of the isotopically enriched atom of a compound provided herein is no less than the natural abundance of the isotope specified.

In certain embodiments, at least one of the atoms of a compound provided herein, as specified as deuterium-enriched, has deuterium enrichment of no less than about 1%, no less than about 2%, no less than about 6%, no less than about 10%, no less than about 20%, no less than about 60%, no less than about 70%, no less than about 80%, no less than about 90%, or no less than about 98%. In certain embodiments, the atoms of a compound provided herein, as specified as deuterium-enriched, have deuterium enrichment of no less than about 10%, no less than about 2%, no less than about 6%, no less than about 10%, no less than about 20%, no less than about 60%, no less than about 70%, no less than about 80%, no less than about 90%, or no less than about 98%.

In certain embodiments, at least one of the atoms of a compound provided herein, as specified as $^{13}$C-enriched, has carbon-13 enrichment of no less than about 2%, no less than about 6%, no less than about 10%, no less than about 20%, no less than about 60%, no less than about 70%, no less than about 80%, no less than about 90%, or no less than about 98%. In certain embodiments, the atoms of a compound provided herein, as specified as $^{13}$C-enriched, have carbon-13 enrichment of no less than about 1%, no less than about 2%, no less than about 6%, no less than about 10%, no less than about 20%, no less than about 60%, no less than about 70%, no less than about 80%, no less than about 90%, or no less than about 98%.

In certain embodiments, a compound provided herein is isolated or purified. In certain embodiments, a compound provided herein has a purity of at least about 60%, at least about 70%, at least about 80%, at least about 90%, at least about 96%, at least about 98%, at least about 99%, or at least about 99.6% by weight.

The compounds provided herein are intended to encompass all possible stereoisomers, unless a particular stereochemistry is specified. Where a compound provided herein contains an alkenyl group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

A compound provided herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

In certain embodiments, the compounds provided herein are inhibitors of a casein kinase 1. In certain embodiments, the compounds provided herein are inhibitors of casein kinase 1α (CK1α). In certain embodiments, the compounds provided herein are selective inhibitors of casein kinase 1α (CK1α). In certain embodiments, the compounds provided herein are inhibitors of human casein kinase 1α (CK1α). In certain embodiments, the compounds provided herein are selective inhibitors of human casein kinase 1α (CK1α). The CK1α inhibitory activity of the compounds provided herein are determined according to the procedures described in International Publication No. WO 2017/021970, the disclosure of which is incorporated herein by reference in its entirety.

When a compound provided herein contains an acidic or basic moiety, it can also be provided as a pharmaceutically acceptable salt (See, Berge et al., *J. Pharm. Sci.* 1977, 77, 1-19; and "Handbook of Pharmaceutical Salts, Properties, and Use," Stahl and Wermuth, Ed.; Wiley-VCH and VHCA, Zurich, 2011).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,6-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid. In certain embodiments, the compounds provided herein are hydrochloride salts.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of a compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1972, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1986; Wang et al., *Curr. Pharm. Design* 1999, 6, 276-287; Pauletti et al., *Adv. Drug. Delivery Rev.* 1997, 27, 236-267; Mizen et al., *Pharm. Biotech.* 1998, 11, 346-376; Gaignault et al., *Pract. Med. Chem.* 1997, 771-797; Asghamejad in "Transport Processes in Pharmaceutical Systems," Amidon et al., Ed., *Marcell Dekker*, 186-218, 2000; Balant et al., *Eur. J. Drug Metab. Pharmacokinet.* 1990, 16, 143-63; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 87, 1-39; Bundgaard, *Controlled Drug Delivery* 1987, 17, 179-97; Bundgaard, *Adv. Drug Delivery Rev.* 1992, 8, 1-38; Fleisher et al., *Adv. Drug Delivery Rev.* 1997, 19, 116-130; Fleisher et al., *Methods Enzymol.* 1986, 112, 370-381; Farquhar et al., *J. Pharm. Sci.* 1983, 72, 324-326; Freeman et al., *J. Chem. Soc., Chem. Commun.* 1991, 876-877; Friis and Bundgaard, *Eur. J Pharm. Sci.* 1997, 4, 49-69; Gangwar et al., *Des. Biopharm. Prop. Prodrugs Analogs,* 1977, 409-421; Nathwani and Wood, Drugs 1993, 46, 877-94; Sinhababu and Thakker, *Adv. Drug Delivery Rev.* 1997, 19, 241-273; Stella et al., *Drugs* 1986, 29, 466-73; Tan et al., *Adv. Drug Delivery Rev.* 1999, 39, 117-161; Taylor, *Adv. Drug Delivery Rev.* 1997, 19, 131-148; Valentino and Borchardt, *Drug Discovery Today* 1997, 2, 148-166; Wiebe and Knaus, *Adv. Drug Delivery Rev.* 1999, 39, 73-80; and Waller et al., *Br. J. Clin. Pharmac.* 1989, 28, 497-607.

Methods of Synthesis

The compounds provided herein can be prepared, isolated, or obtained by any method known to one of ordinary skill in the art. In certain embodiments, a compound of Formula II is synthesized as shown in Scheme I, wherein L is chloro, bromo, iodo, or —OSO²R$^{1a}$; and R$^1$, R$^3$, R$^{1a}$, R$^{2a}$, R$^{2b}$, R$^{2c}$, R$^{2d}$, U, V, W, X, Y, and Z are each as defined herein. Compound I-1 is coupled with compound I-2, for example, under the Suzuki coupling conditions, to form a compound of Formula II.

Scheme I

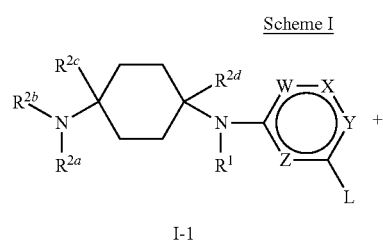

I-1

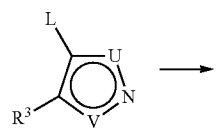

I-2

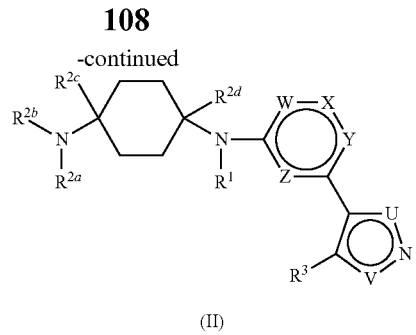

(II)

In certain embodiments, a compound of Formula II is synthesized as shown in Scheme II, wherein R$^1$, R$^3$, R$^{2a}$, R$^{2b}$, R$^{2c}$, R$^{2d}$, L, U, V, W, X, Y, and Z are each as defined herein. Compound I-3 is coupled with compound I-4, for example, under the Suzuki coupling conditions, to form a compound of Formula II.

Scheme II

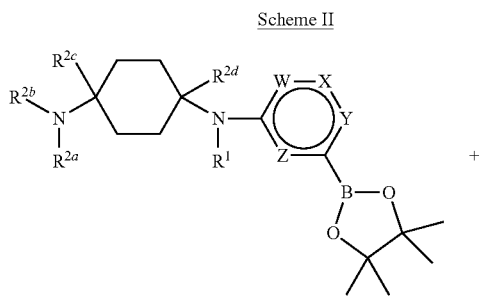

(II)

In certain embodiments, a compound of Formula IA is synthesized as shown in Scheme III, wherein L is chloro, bromo, iodo, or —OSO²R$^{1a}$; and R$^1$, R$^3$, R$^4$, R$^5$, R$^{1a}$, R$^{2a}$, R$^{2b}$, R$^{2c}$, R$^{2d}$, W, X, Y, and Z are each as defined herein. Compound IA-1 is coupled with compound IA-2, for example, under the Suzuki coupling conditions, to form a compound of Formula IA.

Scheme III

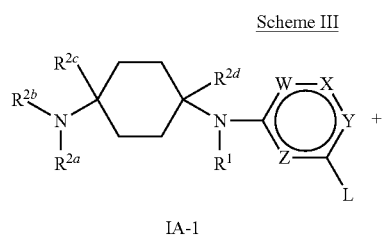

IA-1

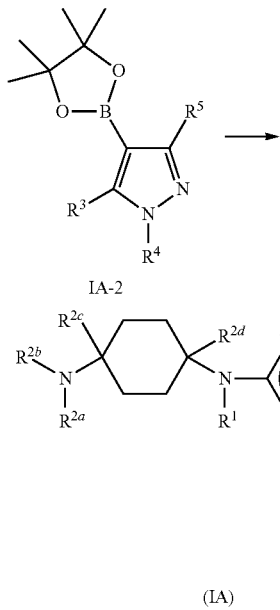

IA-2

(IA)

In certain embodiments, a compound of Formula IA is synthesized as shown in Scheme IV, wherein $R^1$, $R^3$, $R^4$, $R^5$, $R^{2a}$, $R^{2b}$, $R^{2c}$, $R^{2d}$, L, W, X, Y, and Z are each as defined herein. Compound IA-3 is coupled with compound IA-4, for example, under the Suzuki coupling conditions, to form a compound of Formula IA.

Scheme IV

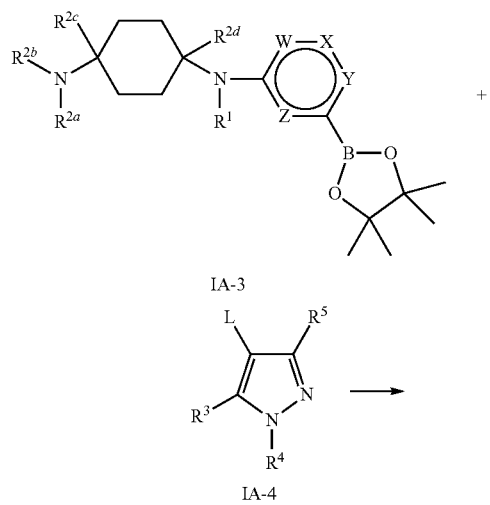

IA-3

IA-4

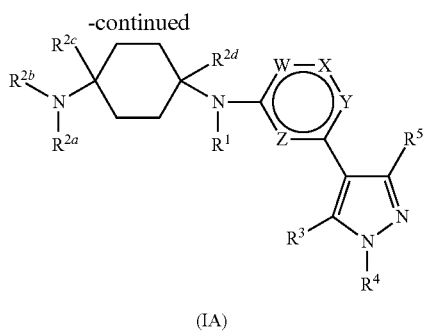

(IA)

Additional synthetic procedures for the synthesis of a compound provided herein include those described in International Publication No. WO 2017/021969, the disclosure of which is incorporated herein by reference in its entirety.

Pharmaceutical Compositions

In one embodiment, provided herein is a pharmaceutical composition comprising a compound provided herein, e.g., a compound of Formula I or IA, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and a pharmaceutically acceptable excipient.

In one embodiment, a pharmaceutical composition provided herein is formulated in a dosage form for oral administration, which comprises a compound provided herein, e.g., a compound of Formula I or IA, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; and a pharmaceutically acceptable excipient.

In another embodiment, a pharmaceutical composition provided herein is formulated in a dosage form for parenteral administration, which comprises a compound provided herein, e.g., a compound of Formula I or IA, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and a pharmaceutically acceptable excipient. In one embodiment, a pharmaceutical composition provided herein is formulated in a dosage form for intravenous administration. In another embodiment, a pharmaceutical composition provided herein is formulated in a dosage form for intramuscular administration. In yet another embodiment, a pharmaceutical composition provided herein is formulated in a dosage form for subcutaneous administration.

In yet another embodiment, a pharmaceutical composition provided herein is formulated in a dosage form for topical administration, which comprise a compound provided herein, e.g., a compound of Formula I or IA, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; and a pharmaceutically acceptable excipient.

In one embodiment, a pharmaceutical composition provided herein is formulated as a cream for topical administration, which comprises a compound provided herein, e.g., a compound of Formula I or IA, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and a pharmaceutically acceptable excipient. In one embodiment, the cream provided herein comprises a compound provided herein, e.g., a compound of Formula I or IA, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and one or more pharmaceutically acceptable excipients selected from the group consisting of water, octyldodecanol, mineral oil, stearyl alcohol, cocamide DEA, polysorbate 70, myristyl alcohol, sorbitan monostearate, lactic acid, and benzyl alcohol. In another embodiment, the cream provided herein comprises a compound provided herein, e.g., a compound of Formula I or IA, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and water, octyldodecanol, mineral oil, stearyl alcohol, cocamide DEA, polysorbate 70, myristyl alcohol, sorbitan monostearate, lactic acid, and benzyl alcohol.

In another embodiment, a pharmaceutical composition provided herein is formulated as a gel for topical administration, which comprises a compound provided herein, e.g., a compound of Formula I or IA, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and a pharmaceutically acceptable excipient. In one embodiment, the gel provided herein comprises a compound provided herein, e.g., a compound of Formula I or IA, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and one or more pharmaceutically acceptable excipients selected from the group consisting of water, isopropyl alcohol, octyldodecanol, dimethicone copolyol 190, carbomer 980, sodium hydroxide, and docusate sodium. In another embodiment, the gel provided herein comprises a compound provided herein, e.g., a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and water, isopropyl alcohol, octyldodecanol, dimethicone copolyol 190, carbomer 980, sodium hydroxide, and docusate sodium.

In yet another embodiment, a pharmaceutical composition provided herein is formulated as a lacquer for topical administration, which comprises a compound provided herein, e.g., a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient. In one embodiment, the lacquer provided herein comprises a compound provided herein, e.g., a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and one or more pharmaceutically acceptable excipients selected from the group consisting of ethyl acetate, isopropyl alcohol, and butyl monoester of poly(methylvinyl ether/maleic acid) in isopropyl alcohol.

The compound provided herein may be administered alone, or in combination with one or more other compounds provided herein. The pharmaceutical compositions that comprise a compound provided herein, e.g., a compound of Formula I or IA, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd Edition, Rathbone et al., Eds., Marcel Dekker, Inc.: New York, NY, 2008).

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1600); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-681, AVICEL-PH-106 (FMC Corp., Marcus Hook, PA); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 60 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.6 to about 16% or from about 1 to about 6% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, MD) and CAB-O-SIL® (Cabot Co. of Boston, MA); and mixtures thereof. The pharmaceutical compositions provided herein may contain about 0.1 to about 6% by weight of a lubricant.

Suitable glidants include, but are not limited to, colloidal silicon dioxide, CAB-O-SIL® (Cabot Co. of Boston, MA), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,246; 4,409,239; and 4,410,646. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-360-dimethyl ether, polyethylene glycol-660-dimethyl ether, polyethylene glycol-760-dimethyl ether, wherein 360, 660, and 760 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 7,360,468.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid.

Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, KS).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, CA), and BIOJECT™ (Bioject Medical Technologies Inc., Tualatin, OR).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (*theobroma* oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 60 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient (s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,846,770; 3,917,899; 3,637,809; 3,698,123; 4,008,719; 6,774,633; 6,069,696; 6,691,777; 6,120,648; 6,073,643; 6,739,477; 6,364,667; 6,739,480; 6,733,677; 6,739,108; 6,891,474; 6,922,367; 6,972,891; 6,980,946; 6,993,866; 7,046,830; 7,087,324; 7,113,943; 7,197,360; 7,248,373; 7,274,970; 7,277,981; 7,377,471; 7,419,971; 7,689,648; 7,713,368; and 7,799,600.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, NJ); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core that contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hy droxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, DE) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 6,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 6,712,069 and 6,798,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1996, 36, 1-21; Verma et al., *Drug Development and Industrial Pharmacy* 2000, 27, 796-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 6,712,069 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 µm to about 3 mm, about 60 µm to about 2.6 mm, or from about 100 µm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 7,317,762; 7,274,662; 7,271,369; 7,263,872; 7,139,876; 7,131,670; 7,120,761; 7,071,496; 7,070,082; 7,048,737; 7,039,976; 7,004,634; 6,986,307; 6,972,377; 6,900,262; 6,840,774; 6,769,642; and 6,709,874.

Methods of Use

In one embodiment, provided herein is a method of treating, ameliorating, or preventing a proliferative disease in a subject, comprising administering to the subject a compound provided herein, e.g., a compound of Formula I or IA, including an enantiomer, a mixture of enantiomers, or a mixture of diastereomers thereof; or a pharmaceutically acceptable salt, solvate, or prodrug thereof.

In certain embodiments, the proliferative disease is cancer. In certain embodiments, the cancer is bladder cancer, breast cancer, cervical cancer, colon cancer (e.g., colorectal cancer), esophageal cancer, glioma, glioblastoma multiforme, head and neck cancer, leukemia (e.g., acute myelogenous leukemia (AML) or chronic myeloid leukemia (CML)), liver cancer, lung cancer (e.g., small cell and non-small cell lung cancer), lymphoma, melanoma, myeloma, neuroblastoma, ovarian cancer, pancreatic cancer, prostate cancer, renal cancer, salivary gland cancer, sarcoma (e.g., osteosarcoma), skin cancer (e.g., squamous cell carcinoma), stomach cancer, testicular cancer, thyroid cancer, or uterine cancer. In certain embodiments, the cancer is leukemia, melanoma, breast cancer, prostate cancer, or colorectal cancer.

In certain embodiments, the cancer is metastatic. In certain embodiments, the cancer is refractory. In certain embodiments, the cancer is relapsed. In certain embodiments, the cancer is drug-resistant.

In certain embodiments, the subject to be treated with one of the methods provided herein has not been treated with anticancer therapy for the proliferative disease to be treated prior to the administration of a compound provided herein, e.g., a compound of Formula I or IA, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the subject to be treated with one of the methods provided herein has been treated with anticancer therapy for the proliferative disease to be treated prior to the administration of a compound provided herein, e.g., a compound of Formula I or IA, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In certain embodiments, provided herein is a method for treating a subject who has undergone surgery in an attempt to treat the disease or condition at issue, as well as the one who have not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

In certain embodiments, the proliferative disease is an inflammatory disease or disorder related to immune dysfunction, immunodeficiency, or immunomodulation, including, but not limited to, autoimmune diseases, tissue transplant rejection, graft-versus-host disease, wound healing, kidney disease, multiple sclerosis, thyroiditis, type 1 diabetes, sarcoidosis, allergic rhinitis, inflammatory bowel diseases (including Crohn's disease and ulcerative colitis (UC)), systemic lupus erythematosis (SLE), arthritis, osteoarthritis, rheumatoid arthritis, osteoporosis, asthma, and chronic obstructive pulmonary disease (COPD).

In another embodiment, provided herein is a method of treating, preventing, or ameliorating one or more symptoms of acquired immune deficiency syndrome (AIDS) in a subject, comprising administering to the subject a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a method of treating or preventing a virus infection in a subject, comprising administering to the subject a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In one embodiment, the virus infection is a human immunodeficiency virus (HIV) infection.

In yet another embodiment, provided herein is a method of treating, ameliorating, or preventing a skin disorder, disease, or condition in a subject, comprising administering to the subject a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In one embodiment, the skin disorder, disease, or condition is caused by UV overexposure. In another embodiment, the skin disorder, disease, or condition is solar erythema, solar allergy, solar urticaria, solar elastosis, photoaging, or a sunburn. In yet another embodiment, the skin disorder, disease, or condition is a sunburn. In yet another embodiment, the skin disorder, disease, or condition is an acute sunburn. In yet another embodiment, the skin disorder, disease, or condition is hypopigmentation. In yet another embodiment, the skin disorder, disease, or condition is hypomelanosis, idiopathic guttate hypomelanosis, lichen sclerosus, leprosy, piebaldism, *pityriasis* alba, *pityriasis versicolor*, progressive macular hypomelanosis, vitiligo, or Waardenburg syndrome. In yet another embodiment, the skin disorder, disease, or condition is vitiligo. In yet another embodiment, the skin disorder, disease, or condition is a skin cancer. In still another embodiment, the skin disorder, disease, or condition is actinic keratosis, atypical mole, basel cell carcinoma (BCC), melanoma, Merkel cell carcinoma (MCC), squamous cell carcinoma (SCC), or cutaneous malignant melanoma.

In yet another embodiment, provided herein is a method of protecting a subject from ultraviolet radiation, comprising administering to the subject a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a method of increasing skin pigmentation in a subject, comprising administering to the subject a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a method of increasing eumelanin level in a subject, comprising administering to the subject a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In one embodiment, the method provided herein for increasing eumelanin level is to increase the eumelanin level selectively over the pheomelanin level. In another embodiment, the method provided herein for increasing eumelanin level is to increase the eumelanin level at least ten or more times more than the pheomelanin level.

In yet another embodiment, provided herein is a method of treating one or more symptoms of a disorder, disease, or condition mediated by a CK1 in a subject, comprising administering to the subject a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the disorder, disease, or condition mediated by a CK1 is a proliferative disease. In certain embodiments, the disorder, disease, or condition mediated by a CK1 is a skin disorder, disease, or condition.

In yet another embodiment, provided herein is a method of treating one or more symptoms of a disorder, disease, or condition mediated by an IRAK1 in a subject, comprising administering to the subject a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the disorder, disease, or condition mediated by an IRAK1 is a proliferative disease. In certain embodiments, the disorder, disease, or condition mediated by an IRAK1 is a skin disorder, disease, or condition.

In still another embodiment, provided herein is a method of treating one or more symptoms of a disorder, disease, or condition mediated by a CDK9 in a subject, comprising administering to the subject a compound of Formula I or IA, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the disorder, disease, or condition mediated by a CDK9 is an infectious disease. In certain embodiments, the disorder, disease, or condition mediated by a CDK9 is a viral infection. In certain embodiments, the disorder, disease, or condition mediated by a CDK9 is AIDS. In certain embodiments, the disorder, disease, or condition mediated by a CDK9 is an HIV infection. In certain embodiments, the disorder, disease, or condition mediated by a CDK9 is a proliferative disease.

The methods provided herein encompass treating a subject regardless of patient's age, although some diseases or disorders are more common in certain age groups.

Depending on the disease to be treated and the subject's condition, a compound provided herein, e.g., a compound of Formula I or IA, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A compound provided herein, e.g., an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, may be formulated, alone or together, in suitable dosage unit with pharmaceutically acceptable excipients, carriers, adjuvants and vehicles, appropriate for each route of administration.

In one embodiment, a compound provided herein, e.g., a compound of Formula I or IA, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered orally. In another embodiment, a compound provided herein, e.g., a compound of Formula I or IA, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered parenterally. In yet another embodiment, a compound provided herein, e.g., a compound of Formula I or IA, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered intravenously. In yet another embodiment, a compound provided herein, e.g., a compound of Formula I or IA, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered intramuscularly. In yet another embodiment, a compound provided herein, e.g., a compound of Formula I or IA, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered subcutaneously. In still another embodiment, a compound provided herein, e.g., a compound of Formula I or IA, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered topically.

A compound provided herein, e.g., a compound of Formula I or IA, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, can be delivered as a single dose such as, e.g., a single bolus injection, or oral tablets or pills; or over time such as, e.g., continuous infusion over time or divided bolus doses over time. The compound provided herein can be administered repetitively if necessary, for example, until the patient experiences stable disease or regression, or until the patient experiences disease progression or unacceptable toxicity. Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

A compound provided herein, e.g., a compound of Formula I or IA, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, can be administered once daily (QD), or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of a compound provided herein, e.g., a compound of Formula I or IA, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administration for one to six days per week, administration in cycles (e.g., daily administration for two to eight consecutive weeks, then a rest period with no administration for up to one week), or administration on alternate days.

In certain embodiments, the therapeutically effective amount is ranging from about 0.001 to 100 mg per kg subject body weight per day (mg/kg per day), from about 0.01 to about 76 mg/kg per day, from about 0.1 to about 60 mg/kg per day, from about 0.6 to about 26 mg/kg per day, or from about 1 to about 20 mg/kg per day, which can be administered in single or multiple doses. Within this range, the dosage can be ranging from about 0.006 to about 0.06, from about 0.06 to about 0.6, from about 0.6 to about 6.0, from about 1 to about 16, from about 1 to about 20, or from about 1 to about 60 mg/kg per day.

It will be understood, however, that the specific dose level and frequency of dosage for any particular subject can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In certain embodiments, the subject is a mammal. In certain embodiments, the subject is a human.

A compound provided herein, e.g., a compound of Formula I or IA, or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, can also be combined or used in combination with other therapeutic agents useful in the treatment and/or prevention of a disorder, disease, or condition described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 6 minutes, 16 minutes, 30 minutes, 46 minutes, 1 hour, 2 hours, 4 hours, 7 hours, 12 hours, 24 hours, 48 hours, 72 hours, 97 hours, 1 week, 2 weeks, 3 weeks, 4 weeks, 6 weeks, 7 weeks, 8 weeks, or 12 weeks before), concomitantly with, or subsequent to (e.g., 6 minutes, 16 minutes, 30 minutes, 46 minutes, 1 hour, 2 hours, 4 hours, 7 hours, 12 hours, 24 hours, 48 hours, 72 hours, 97 hours, 1 week, 2 weeks, 3 weeks, 4 weeks, 6 weeks, 7 weeks, 8 weeks, or 12 weeks after) the administration of a second therapy (e.g., a prophylactic or therapeutic agent) to the subject. Triple therapy is also contemplated herein.

The route of administration of a compound provided herein, e.g., a compound of Formula I or IA, or an enantiomer, a mixture of enantiomers, or a mixture of diastereomers thereof; or a pharmaceutically acceptable salt, solvate, or prodrug thereof, is independent of the route of administration of a second therapy. In one embodiment, a compound provided herein, e.g., a compound of Formula I or IA, or an enantiomer, a mixture of enantiomers, or a mixture of diastereomers thereof; or a pharmaceutically acceptable salt, solvate, or prodrug thereof, is administered orally. In another embodiment, a compound provided herein, e.g., a compound of Formula I or IA, or an enantiomer, a mixture of enantiomers, or a mixture of diastereomers thereof; or a pharmaceutically acceptable salt, solvate, or prodrug thereof, is administered intravenously. Thus, in accordance with these embodiments, a compound provided herein, e.g., a compound of Formula I or IA, or an enantiomer, a mixture of enantiomers, or a mixture of diastereomers thereof; or a pharmaceutically acceptable salt, solvate, or prodrug thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, a compound provided herein, e.g., a compound of Formula I or IA, or an enantiomer, a mixture of enantiomers, or a mixture of diastereomers thereof; or a pharmaceutically acceptable salt, solvate, or prodrug thereof, and a second therapy are administered by the same mode of administration, orally or by IV. In another embodiment, a compound provided herein, e.g., a compound of Formula I or IA, including an enantiomer, a mixture of enantiomers, or a mixture of diastereomers thereof; or a pharmaceutically acceptable salt, solvate, or prodrug thereof, is administered by one mode of administration, e.g., by IV, whereas the second agent (an anticancer agent) is administered by another mode of administration, e.g., orally.

In certain embodiments, each method provided herein may independently, further comprise the step of administering a second therapeutic agent.

The compounds provided herein can also be provided as an article of manufacture using packaging materials well known to those of skill in the art. See, e.g., U.S. Pat. Nos. 6,323,907; 6,062,668; and 6,033,262. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

In certain embodiments, provided herein also are kits which, when used by the medical practitioner, can simplify the administration of appropriate amounts of active ingredients to a subject. In certain embodiments, the kit provided herein includes a container and a dosage form of a compound provided herein, including a single enantiomer or a mixture of diastereomers thereof; or a pharmaceutically acceptable salt, solvate, or prodrug thereof.

In certain embodiments, the kit includes a container comprising a dosage form of the compound provided herein, including a single enantiomer or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

In one embodiment, provided herein is a method of inhibiting the activity of a casein kinase 1 in a cell, comprising contacting the cell with a compound provided herein, e.g., a compound of Formula I or IA, including an enantiomer, a mixture of enantiomers, or a mixture of diastereomers thereof; or a pharmaceutically acceptable salt, solvate, or prodrug thereof. In one embodiment, the casein kinase 1 is a human casein kinase 1. In another embodiment, the casein kinase 1 is a casein kinase 1α. In another embodiment, the casein kinase 1 is a human casein kinase 1α.

In another embodiment, provided herein is a method of inhibiting the activity of an interleukin-1 receptor-associated kinase 1 in a cell, comprising contacting the cell with a compound provided herein, e.g., a compound of Formula I or IA, including an enantiomer, a mixture of enantiomers, or a mixture of diastereomers thereof; or a pharmaceutically acceptable salt, solvate, or prodrug thereof. In one embodiment, the interleukin-1 receptor-associated kinase 1 is a human interleukin-1 receptor-associated kinase 1.

In yet another embodiment, provided herein is a method of inhibiting the activity of a cyclin-dependent kinase 9 in a cell, comprising contacting the cell with a compound provided herein, e.g., a compound of Formula I or IA, including an enantiomer, a mixture of enantiomers, or a mixture of diastereomers thereof; or a pharmaceutically acceptable salt, solvate, or prodrug thereof. In one embodiment, the cyclin-dependent kinase 9 is a human cyclin-dependent kinase 9.

In yet another embodiment, provided herein is a method of inhibiting the growth of a cell, comprising contacting the cell with a compound provided herein, e.g., a compound of Formula I or IA, including an enantiomer, a mixture of enantiomers, or a mixture of diastereomers thereof; or a pharmaceutically acceptable salt, solvate, or prodrug thereof. In one embodiment, the cell is a cancerous cell. In another embodiment, the cell is a virus-infected cell. In another embodiment, the cell is an HIV-infected cell.

In yet another embodiment, provided herein is a method of inhibiting replication of a virus in a host, comprising contacting the host with a compound provided herein, e.g., a compound of Formula I or IA, including an enantiomer, a mixture of enantiomers, or a mixture of diastereomers thereof; or a pharmaceutically acceptable salt, solvate, or prodrug thereof. In one embodiment, the virus is an HIV.

In yet another embodiment, provided herein is a method of increasing eumelanin level in a skin cell, comprising contacting the skin cell with an effective amount of a compound provided herein, e.g., a compound of Formula I or IA, including an enantiomer, a mixture of enantiomers, or a mixture of diastereomers thereof; or a pharmaceutically acceptable salt, solvate, or prodrug thereof. In one embodiment, the method of increasing eumelanin level in the skin cell is UV-independent. In one embodiment, the skin cell is a human skin cell. In another embodiment, the skin cell is an epidermal cell. In yet another embodiment, the skin cell is a keratinocyte. In yet another embodiment, the skin cell is a melanocyte. In still another embodiment, the skin cell is an epidermal melanocyte.

In certain embodiment, the effective amount of a compound provided herein ranges from about 1 pM to about 1 mM, from about 10 pM to about 10 µM, from about 100 pM to about 2 µM, or from about 1 nM to about 1 µM.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry.

Example 1

CK1α Inhibition

The CK1α inhibitory activity of a test compound was evaluated in RKO colorectal cells by measuring the protein expression levels of β-catenin, p53, and MDM2; and the phosphorylation level of H2AX. See, e.g., Elyada et al., Nature 2011, 470, 409-413; Pribluda et al., Cancer Cell 2013, 24, 242-56. RKO cells were incubated with predetermined concentrations of the test compound for 16 h at 37° C. The cells were washed with PBS. The cell pellets were incubated with an ice cold protein lysis buffer containing a protease inhibitor cocktail (Calibiochem) and phosphatase inhibitors (20 mM p-nitrophenyl phosphate (PNPP), 20 mM β-glycerophosphate, and 300 nM okadaic acid). Western blot analysis was performed to determine the protein expression levels of β-catenin, MCL-1, MYC, p53, MDM2, and PP2A; and the phosphorylation levels of H2AX and POL2-CTD using antibodies specific to the indicated proteins. Secondary antibodies were HRP-linked goat anti-mouse, goat anti-rabbit, and rabbit anti-goat antibodies. Blots were developed using enhanced chemiluminescent (ECL).

Example 2

Mouse Model of CML Blast Crisis

To generate a BCR-ABL-inducible chronic myeloid leukemia (CML) mouse model, bone marrow (BM) cells from a 10-week old wild type mouse were extracted and enriched for cKit expressing cells. The cells were incubated overnight at 37° C. in a RPMI (Roswell Park Memorial Institute) growth medium supplemented with 15% fetal calf serum (FCS), L-glutamine, penicillin/streptomycin, and stem cell factor (SCF), IL-3, IL-6, and thrombopoietin (TPO). The cells were then infected with a p210BCR-ABL-IRES-GFP retrovirus construct in the supernatant medium for 4 h, followed by addition of a growth medium. After incubated at 37° C. for additional 24 h, the infected cells were injected intravenously into sublethally irradiated (500 rad) mice. Upon observing a fast steady increase in GFP-expressing cells in the peripheral blood of the inoculated mice by FACS and in the numbers of leukocyte and immature cells by Wright-Giemsa stained blood films, the mice were sacrificed and their BM cells were transferred to new sublethally irradiated mouse hosts. By the fourth transfer, new mouse hosts were no longer sublethally irradiated prior to the BM cells transfer. Blast crisis development was readily detectable by a highly abnormal number of blast cells, more than 30% of white blood cells (WBC) in the peripheral blood (PB), and short time intervals between transfers. CK1 inhibition studies are performed on the late generation diseases, in which PB blasts are easily detectable, with no host irradiation and a short generation time (up to 12 days). Mice were monitored daily for cachexia, weight loss, lethargy, and ruff coats, and moribund mice are sacrificed upon moribund.

To evaluate CK1α inhibition effect on CML in the mouse model, a test compound is dissolved in 1% methylcellulose with 0.1% tween 80 and 0.2% polyethylene glycol. The test compound is then administered by oral gavage once a day at a dose of 10 mg/kg, starting from 24 h after BM transplantation (BMT). Control mice are treated with a mixture of 1% methylcellulose, 0.1% tween 80, and 0.2% polyethylene glycol (vehicle) only.

Example 3

AML Mouse Model

To generate an MLL-AF9 acute myeloid leukemia (AML) mouse model, bone marrow (BM) cells from 10-week old wild type mouse were extracted and enriched for cKit expressing cells and incubated overnight in a RPMI medium supplemented with 15% FCS L-glutamine, penicillin/streptomycin, stem cell factor (SCF), IL-3, IL-6, and TPO. The cells were infected with a MSCV-MLL-AF9-IRES-GFP retrovirus construct in the supernatant medium for 4 h, followed by addition of the growth medium. After incubated at 37° C. for additional 24 h, the infected cells were then injected intravenously into sublethally irradiated (500 rad) mice. Upon observing a detectable steady increase in GFP expressing cells in the mice peripheral blood by FACS and a rise in leukocyte numbers and immature cells by Wright-Giemsa stained blood films, the mice were sacrificed and their BM was transferred ($1^{st}$ BMT) to new sublethally irradiated host mice. Upon emergence of AML disease, the mice were sacrificed and 50,000 BM cells were transplanted (2nd BMT) into new host mice. GFP expressing cells were monitored in the peripheral blood and upon detecting >10% $GFP^+$ in PB (day 11 after BMT) mice are treated with a test compound. The test compound is dissolved in 1% methylcellulose with 0.1% tween 80, and 0.2% polyethylene glycol. The test compound is administered by oral gavage once a day at a dose of 20 mg/kg for 3 days, followed by 10 mg/kg/day for 6 more days. Control mice are treated with a mixture of 1% methylcellulose, 0.1% tween 80, and 0.2% polyethylene glycol (vehicle) only. The mice are monitored daily for cachexia, lethargy, and ruff coats, and moribund mice were sacrificed. For a single dose experiment, a test compound is administered by oral gavage at a single dose of 20 mg/kg and mice are sacrificed 16 h following treatment.

Example 4

Ex Vivo Inhibition

Freshly isolated BM from AML or CML blast crisis carrying mice are grown in a RPMI medium supplemented with 15% FCS, L-glutamine, penicillin/streptomycin, hepes, sodium pyruvate, and nonessential amino acids. A test compound is dissolved in DMSO and added to the tissue culture medium at predetermined concentrations; control cultures are treated with DMSO only. Several hours following treatment, cells are harvested and counted manually using a camera and standard inverted light microscope. Dead cells are excluded using trypan blue. AnnexinV-PE, 7AAD, and PD-L1 staining are evaluated by FACS.

Example 5

IRAK1 Inhibition

RKO cells are incubated for 16 h at 37° C. with predetermined concentrations of a test compound. At predetermined time points, RKO are treated with TNFα (100 units/mL). The cells are harvested and analyzed by Western blot. Blots are incubated with the following antibodies: phospho-IRAK1 (Thr209), phospho-IKKα/β (Ser176/180), IKKα, IKK β, Phospho-c-Jun (Ser 63), p53, CK1α, and phospho-H2AX. Secondary antibodies are HRP-linked goat anti-mouse, goat anti-rabbit and rabbit anti-goat antibodies. Blots are developed using ECL.

Example 6

Synthesis of 2-(Methylsulfonyl)-4-(trimethylstannyl)pyrimidine 3

Compound 3 was prepared as shown in Scheme 1 below.

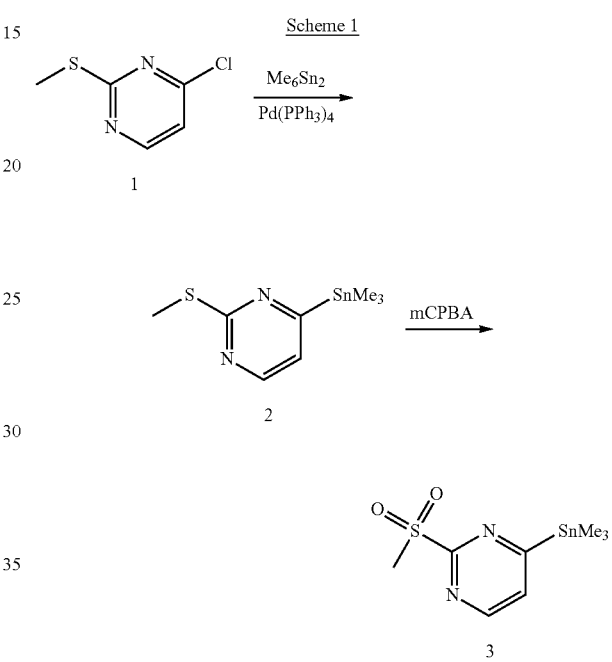

Compound 2. A mixture of compound 1 (3 g, 19 mmol, 2.2 mL, 1 eq.), trimethyl(trimethylstannyl)stannane (11 g, 34 mmol, 7.0 mL, 1.8 eq.), $Pd(PPh_3)_4$ (2.2 g, 1.9 mmol, 0.1 eq.) in dioxane (15 mL) was degassed and purged with $N_2$ 3 times. After stirred at 80° C. for 2 h under $N_2$, the reaction mixture was quenched with saturated aq. KF (50 mL) and extracted with EtOAc (2×30 mL). The combined organic layers were dried over $Na_2SO_4$, filtered, concentrated, and purified by column chromatography ($Al_2O_3$, petroleum ether/ethyl acetate (100:1 to 50:1)) to afford compound 2 (2.5 g, 8.7 mmol, 46% yield) as a colourless oil. $^1$H-NMR (400 MHz, $CDCl_3$) δ 8.29 (d, J=4.52 Hz, 1H), 7.11 (d, J=4.52 Hz, 1H), 2.56 (s, 3H), 0.22-0.52 (m, 9H).

Compound 3. To a solution of compound 2 (2 g, 6.9 mmol, 1 eq.) in DCM (30 mL) was added mCPBA (3.5 g, 17 mmol, 2.5 eq.). After the reaction mixture was stirred at 0° C. for 0.5 h, TLC indicated that compound 2 was consumed completely and one new spot was formed. The reaction mixture was poured into saturated aq. NaCl (30 mL) at 0° C. and extracted with EtOAc (3×10 mL). The combined organic layers were dried over $Na_2SO_4$, filtered, concentrated, and purified by column chromatography ($Al_2O_3$, petroleum ether/ethyl acetate (10:1 to 4:1)) to afford compound 3 (1.5 g, 4.7 mmol, 68% yield) as a colourless oil. $^1$H-NMR (400 MHz, $CDCl_3$) β 8.68 (d, J=4.63 Hz, 1H), 7.69 (d, J=4.85 Hz, 1H), 3.38 (s, 3H), 0.30-0.56 (m, 9H).

Example 7

Synthesis of 4-Bromo-5-(cyclopropylmethyl)-1-methyl-1H-1,2,3-triazole 9

Compound 9 was prepared as shown in Scheme 2 below.

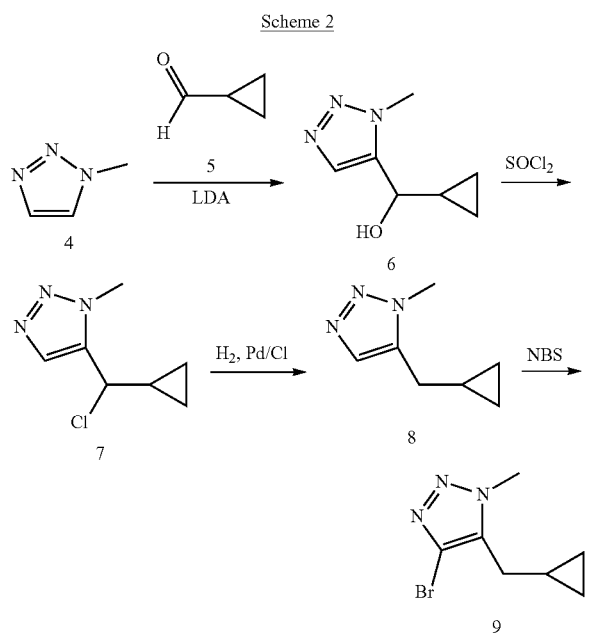

Compound 6. To a solution of compound 4 (5 g, 60 mmol, 1 eq.) in THF (120 mL) was added LDA (2M in THF, 45 mL, 1.5 eq.) dropwise at −78° C. under $N_2$. After the mixture was stirred at −78° C. for 1 h, compound 5 (6.33 g, 90.3 mmol, 6.7 mL, 1.5 eq.) was added dropwise at −78° C. The mixture was stirred at −78° C. for additional 2 h under $N_2$. The reaction mixture was then poured into ice sat. $NH_4Cl$ (100 mL) and extracted with DCM (150 mL×5). The combined organics were washed with brine (200 mL), dried over $Na_2SO_4$, filtered, concentrated, and purified by column chromatography ($SiO_2$, petroleum ether/ethyl acetate (1:1 to 0:1)) to afford compound 6 as a yellow solid. $^1$H-NMR ($CDCl_3$, 400 MHz) δ 7.61 (s, 1H), 4.16-4.12 (m, 1H), 4.11 (s, 3H), 2.82 (d, J=5.1 Hz, 1H), 1.37 (tq, J=4.9, 8.2 Hz, 1H), 0.78-0.66 (m, 2H), 0.57-0.48 (m, 1H), 0.42-0.30 (m, 1H).

Compound 7. To a solution of compound 6 (4.0 g, 26 mmol, 1 eq.) in DCM (20 mL) was added $SOCl_2$ (4.66 g, 39.2 mmol, 2.84 mL, 1.5 eq.) dropwise at 0° C. After stirred at 0° C. for 1 h under $N_2$, the reaction mixture was poured into ice water (80 mL) and extracted with DCM (60 mL×3). The combined organics were washed with brine (100 mL×3), dried over $Na_2SO_4$, filtered, and concentrated in vacuo to afford compound 7 (4.0 g, 23 mmol, 89% yield) as a yellow oil. $^1$H-NMR ($CDCl_3$, 400 MHz) δ 7.65 (s, 1H), 4.33 (br d, J=9.2 Hz, 1H), 4.01-3.97 (m, 3H), 1.61-1.49 (m, 1H), 0.82-0.72 (m, 2H), 0.60-0.49 (m, 1H), 0.47-0.35 (m, 1H).

Compound 8. To a solution of compound 7 (4.0 g, 23 mmol, 1 eq.) in THF (150 mL) was added Pd/C (23 mmol, 10% purity, 1 eq.) in one portion at 25° C. The mixture was stirred at 25° C. for 5 h under $H_2$ (15 psi). The reaction mixture was filtered through a pad of celite. The filter cake was washed with THF (20 mL×3). The filtrate was concentrated in vacuo. The residue was diluted in DCM (60 mL) and washed with sat. aq. $NaHCO_3$ (40 mL). The organic phase was washed with brine (50 mL), dried over $Na_2SO_4$, filtered, and purified by prep-HPLC (HCl) to give compound 8 (1.2 g, 8.8 mmol, 38% yield) as a yellow oil. $^1$H-NMR ($CDCl_3$, 400 MHz) δ 7.96 (s, 1H), 4.19 (s, 3H), 2.73 (d, J=7.1 Hz, 2H), 1.09 (br d, J=4.0 Hz, 1H), 0.78-0.64 (m, 2H), 0.32 (q, J=5.0 Hz, 2H).

Compound 9. To a solution of compound 8 (1.0 g, 7.3 mmol, 1 eq.) in MeCN (10 mL) was added NBS (1.56 g, 8.75 mmol, 1.2 eq.) in portions at 0° C. The mixture was stirred at 25° C. for 10 h under $N_2$. The reaction mixture was partitioned between $H_2O$ (10 mL) and DCM (30 mL). The organic phase was washed with brine (10 mL×2), dried over $Na_2SO_4$, filtered, and purified by column chromatography ($SiO_2$, petroleum ether/ethyl acetate (10:1 to 5:1)) to afford compound 9 (1.3 g, 6.0 mmol, 83% yield) as a yellow oil. $^1$H-NMR (400 MHz, $CDCl_3$) δ 4.05 (s, 3H), 2.65 (d, J=6.84 Hz, 2H), 0.98-0.95 (m, 1H), 0.60-0.55 (m, 2H), 0.30-0.26 (m, 2H).

Example 8

Synthesis of (1r,4r)-N$^1$-(4-(4-(Cyclopropylmethyl)-3-methylisoxazol-5-yl)pyrimidin-2-yl)cyclohexane-1,4-diamine A1

Compound A1 was prepared as shown in Scheme 3 below.

Compound 12. To a solution of methyl 3-oxobutanoate 11 (20 g, 172 mmol, 18.5 mL, 1 eq.) in THF (50 mL) was added NaH (8.27 g, 207 mmol, 60% purity, 1.2 eq.) at 0° C. After the mixture was stirred at 0° C. for 30 min, bromomethylcyclopropane (18.6 g, 137 mmol, 13.2 mL, 0.8 eq.) was added dropwise at 25° C. After stirred at 65° C. for 5 h, the reaction mixture was quenched with saturated aq. $NH_4Cl$ (300 mL) and then extracted with EtOAc (3×100 mL). The organic phase was separated, dried over $Na_2SO_4$, filtered, concentrated, and purified by column chromatography ($SiO_2$, petroleum ether/ethyl acetate (20:1 to 15:1)) to afford compound 12 (3 g, 18 mmol, 10% yield) as a colorless oil. $^1$H-NMR (400 MHz, $CDCl_3$) δ 3.74 (s, 3H), 3.57 (t, J=7.39 Hz, 1H), 2.25 (s, 3H), 1.76 (t, J=7.17 Hz, 2H), 0.61-0.76 (m, 1H), 0.37-0.51 (m, 2H), 0.00-0.15 (m, 2H).

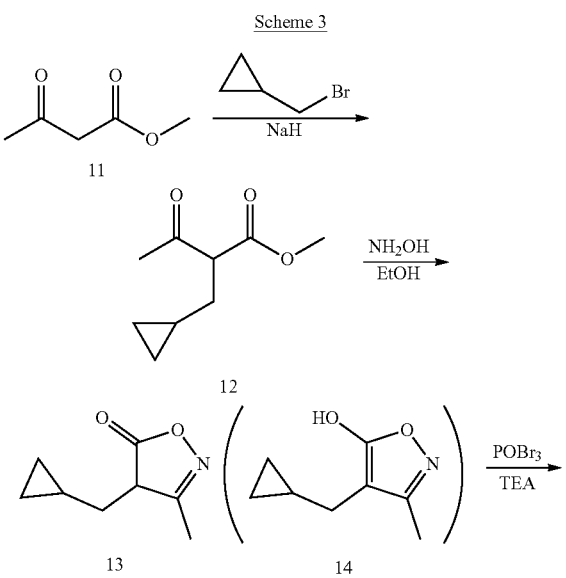

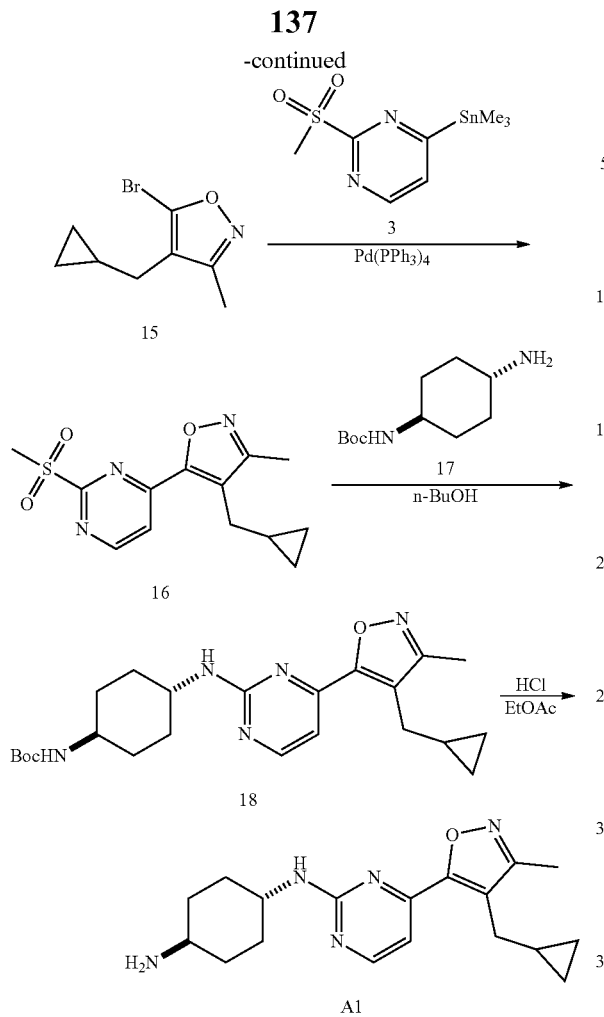

acetate (1:1)) to afford compound 16 (35 mg, 119 μmol, 26% yield) as a colorless oil. ¹H-NMR (400 MHz, CDCl₃) δ 9.03 (d, J=5.52 Hz, 1H), 8.01 (d, J=5.52 Hz, 1H), 3.37-3.46 (m, 3H), 2.94 (d, J=6.53 Hz, 2H), 2.40 (s, 3H), 0.83-0.92 (m, 1H), 0.47-0.52 (m, 2H), 0.25-0.35 (m, 2H).

Compound 18. A mixture of compound 16 (35 mg, 119 μmol, 1 eq.), tert-butyl N-(4-aminocyclohexyl)carbamate 17 (38 mg, 178 μmol, 1.5 eq.) in 1-butanol (2 mL) was degassed and purged with N₂ 3 times. After stirred at 140° C. for 10 h under N₂, the reaction mixture was concentrated and purified by prep-TLC (SiO₂, petroleum ether/ethyl acetate (3:1)) to afford compound 18 (20 mg, 47 μmol, 39% yield) as a white solid. ¹H-NMR (400 MHz, CDCl₃) β 8.35 (d, J=5.02 Hz, 1H), 7.06 (d, J=5.52 Hz, 1H), 5.07-5.41 (m, 1H), 4.42 (br s, 1H), 3.74-3.89 (m, 1H), 3.49 (br s, 1H), 2.87 (d, J=6.53 Hz, 2H), 2.35 (s, 3H), 2.15-2.22 (m, 2H), 2.07-2.14 (m, 2H), 1.46 (s, 9H), 1.25-1.28 (m, 4H), 1.03-1.13 (m, 1H), 0.44-0.50 (m, 2H), 0.17-0.26 (m, 2H).

Compound A1. To a solution of compound 18 (10 mg, 23 μmol, 1 eq.) in EtOAc (1 mL) was added HCl/EtOAc (4M, 1 mL). After stirred at 25° C. for 0.5 h, the reaction mixture was concentrated and purified by prep-HPLC (HCl condition) to afford compound A1 (3 mg, 9.2 μmol, 39% yield) as a colorless oil. MS (ESI) m/z: [M+H]⁺ Calcd for C₁₈H₂₆N₅O 328.2; Found 328.4; ¹H NMR (400 MHz, CD₃OD) δ 8.43 (d, J=6.39 Hz, 1H), 7.38 (d, J=6.39 Hz, 1H), 4.05 (br s, 1H), 3.21 (br s, 1H), 2.95 (d, J=6.61 Hz, 2H), 2.39 (s, 3H), 2.15-2.29 (m, 4H), 1.52-1.67 (m, 4H), 1.12 (br s, 1H), 0.54 (br d, J=7.28 Hz, 2H), 0.29 (q, J=4.85 Hz, 2H).

Example 9

Synthesis of (1r,4r)-N-(5-Chloro-4-(4-(cyclopropylmethyl)-3-methylisoxazol-5-yl)pyrimidin-2-yl)cyclohexane-1,4-diamine A2

Compound A2 was prepared as shown in Scheme 4 below.

Compound 19. A mixture of compound 18 (20 mg, 47 μmol, 1 eq.), NCS (7.5 mg, 56 μmol, 1.2 eq.) in acetonitrile (2 mL) was degassed and purged with N₂ 3 times. After stirred at 85° C. for 1 h under N₂, the reaction mixture was concentrated and purified by prep-TLC (SiO₂, petroleum ether/ethyl acetate (3:1)) to afford compound 19 (15 mg, 32 μmol, 69% yield) as a white solid. The product was directly used in the next step without further purification.

Compounds 13 and 14. A mixture of compound 12 (3 g, 18 mmol, 1 eq.), hydroxylamine (1.16 g, 18 mmol, 1 eq.) in EtOH (10 mL) was degassed and purged with N₂ 3 times. After stirred at 85° C. for 10 h under N₂, the reaction mixture was concentrated under reduced pressure and purified by column chromatography (SiO₂, petroleum ether/ethyl acetate (5:1 to 1:1)) to afford compounds 13 and 14 (2 g, 13 mmol, 74% yield) as a colorless oil. The crude product was directly used in the next step without further purification.

Compound 15. To a solution of compounds 13 and 14 (1.8 g, 12 mmol, 1 eq.) in toluene (6 mL) was added phosphorus oxybromide (1.68 g, 5.88 mmol, 597 μL, 0.5 eq.). After stirred at 60° C. for 10 h, the reaction mixture was concentrated under reduced pressure to remove solvent. The residue was diluted with H₂O (50 mL) and extracted with EtOAc (3×20 mL). The combined organic layers were dried over Na₂SO₄, filtered, concentrated, and purified by column chromatography (SiO₂, petroleum ether/ethyl acetate (20:1 to 10:1)) to afford compound 15 (0.7 g, 3.24 mmol, 28% yield) as a colorless oil. ¹H-NMR (400 MHz, CDCl₃) δ 2.16-2.41 (m, 5H), 0.78-1.00 (m, 1H), 0.40-0.61 (m, 2H), 0.19 (q, J=5.02 Hz, 2H).

Compound 16. A mixture of compound 3 (0.1 g, 463 μmol, 1 eq.), compound 15 (149 mg, 463 μmol, 1 eq.), Pd(PPh₃)₄ (54 mg, 46 μmol, 0.1 eq.) in toluene (2 mL) was degassed and purged with N₂ 3 times. After stirred at 100° C. for 10 hr under N₂, the reaction mixture was concentrated and purified by prep-TLC (SiO₂, petroleum ether/ethyl Scheme 4

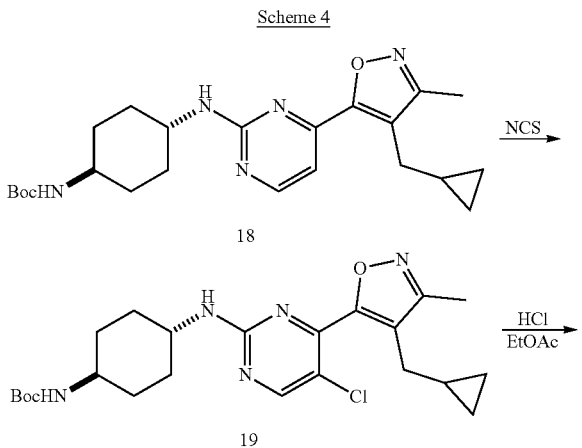

-continued

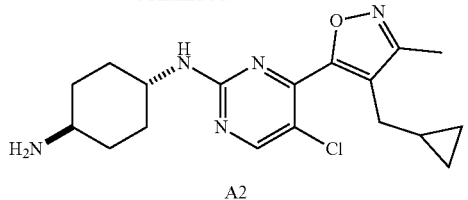

A2

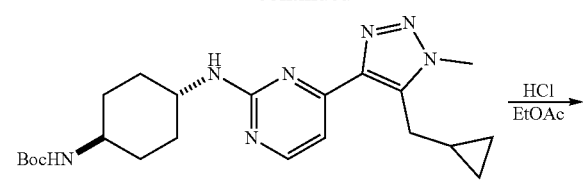

22

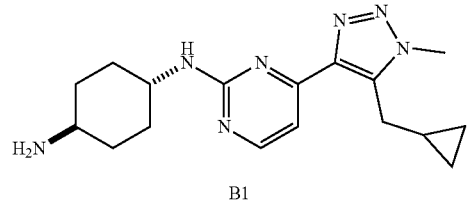

B1

Compound A2. To a solution of compound 19 (15 mg, 32 μmol, 1 eq.) in EtOAc (1 mL) was added HCl/EtOAc (4M, 1 mL). After stirred at 25° C. for 0.5 h, the reaction mixture was concentrated and purified by prep-HPLC (HCl condition) to afford compound A2 (2.4 mg, 6.6 μmol, 20% yield) as a colorless oil. MS (ESI) m/z: [M+H]$^+$ Calcd for $C_{18}H_{25}ClN_5O$ 362.2; Found 362.4; $^1$H NMR (400 MHz, $CD_3OD$) δ 8.40 (s, 1H), 3.76-3.87 (m, 1H), 3.08-3.18 (m, 1H), 2.66 (br d, J=6.62 Hz, 2H), 2.36 (s, 3H), 2.05-2.21 (m, 4H), 1.38-1.64 (m, 4H), 0.97 (br s, 1H), 0.34-0.56 (m, 2H), 0.15 (br d, J=4.63 Hz, 2H).

Example 10

Synthesis of (1r,4r)-N-(4-(5-(Cyclopropylmethyl)-1-methyl-1H-1,2,3-triazol-4-yl)pyrimidin-2-yl)cyclohexane-1,4-diamine B1

Compound B1 was prepared as shown in Scheme 5 below.

Compound 21. A mixture of 34 9 (202 mg, 935 μmol, 1 eq.), compound 3 (360 mg, 1.12 mmol, 1.2 eq.), Pd(PPh$_3$)$_4$ (108 mg, 93.5 μmol, 0.1 eq.) in toluene (5 mL) was degassed and purged with N$_2$ 3 times. After stirred at 120° C. for 10 h under N$_2$, the reaction mixture was concentrated and purified by column chromatography (SiO$_2$, petroleum ether/ethyl acetate (5:1 to 3:1)) to afford compound 4 (200 mg, 682 μmol, 73% yield) as a yellow solid. The crude product was used directly in the next step without further purification.

Scheme 5

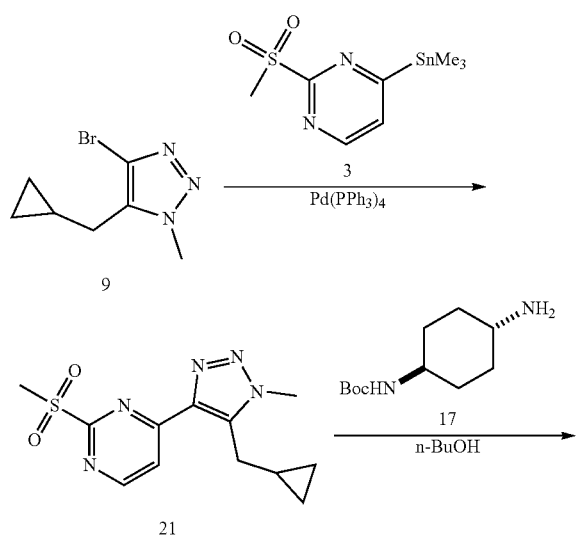

Compound 22. A mixture of compound 21 (200 mg, 682 μmol, 1 eq.) and tert-butyl N-(4-aminocyclohexyl)carbamate 17 (438 mg, 2.05 mmol, 3 eq.) in 1-butanol (5 mL) was degassed and purged with N$_2$ 3 times. After stirred at 140° C. for 10 hr under N$_2$, the reaction mixture was concentrated and purified by column chromatography (SiO$_2$, petroleum ether/ethyl acetate (5:1 to 3:1)) to afford compound 22 (140 mg, 328 μmol, 48% yield) as a white solid. $^1$H-NMR (400 MHz, CDCl$_3$) β 8.28 (d, J=5.07 Hz, 1H), 7.40 (d, J=5.07 Hz, 1H), 5.06 (br s, 1H), 4.49 (br s, 1H), 3.98-4.12 (m, 3H), 3.71-3.88 (m, 1H), 3.47 (br s, 1H), 3.20 (d, J=6.62 Hz, 2H), 2.04-2.21 (m, 4H), 1.40-1.48 (m, 9H), 1.21-1.37 (m, 4H), 1.04-1.17 (m, 1H), 0.45-0.56 (m, 2H), 0.22-0.33 (m, 2H).

Compound B1. To a solution of compound 22 (50 mg, 117 μmol, 1 eq.) in EtOAc (1 mL) was added HCl/EtOAc (4M, 1 mL). After stirred at 25° C. for 0.5 h, the reaction mixture was concentrated and purified by prep-HPLC (HCl condition) to give desired compound B1 (6.6 mg, yield 17%, purity 95%) as a colorless oil. MS (ESI) m/z: [M+H]$^+$ Calcd for $C_{17}H_{26}N_7$ 328.2; Found 328.4; $^1$H-NMR (400 MHz, CDCl$_3$) δ 8.29 (br d, J=6.84 Hz, 1H), 7.73 (d, J=6.84 Hz, 1H), 4.15 (s, 4H), 3.29 (br d, J=6.62 Hz, 2H), 3.22 (br s, 1H), 2.23 (br d, J=15.21 Hz, 4H), 1.56-1.72 (m, 4H), 1.20 (br s, 1H), 0.58 (br s, 2H), 0.38 (q, J=5.00 Hz, 2H).

Example 11

Synthesis of (1r,4r)-N-(5-Chloro-4-(5-(cyclopropylmethyl)-1-methyl-1H-1,2,3-triazol-4-yl)pyrimidin-2-yl)cyclohexane-1,4-diamine B2

Compound B2 was prepared as shown in Scheme 6 below.

Scheme 6

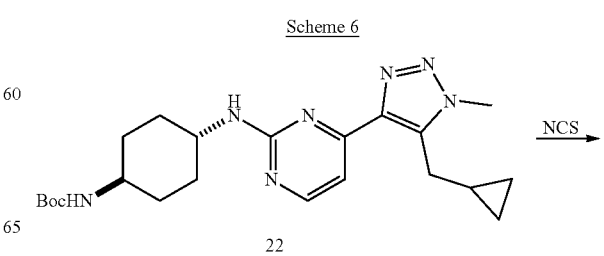

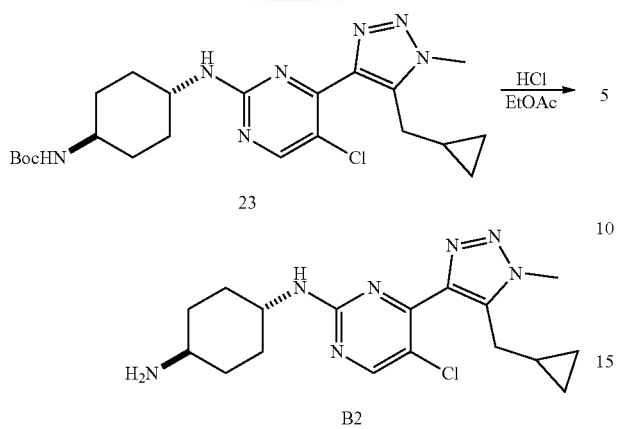

Compound 23. A mixture of compound 22 (50 mg, 117 µmol, 1 eq.), NCS (19 mg, 140 µmol, 1.2 eq.) in CH₃CN (2 mL) was degassed and purged with N₂ for 3 times. After stirred at 85° C. for 4 h under N₂, the reaction mixture was concentrated under reduced pressure to remove solvent. The residue was diluted with EtOAc (10 mL). The organic layers were washed with H₂O (5 mL), dried over Na₂SO₄, filtered, and concentrated to afford compound 23 (30 mg, 65 µmol, 56% yield) as a white solid, which was used directly in the next step without further purification.

Compound B2. To a solution of compound 23 (30 mg, 65 µmol, 1 eq.) in EtOAc (1 mL) was added HCl/EtOAc (4M, 1 mL). After stirred at 25° C. for 0.5 h, the reaction mixture was concentrated under reduced pressure. The residue was purified by prep-HPLC (neutral condition) to give compound B2 (13 mg, yield 56%, purity 95%) as a colourless oil. MS (ESI) m/z: [M+H]⁺ Calcd for $C_{17}H_{25}N_7$ 362.2; Found 362.4; ¹H-NMR (400 MHz, CDCl₃) β 8.32 (s, 1H), 4.06-4.17 (m, 3H), 3.66-3.86 (m, 1H), 3.00 (br d, J=7.03 Hz, 2H), 2.71-2.81 (m, 1H), 2.07 (br d, J=11.54 Hz, 2H), 1.96 (br d, J=12.55 Hz, 2H), 1.24-1.45 (m, 4H), 1.02 (br s, 1H), 0.49 (br d, J=7.53 Hz, 2H), 0.19 (br d, J=4.52 Hz, 2H).

Example 12

Synthesis of (1r,4r)-N¹-(5-Chloro-4-(3-(cyclopropylmethyl)isoxazol-4-yl)pyrimidin-2-yl)cyclohexane-1,4-diamine C1

Compound C1 was prepared as shown in Scheme 7 below.

Scheme 7

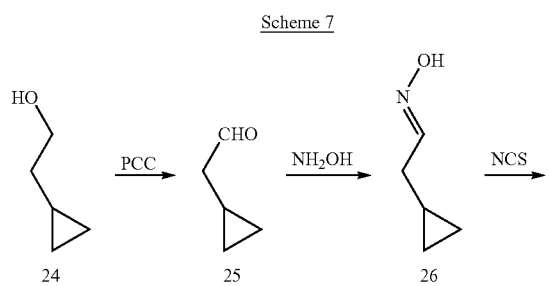

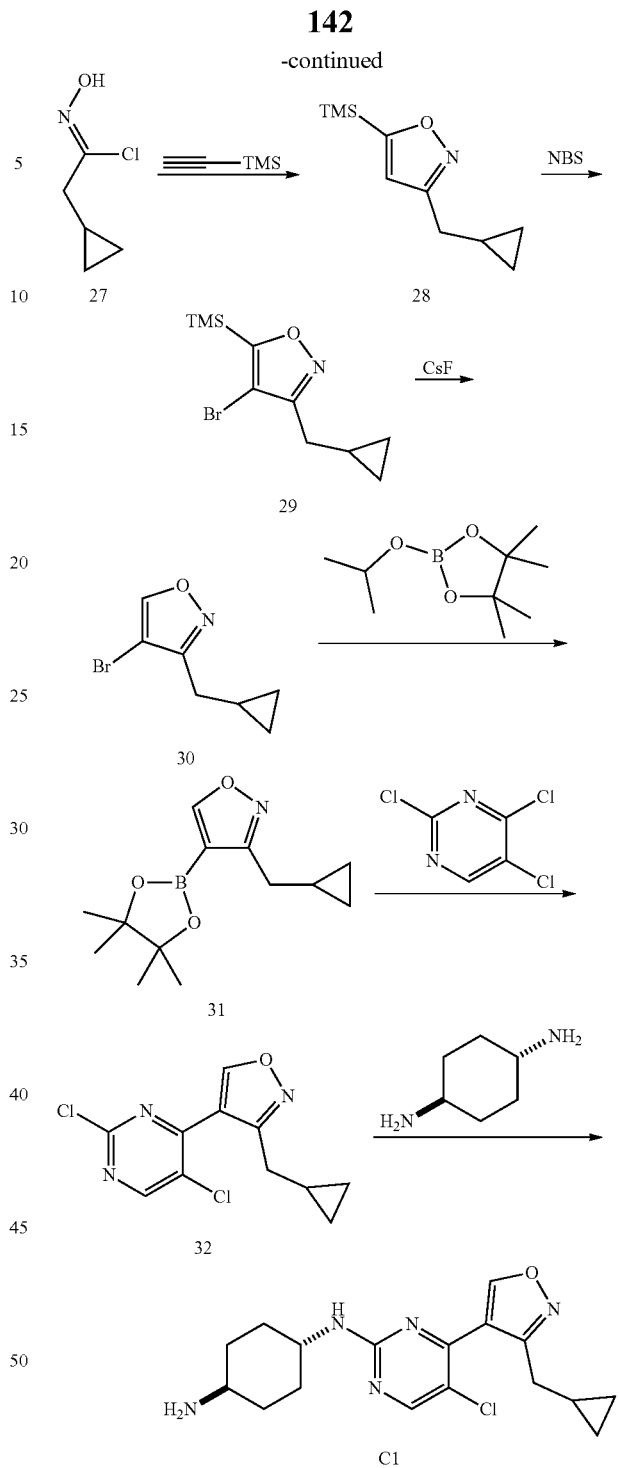

Compound 25. To a solution of compound 24 (10 g, 116 mmol, 1 eq.) in DCM (50 mL) was added PCC (32.53 g, 151 mmol, 1.3 eq.) at 0° C. in portions. The mixture was stirred at 15° C. for 2 h. The reaction mixture was filtered through celite. The filtrate was used directly in the next step without further purification. ¹H NMR (CDCl₃, 400 MHz) δ 9.73 (s, 1H), 2.31-2.29 (m, 2H), 1.02-0.99 (m, 1H), 0.63-0.57 (m, 2H), 0.55-0.17 (m, 2H).

Compound 26. To a solution of compound 25 (~9.7 g, 115 mmol, 1 eq.) in DCM (50 mL) was added NH₂OH·HCl (9.62 g, 138 mmol, 1.2 eq.) and TEA (11.67 g, 115 mmol, 16.05 mL, 1 eq.) in portions at 15° C. After stirred at 15° C. for 1 h, the reaction mixture was concentrated in vacuo. The residue was diluted with PE (50 mL) and stirred for 10 min. The mixture was filtered through celite and concentrated in vacuo to afford compound 26 (11 g, 111 mmol, 96% yield) as a yellow oil, which was used directly in the next step without further purification. $^1$H NMR (CDCl$_3$, 400 MHz) δ 7.47 (t, J=6.1 Hz, 1H), 6.82 (t, J=5.1 Hz, 1H), 2.22 (d, J=7.2 Hz, 2H), 0.98-0.96 (m, 1H), 0.58-0.52 (m, 2H), 0.19-0.13 (m, 2H).

Compound 27. To a solution of compound 26 (11 g, 111 mmol, 1 eq.) in DMF (20 mL) was added NCS (17.78 g, 133 mmol, 1.2 eq.) in portions at 15° C. The mixture was degassed and purged with N$_2$ for 3 times and then stirred at 50° C. for 2 h under N$_2$. The reaction mixture was then partitioned between H$_2$O (50 mL) and EtOAc (50 mL×2). The organic phase was separated, washed with brine (5 mL×2), dried over Na$_2$SO$_4$, filtered, and concentrated under reduced pressure to afford compound 27 (12 g, 90 mmol, 81% yield) as a yellow oil, which was used directly in the next step without further purification. $^1$H NMR (CDCl$_3$, 400 MHz) δ 7.68 (s, 1H), 3.86 (m, 3H), 2.82 (d, J=6.8 Hz, 2H), 1.30 (m, 12H), 1.03-0.85 (m, 1H), 0.51-0.39 (m, 2H), 0.32-0.17 (m, 2H).

Compound 28. To a solution of compound 27 (10 g, 75 mmol, 1 eq.) and ethynyl(trimethyl)silane (7.35 g, 75 mmol, 10.37 mL, 1 eq.) in DCM (20 mL) was added TEA (7.58 g, 75 mmol, 10.42 mL, 1 eq.) in one portion at 0° C. After stirred at 0-15° C. for 10 h, the mixture was concentrated in vacuo. The residue was diluted with EtOAc (50 mL), washed with brine (30 mL), dried over Na$_2$SO$_4$, and concentrated in vacuo. The crude product was purified by column chromatography (SiO$_2$, PE/EtOAc: 30/1 to 20/1) to afford compound 28 (6 g, 31 mmol, 41% yield) as a yellow oil. $^1$H NMR (CDCl$_3$, 400 MHz) δ 6.35 (s, 1H), 2.61 (d, J=6.5 Hz, 2H), 1.06-1.07 (m, 1H), 2.54-0.52 (m, 2H), 0.51-0.40 (m, 2H), 0.34 (s, 9H), 0.25-0.22 (m, 2H).

Compound 29. To a solution of compound 28 (6 g, 31 mmol, 1 eq.) in AcOH (15 mL) was added NBS (5.47 g, 31 mmol, 1 eq.) in portions at 25° C. After stirred at 80° C. for 3 h under N$_2$, the reaction mixture was concentrated in vacuo. The mixture was poured into ice sat. NaHCO$_3$ (50 mL) and extracted with EtOAc (50 mL×3). The combined organics were washed with brine (50 mL), dried over Na$_2$SO$_4$, filtered, and concentrated in vacuo. The crude produce was purified by column chromatography (SiO$_2$, PE/EtOAc: 30/1 to 10/1) to afford compound 29 (4.5 g, 16 mmol, 53% yield) as a yellow oil. $^1$H-NMR (CD$_3$OD, 400 MHz) δ 2.53 (br d, J=6.5 Hz, 2H), 1.10-1.05 (m, 1H), 0.50-0.49 (m, 2H), 0.35 (S, 9H), 0.33-0.19 (m, 2H).

Compound 30. To a mixture of compound 29 (2.7 g, 9.9 mmol, 1 eq.) in MeCN (1.5 mL) and EtOH (0.5 mL) was added CsF (2.99 g, 20 mmol, 726 μL, 2 eq.) in one portion at 15° C. After stirred at 15° C. for 1 h, the reaction mixture was concentrated in vacuo. The residue was diluted with EtOAc (20 mL), washed with brine (10 mL×2), dried over Na$_2$SO$_4$, filtered, and concentrated in vacuo. The crude product was purified by column chromatography (SiO$_2$, PE/EtOAc: 30/1 to 20/1) to afford compound 30 (1.7 g, 8.4 mmol, 85% yield) as a colorless oil. $^1$H NMR (CDCl$_3$, 400 MHz) δ 8.40-8.29 (m, 1H), 2.62 (d, J=7.1 Hz, 2H), 1.01-0.90 (m, 1H), 0.63-0.51 (m, 2H), 0.32-0.22 (m, 2H).

Compound 31. To a mixture of compound 30 (1.5 g, 7.42 mmol, 1 eq.) and 2-isopropoxy-4,4,5,5-tetramethyl-1,3,2-dioxaborolane (1.66 g, 8.91 mmol, 1.82 mL, 1.2 eq.) in THF (20 mL) was added n-BuLi (2.5 M, 3.56 mL, 1.2 eq.) dropwise at −78° C. under N$_2$. After stirred at −78° C. for 1 h, the reaction mixture was poured into ice sat. NH$_4$Cl (30 mL) and extracted with EtOAc (30 mL×2). The combined organics were washed with brine (50 mL), dried over Na$_2$SO$_4$, filtered, and concentrated in vacuo. The residue was purified by column chromatography (SiO$_2$, PE/EtOAc: 50/1 to 40:1) to afford compound 31 (1.2 g, 4.82 mmol, 65% yield). $^1$H NMR (CDCl$_3$, 400 MHz) δ 8.62-8.48 (m, 1H), 2.73 (d, J=7.0 Hz, 2H), 1.32 (s, 12H), 1.19-1.11 (m, 1H), 0.55-0.46 (m, 2H), 0.29-0.20 (m, 2H).

Compound 32. A mixture of 2,4,5-trichloropyrimidine (491 mg, 2.68 mmol, 1 eq.), compound 31 (0.8 g, 3.21 mmol, 1.2 eq.), aq. Na$_2$CO$_3$ (2 M, 4.01 mL, 3 eq.), and 4-di(tert-butyl)phosphanyl-N,N-dimethyl-aniline dichloropalladium (189.49 mg, 268 μmol, 189 μL, 0.1 eq.) in DME (8 mL) was degassed and purged with N$_2$ for 3 times and then stirred at 85° C. for 2 h under N$_2$. The reaction mixture was concentrated in vacuo. The mixture was diluted H$_2$O (20 mL) and then extracted with EtOAc (30 mL×3). The combined organic layers were washed with brine (20 mL), dried over Na$_2$SO$_4$, filtered, and concentrated under reduced pressure. The residue was purified by column chromatography (SiO$_2$, PE/EtOAc: 4/1 to 2:1) to afford compound 32 (0.5 g, 1.85 mmol, 69% yield). $^1$H NMR (CDCl$_3$, 400 MHz) δ 9.15 (s, 1H), 8.53-8.45 (m, 1H), 2.84 (d, J=6.8 Hz, 2H), 1.05-0.99 (m, 1H), 0.40-0.31 (m, 2H), 0.17-0.05 (m, 2H).

Compound C1. A mixture of trans-cyclohexane-1,4-diamine (507 mg, 4.44 mmol, 4 eq.), compound 32 (0.3 g, 1.11 mmol, 1 eq.) in n-BuOH (5 mL) was degassed and purged with N$_2$ for 3 times. After stirred at 160° C. for 2 h under N$_2$, the reaction mixture was partitioned between H$_2$O (10 mL) and EtOAc (15 mL). The organic phase was separated, washed with brine (10 mL×2), dried over Na$_2$SO$_4$, filtered, and concentrated under reduced pressure. The residue was purified by prep-HPLC (HCl condition) to afford compound C1 (0.147 g, 0.421 mmol, 38% yield, 100% purity). $^1$H NMR (CD$_3$OD, 400 MHz) δ 9.63 (s, 1H), 8.47 (s, 1H), 3.94 (br s, 1H), 3.19 (br s, 1H), 3.01 (d, J=6.9 Hz, 2H), 3.05-2.91 (m, 1H), 2.22-2.11 (m, 4H), 1.65-1.50 (m, 4H), 1.19-1.05 (m, 1H), 0.62-0.47 (m, 2H), 0.23 (q, J=4.9 Hz, 2H).

Example 13

Synthesis of (1r,4r)-4-((5-Chloro-4-(3-(cyclopropylmethyl)isoxazol-4-yl)pyrimidin-2-yl)amino)cyclohexan-1-ol C2

Compound C2 was prepared as shown in Scheme 8 below.

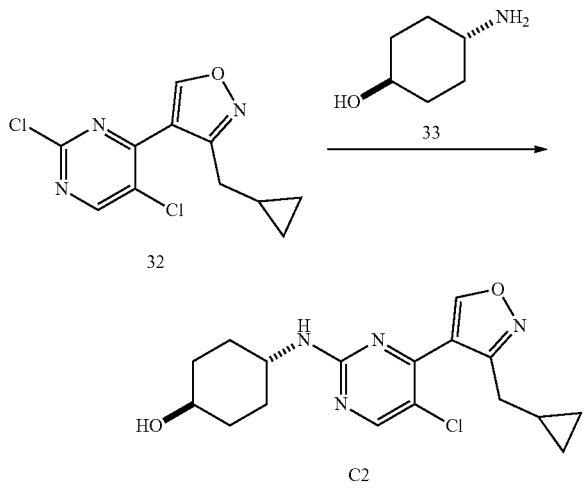

Compound C2. A mixture of trans-4-aminocyclohexanol (21.32 mg, 185 µmol, 2.5 eq.) and compound 32 (0.02 g, 74 µmol, 1 eq.) in n-BuOH (5 mL) was degassed and purged with $N_2$ for 3 times and then stirred at 160° C. for 2 h under $N_2$. The reaction mixture was concentrated under reduced pressure. The residue was purified by prep-HPLC (HCl condition) to afford compound C2 (6.7 mg, 19 µmol, 26% yield). $^1$H NMR (CD$_3$OD, 400 MHz) δ 9.62 (s, 1H), 8.41 (s, 1H), 3.86 (br s, 1H), 3.68-3.48 (m, 1H), 3.01 (d, J=6.9 Hz, 2H), 2.17-1.98 (m, 4H), 1.54-1.36 (m, 4H), 1.28-1.08 (m, 1H), 1.21-1.07 (m, 1H), 0.71-0.35 (m, 2H), 0.24 (q, J=4.8 Hz, 2H).

Example 14

Synthesis of (1r,4r)-4-((4-(4-(Cyclopropylmethyl)-3-methylisoxazol-5-yl)pyrimidin-2-yl)amino)cyclohexan-1-ol C3 and (1r,4r)-4-((5-Chloro-4-(4-(cyclopropylmethyl)-3-methylisoxazol-5-yl)pyrimidin-2-yl)amino)cyclohexan-1-ol C4

Compounds C3 and C4 were prepared as shown in Scheme 9 below.

Compound C3. A mixture of compound 16 (59 mg, 511 µmol, 2.5 eq.) and compound 33 (60 mg, 204 µmol, 1 eq.) in t-BuOH (5 mL) was stirred at 140° C. for 2 h. The reaction mixture was concentrated in vacuo. The residue was partitioned between H$_2$O (5 mL) and DCM (10 mL). The organic phase was separated, washed with brine (10 mL), dried over Na$_2$SO$_4$, filtered, and concentrated in vacuo. The crude product was purified by orep-TLC (EtOAc) to afford compound C3 (40 mg, 122 µmol, 60% yield). $^1$H NMR (CD$_3$OD, 400 MHz) δ 8.39 (d, J=6.5 Hz, 1H), 7.39 (d, J=6.5 Hz, 1H), 4.07 (br s, 1H), 3.70-3.55 (m, 1H), 2.95 (d, J=6.7 Hz, 2H), 2.39 (s, 3H), 2.17-2.00 (m, 4H), 1.63-1.35 (m, 4H), 1.12 (br s, 1H), 0.54 (br d, J=7.0 Hz, 2H), 0.30 (q, J=5.1 Hz, 2H).

Compound C4. To a solution of compound C3 (20.0 mg, 61 µmol, 1 eq.) in MeCN (5 mL) was added NCS (8.1 mg, 61 µmol, 1.0 eq.) in portions at 25° C. The mixture was degassed and purged with $N_2$ for 3 times. Then the mixture was warmed to 80° C. and stirred for 12 h under $N_2$. The reaction mixture was concentrated in vacuo. The residue was purified by prep-HPLC (neutral condition) to afford compound C4 (10.5 mg, 29 µmol, 47% yield). $^1$H NMR (CD$_3$OD, 400 MHz) δ 8.36 (s, 1H), 3.78 (br s, 1H), 3.58 (br s, 1H), 2.69 (br s, 2H), 2.35 (s, 3H), 2.11-1.91 (m, 4H), 1.45-1.31 (m, 4H), 1.00 (br s, 1H), 0.47 (br d, J=7.2 Hz, 2H), 0.24-0.09 (m, 2H).

Example 15

Synthesis of (1r,4r)-4-((4-(5-(Cyclopropylmethyl)-1-methyl-1H-1,2,3-triazol-4-yl)pyrimidin-2-yl)amino)cyclohexan-1-ol C5 and (1r,4r)-4-((5-Chloro-4-(5-(cyclopropylmethyl)-1-methyl-1H-1,2,3-triazol-4-yl)pyrimidin-2-yl)amino)cyclohexan-1-ol C6

Compounds C5 and C6 were prepared as shown in Scheme 10 below.

Compound C5. A mixture of compound 33 (0.2 g, 1.70 mmol, 2.5 eq.) and compound 21 (0.2 g, 682 µmol, 1 eq.) in t-BuOH (5 mL) was stirred at 140° C. for 2 h under $N_2$. The reaction mixture was cooled down to 25° C. and concentrated in vacuo. The residue was purified by prep-HPLC (neural condition) to afford compound C5 (0.11 g, 335 µmol, 49% yield). $^1$H NMR (CD$_3$OD, 400 MHz) δ 8.25 (d, J=5.3 Hz, 1H), 7.26 (d, J=5.3 Hz, 1H), 4.10 (s, 3H), 3.86 (br s, 1H), 3.68-3.56 (m, 1H), 3.33-3.32 (m, 2H), 2.12-1.98 (m, 4H), 1.50-1.36 (m, 4H), 1.17 (br s, 1H), 0.58-0.50 (m, 2H), 0.39-0.32 (m, 2H).

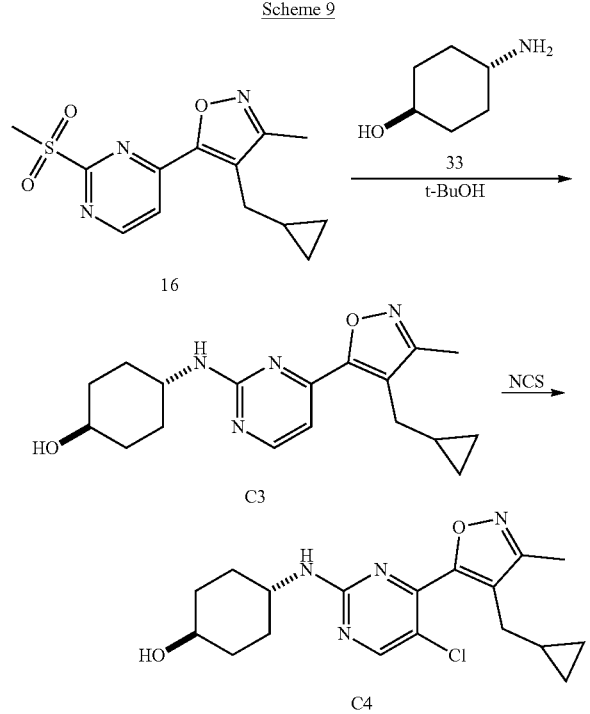

Scheme 9

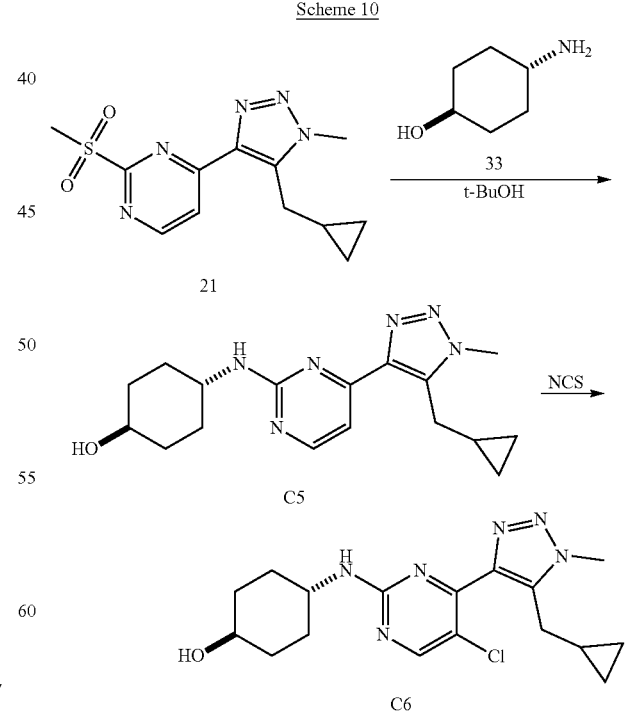

Scheme 10

Compound C6. To a solution of compound C5 (50 mg, 152 µmol, 1 eq.) in MeCN (5 mL) was added NCS (24 mg, 183 µmol, 1.2 eq.) in one portion at 25° C. The mixture was warmed to 80° C. and stirred for 0.5 hr under N₂. The reaction mixture was concentrated in vacuo. The residue was purified by prep-HPLC (HCl condition) to afford compound C6 (24 mg, 67 µmol, 44% yield). ¹H NMR (CD₃OD, 400 MHz) δ 8.31 (s, 1H), 4.12 (s, 3H), 3.77 (br s, 1H), 3.58 (br s, 1H), 3.01 (br d, J=6.7 Hz, 2H), 2.12-1.89 (m, 4H), 1.47-1.28 (m, 4H), 1.04 (br s, 1H), 0.50 (br d, J=7.7 Hz, 2H), 0.21 (br d, J=4.5 Hz, 2H).

Example 16

Synthesis of (1r,4r)-N-(4-(5-(Cyclopropylmethyl)-1-methyl-1H-1,2,3-triazol-4-yl)-5-ethylpyrimidin-2-yl)cyclohexane-1,4-diamine C7

Compound C7 was prepared as shown in Scheme 11 below.

Compound 34. To a solution of compound 9 (0.5 g, 2.31 mmol, 1 eq.) and TMEDA (323 mg, 2.78 mmol, 419 µL, 1.2 eq.) in THF (20 mL) was added dropwise n-BuLi (2.5 M, 1.11 mL, 1.2 eq.) at −78° C. under N₂. After addition, the mixture was stirred at this temperature for 15 min. Bu₃SnCl (1.13 g, 3.47 mmol, 934 µL, 1.5 eq.) was added dropwise at −78° C. The mixture was stirred at −78° C. for 25 mins. The reaction mixture was poured into sat. NH₄Cl (20 mL) and extracted with EtOAc (30 mL×3). The combined organics were washed with sat. KF (30 mL), brine (30 mL), dried over Na₂SO₄, and concentrated in vacuo. The residue was purified by column chromatography (Al₂O₃, PE/EtOAc: 7/1 to 6/1) to afford compound 34 (0.6 g, 1.41 mmol, 61% yield) as a colorless oil. ¹H NMR (CDCl₃, 400 MHz) δ 3.85 (s, 3H), 2.46 (d, J=6.3 Hz, 2H), 1.41-1.31 (m, 6H), 1.19-1.10 (m, 6H), 1.00-0.89 (m, 6H), 0.71 (t, J=7.2 Hz, 9H), 0.52-0.50 (m, 1H), 0.42-0.33 (m, 2H), 0.04-0.03 (m, 2H).

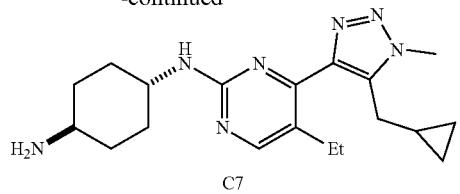

C7

Compound 36. A mixture of compound 34 (100 mg, 234 µmol, 1 eq.), compound 35 (62 mg, 352 µmol, 1.5 eq.), Pd(PPh₃)₄ (27 mg, 23 µmol, 0.1 eq.), and LiCl (20 mg, 469 µmol, 2 eq.) in toluene (1 mL) was degassed and purged with N₂ for 3 times. Then the mixture was stirred at 100° C. for 5 h under N₂. The reaction mixture was cooled down to 25° C. and poured into sat. KF (10 mL) and stirred for 20 min. Then the mixture was extracted with EtOAc (10 mL×2). The combined organics were washed with brine (20 mL), dried over Na₂SO₄, and concentrated in vacuo to afford crude compound 36 (40 mg) as a yellow solid, which was used directly in the next step without further purification.

Compound C7. A mixture of compound 36 (30 mg, 108 µmol, 1 eq.) and compound 37 (31 mg, 270 µmol, 2.5 eq.) in n-BuOH (0.5 mL) was stirred at 140° C. for 3 h. The mixture was cooled down to 25° C. and concentrated in vacuo. The residue was purified by prep-HPLC (HCl condition) to afford compound C7 (7.5 mg, 21 µmol, 20% yield) as a brown oil. ¹H NMR (CD₃OD, 400 MHz) δ 8.19 (s, 1H), 4.15 (s, 3H), 4.11-3.96 (m, 1H), 3.22 (s, 2H), 3.21-3.18 (m, 1H), 3.15 (q, J=7.4 Hz, 2H), 2.25-2.16 (m, 4H), 1.68-1.56 (m, 4H), 1.22 (t, J=7.4 Hz, 3H), 1.11 (br s, 1H), 0.56 (br d, J=7.4 Hz, 2H), 0.30 (br d, J=4.5 Hz, 2H).

Example 17

Synthesis of (1r,4r)-N-(4-(5-(Cyclopropylmethyl)-1-methyl-1H-1,2,3-triazol-4-yl)-5-fluoropyrimidin-2-yl)cyclohexane-1,4-diamine C8

Compound C8 was prepared as shown in Scheme 12 below.

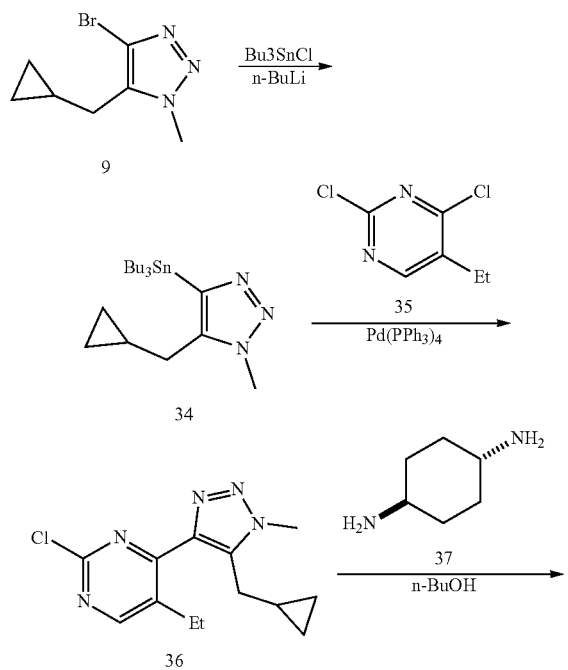

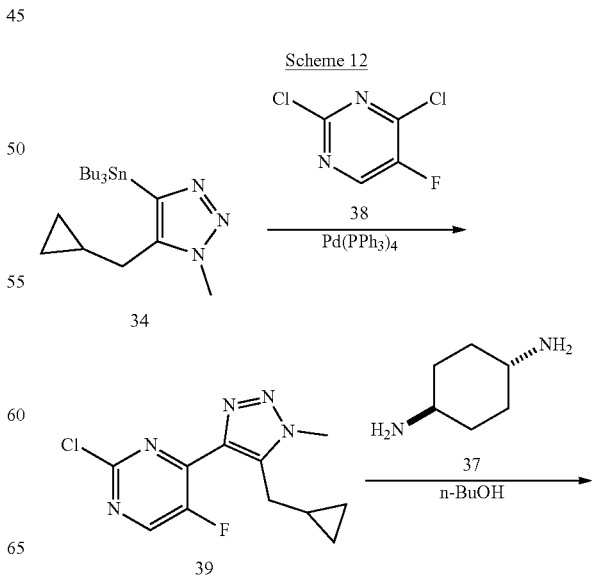

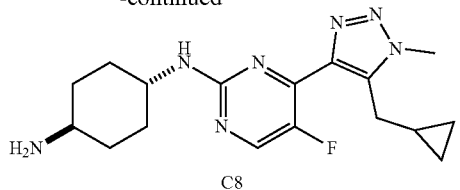

Compound 39. A mixture of compound 34 (150 mg, 352 µmol, 1 eq.), compound 38 (588 mg, 3.52 mmol, 10 eq.), BINAP (88 mg, 141 µmol, 0.4 eq.), and Pd₂(dba)₃ (65 mg, 70 µmol, 0.2 eq.) in toluene (10 mL) was degassed and purged with N₂ for 3 times. Then the mixture was stirred at 100° C. for 8 h under N₂. The mixture was cooled down to 25° C. and partitioned between sat. KF (20 mL) and EtOAc (20 mL). The organic phase was separated, washed with brine (15 mL), dried over Na₂SO₄, and concentrated in vacuo. The residue was purified by column chromatography (PE/EtOAc: 10/1 to 3/1) to afford compound 39 (80 mg, 299 µmol, 85% yield). ¹H NMR (CDCl₃, 400 MHz) δ 8.56 (d, J=2.6 Hz, 1H), 4.14 (s, 3H), 3.16 (d, J=6.8 Hz, 2H), 1.15-0.93 (m, 1H), 0.60-0.44 (m, 2H), 0.42-0.21 (m, 2H).

Compound C8. To a solution of compound 39 (30 mg, 112 µmol, 1 eq.) and compound 38 (38 mg, 336 µmol, 3 eq.) in n-BuOH (0.5 mL) was stirred at 140° C. for 3 h. The mixture was cooled down to 25° C. and concentrated in vacuo. The residue was purified by prep-HPLC (neutral condition) to compound C8 (13 mg, 38 µmol, 34% yield). ¹H NMR (CD₃OD, 400 MHz) δ 8.27 (d, J=3.4 Hz, 1H), 4.13 (s, 3H), 3.82-3.69 (m, 1H), 3.20 (d, J=6.7 Hz, 2H), 2.79-2.66 (m, 1H), 2.16-2.03 (m, 2H), 1.98-1.89 (m, 2H), 1.43-1.25 (m, 4H), 1.10 (br d, J=6.5 Hz, 1H), 0.58-0.48 (m, 2H), 0.34-0.25 (m, 2H).

Example 18

Synthesis of (1r,4r)-4-((4-(5-(Cyclopropylmethyl)-1-methyl-1H-1,2,3-triazol-4-yl)-5-fluoropyrimidin-2-yl)amino)cyclohexan-1-ol C9

Compound C9 was prepared as shown in Scheme 13 below.

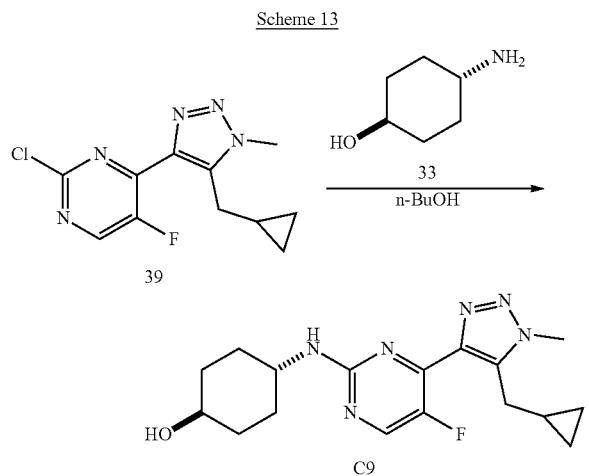

Scheme 13

Compound C9. To a solution of compound 39 (10 mg, 37 µmol, 1 eq.) and compound 33 (13 mg, 112 µmol, 3 eq.) in n-BuOH (0.5 mL) was stirred at 140° C. for 11 h. The mixture was cooled down to 25° C. and concentrated in vacuo. The residue was purified by prep-HPLC (HCl condition) to afford compound C9 (2.0 mg, 5.8 µmol, 15% yield) as a yellow oil. ¹H NMR (CD₃OD, 400 MHz) δ 8.43 (d, J=4.3 Hz, 1H), 4.16 (s, 3H), 3.96-3.82 (m, 1H), 3.67-3.54 (m, 1H), 3.24 (d, J=6.8 Hz, 2H), 2.13-2.07 (m, 2H), 2.03 (br d, J=9.4 Hz, 2H), 1.54-1.42 (m, 4H), 1.21-1.09 (m, 1H), 0.61-0.51 (m, 2H), 0.40-0.28 (m, 2H).

Example 19

Synthesis of (1r,4r)-N-(4-(5-(Cyclopropylmethyl)-1-methyl-1H-1,2,3-triazol-4-yl)-5-(trifluoromethyl)pyrimidin-2-yl)cyclohexane-1,4-diamine C10

Compound C10 was prepared as shown in Scheme 14 below.

Compound 41. A mixture of compound 34 (0.1 g, 235 µmol, 1 eq.), compound 40 (102 mg, 469 µmol, 2 eq.), CsF (71 mg, 469 µmol, 2 eq.), and Pd(dppf)Cl₂ (17 mg, 23 µmol, 0.1 eq.) in dioxane (3 mL) was degassed and purged with N₂ for 3 times. Then the mixture was stirred at 100° C. for 5 h under N₂. The reaction mixture was cooled down to 25° C. and partitioned between sat. KF (20 mL) and EtOAc (10 mL×3). The organic phase was separated, washed with brine (20 mL), dried over Na₂SO₄, and concentrated in vacuo. The residue was purified by prep-TLC (PE/EtOAc: 3:1) to afford compound 41 (10 mg, 20 µmol, 9% yield, 65% purity) as a yellow oil. LCMS (M+H⁺)=318.

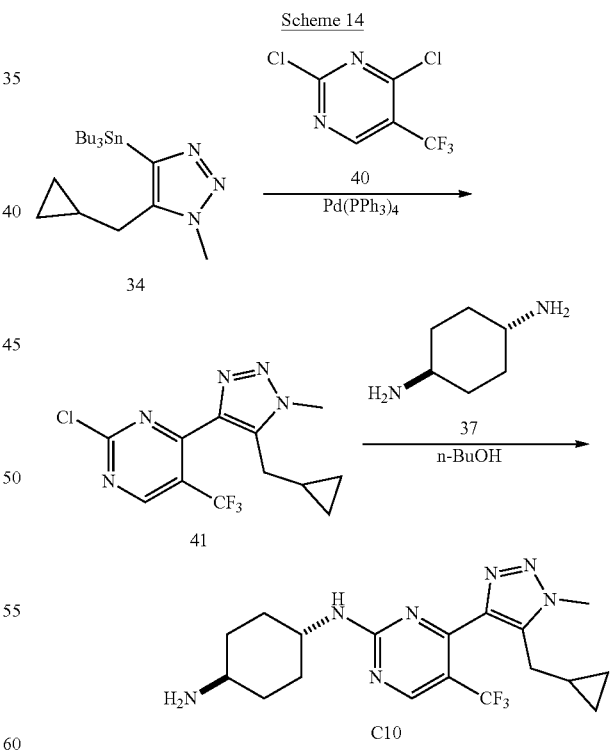

Scheme 14

Compound C10. A mixture of compound 41 (5 mg, 16 µmol, 1 eq.) and compound 37 (5 mg, 47 µmol, 3 eq.) in n-BuOH (0.5 mL) was stirred at 140° C. for 11 h. The mixture was cooled down to 25° C. and concentrated in vacuo. The residue was purified by prep-HPLC (HCl condition) to afford compound C10 (1.2 mg, 3 µmol, 19% yield)

as a yellow oil. $^1$H NMR (CD$_3$OD, 400 MHz) δ 8.52 (s, 1H), 4.93-4.92 (m, 1H), 4.56 (s, 1H), 4.16 (s, 3H), 3.29-3.28 (m, 2H), 2.16 (br s, 4H), 1.74-1.58 (m, 4H), 1.20 (s, 1H), 0.57 (br d, J=8.3 Hz, 2H), 0.37 (br d, J=4.8 Hz, 2H).

Example 20

Synthesis of (1r,4r)-N-(4-(5-(Cyclopropylmethyl)-1-methyl-1H-1,2,3-triazol-4-yl)-5-vinylpyrimidin-2-yl)cyclohexane-1,4-diamine C11

Compound C11 was prepared as shown in Scheme 15 below.

Compound 44. A mixture of compound 42 (1.0 g, 4.22 mmol, 1.5 eq.), compound 43 (1.2 g, 2.82 mmol, 1 eq.), Pd(PPh$_3$)$_4$ (325 mg, 282 µmol, 0.1 eq.), and LiCl (239 mg, 5.63 mmol, 2 eq.) in toluene (10 mL) was degassed and purged with N$_2$ for 3 times. Then the mixture was stirred at 100° C. for 8 h under N$_2$. The reaction mixture was cooled down to 25° C. and partitioned between sat. KF (30 mL) and EtOAc (40 mL). The organic phase was separated, washed with brine (20 mL), dried over Na$_2$SO$_4$, and concentrated in vacuo. The residue was purified by column chromatography (PE/EtOAc: 10/1 to 3/1) to afford compound 44 (400 mg, 1.18 mmol, 42% yield). $^1$H NMR (CDCl$_3$, 400 MHz) δ 8.72 (s, 1H), 4.11 (s, 3H), 3.00 (d, J=6.7 Hz, 2H), 2.57 (s, 3H), 1.07-0.92 (m, 1H), 0.57-0.46 (m, 2H), 0.32-0.17 (m, 2H).

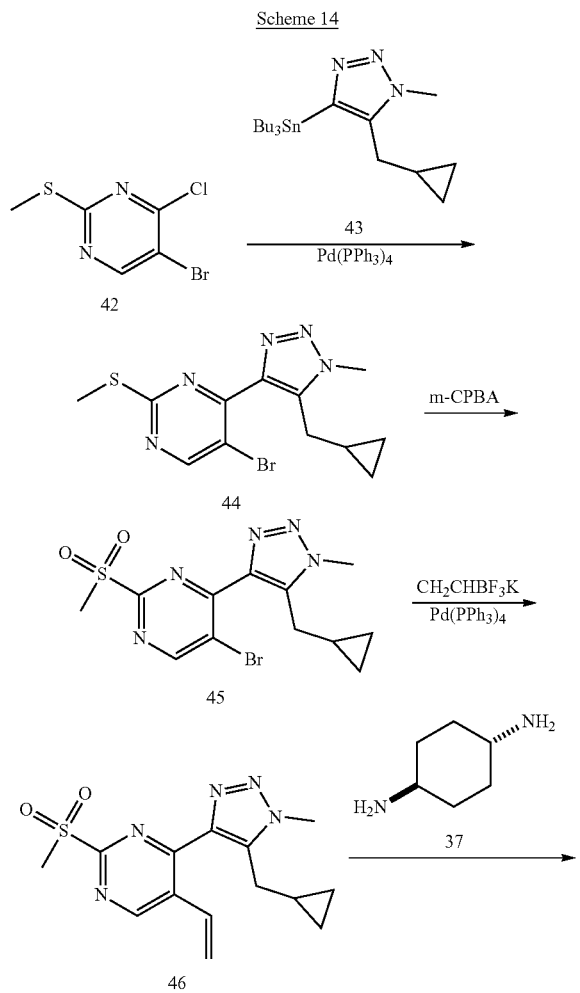

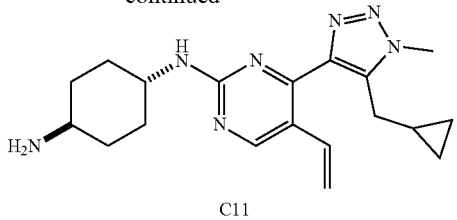

Compound 45. To a solution of compound 44 (70 mg, 206 µmol, 1 eq.) in DCM (10 mL) was added m-CPBA (111 mg, 514 µmol, 80% purity, 2.5 eq.) in portions at 0° C. The mixture was stirred at 0-15° C. for 1 h under N$_2$. The reaction mixture was poured into sat. NaHCO$_3$ (20 mL) and extracted with DCM (20 mL×2). The combined organics were poured into sat. Na$_2$SO$_3$ (20 mL) and stirred for 5 min. The organic phase was separated and washed with brine (40 mL), dried over Na$_2$SO$_4$, and concentrated in vacuo. The residue was purified by column chromatography (PE/EtOAc: 10:1 to 3:1) to afford compound 45 (70 mg, 188 µmol, 91% yield). $^1$H NMR (CDCl$_3$, 400 MHz) δ 9.07 (s, 1H), 4.15 (s, 3H), 3.36 (s, 3H), 3.15 (d, J=6.7 Hz, 2H), 1.14-1.02 (m, 1H), 0.61-0.50 (m, 2H), 0.34 (q, J=4.9 Hz, 2H).

Compound 46. A mixture of compound 45 (38 mg, 62 µmol, 1 eq.), trifluoro(vinyl)-λ$^4$-borane, potassium salt (8 mg, 62 µmol, 1 eq.), Na$_2$CO$_3$ (20 mg, 185 µmol, 3 eq.), and Pd(PPh$_3$)$_4$ (7 mg, 6.2 µmol, 0.1 eq.) in dioxane (1.5 mL) and H$_2$O (0.3 mL) was degassed and purged with N$_2$ for 3 times. Then the mixture was stirred at 80° C. for 2 h under N$_2$. The mixture was cooled down to 25° C. and filtered through celite. The filtrate was concentrated in vacuo. The residue was purified by prep-TLC (PE/EtOAc: 1/1) to afford compound 46 (18 mg, 56 µmol, 91% yield) as a yellow oil. $^1$H NMR (CDCl$_3$, 400 MHz) δ 9.02 (s, 1H), 7.85 (dd, J=11.1, 17.6 Hz, 1H), 5.91 (d, J=17.6 Hz, 1H), 5.67 (d, J=11.4 Hz, 1H), 4.14 (s, 3H), 3.37 (s, 3H), 3.24 (d, J=6.8 Hz, 2H), 1.12-1.10 (br s, 1H), 0.56-0.50 (m, 2H), 0.36 (q, J=5.1 Hz, 2H).

Compound C11. A mixture of compound 46 (18 mg, 56 µmol, 1 eq.) and compound 37 (10 mg, 85 µmol, 1.5 eq.) in t-BuOH (0.5 mL) was stirred at 100° C. for 3 h. The mixture was cooled down to 25° C. and concentrated in vacuo. The residue was purified by prep-HPLC (HCl) to afford compound C11 (2.6 mg, 7.4 µmol, 13% yield) as a brown oil. $^1$H NMR (CD$_3$OD, 400 MHz) δ 8.47 (s, 1H), 7.45 (br s, 1H), 5.69 (d, J=17.6 Hz, 1H), 5.38 (d, J=11.0 Hz, 1H), 4.84-4.79 (m, 1H), 4.15 (s, 3H), 4.12-3.95 (m, 1H), 3.19 (br d, J=6.5 Hz, 2H), 2.20 (br d, J=15.3 Hz, 4H), 1.69-1.53 (m, 4H), 1.19-1.07 (m, 1H), 0.56 (br d, J=7.2 Hz, 2H), 0.32 (br s, 2H).

Example 21

Synthesis of (1r,4r)-N-(5-Cyclopropyl-4-(5-(cyclopropylmethyl)-1-methyl-1H-1,2,3-triazol-4-yl)pyrimidin-2-yl)cyclohexane-1,4-diamine C12

Compound C12 was prepared as shown in Scheme 16 below.

Scheme 16

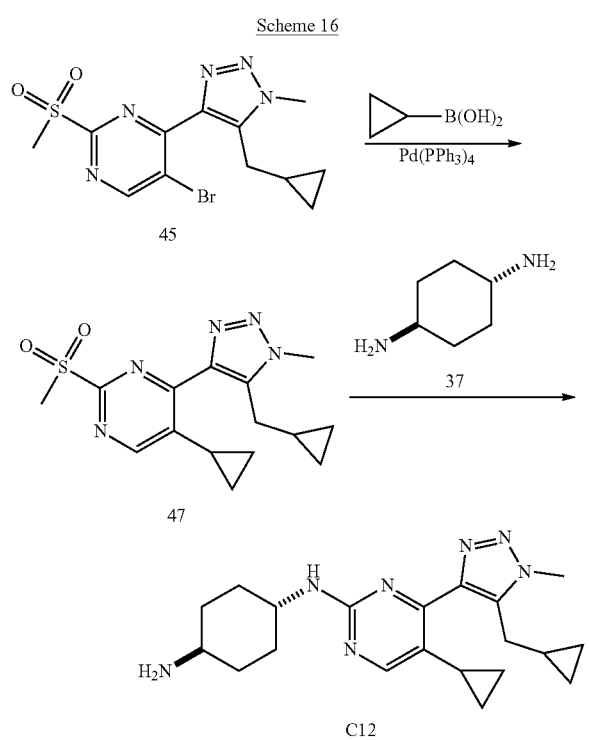

Compound 47. A mixture of cyclopropylboronic acid (16 mg, 188 μmol, 1 eq.), compound 45 (70 mg, 188 μmol, 1 eq.), K$_2$CO$_3$ (51.98 mg, 376 μmol, 2 eq.), and Pd(PPh$_3$)$_4$ (21.73 mg, 19 μmol, 0.1 eq.) in toluene (5 mL) was stirred at 80° C. for 2 h under N$_2$. The mixture was cooled down to 25° C. and concentrated in vacuo. The residue was purified by prep-TLC (PE/EtOAc: 1/1) to afford compound 47 (10 mg, 30 μmol, 16% yield). LCMS (M+H$^+$)=334.

Compound C12. To a solution of compound 37 (6.8 mg, 60 μmol, 2 eq.) and compound 47 (10 mg, 30 μmol, 1 eq.) in t-BuOH (0.5 mL) was stirred at 160° C. for 10 h. The mixture was cooled down to 25° C. and concentrated in vacuo. The residue was purified by prep-HPLC (neutral condition and HCl condition) to afford compound C12 (1.0 mg, 2.4 μmol, 8% yield, 97% purity). $^1$H NMR (CD$_3$OD, 400 MHz) δ 8.06 (s, 1H), 4.15 (s, 3H), 3.72 (s, 1H), 3.16 (br d, J=5.3 Hz, 2H), 2.54 (br s, 1H), 2.22-2.12 (m, 4H), 1.58 (br t, J=9.3 Hz, 4H), 1.10 (br s, 1H), 0.96 (br d, J=8.3 Hz, 2H), 0.56 (br d, J=5.4 Hz, 5H), 0.27 (br s, 2H).

Example 22

Synthesis of (1r,4r)-N-(5-Chloro-4-(5-(cyclopropylmethyl)-2H-1,2,3-triazol-4-yl)pyrimidin-2-yl)cyclohexane-1,4-diamine C13

Compound C13 was prepared as shown in Scheme 17 below.

Scheme 17

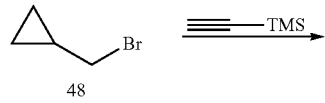

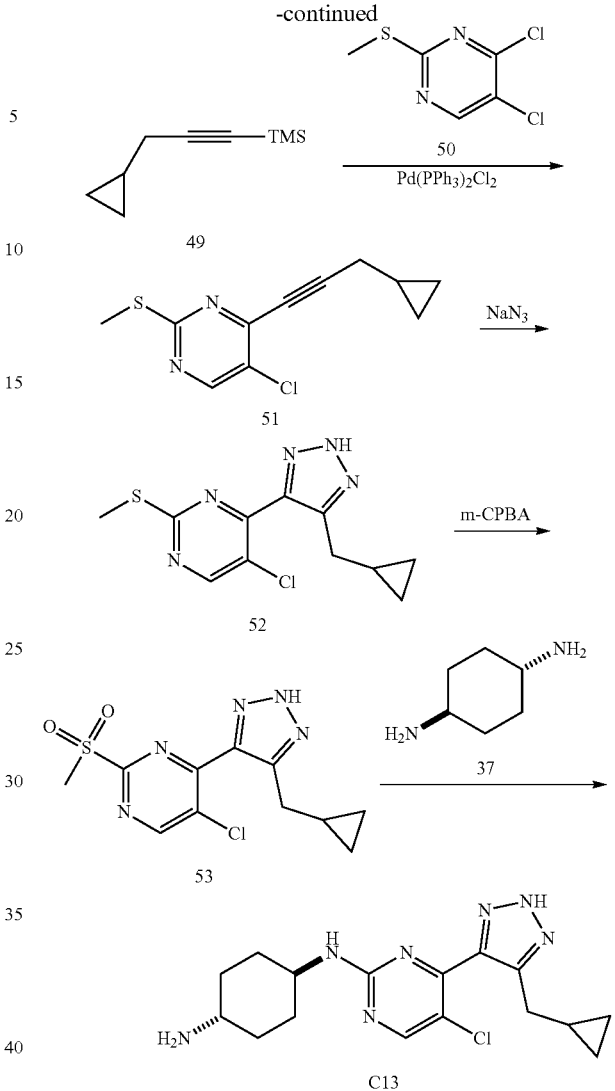

Compound 49. To a solution of ethynyl(trimethyl)silane (15 g, 153 mmol, 21.16 mL, 1 eq.) in THF (100 mL) was added n-BuLi (2.5 M, 73.31 mL, 1.2 eq.) dropwise at −78° C. under N$_2$. The mixture was stirred at 0° C. for 10 min. Then HMPA (41.05 g, 229 mmol, 40.25 mL, 1.5 eq.) was added dropwise at −78° C. The mixture was stirred at −78° C. for 20 min under N$_2$. Then compound 48 (20.62 g, 153 mmol, 14.62 mL, 1 eq.) was added dropwise at −78° C. Then the mixture was stirred −78-25° C. for 9.5 h. The reaction mixture was poured into ice sat. NH$_4$Cl (100 mL) and extracted with MTBE (150 mL). The organic phase was washed with brine (200 mL), dried over Na$_2$SO$_4$, and concentrated in vacuo. The residue was purified by column chromatography (SiO$_2$, hexane) to afford compound 49 (21 g, 138 mmol, 90% yield) as a yellow liquid. $^1$H NMR (CDCl$_3$, 400 MHz) δ 2.31 (d, J=5.6 Hz, 2H), 0.95-0.91 (m, 1H), 0.50-0.39 (m, 2H), 0.28-0.22 (m, 2H), 0.17-0.14 (m, 9H).

Compound 51. To a mixture of compound 49 (976 mg, 5.13 mmol, 2 eq.), compound 50 (0.5 g, 2.56 mmol, 1 eq.), Pd(PPh$_3$)$_2$Cl$_2$ (360 mg, 512 μmol, 0.2 eq.), and CuI (244 mg, 1.28 mmol, 0.5 eq.) in THF (10 mL) was added TBAF (1 M, 2.56 mL, 1 eq.) in one portion at 0° C. under N$_2$. The reaction mixture was stirred at 60° C. under N$_2$ for 10 h. The mixture was partitioned between H₂O (100 mL) and EtOAc (200 mL). The combined organic phase were washed with brine (200 mL), dried over Na₂SO₄, and concentrated in vacuo. The residue was purified by column chromatography (SiO₂, PE/EtOAc: 1/0 to 50/1) and prep-TLC (PE/EtOAc: 20:1) to afford compound 51 (0.3 g, 1.26 mmol, 49% yield) as a brown oil. ¹H NMR (CDCl₃, 400 MHz) δ 8.47 (s, 1H), 2.61 (d, J=5.9 Hz, 2H), 2.56 (s, 3H), 1.13-1.03 (m, 1H), 0.61-0.52 (m, 2H), 0.36 (q, J=4.9 Hz, 2H).

Compound 52. A mixture of NaN₃ (123 mg, 1.88 mmol, 1.5 eq.), compound 51 (300 mg, 1.26 mmol, 1 eq.), CuSO₄·5H₂O (376.51 mg, 1.51 mmol, 1.2 eq.), and sodium (2R)-2-[(1S)-1,2-dihydroxyethyl]-4-hydroxy-5-oxo-2H-furan-3-olate (299 mg, 1.51 mmol, 1.2 eq.) in DMF (5 mL) was stirred at 20° C. for 12 h. The reaction mixture was partitioned between H₂O (10 mL) and EtOAc (20 mL×2). The organic phase was separated and dried over Na₂SO₄ and concentrated in vacuo. The residue was purified by column chromatography (SiO₂, PE/EtOAc: 10/1 to 5:1) to afford compound 52 (20 mg, 71 μmol, 6% yield) as a yellow oil. ¹H NMR (CDCl₃, 400 MHz) δ 11.82 (br s, 1H), 8.60 (s, 1H), 3.01 (d, J=7.0 Hz, 2H), 2.60 (s, 3H), 1.17-0.97 (m, 1H), 0.59 (br d, J=7.4 Hz, 2H), 0.38-0.13 (m, 2H).

Compound 53. To a solution of compound 52 (15 mg, 53 μmol, 1 eq.) in DCM (10 mL) was added m-CPBA (29 mg, 133 μmol, 80% purity, 2.5 eq.) in portions at −78° C. The mixture was stirred at −78 to 0° C. for 1 h under N₂. The reaction mixture was poured into sat. Na₂SO₃ (10 mL) and and stirred for 5 min. Then the mixture was extracted with DCM (20 mL×2). The combined organic layers were poured into sat. NaHCO₃ (10 mL). The organic layer was washed with brine (20 mL), dried over Na₂SO₄, filtered, and concentrated in vacuo to give compound 53 (16 mg, 51 μmol, 96% yield) as a yellow solid. H NMR (CDCl₃, 400 MHz) δ 8.96 (s, 1H), 3.39 (s, 3H), 3.12 (d, J=7.2 Hz, 2H), 0.97 (br t, J=7.5 Hz, 1H), 0.70-0.60 (m, 2H), 0.34 (q, J=5.0 Hz, 2H).

Compound C13. A mixture of compound 53 (0.015 g, 48 μmol, 1 eq.) and compound 37 (10.92 mg, 96 μmol, 2 eq.) in t-BuOH (0.5 mL) was stirred at 140° C. for 2 h. The mixture was concentrated in vacuo. The residue was purified by prep-HPLC (HCl condition) to afford compound C13 (1.7 mg, 4.9 μmol, 10% yield). ¹H NMR (CD₃OD, 400 MHz) δ 8.40 (s, 1H), 3.93-3.75 (m, 1H), 3.15 (br s, 1H), 2.93 (d, J=7.0 Hz, 2H), 2.19 (br d, J=10.8 Hz, 2H), 2.12 (br d, J=11.2 Hz, 2H), 1.57-1.46 (m, 4H), 1.11 (s, 1H), 0.61-0.47 (m, 2H), 0.23 (q, J=5.1 Hz, 2H).

Example 23

Synthesis of (1r,4r)-N-(5-Chloro-4-(4-(cyclopropylmethyl)-1H-pyrazol-5-yl)pyrimidin-2-yl)cyclohexane-1,4-diamine C14

Compound C14 was prepared as shown in Scheme 18 below.

Scheme 18

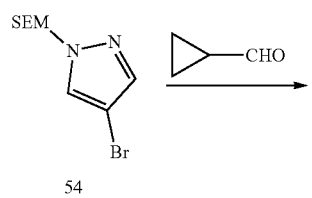

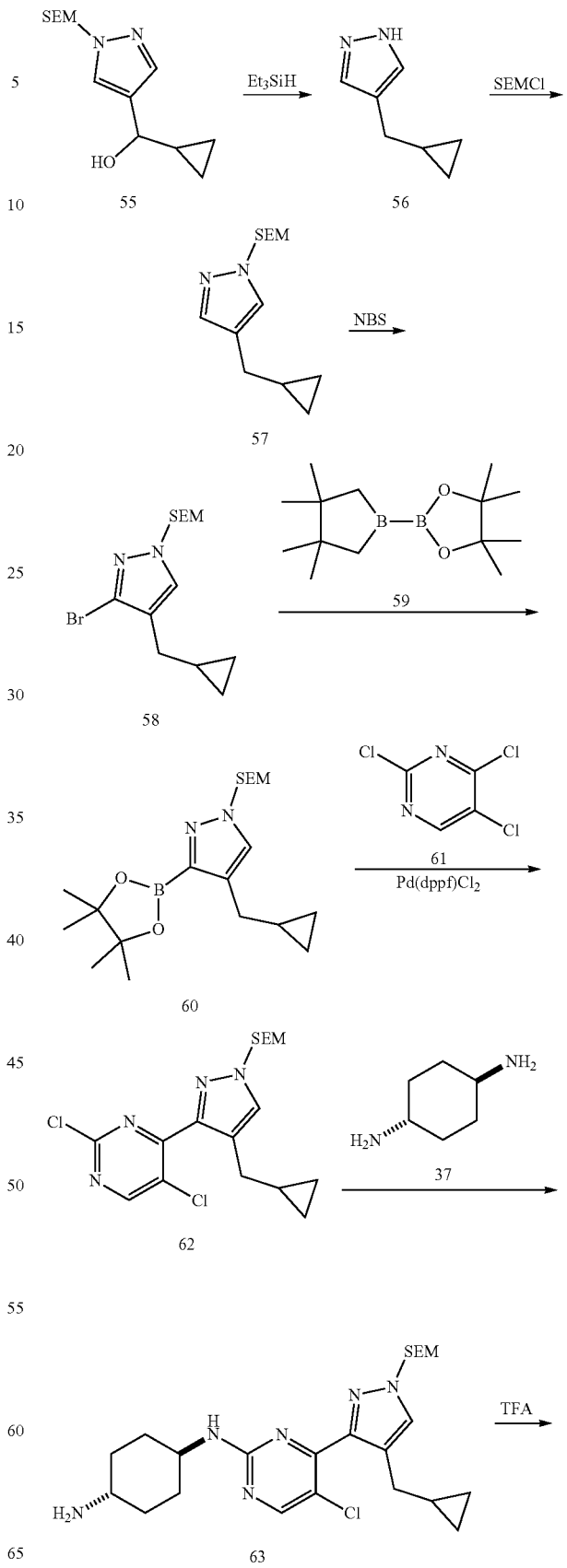

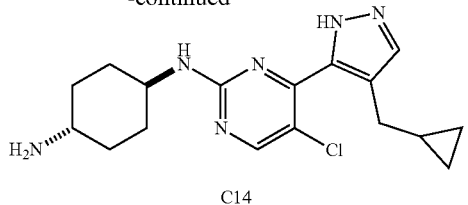

C14

Compound 55. To a solution of compound 54 (7.58 g, 108 mmol, 8.09 mL, 2 eq.) in THF (200 mL) was added n-BuLi (2.5 M, 26 mL, 1.2 eq.) dropwise at −78° C. under $N_2$. The mixture was stirred at −78° C. for 0.5 h. Then cyclopropyl aldehyde (15 g, 54 mmol, 1 eq.) was added dropwise at −78° C. The mixture was stirred at −78° C. for 0.5 h under $N_2$. The reaction mixture was poured into ice $NH_4Cl$ (100 mL) and extracted with EtOAc (150 mL×2). The combined organic layers were washed with brine (150 mL), dried over $Na_2SO_4$, and concentrated in vacuo. The residue was purified by column chromatography ($SiO_2$, PE/EtOAc: 10/1 to 2/1) to afford compound 55 (4.69 g, 17 mmol, 32% yield) as a yellow oil. $^1$H NMR ($CDCl_3$, 400 MHz) δ 7.38 (d, J=1.7 Hz, 1H), 6.35 (d, J=1.6 Hz, 1H), 5.60-5.41 (m, 2H), 4.23-4.12 (m, 1H), 3.51 (t, J=8.4 Hz, 2H), 3.31 (br d, J=3.3 Hz, 1H), 1.41-1.29 (m, 1H), 0.89-0.78 (m, 2H), 0.68-0.43 (m, 3H), 0.30 (qd, J=4.8, 9.7 Hz, 1H), 0.03-0.25 (m, 9H).

Compound 56. To a solution of compound 55 (4.6 g, 17 mmol, 1 eq.) in DCM (17 mL) was added TFA (39 g, 343 mmol, 25.38 mL, 20 eq.) and triethylsilane (9.96 g, 86 mmol, 13.69 mL, 5 eq.) in one portion at 25° C. The mixture was stirred at 60° C. for 12 h. The reaction mixture was concentrated in vacuo. The mixture was poured into ice $NaHCO_3$ (100 mL) and extracted with EtOAc (50 mL×3). The combined organic layers were washed with brine (50 mL), dried over $Na_2SO_4$, filtered, and concentrated in vacuo. The residue was purified by column chromatography ($SiO_2$, PE/EtOAc: 10/1 to 2/1) to afford compound 56 (2.0 g, 16 mmol, 96% yield) as a yellow oil. $^1$H NMR ($CDCl_3$, 400 MHz) δ 12.76 (br s, 1H), 7.64 (s, 1H), 6.39-6.04 (m, 1H), 2.67 (d, J=7.0 Hz, 2H), 1.18-0.95 (m, 1H), 0.72-0.49 (m, 2H), 0.34-0.07 (m, 2H).

Compound 57. To solution of compound 56 (2 g, 16 mmol, 1 eq.) in THF (50 mL) was add NaH (786 mg, 30 mmol, 60% purity, 1.2 eq.) in portions at 0° C. under $N_2$. Then the mixture was stirred at 0° C. for 30 min. SEM-Cl (4.09 g, 25 mmol, 4.35 mL, 1.5 eq.) was added dropwise at 0° C. The mixture was stirred at 0-30° C. for 2 h under $N_2$. The reaction mixture was poured into ice sat. $NH_4Cl$ (100 mL) and extracted with EtOAc (50 mL×2). The combined organic layers were washed with brine (50 mL), dried over $Na_2SO_4$, and concentrated in vacuo. The residue was purified by column chromatography ($SiO_2$, PE/EtOAc: 20/1 to 1/1) to afford compound 57 (4 g, 16 mmol, 97% yield) as a yellow oil. $^1$H NMR ($CDCl_3$, 400 MHz) δ 7.45 (dd, J=2.0, 15.8 Hz, 1H), 5.39 (d, J=17.6 Hz, 2H), 3.60-3.42 (m, 2H), 2.60 (dd, J=6.8, 19.0 Hz, 2H), 1.10-0.94 (m, 1H), 0.94-0.81 (m, 2H), 0.61-0.41 (m, 2H), 0.27-0.14 (m, 2H), −0.03 (d, J=3.3 Hz, 9H).

Compound 58. To solution of compound 57 (4 g, 15.85 mmol, 1 eq.) in MeCN (0.5 mL) was addd NBS (2.82 g, 15.85 mmol, 1 eq.) in portions at 0° C. Then the mixture was stirred at 0-30° C. for 2.5 h. The reaction mixture was poured into $H_2O$ (30 mL) and concentrated in vacuo. Then the mixture was partitioned between $H_2O$ (20 mL) and EtOAc (50 mL). The organic phase was separated, washed with brine (30 mL), dried over $Na_2SO_4$, and concentrated in vacuo. The residue was purified by column chromatography ($SiO_2$, PE/EtOAc: 20/1 to 1/1) to afford compound 58 (2.1 g, 3 mmol, 38% yield) as a yellow oil. $^1$H NMR ($CDCl_3$, 400 MHz) δ 7.59-7.40 (m, 2H), 5.55-5.24 (m, 4H), 3.60-3.52 (m, 4H), 2.74-2.51 (m, 4H), 1.17-1.02 (m, 2H), 0.96-0.85 (m, 4H), 0.54-0.44 (m, 4H), 0.34-0.18 (m, 4H), −0.02 (d, J=2.3 Hz, 18H).

Compound 60. To a mixture of compound 58 (2.0 g, 3.02 mmol, 1 eq.) and compound 59 (1.68 g, 9.05 mmol, 1.85 mL, 3 eq.) in THF (30 mL) was added n-BuLi (2.5 M, 2.90 mL, 2.4 eq.) dropwise at −78° C. under $N_2$. The mixture was stirred at −78° C. for 0.5 h. The mixture was poured into ice $NH_4Cl$ (50 mL) and extracted with EtOAc (50 mL×2). The combined organics were washed with brine (50 mL), dried over $Na_2SO_4$, and concentrated in vacuo. The residue was purified by column chromatography ($SiO_2$, PE/EtOAc: 10/1 to 3/1) to afford compound 60 (0.8 g, 2 mmol, 70% yield) as a yellow oil. $^1$H NMR ($CDCl_3$, 400 MHz) δ 7.79-7.69 (m, 2H), 5.50-5.36 (m, 4H), 3.62-3.51 (m, 4H), 2.92-2.67 (m, 4H), 1.31 (s, 24H), 1.11-1.01 (m, 2H), 0.93-0.88 (m, 4H), 0.48-0.37 (m, 4H), 0.34-0.21 (m, 4H), −0.02 (s, 18H).

Compound 62. A mixture of compound 61 (242 mg, 1.32 mmol, 1 eq.), compound 60 (1 g, 1.32 mmol, 1 eq.), Pd(dppf)$Cl_2$ (97 mg, 132 μmol, 0.1 eq.), and $K_2CO_3$ (365 mg, 2.64 mmol, 2 eq.) in dioxane:MeCN:$H_2O$ (2:2:1; 5 mL) was degassed and purged with $N_2$ for 3 times. Then the mixture was stirred at 80° C. for 2 h under $N_2$. The reaction mixture was partitioned between $H_2O$ (20 mL) and EtOAc (30 mL). The organic phase was separated, washed with brine (10 mL), dried over $Na_2SO_4$, filtered, and concentrated in vacuo. The residue was purified by column chromatography ($SiO_2$, PE/EtOAc: 20/1 to 3/1) to afford compound 62 (0.5 g, 626 μmol, 47% yield) as a yellow oil. $^1$H NMR ($CDCl_3$, 400 MHz) δ 8.58-8.53 (m, 2H), 8.34-8.25 (m, 2H), 5.58-5.53 (m, 3H), 3.69-3.58 (m, 4H), 3.20-3.07 (m, 4H), 0.96-0.84 (m, 6H), 0.50-0.39 (m, 4H), 0.34-0.22 (m, 4H), 0.01-(−0.04) (m, 18H). 2.7 Preparation of Compound 11—Notebook Page: ET18031-630

Compound 63. A mixture of compound 37 (143 mg, 1.25 mmol, 5 eq), compound 62 (100 mg, 250 μmol, 1 eq.) in n-BuOH (1 mL) was stirred at 140° C. for 4 h. The reaction mixture was partitioned between $H_2O$ (20 mL) and EtOAc (30 mL). The organic phase was separated, washed with brine (10 mL), dried over $Na_2SO_4$, filtered, and concentrated in vacuo to give compound 63 (0.230 g, 96% yield) as a yellow oil. $^1$H NMR ($CDCl_3$, 400 MHz) δ 8.36 (br s, 1H), 8.25-8.19 (m, 2H), 8.14 (br s, 1H), 5.53 (s, 2H), 5.44 (s, 2H), 4.91 (br d, J=5.3 Hz, 2H), 3.81 (br s, 2H), 3.66-3.58 (m, 4H), 3.12 (br d, J=5.6 Hz, 2H), 2.98 (br s, 2H), 2.74 (br s, 1H), 2.29-2.09 (m, 4H), 1.52-1.26 (m, 16H), 1.14-1.02 (m, 2H), 0.94-0.90 (m, 4H), 0.43 (br s, 4H), 0.19 (br t, J=5.0 Hz, 3H), 0.00 (s, 16H).

Compound C14. To a mixture of compound 63 (0.23 g, 241 μmol, 1 eq.) in DCM (2 mL) was added TFA (27 mg, 241 μmol, 17.85 μL, 1 eq.) dropwise at 0° C. The mixture was stirred at 0-30° C. for 2 h. The reaction mixture was poured into $NaHCO_3$ (10 mL) and DCM (15 mL×2). The organic phase was separated and washed with brine (15 mL), dried over $Na_2SO_4$, filtered, and concentrated in vacuo. The residue was purified by prep-HPLC (basic condition) to afford compound C14 (13 mg, 38 μmol, 16% yield). $^1$H NMR (CD$_3$OD, 400 MHz) δ 8.27 (br s, 1H), 8.19 (s, 1H), 3.81 (br s, 1H), 3.00 (br d, J=6.9 Hz, 2H), 2.86 (br s, 1H), 2.10 (br s, 2H), 2.01 (br s, 2H), 1.46-1.34 (m, 4H), 1.11 (br s, 1H), 0.49 (br d, J=7.4 Hz, 2H), 0.21 (br d, J=4.5 Hz, 2H).

Hz, 2H), 2.10-1.96 (m, 4H), 1.45-1.32 (m, 4H), 1.13 (br s, 1H), 0.51 (br s, 2H), 0.23 (br s, 2H).

Example 24

Synthesis of (1r,4r)-4-((5-Chloro-4-(4-(cyclopropyl-methyl)-1H-pyrazol-5-yl)pyrimidin-2-yl)amino)cyclohexan-1-ol C15

Compound C15 was prepared as shown in Scheme 19 below.

Example 25

Synthesis of (1r,4r)-N¹-(5-Fluoro-4-(5-(cyclopropyl-methyl)-1-methyl-1H-pyrazol-4-yl)pyrimidin-2-yl)-N⁴-(pent-4-yn-1-yl)cyclohexane-1,4-diamine AA1

Compound AA1 was prepared as shown in Scheme A1 below.

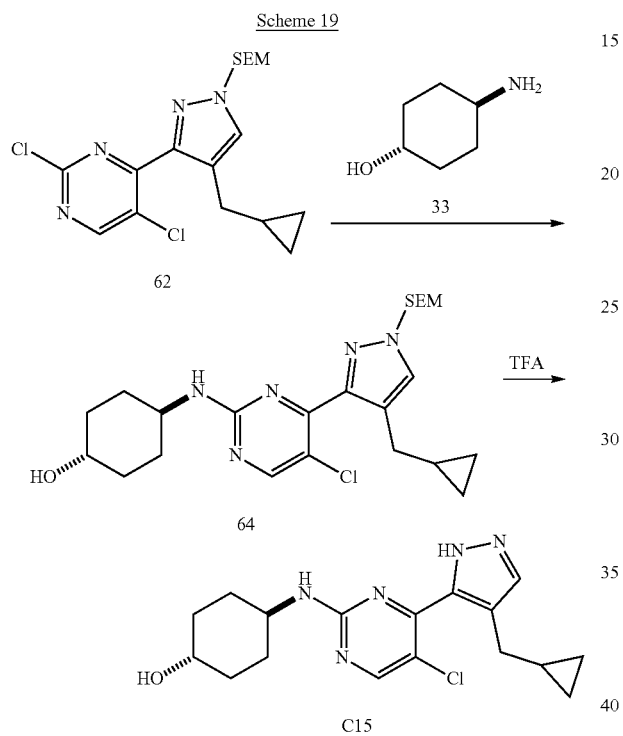

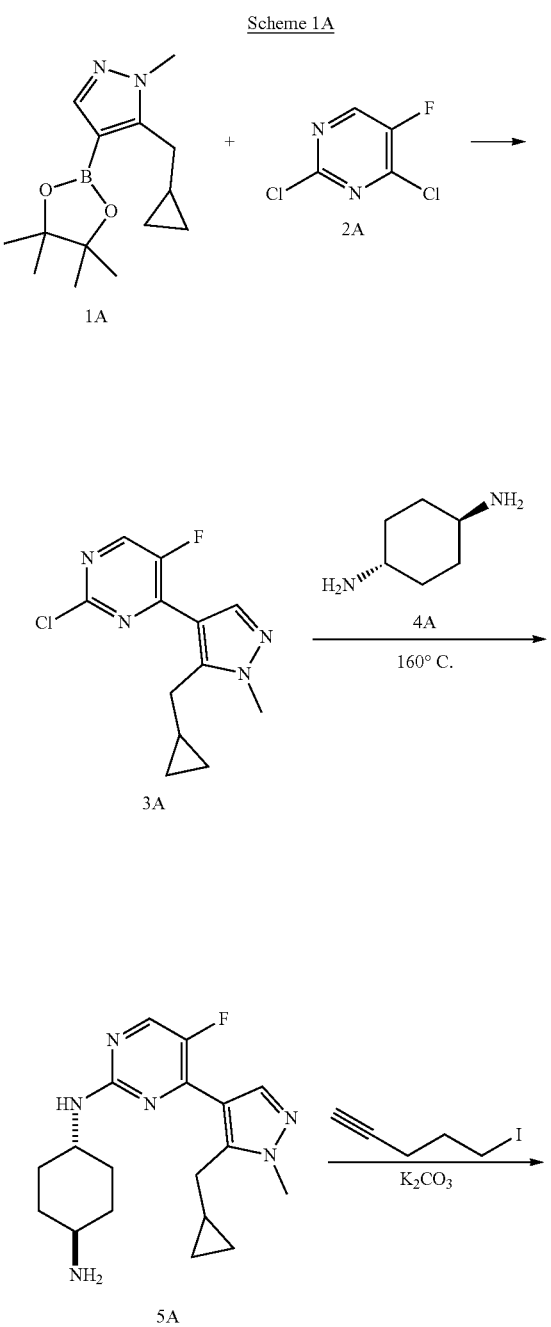

Compound 64. A mixture of compound 62 (200 mg, 250 µmol, 1 eq.) and compound 33 (72 mg, 626 µmol, 2.5 eq.) in n-BuOH (1 mL) was stirred at 140° C. for 4 h. The reaction mixture was partitioned between H₂O (20 mL) and EtOAc (30 mL). The organic phase was separated, washed with brine (10 mL), dried over Na₂SO₄, filtered, and concentrated in vacuo to afford compound 64 (0.15 g, 63% yield) as a yellow oil. ¹H NMR (CDCl₃, 400 MHz) δ 8.28-8.06 (m, 4H), 5.54 (s, 4H), 4.98 (br s, 2H), 3.82 (br s, 2H), 3.11 (br d, J=6.0 Hz, 4H), 2.15 (br d, J=10.5 Hz, 4H), 2.02 (br s, 4H), 1.44-1.40 (m, 4H), 1.36-1.22 (m, 8H), 1.06 (br s, 2H), 0.49-0.36 (m, 4H), 0.23-0.13 (m, 4H), 0.00 (s, 18H).

Compound C15. To a solution of compound 64 (0.14 g, 146 µmol, 1 eq.) in DCM (1.5 mL) was added TFA (1.08 g, 9.45 mmol, 700 µL, 65 eq.) at 0° C. The mixture was stirred at 0-30° C. for 0.5 h. The reaction mixture was poured into NaHCO₃ (10 mL) and extracted with EtOAc (15 mL×2). The organic phase was separated and washed with brine (15 mL), dried over Na₂SO₄, and concentrated in vacuo. The residue was purified by prep-HPLC (basic condition) to afford compound C15 (18.5 mg, 36% yield). ¹H NMR (CD₃OD, 400 MHz) δ 8.26 (br s, 1H), 8.18 (s, 1H), 4.60 (br s, 1H), 3.81 (br s, 1H), 3.68-3.54 (m, 1H), 3.01 (br d, J=6.3

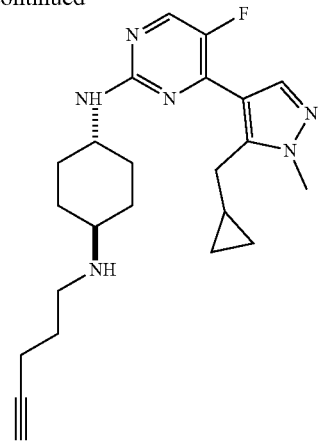

AA1

Compound 3A. A mixture of compound 1A (0.25 g, 954 μmol, 1 eq.), compound 2A (159 mg, 954 μmol, 1 eq.), Pd(dppf)Cl₂ (70 mg, 96 μmol, 0.1 eq.), and K₂CO₃ (264 mg, 1.91 mmol, 2 eq.) in dioxane:MeCN:H₂O (2:2:1) (3 mL) was degassed and purged with N₂ for 3 times at 25° C. After stirred at 90° C. for 10 h, the reaction mixture was cooled to 25° C. and partitioned between H₂O (10 mL) and EtOAc (10 mL). The organic phase was separated, washed with brine (10 mL), dried over Na₂SO₄, and concentrated in vacuo to give a residue. The residue was purified by prep-TLC (PE:EtOAc (3:1)) to give compound 3A (0.2 g, 750 μmol, 79% yield). ¹H NMR (CDCl₃, 400 MHz) δ 8.37 (d, J=3.1 Hz, 1H), 8.07 (d, J=4.3 Hz, 1H), 3.95 (s, 3H), 3.22 (d, J=6.7 Hz, 2H), 1.14-0.96 (m, 1H), 0.54-0.44 (m, 2H), 0.38 (q, J=4.9 Hz, 2H).

Compound 5A. A mixture of compound 3A (0.17 g, 637 μmol, 1 eq.) and compound 4A (364 mg, 3.19 mmol, 5 eq.) in n-BuOH (5 mL) was degassed and purged with N₂ for 3 times at 25° C. After stirred at 160° C. for 5 h, the reaction mixture was cooled to 25° C. and partitioned between H₂O (10 mL) and EtOAc (15 mL). The organic phase was separated, washed with brine (10 mL), dried over Na₂SO₄, and concentrated in vacuo to give a residue. The residue was purified by prep-HPLC (neutral condition) to give compound 5A (0.12 g, 55% yield). ¹H-NMR (CDCl₃, 400 MHz) δ 8.09 (d, J=3.5 Hz, 1H), 8.02 (d, J=4.2 Hz, 1H), 4.85 (br d, J=8.2 Hz, 1H), 3.91 (s, 3H), 3.84-3.72 (m, 1H), 3.22 (d, J=6.4 Hz, 2H), 2.87-2.77 (m, 1H), 2.17 (br d, J=11.5 Hz, 2H), 1.99 (br d, J=11.9 Hz, 2H), 1.40-1.24 (m, 4H), 1.16-1.04 (m, 1H), 0.53-0.46 (m, 2H), 0.28-0.22 (m, 2H).

5-Iodopent-1-yne. A mixture of 5-chloropent-1-yne (0.5 g, 4.9 mmol, 1 eq.) and NaI (2.2 g, 15 mmol, 3 eq.) in acetone (5 mL) was stirred at 80° C. for 12 h. The mixture was filtered and the filtrate was concentrated in vacuo to give 5-iodopent-1-yne (0.4 g), which was used directly in the next step without further purification. ¹H-NMR (CDCl₃, 400 MHz) δ 3.31 (t, J=6.7 Hz, 2H), 2.35-2.29 (m, 2H), 2.02-1.95 (m, 3H).

Compound AA1. A mixture of compound 5A (0.1 g, 290 μmol, 1 eq.), 5-iodopent-1-yne (45 mg, 232 μmol, 0.8 eq.), and K₂CO₃ (48 mg, 348 μmol, 143 μL, 1.2 eq.) in DMF (1.5 mL) was stirred at 25° C. for 12 h under N₂. The reaction mixture was partitioned between H₂O (10 mL) and EtOAc (10 mL). The organic phase was separated, washed with brine (10 mL), dried over Na₂SO₄, and concentrated in vacuo to give a residue. The residue was purified by prep-HPLC (HCl condition) to give AA1 (30 mg, 23% yield) as a HCl salt. ¹H-NMR (400 MHz, CD₃OD) δ 8.36 (d, J=5.7 Hz, 1H), 8.21 (d, J=4.9 Hz, 1H), 4.15-4.00 (m, 1H), 3.96 (s, 3H), 3.34-3.32 (m, 2H), 3.28-3.23 (m, 1H), 3.23-3.16 (m, 2H), 2.43-2.39 (m, 2H), 2.39-2.36 (m, 1H), 2.28 (br dd, J=9.8, 20.0 Hz, 4H), 2.02-1.90 (m, 2H), 1.76-1.54 (m, 4H), 1.26-1.12 (m, 1H), 0.60-0.51 (m, 2H), 0.42-0.29 (m, 2H).

Example 26

Synthesis of N-((1r,4r)-4-((5-Chloro-4-(5-(cyclopropylmethyl)-1-methyl-1H-pyrazol-4-yl)pyrimidin-2-yl)amino)cyclohexyl)pent-4-ynamide AA2

Compound AA2 was prepared as shown in Scheme 2A below.

Scheme 2A

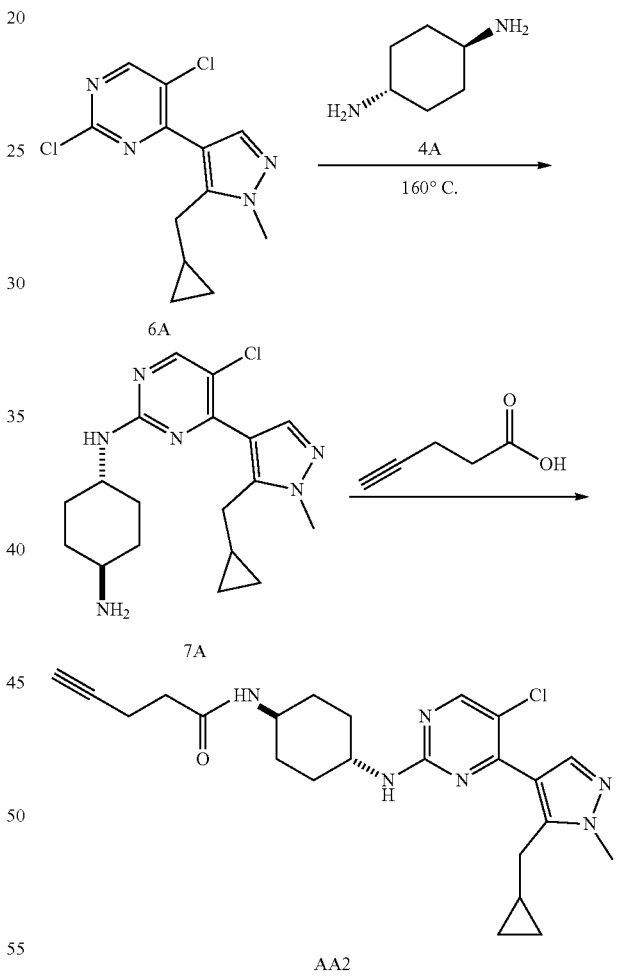

AA2

Compound 7A. A mixture of compound 6A (2.5 g, 8.83 mmol, 1 eq.) and compound 4A (5.04 g, 44 mmol, 5 eq.) in n-BuOH (5 mL) was degassed and purged with N₂ for 3 times at 25° C. After stirred at 160° C. for 2 h, the reaction mixture was cooled to 25° C. and partitioned between H₂O (10 mL) and EtOAc (15 mL). The organic phase was separated, washed with brine (10 mL×2), dried over Na₂SO₄, and concentrated in vacuo to give a residue. The residue was purified by prep-HPLC (neutral condition) to give compound 7A (2.7 g, 85% yield). ¹H-NMR (400 MHz, CD$_3$OD) δ 8.19 (s, 1H), 8.06 (br s, 1H), 3.90 (s, 3H), 3.85-3.69 (m, 1H), 3.13 (br d, J=6.5 Hz, 2H), 2.90-2.73 (m, 1H), 2.14-1.90 (m, 4H), 1.45-1.25 (m, 4H), 1.07-0.92 (m, 1H), 0.51-0.40 (m, 2H), 0.16 (br d, J=4.8 Hz, 2H).

Compound AA2. A mixture of compound 7A (500 mg, 1.39 mmol, 1 eq.), pent-4-ynoic acid (143 mg, 1.45 mmol, 1.05 eq.), HATU (579 mg, 1.52 mmol, 1.1 eq.), and TEA (280 mg, 2.77 mmol, 386 μL, 2 eq.) in DMF (5 mL) was stirred at 25° C. for 2 h under N$_2$. The reaction mixture was partitioned between H$_2$O (10 mL) and EtOAc (10 mL). The organic phase was separated, washed with brine (10 mL), dried over Na$_2$SO$_4$, and concentrated in vacuo to give a residue. The residue was purified by prep-HPLC (HCl condition) to give compound AA2 (0.375 g, 57% yield) as a HCl salt. $^1$H-NMR (400 MHz, CD$_3$OD) δ 8.36-7.97 (m, 2H), 3.93 (s, 3H), 3.90-3.84 (m, 1H), 3.75-3.65 (m, 1H), 3.17 (d, J=6.4 Hz, 2H), 2.52-2.33 (m, 4H), 2.26 (t, J=2.6 Hz, 1H), 2.15-1.92 (m, 4H), 1.56-1.30 (m, 4H), 1.13-0.98 (m, 1H), 0.51 (br d, J=7.7 Hz, 2H), 0.23 (br d, J=4.5 Hz, 2H).

Example 27

Synthesis of (1r,4r)-N$^1$-(5-Chloro-4-(5-(cyclopropylmethyl)-1-methyl-1H-pyrazol-4-yl)pyrimidin-2-yl)-N$^4$-(pent-4-yn-1-yl)cyclohexane-1,4-diamine AA3

Compound AA3 was prepared as shown in Scheme 3A below.

Scheme 3A

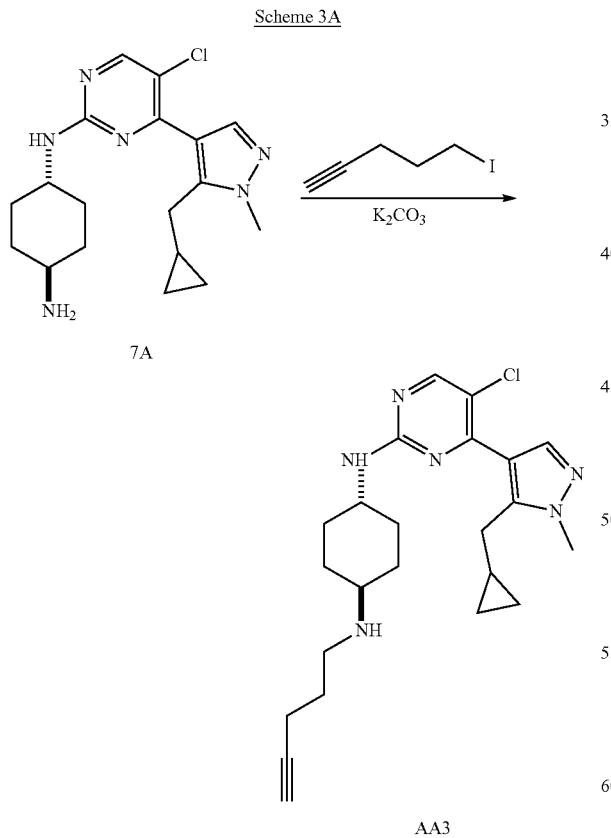

AA3

Compound AA3. To a solution of compound 7A (100 mg, 277 μmol, 1 eq.) in DMF (5 mL) was added K$_2$CO$_3$ (57 mg, 416 μmol, 1.5 eq.) at 25° C. After the mixture was stirred at 25° C. for 30 mins, 5-iodopent-1-yne (54 mg, 277 μmol, 1 eq.) in DMF (5 mL) was added. The mixture was stirred at 25° C. for 2 h. The reaction mixture was then filtered, concentrated, and purified by prep-HPLC (neutral condition) to give compound AA3 (13 mg, 11% yield). $^1$H NMR (CD$_3$OD, 400 MHz) δ 8.19 (s, 1H), 7.96-8.14 (m, 1H), 3.87-3.98 (m, 3H), 3.71-3.86 (m, 1H), 3.03-3.26 (m, 2H), 2.69-2.87 (m, 2H), 2.49-2.68 (m, 1H), 2.15-2.36 (m, 3H), 1.96-2.15 (m, 4H), 1.74 (quin, J=7.18 Hz, 2H), 1.22-1.45 (m, 4H), 1.01 (br d, J=6.40 Hz, 1H), 0.47 (br d, J=7.53 Hz, 2H), 0.17 (br d, J=4.64 Hz, 2H).

Example 28

Synthesis of N-((1r,4r)-4-((5-Chloro-4-(5-(cyclopropylmethyl)-1-methyl-1H-pyrazol-4-yl)pyrimidin-2-yl)amino)cyclohexyl)pentanamide AA4

Compound AA4 was prepared as shown in Scheme 4A below.

Scheme 4A

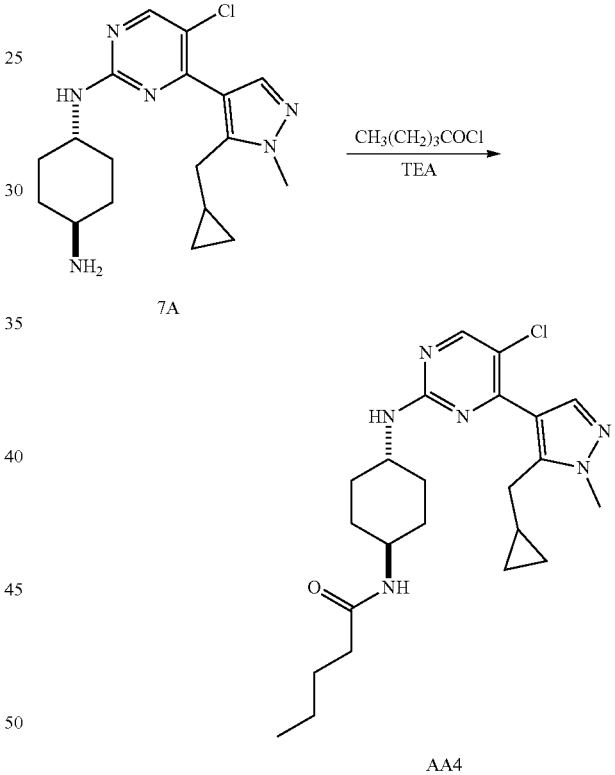

AA4

Pentanoyl chloride. To a solution of pentanoic acid (500 mg, 4.9 mmol, 532 μL, 1 eq.) in DCM (3 mL) was added oxalyl chloride (684 mg, 5.4 mmol, 471.39 μL, 1.1 eq.) at 0° C., followed by two drops of DMF at 0° C. After stirred at 25° C. for 1 h, the reaction mixture was concentrated in vacuo to yield pentanoyl chloride (600 mg), which was directly in the next step without further purification.

Compound AA4. To a solution of compound 7A (50 mg, 139 μmol, 1 eq.) in DCM (2 mL) was added TEA (21 mg, 208 μmol, 28.93 μL, 1.5 eq.) at 0° C. After stirred at 0° C. for 10 min, pentanoyl chloride (17 mg, 139 μmol, 17 μL, 1 eq.) in DCM (0.5 mL) was added dropwise at 0° C. After stirred at 25° C. for 1 h, the reaction mixture was then partitioned between H$_2$O (10 mL) and EtOAc (20 mL). The organic phase was separated, dried over Na$_2$SO$_4$, and concentrated in vacuo to give a residue. The residue was purified by prep-HPLC (HCl condition) to give compound AA4 (13 mg, yield 32%, purity 95%). $^1$H NMR (CD$_3$OD, 400 MHz) δ 8.20-8.49 (m, 2H), 3.94 (s, 4H), 3.68 (tt, J=11.33, 3.89 Hz, 1H), 3.20 (d, J=6.39 Hz, 2H), 2.06-2.24 (m, 4H), 1.93-2.03 (m, 2H), 1.26-1.67 (m, 8H), 1.02-1.15 (m, 1H), 0.94 (t, J=7.39 Hz, 3H), 0.46-0.60 (m, 2H), 0.27 (br d, J=4.63 Hz, 2H).

Example 29

Synthesis of N$^1$-(5-Chloro-4-(5-(cyclopropylmethyl)-1-methyl-1H-pyrazol-4-yl)pyrimidin-2-yl)bicyclo[2.2.1]heptane-1,4-diamine AB1

Compound AB1 was prepared as shown in Scheme 5A below.

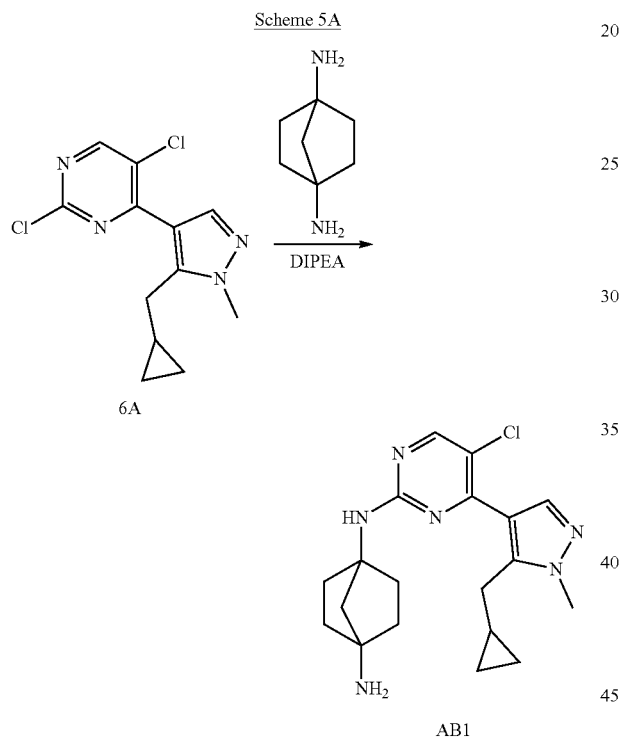

Compound AB1. A mixture of compound 6A (75 mg, 265 μmol, 1 eq.), bicyclo[2.2.1]heptane-1,4-diamine (47 mg, 371 μmol, 1.4 eq.), and DIPEA (103 mg, 795 μmol, 138 μL, 3 eq.) in DMSO (1 mL) was degassed and purged with N$_2$ for three times at 25° C. After stirred at 140° C. for 10 h under N$_2$, the reaction mixture was purified by prep-HPLC (HCl) to give compound AB1 (21 mg, yield 21%, purity 95%). $^1$H NMR (400 MHz, CD$_3$OD) δ 8.46 (s, 1H), 8.15 (s, 1H), 3.98 (s, 3H), 3.05-3.24 (m, 1H), 3.15 (d, J=6.53 Hz, 2H), 1.87-2.32 (m, 10H), 0.95 (br t, J=5.02 Hz, 1H), 0.48 (br d, J=7.53 Hz, 2H), 0.14 (d, J=5.52 Hz, 2H).

Example 30

Synthesis of N$^1$-(5-Chloro-4-(5-(cyclopropylmethyl)-1-methyl-1H-pyrazol-4-yl)pyrimidin-2-yl)bicyclo[2.2.2]octane-1,4-diamine AB2

Compound AB2 was prepared as shown in Scheme 6A below.

Compound 8A. A mixture of compound 6A (60 mg, 212 μmol, 1 eq.), tert-butyl N-(1-amino-4-bicyclo[2.2.2]octanyl)carbamate (51 mg, 212 μmol, 1 eq.), and DIPEA (41 mg, 318 μmol, 55 μL, 1.5 eq.) in DMSO (2 mL) was degassed and purged with N$_2$ for three times at 25° C. After stirred at 140° C. for 10 h under N$_2$, the reaction mixture was partitioned between H$_2$O (5 mL) and EtOAc (10 mL). The organic phase was separated, dried over Na$_2$SO$_4$ and concentrated in vacuo to give compound 8A (60 mg), which was used directly in the next step without further purification.

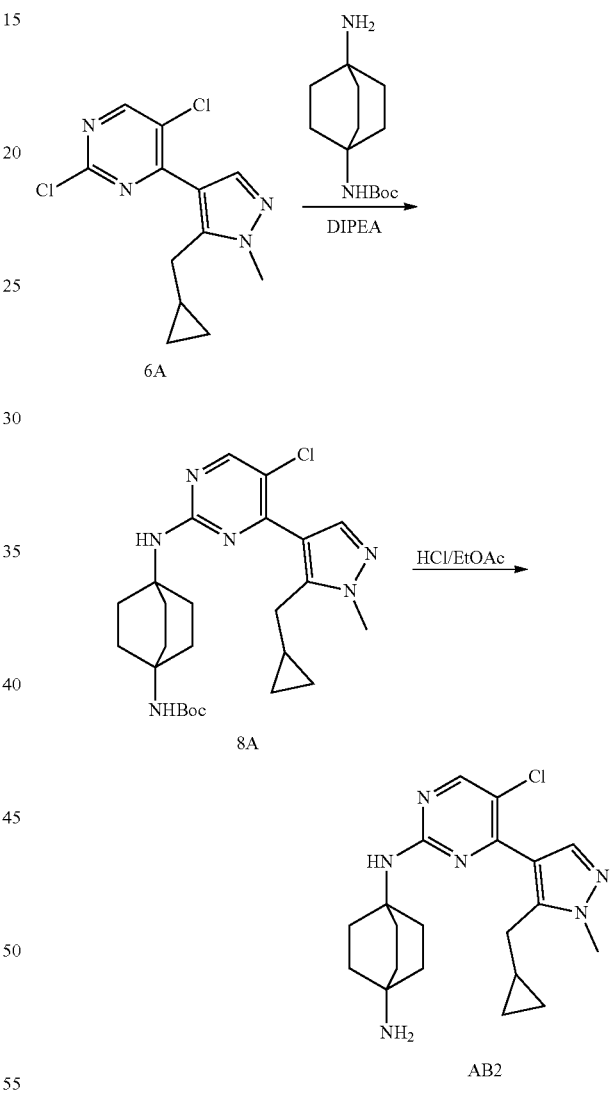

Compound AB2. To a solution of compound 8A (60 mg, 123 μmol, 1 eq.) in EtOAc (3 mL) was added HCl/EtOAc (4 M, 31 μL, 1 eq.) at 25° C. After stirred at 25° C. for 0.5 h, the reaction mixture was concentrated in vacuo to give a residue. The residue was then purified by prep-HPLC (neutral condition) to give compound AB2 (9.6 mg, yield 20%, purity 95%). $^1$H NMR (400 MHz, CD$_3$OD) δ 8.20 (s, 1H), 7.90 (s, 1H), 3.91 (s, 3H), 3.09 (d, J=6.62 Hz, 2H), 2.04-2.17 (m, 6H), 1.64-1.76 (m, 6H), 0.86-1.01 (m, 1H), 0.34-0.51 (m, 2H), 0.00-0.14 (m, 2H).

Example 31

Synthesis of (1r,4r)-N¹-(5-Chloro-4-(5-(cyclopropylmethyl)-1-methyl-1H-pyrazol-4-yl)pyrimidin-2-yl)-N⁴-pentylcyclohexane-1,4-diamine AA5 and (1r,4r)-N¹-(5-Chloro-4-(5-(cyclopropylmethyl)-1-methyl-1H-pyrazol-4-yl)pyrimidin-2-yl)-N⁴,N⁴-dipentylcyclohexane-1,4-diamine AA6

Compounds AA5 and AA6 were prepared as shown in Scheme 7A below.

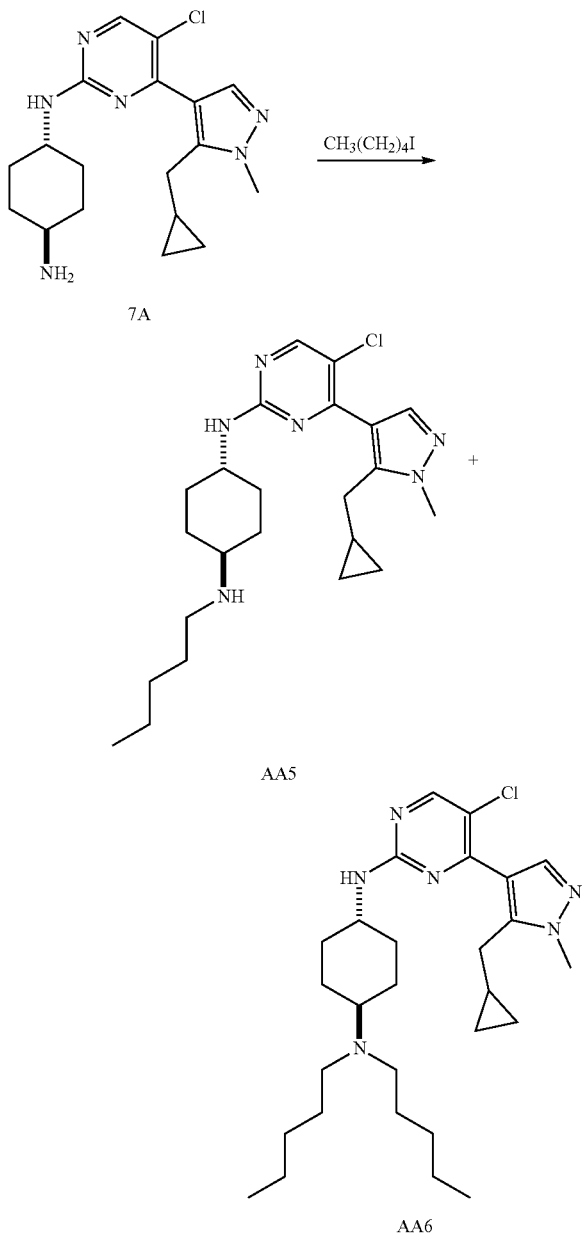

Compounds AA5 and AA6. To a solution of compound 7A (40 mg, 111 μmol, 1 eq.) in DMF (3 mL) was added $K_2CO_3$ (18.38 mg, 133 μmol, 1.2 eq.) at 25° C. After addition, the mixture was stirred at this temperature for 30 min and then 1-iodopentane (21.95 mg, 111 μmol, 1 eq.) in DMF (3 mL) was added. The mixture was stirred at 25° C. for 2 h. The reaction mixture was filtered and concentrated. The residue was purified by prep-HPLC (HCl condition) to afford compound AA5 (12 mg, 28 μmol, 25% yield) as a colorless oil and compound AA6 (7 mg, 14 μmol, 13% yield) as a colorless oil.

Compound AA5: MS (ESI) m/z: [M+H]⁺ Calcd for $C_{23}H_{36}ClN_6$ 431.3; Found 431.5; ¹H NMR (CD₃OD, 400 MHz) δ 8.32-8.55 (m, 2H), 3.87-4.15 (m, 4H), 3.13-3.25 (m, 3H), 3.00-3.09 (m, 2H), 2.15-2.35 (m, 4H), 1.68-1.78 (m, 2H), 1.52-1.67 (m, 4H), 1.33-1.48 (m, 4H), 1.03-1.14 (m, 1H), 1.02-1.16 (m, 1H), 0.91-1.02 (m, 3H), 0.45-0.64 (m, 2H), 0.24-0.32 (m, 2H). 431.5

Compound AA6: MS (ESI) m/z: [M+H]⁺ Calcd for $C_{28}H_{46}ClN_6$ 501.2; Found 501.6; ¹H NMR (CD₃OD, 400 MHz) δ 8.14-8.41 (m, 2H), 3.84-4.06 (m, 4H), 3.43 (t, J=11.91 Hz, 1H), 3.06-3.28 (m, 6H), 2.12-2.33 (m, 4H), 1.69-1.84 (m, 6H), 1.50-1.65 (m, 2H), 1.37-1.46 (m, 8H), 1.01-1.14 (m, 1H), 0.97 (t, J=6.84 Hz, 6H), 0.45-0.55 (m, 2H), 0.15-0.30 (m, 2H). 501.6

Example 32

Synthesis of (1r,4r)-N-(3-Aminopropyl)-N⁴-(5-chloro-4-(5-(cyclopropylmethyl)-1-methyl-1H-pyrazol-4-yl)pyrimidin-2-yl)cyclohexane-1,4-diamine AA7 and (Z)-Cyclooct-4-en-1-yl (3-(((1r,4r)-4-((5-chloro-4-(5-(cyclopropylmethyl)-1-methyl-1H-pyrazol-4-yl)pyrimidin-2-yl)amino)cyclohexyl)amino)propyl)carbamate AA8

Compounds AA7 and AA8 were prepared as shown in Scheme 8A below.

Compound 9A. A mixture of compound 7A (27.25 mg, 76 μmol, 1 eq.), tert-butyl (3-bromopropyl)carbamate (21.57 mg, 91 μmol, 1.2 eq.) and $K_2CO_3$ (31.31 mg, 227 μmol, 3 eq.) in DMF (2 mL) was degassed and purged with $N_2$ for 3 times and then stirred at 50° C. for 6 h under $N_2$ atmosphere. The reaction mixture was partitioned between $H_2O$ (10 mL) and EtOAc (10 mL). The organic phase was separated, washed with brine (10 mL×3), dried over $Na_2SO_4$, filtered, and concentrated under reduced pressure. The residue was purified by prep-HPLC (HCl condition) to afford compound 9A (8.1 mg, 16 μmol, 21% yield) as a yellow oil. ¹H NMR (CD₃OD, 400 MHz) δ 8.19 (s, 1H), 8.14-7.98 (m, 1H), 3.91 (s, 3H), 3.80 (br t, J=10.8 Hz, 1H), 3.16-3.03 (m, 4H), 2.67 (t, J=7.3 Hz, 2H), 2.55 (br t, J=10.8 Hz, 1H), 2.12-2.02 (m, 4H), 1.68 (quin, J=6.9 Hz, 2H), 1.44 (s, 9H), 1.37-1.23 (m, 4H), 1.07-0.94 (m, 1H), 0.54-0.41 (m, 2H), 0.17 (q, J=5.0 Hz, 2H).

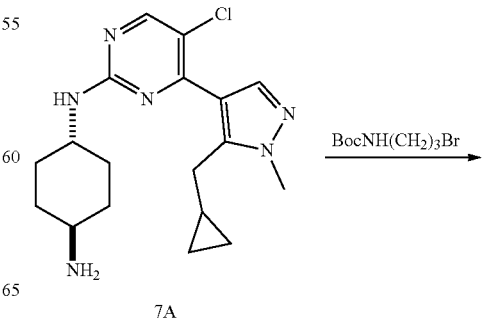

Scheme 8A

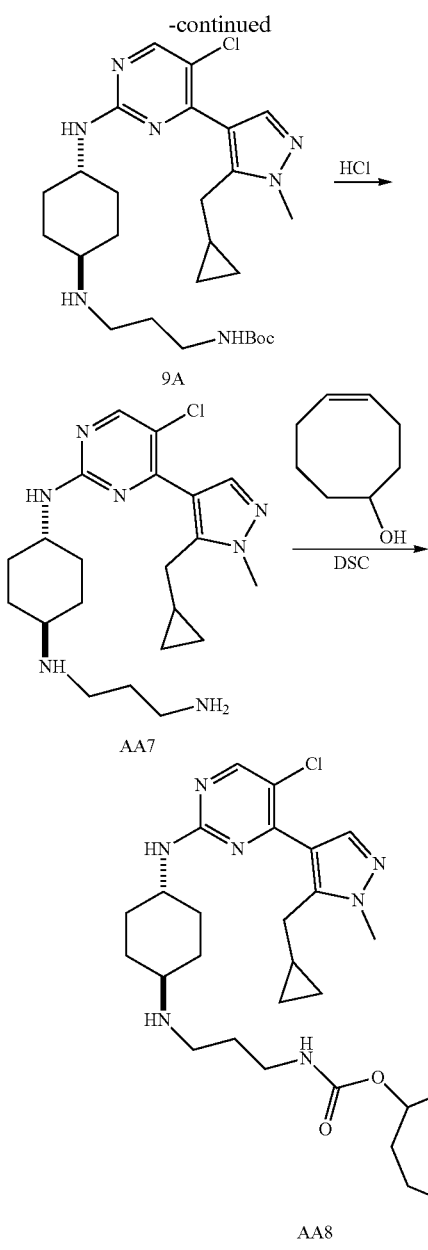

9A

AA7

AA8

Compound AA7. A mixture of compound A9 (200 mg, 386 μmol, 1 eq.) in EtOAc (5 mL) was added HCl/EtOAc (4 M, 965 μL, 10 eq.) in one portion. After stirred at 25° C. for 0.5 h, the reaction mixture was filtered and the filter cake was washed with EtOAc (5 mL×3). The filter cake was dried in vacuo to afford crude compound AA7 (150 mg), which was used directly in the next step without further purification. Some of the crude product (15 mg) was purified by preo-HPLC (HCl condition) to afford compound AA7 (4.5 mg). $^1$H NMR (CD$_3$OD, 400 MHz) δ 8.51 (br s, 1H), 8.44 (s, 1H), 4.18-4.02 (m, 1H), 3.98 (s, 3H), 3.28-3.16 (m, 5H), 3.12 (br t, J=7.6 Hz, 2H), 2.40-2.22 (m, 4H), 2.19-2.09 (m, 2H), 1.80-1.48 (m, 4H), 1.12 (br s, 1H), 0.56 (br d, J=7.5 Hz, 2H), 0.31 (br d, J=4.5 Hz, 2H).

Compound AA8. A mixture of (Z)-cyclooct-4-en-1-ol (42 mg, 330 μmol, 1.5 eq.), N,N'-disuccinimidyl carbonate (DSC) (101 mg, 396 μmol, 1.8 eq.), and TEA (40 mg, 396 μmol, 1.8 eq.) in MeCN (0.5 mL) was degassed and purged with N$_2$ for 3 times. After stirred at 25° C. for 4 h under N$_2$, the mixture was added into a mixture of compound AA7 (91.98 mg, 220 μmol, 1 eq.) and TEA (40 mg, 396 μmol, 1.8 eq.) in DMF (0.5 mL) dropwise at 25° C. under N$_2$. After stirred at 25° C. for 0.5 h under N$_2$, the reaction mixture was filtered and the filtrate was concentrated in vacuo. The mixture was purificated by prep-HPLC (HCl) to afford compound AA8 (8.9 mg, 16 μmol, 7% yield) as a yellow oil. $^1$H NMR (CD$_3$OD, 400 MHz) δ 8.47 (br s, 1H), 8.42 (s, 1H), 5.75-5.50 (m, 2H), 4.70 (br s, 1H), 4.15-4.00 (m, 1H), 3.96 (s, 3H), 3.29-3.18 (m, 4H), 3.14-2.97 (m, 2H), 2.62-2.49 (m, 2H), 2.44-2.32 (m, 1H), 2.25 (br d, J=13.2 Hz, 2H), 2.21-2.13 (m, 2H), 2.10-2.00 (m, 1H), 1.95-1.81 (m, 4H), 1.73 (br dd, J=4.6, 9.9 Hz, 1H), 1.68-1.34 (m, 7H), 1.10 (br s, 1H), 0.54 (br d, J=7.3 Hz, 2H), 0.30 (br s, 1H).

Example 33

Synthesis of Cyclooctyl (3-(((1r,4r)-4-((5-chloro-4-(5-(cyclopropylmethyl)-1-methyl-1H-pyrazol-4-yl)pyrimidin-2-yl)amino)cyclohexyl)amino)propyl)carbamate AA9

Compound AA9 was prepared as shown in Scheme 9A below.

Scheme 9A

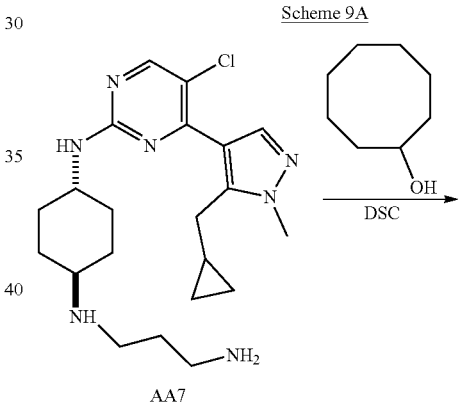

AA7

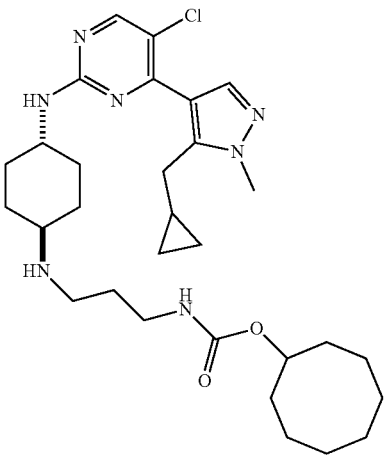

AA9

Compound AA9. A mixture of cyclooctanol (15.52 mg, 121 µmol, 1.1 eq.), DSC (33.82 mg, 132 µmol, 1.2 eq.), and TEA (15.59 mg, 154 µmol, 21.44 µL, 1.4 eq.) in MeCN (0.5 mL) was degassed and purged with $N_2$ for 3 times and stirred at 25° C. for 4 h under $N_2$. The mixture was added into a mixture of compound AA7 (0.05 g, 110 µmol, 1 eq.) and TEA (15.59 mg, 154 µmol, 21.44 µL, 1.4 eq.) in DMF (0.5 mL) dropwise at 25° C. under $N_2$. The mixture was stirred at 25° C. for 0.5 h under $N_2$. The reaction mixture was then concentrated under reduced pressure. The residue was filtered. The filtrate was purified by prep-HPLC (HCl) to afford compound AA9 (6.6 mg, 11 µmol, 10% yield) as a yellow oil. $^1$H NMR ($CD_3OD$, 400 MHz) δ 8.52-8.32 (m, 2H), 4.17-3.85 (m, 4H), 3.25-3.18 (m, 4H), 3.08 (br t, J=7.5 Hz, 2H), 2.66-2.48 (m, 1H), 2.26 (br d, J=10.3 Hz, 4H), 1.94-1.75 (m, 6H), 1.71-1.43 (m, 14H), 1.10 (br s, 1H), 0.54 (br d, J=7.5 Hz, 2H), 0.29 (br s, 2H).

Example 34

Synthesis of (E)-Cyclooct-4-en-1-yl (3-(((1r,4r)-4-((5-chloro-4-(5-(cyclopropylmethyl)-1-methyl-1H-pyrazol-4-yl)pyrimidin-2-yl)amino)cyclohexyl)amino)propyl)carbamate AA10

Compound AA10 was prepared as shown in Scheme 10A below.

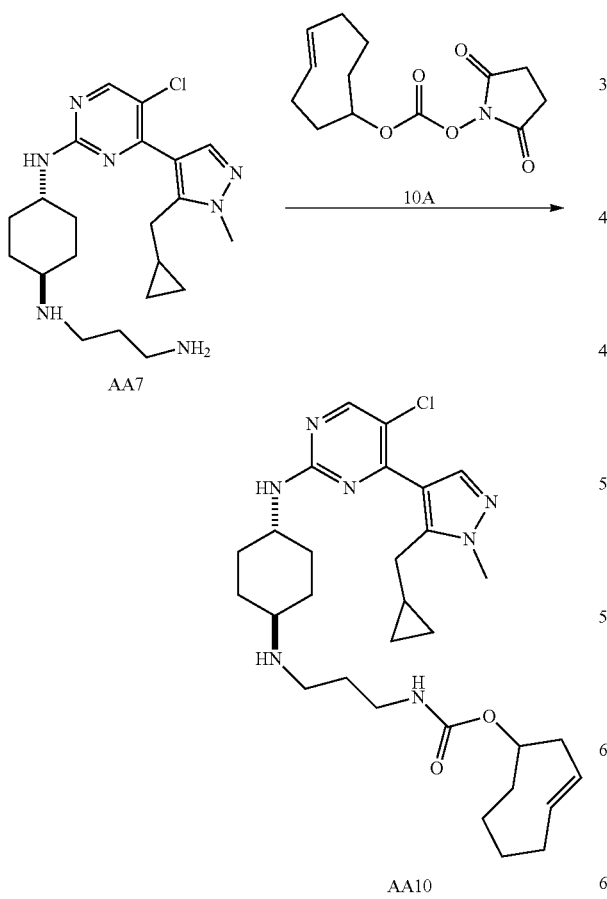

Compound AA10. A mixture of compound 7A (0.28 g, 616 µmol, 1 eq.), TEA (125 mg, 1.23 mmol, 172 µL, 2 eq.) in DCM (1 mL) was degassed and purged with $N_2$ for 3 times. A solution of compound 10A (165 mg, 616 µmol, 1 eq.) in DCM (1 mL) was added dropwise at 0° C. under $N_2$. The mixture was stirred at 0-25° C. for 0.5 h under $N_2$. The reaction mixture was filtered and the filtrate was concentrated in vacuo. The mixture was purificated by prep-HPLC (HCl condition) to afford compound AA10 (131 mg, 217 µmol, 35% yield). $^1$H NMR ($CD_3OD$, 400 MHz) δ 8.66-8.35 (m, 2H), 5.81-5.28 (m, 2H), 4.83-4.28 (m, 1H), 4.09 (br s, 1H), 3.98 (s, 3H), 3.26 (br d, J=5.3 Hz, 5H), 3.10 (br s, 2H), 2.46-2.15 (m, 7H), 2.03-1.88 (m, 5H), 1.80-1.34 (m, 8H), 1.13 (br s, 1H), 0.57 (br d, J=6.3 Hz, 2H), 0.32 (br s, 2H).

Example 35

Synthesis of N-(2-(2-(2-(2-(((1r,4r)-4-((5-Chloro-4-(5-(cyclopropylmethyl)-1-methyl-1H-pyrazol-4-yl)pyrimidin-2-yl)amino)cyclohexyl)amino)ethoxy)ethoxy)ethoxy)ethyl)-5-((3aS,4S,6aR)-2-oxohexahydro-1H-thieno[3,4-d]imidazol-4-yl)pentanamide AA11

Compound AA11 was prepared as shown in Scheme 11A below.

Compound 12A. A mixture of compound 11A (0.22 g, 1.41 mmol, 2 eq.) and compound 6A (0.2 g, 706 µmol, 1 eq.) in n-BuOH (5 mL) was degassed and purged with $N_2$ for 3 times. After stirred at 160° C. for 5 h, the reaction mixture was partitioned between $H_2O$ (10 mL) and DCM (15 mL). The organic phase was separated, washed with brine (10 mL×2), dried over $Na_2SO_4$, and concentrated in vacuo. The residue was purified by prep-TLC (PE/EtOAc: 1:1) to afford compound 12A (0.24 g, 594 µmol, 84% yield). $^1$H NMR ($CDCl_3$, 400 MHz) δ 8.26-8.05 (m, 2H), 4.95 (br d, J=7.4 Hz, 1H), 3.97 (s, 4H), 3.92 (s, 3H), 3.06 (br d, J=6.5 Hz, 2H), 2.06 (br dd, J=4.0, 12.4 Hz, 2H), 1.88-1.76 (m, 2H), 1.74-1.58 (m, 4H), 1.09-0.97 (m, 1H), 0.54-0.42 (m, 2H), 0.23-0.14 (m, 2H).

Scheme 11A

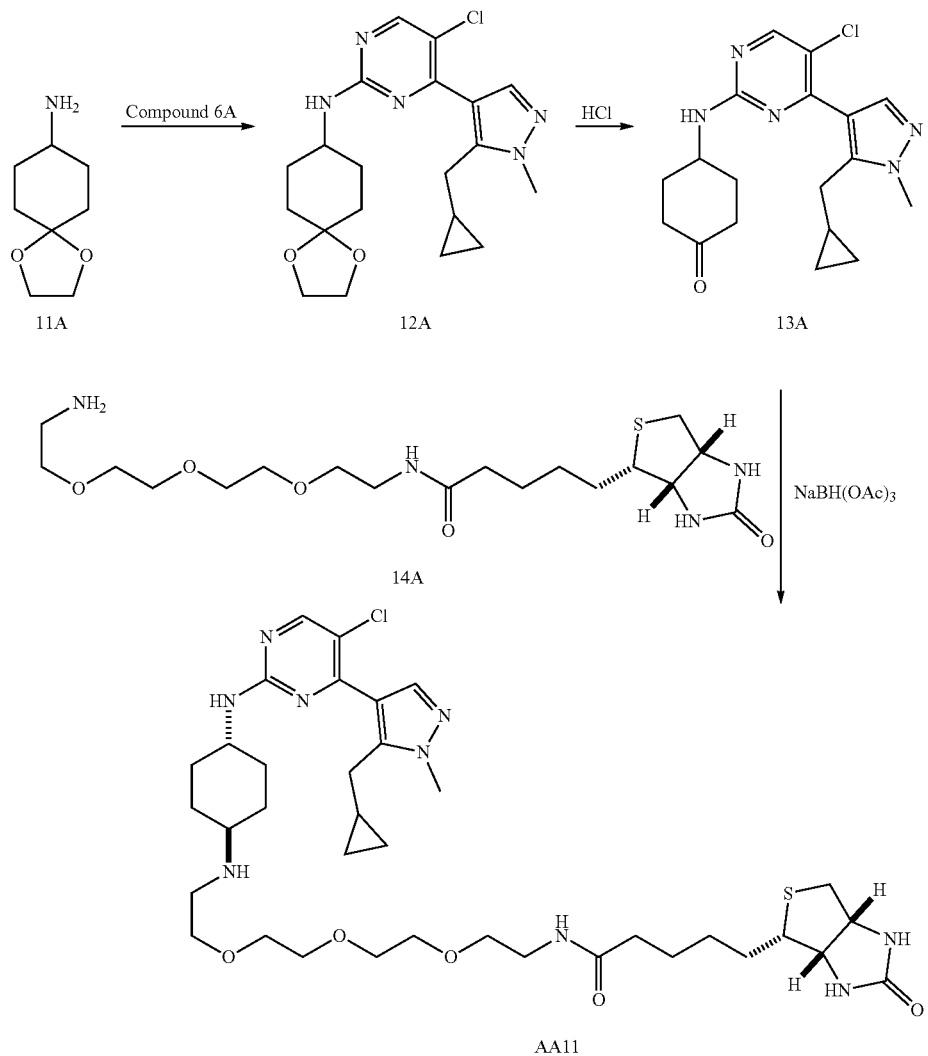

Compound 13A. A mixture of compound 12A (0.22 g, 545 µmol, 1 eq.) in aq. HCl (4 M, 2.72 mL, 20 eq.) was stirred at 15° C. for 2 h under $N_2$. The reaction mixture was concentrated in vacuo. The residue was purified by prep-HPLC (HCl condition) to afford compound 13A (0.20 g, 505 µmol, 92.65% yield). $^1$H NMR (CDCl$_3$, 400 MHz) δ 8.30 (br s, 1H), 8.17 (s, 1H), 4.46-4.31 (m, 1H), 3.95 (s, 3H), 3.10 (d, J=6.1 Hz, 2H), 2.69-2.54 (m, 2H), 2.45 (ddd, J=5.7, 9.7, 15.1 Hz, 2H), 2.35-2.25 (m, 2H), 2.07-1.95 (m, 2H), 1.10-0.95 (m, 1H), 0.58-0.49 (m, 2H), 0.30-0.17 (m, 2H).

Compound AA11. A mixture of compound 13A (92 mg, 255 µmol, 1 eq.) and compound 14A (160 mg, 382 µmol, 1.5 eq.) in MeOH (2 mL) stirred at 15° C. for 5 h. To the mixture was added CH$_3$COOH (31 mg, 510 µmol, 29 µL, 2 eq.) and NaBH(OAc)$_3$ (162 mg, 765 µmol, 3 eq.) in one portion. The reaction mixture was then stirred at 15-50° C. for 24 h under $N_2$. The reaction mixture was cooled to 25° C. and partitioned between H$_2$O (10 mL) and EtOAc (15 mL). The organic phase was separated and washed with brine (10 mL), dried over Na$_2$SO$_4$, and concentrated in vacuo. The residue was purified by prep-HPLC (HCl condition) to afford compound AA11 (20 mg, 25 µmol, 10% yield). $^1$H NMR (CD$_3$OD, 400 MHz) δ 8.42-8.21 (m, 2H), 4.60-4.47 (m, 1H), 4.38-4.25 (m, 1H), 3.90 (br s, 1H), 3.81 (s, 3H), 3.64 (br s, 2H), 3.54 (s, 4H), 3.50 (br s, 2H), 3.42 (br t, J=5.2 Hz, 2H), 3.26 (br t, J=5.2 Hz, 2H), 3.15 (br s, 6H), 3.08 (br d, J=6.5 Hz, 2H), 2.85 (br dd, J=4.3, 13.1 Hz, 1H), 2.64 (br d, J=13.3 Hz, 1H), 2.15 (br t, J=6.8 Hz, 4H), 2.09 (br s, 2H), 1.68-1.38 (m, 8H), 1.36-1.21 (m, 2H), 0.94 (br s, 1H), 0.38 (br d, J=7.2 Hz, 2H), 0.14 (br s, 2H).

Example 36

Synthesis of (1r,4r)-N$^1$-(4-(1-Methyl-3-(tetrahydro-2H-pyran-4-yl)-1H-pyrazol-4-yl)pyrimidin-2-yl)cyclohexane-1,4-diamine AA12

Compound AA12 was prepared as shown in Scheme 12A below.

Compound 16A. To a solution of compound 15A (5.0 g, 31 mmol, 1 eq.) in THF (50 mL) was added LDA (2 M in THF, 17 mL, 1.1 eq.) dropwise at −78° C. under $N_2$. The mixture was stirred at −78° C. for 1 h. TMSCl (3.9 g, 36 mmol, 4.5 mL, 1.15 eq.) was added at −78° C. dropwise.

After stirred at −78° C. for 30 mins, the mixture was poured into sat. NH₄Cl (50 mL) and extracted with EtOAc (50 mL×2). The combined organics were washed with brine (20 mL×3), dried over Na₂SO₄, and concentrated in vacuo. The residue was purified by column chromatography (PE/EtOAc: 5/1 to 1/1) to afford compound 16A (7.0 g, 30 mmol, 97% yield) as a yellow oil. ¹H NMR (CDCl₃, 400 MHz) δ 7.43 (s, 1H), 3.98-3.91 (m, 3H), 0.51-0.39 (m, 9H).

Compound 17A. To a solution of compound 16A (6.2 g, 27 mmol, 1 eq.) in THF (50 mL) was added LDA (2 M, 19.9 mL, 1.5 eq.) in THF dropwise at −78° C. under N₂. The mixture was stirred at −78° C. for 1 h. Tetrahydro-4H-pyran-4-one (4.0 g, 40 mmol, 3.66 mL, 1.5 eq.) was added dropwise at −78° C. The mixture was stirred at −78° C. for 30 mins. The mixture was poured into ice water (50 mL) and extracted with EtOAc (100 mL×2). The combined organics were washed with brine (100 mL×3), dried over Na₂SO₄, filtered, and concentrated in vacuo to give compound 17A (8.0 g, 24 mmol, 90% yield) as a yellow oil. ¹H NMR (CD₃OD, 400 MHz) δ 4.00 (s, 6H), 3.79-3.60 (m, 4H), 2.67-2.52 (m, 1H), 1.98-1.72 (m, 4H), 0.50-0.40 (m, 9H).

Scheme 12A

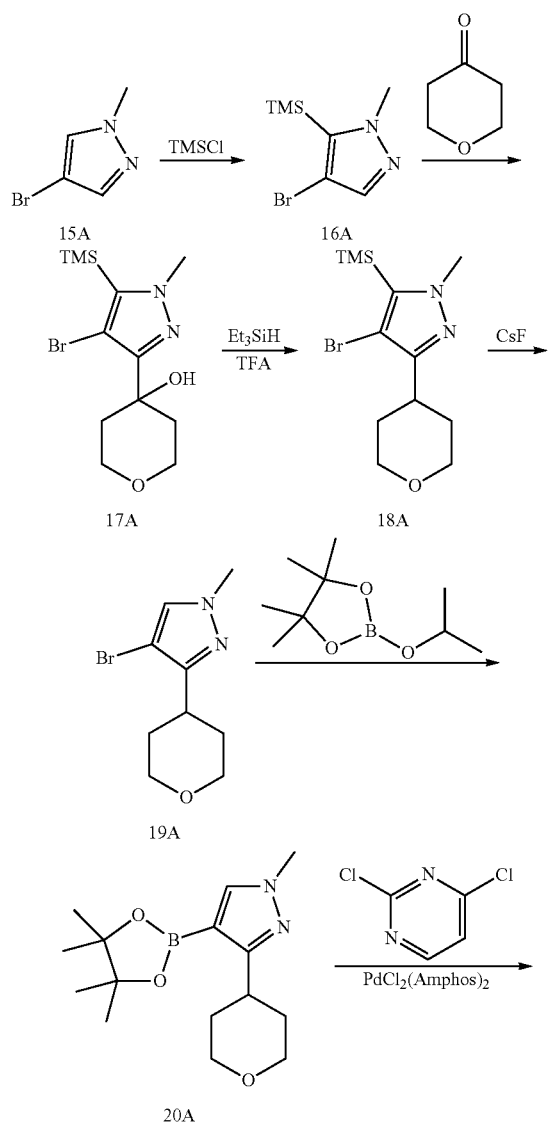

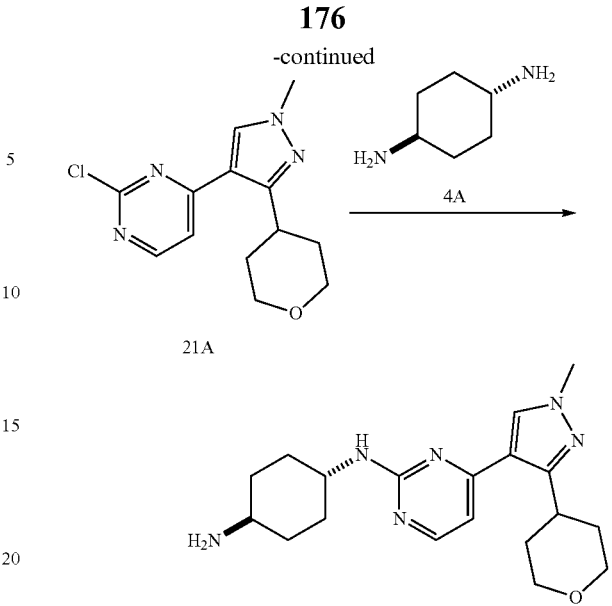

Compound 18A. To a mixture of compound 17A (8.0 g, 24 mmol, 1 eq.) and TFA (54.7 g, 480 mmol, 35.54 mL, 20 eq.) in DCM (50 mL) was added triethylsilane (13.96 g, 120 mmol, 19 mL, 5 eq.) at 15° C. The mixture was stirred at 15-50° C. for 12 h under N₂. The mixture was concentrated in vacuo. The residue was purified by column chromatography (PE/EtOAc: 20/1 to 10/1) to afford compound 18A (6.0 g, 19 mmol, 79% yield) as a yellow oil. ¹H NMR (CDCl₃, 400 MHz) δ 4.06 (br dd, J=2.4, 11.3 Hz, 2H), 3.95-3.86 (m, 3H), 3.45 (s, 1H), 3.54 (dt, J=2.1, 11.7 Hz, 1H), 2.93 (tt, J=3.9, 11.7 Hz, 1H), 2.01-1.79 (m, 4H), 0.49-0.39 (m, 9H).

Compound 19A. To a mixture of compound 18A (5.0 g, 16 mmol, 1 eq.) in EtOH (5 mL) and MeCN (15 mL) was added CsF (4.8 g, 32 mmol, 2 eq.) in one portion at 15° C. The mixture was stirred at 15° C. for 4 h. The reaction mixture was filtered through celite. The filtrate was concentrated in vacuo. The residue was purified by column chromatography (PE/EtOAc: 10/1 to 5/1) to afford compound 19A (3.6 g, 15 mmol, 93% yield) as a yellow oil. ¹H NMR (CDCl₃, 400 MHz) δ 7.32 (s, 1H), 4.06 (br dd, J=2.3, 11.5 Hz, 2H), 3.53 (dt, J=2.1, 11.7 Hz, 2H), 2.93 (tt, J=3.9, 11.7 Hz, 1H), 2.01-1.86 (m, 2H), 1.86-1.76 (m, 2H).

Compound 20A. To a mixture of compound 19A (1.0 g, 4.08 mmol, 1 eq.) and 2-isopropoxy-4,4,5,5-tetramethyl-1,3,2-dioxaborolane (0.9 g, 4.90 mmol, 1.2 eq.) in THF (30 mL) was added n-BuLi (2.5 M, 2.0 mL, 1.2 eq.) dropwise at −78° C. under N₂. The mixture was stirred at −78° C. for 0.5 h. The mixture was poured into sat. NH₄Cl (50 mL) and extracted with EtOAc (30 mL×3). The combined organics were washed with brine (30 mL), dried over Na₂SO₄, and concentrated in vacuo. The residue was purified by column chromatography (PE/EtOAc: 20/1 to 5:1) to afford compound 20A (0.5 g, 1.71 mmol, 42% yield) as a yellow oil. ¹H NMR (CDCl₃, 400 MHz) δ 7.56 (s, 1H), 4.03 (br dd, J=3.5, 10.4 Hz, 2H), 3.82 (s, 3H), 3.51 (dt, J=2.1, 11.7 Hz, 2H), 3.26-2.77 (m, 1H), 1.99-1.88 (m, 2H), 1.83-1.75 (m, 2H), 1.28 (s, 12H).

Compound 21A. A mixture of compound 20A (0.5 g, 1.71 mmol, 1.2 eq.), 2,4-dichloropyrimidine (0.21 g, 1.43 mmol, 1 eq.), aq. Na₂CO₃ (2 M, 2.1 mL, 3 eq.), and PdCl₂(Amphos)₂ (0.1 g, 143 µmol, 0.1 eq.) in DME (3 mL) was degassed and purged with N₂ for 3 times. Then the mixture was stirred at 85° C. for 2 h under N₂. The reaction mixture was cooled down to 25° C. and partitioned between H₂O (20 mL) and EtOAc (20 mL×2). The organic phase was separated, washed with brine (50 mL), dried over Na₂SO₄, and concentrated in vacuo. The residue was purified by prep-TLC (PE/EtOAc: 1:1) to afford compound 21A (90 mg, 323 μmol, 23% yield) as a yellow oil. LCMS (M+H⁺): 279.

Compound AA12. A mixture of compound 21A (90 mg, 323 μmol, 1 eq.) and compound 4A (111 mg, 969 μmol, 3 eq.) in n-BuOH (5 mL) was degassed and purged with N₂ for 3 times. Then the mixture was stirred at 160° C. for 2 h under N₂. The reaction mixture was cooled down to 25° C. and concentrated in vacuo. The residue was purified by prep-HPLC (neutral condition) to afford compound AA12 (8 mg, 22 μmol, 7% yield). ¹H NMR (CD₃OD, 400 MHz) δ 8.09 (br d, J=5.3 Hz, 1H), 8.06 (s, 1H), 6.73 (br d, J=5.4 Hz, 1H), 4.04 (br d, J=10.9 Hz, 2H), 3.88 (s, 3H), 3.86-3.76 (m, 2H), 3.61 (dt, J=2.3, 11.2 Hz, 2H), 2.83 (br s, 1H), 2.15-1.98 (m, 4H), 1.89 (br s, 4H), 1.40 (br s, 4H).

Example 37

Synthesis of (1r,4r)-N¹-(4-(5-Ethyl-1-methyl-3-(tetrahydro-2H-pyran-4-yl)-1H-pyrazol-4-yl)pyrimidin-2-yl)cyclohexane-1,4-diamine AA13

Compound AA13 was prepared as shown in Scheme 13A below.

Scheme 13A

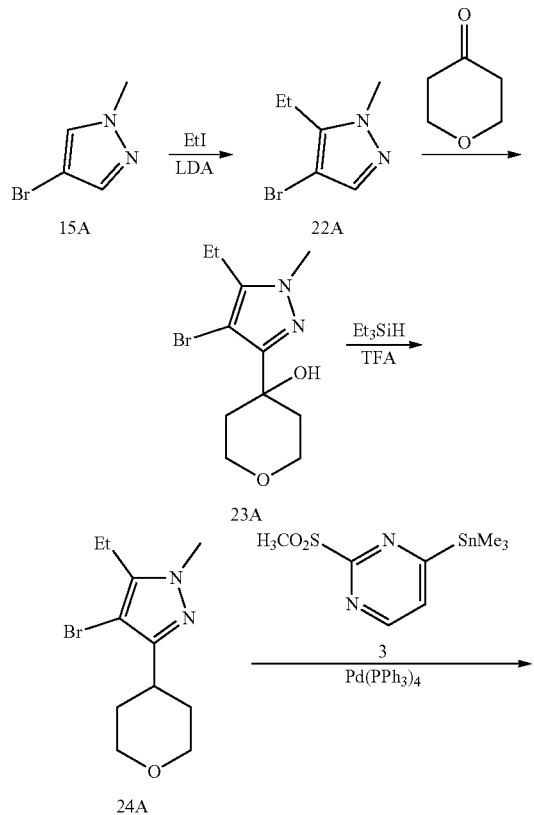

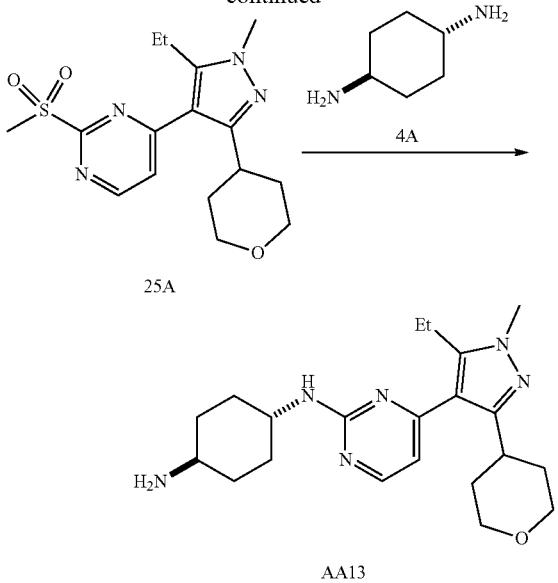

Compound 22A. To a solution of compound 15A (20.0 g, 124 mmol, 1 eq.) in THF (50 mL) was added LDA (2 M, 74.5 mL, 1.2 eq.) dropwise at −78° C. under N₂. The mixture was stirred at −78° C. for 1 h. Iodoethane (25.2 g, 161 mmol, 12.92 mL, 1.3 eq.) was added dropwise at −78° C. The mixture was stirred at −78° C. for 30 mins. The mixture was poured into ice sat. NH₄Cl (50 mL) and extracted with EtOAc (100 mL×2). The combined organics were washed with brine (100 mL), dried over Na₂SO₄, filtered, and concentrated in vacuo. The residue was purified by column chromatography (PE/EtOAc: 5/1 to 1/1) to afford compound 22A (20 g, 106 mmol, 85% yield) as a yellow oil. ¹H NMR (CDCl₃, 400 MHz) δ 7.37 (s, 1H), 3.83 (s, 3H), 2.69 (q, J=7.6 Hz, 2H), 1.18 (t, J=7.6 Hz, 3H).

Compound 23A. To a solution of compound 22A (10.0 g, 53 mmol, 1 eq.) in THF (50 mL) was added LDA (2 M, 26.5 mL, 1 eq.) dropwise at −78° C. under N₂. The mixture was stirred at −78° C. for 1 h. Tetrahydro-4H-pyran-4-one (7.9 g, 79 mmol, 7.29 mL, 1.5 eq.) was added dropwise at −78° C. The mixture was stirred at −78° C. for 30 mins. The mixture was poured into ice sat.NH₄Cl (50 mL) and extracted with EtOAc (100 mL×2). The combined organics were washed with brine (100 mL), dried over Na₂SO₄, and concentrated in vacuo to afford compound 23A (15 g, 52 mmol) as a yellow oil, which was used directly in the next step without further purification. ¹H NMR (CD₃OD, 400 MHz) δ 3.90 (dd, J=2.5, 10.8 Hz, 2H), 3.82 (s, 3H), 3.77-3.73 (m, 2H), 2.73 (d, J=7.7 Hz, 2H), 2.40-2.30 (m, 2H), 1.92-1.87 (m, 2H), 1.18 (d, J=7.0 Hz, 3H).

Compound 24A. To a mixture of compound 23A (15.0 g, 52 mmol, 1 eq.) and TFA (118.3 g, 1.04 mol, 76.81 mL, 20 eq.) in DCM (50 mL) was added triethylsilane (30.16 g, 259.36 mmol, 41.43 mL, 5 eq.) in one portion at 15° C. The mixture was stirred at 15-50° C. for 12 h under N₂. The mixture was cooled down to 25° C. and concentrated in vacuo. The residue was purified by column chromatography (PE/EtOAc: 20/1 to 10/1) to afford compound 24A (14 g, 51 mmol, 99% yield) as a yellow oil. ¹H NMR (CDCl₃, 400 MHz) δ 4.12-4.00 (m, 2H), 3.79 (s, 3H), 3.53 (dt, J=2.0, 11.7 Hz, 2H), 2.89 (tt, J=3.9, 11.7 Hz, 1H), 2.66 (q, J=7.7 Hz, 2H), 2.02-1.88 (m, 2H), 1.86-1.76 (m, 2H), 1.17 (t, J=7.6 Hz, 3H).

Compound 25A. A mixture of compound 23A (0.50 g, 1.83 mmol, 1 eq.), compound 3 (0.65 g, 2.01 mmol, 1.1 eq.) and Pd(PPh$_3$)$_4$ (0.21 g, 183 μmol, 0.1 eq.) in toluene (5 mL) was degassed and purged with N$_2$ for 3 times. The mixture was stirred at 90° C. for 12 h under N$_2$. The reaction mixture was cooled down to 25° C. and concentrated in vacuo. The residue was purified by column chromatography (PE/EtOAc: 10/1 to 8/1) to afford compound 25A (80 mg, 228 μmol, 12% yield) as a yellow oil. $^1$H NMR (CDCl$_3$, 400 MHz) δ 8.87-8.73 (m, 1H), 7.37-7.30 (m, 1H), 4.07 (br d, J=10.8 Hz, 2H), 3.86 (d, J=1.6 Hz, 3H), 3.55 (br t, J=11.7 Hz, 2H), 3.37 (d, J=1.6 Hz, 3H), 3.27 (br d, J=11.0 Hz, 1H), 3.00-2.87 (m, 2H), 2.02-1.92 (m, 2H), 1.84 (br d, J=11.2 Hz, 2H), 1.35-1.29 (m, 3H).

Compound AA13. A mixture of compound 25A (50 mg, 143 μmol, 1 eq.) and compound 4A (49 mg, 428 μmol, 3 eq.) in t-BuOH (5 mL) was degassed and purged with N$_2$ for 3 times. Then the mixture was stirred at 140° C. for 2 h under N$_2$. The reaction mixture was cooled down to 25° C. and concentrated in vacuo. The residue was purified by prep-HPLC (neutral condition) to afford compound AA13 (17.5 mg, 46 μmol, 32% yield). $^1$H NMR (CD$_3$OD, 400 MHz) δ 8.19 (d, J=5.1 Hz, 1H), 6.59 (d, J=5.3 Hz, 1H), 4.06-3.95 (m, 2H), 3.82 (s, 4H), 3.49 (br d, J=1.6 Hz, 2H), 3.32 (br s, 2H), 2.86 (d, J=7.4 Hz, 2H), 2.81-2.71 (m, 1H), 2.09 (br d, J=13.5 Hz, 2H), 1.99-1.84 (m, 4H), 1.80-1.70 (m, 2H), 1.37 (br d, J=9.2 Hz, 4H), 1.22 (t, J=7.5 Hz, 3H).

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound selected from:

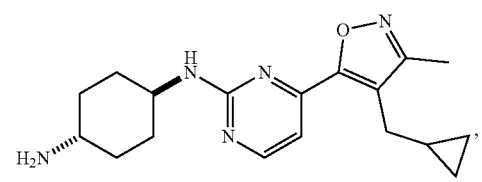

A1

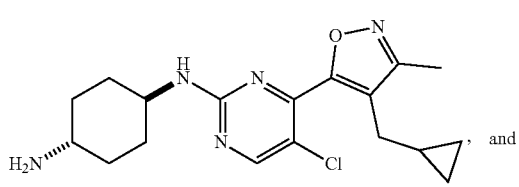

A2

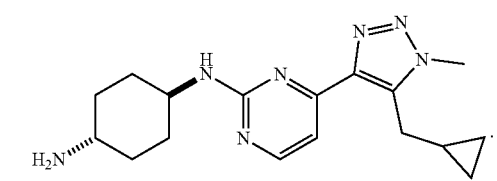

and

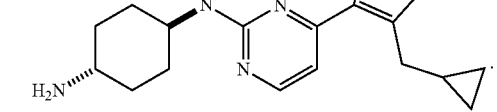

B1

2. A compound selected from:

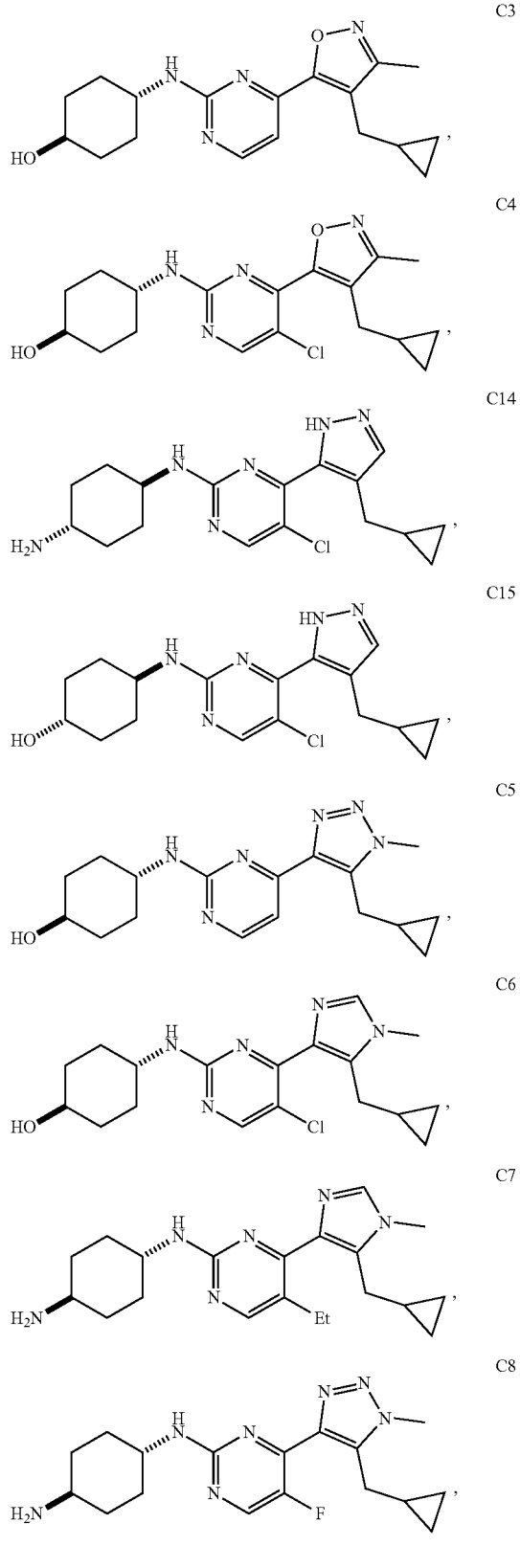

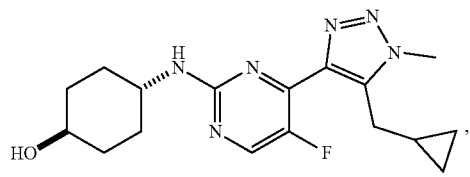
C9
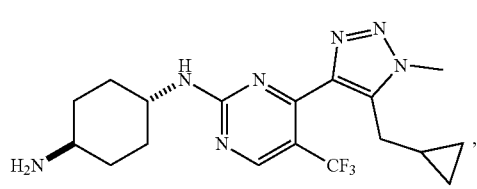
C10
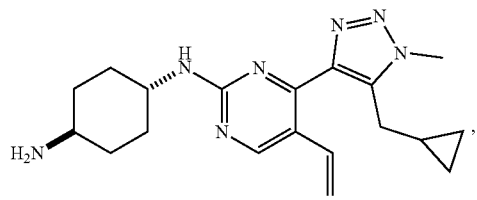
C11
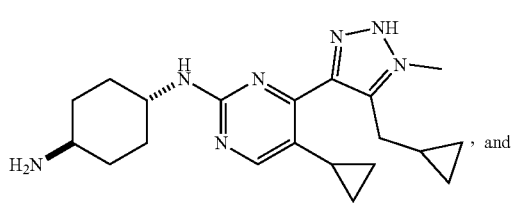
, and
C12
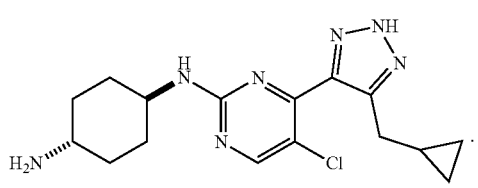
C13
3. A compound having the formula:
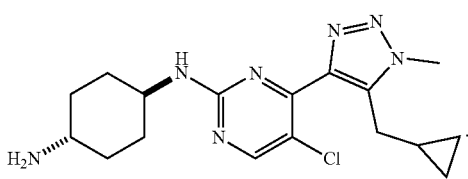
B2
* * * * *